United States Patent [19]
Gordon et al.

[11] Patent Number: 4,862,361
[45] Date of Patent: Aug. 29, 1989

[54] METHODS AND APPARATUS FOR MONITORING CARDIOVASCULAR REGULATION USING HEART RATE POWER SPECTRAL ANALYSIS

[75] Inventors: David Gordon, Chicago, Ill.; Solange Akselrod, Ramat-Ilan, Israel; Richard J. Cohen, Newton Highlands, Mass.; Jerome C. Tu, Monterey Park, Calif.; Stephen K. Burns, Henniker, N.H.; Victoria H. DeLeon, Arlington, Mass.

[73] Assignee: Massachusetts Institute of Technology, Cambridge, Mass.

[21] Appl. No.: 742,114

[22] Filed: Jun. 5, 1985

[51] Int. Cl.$^4$ ................................................ A61B 5/02
[52] U.S. Cl. ............................ 364/413.06; 128/661.04
[58] Field of Search ................ 364/415; 128/663, 661, 128/713, 715, 702, 703

[56] References Cited

U.S. PATENT DOCUMENTS

| | | |
|---|---|---|
| 3,612,041 | 10/1971 | Ragsdale . |
| 3,698,386 | 10/1972 | Fried . |
| 4,170,992 | 10/1979 | Dillman . |
| 4,289,141 | 9/1986 | Coanier ................ 128/713 |
| 4,379,460 | 4/1983 | Judell . |
| 4,422,458 | 12/1983 | Kravath . |
| 4,432,375 | 2/1984 | Angel et al. . |
| 4,463,764 | 8/1984 | Anderson et al. . |
| 4,506,678 | 3/1985 | Russell et al. . |
| 4,519,395 | 5/1985 | Hrushesky ................ 128/671 |
| 4,545,387 | 10/1985 | Balique ................ 128/663 |
| 4,549,551 | 10/1985 | Dyck et al. ................ 128/715 |
| 4,570,225 | 2/1986 | Lundy . |
| 4,573,478 | 3/1986 | Arnold . |

FOREIGN PATENT DOCUMENTS

2527475 12/1976 Fed. Rep. of Germany .

OTHER PUBLICATIONS

"Computer Electrocardiographic Processing", Cesar A. Caceres, Aug. 1972.

"Non Invasive Monitoring Techinques in Neurosurgical Intensive Care", James J. Ackmenn.
Baselli et al., Med. Inform., 10, 223–235 (1985).
Bhargava et al., J. Electrocardiol., 14, 57–60 (1981).
Cary, "A Digital Cardiac Tachometer Synthesizer and Signal Delay", B.S Thesis, Massachusetts Institute of Technology (1983).
de Boer et al., Med. Biol. Eng. Comput., 23, 352–358 (1983).
de Leon et al., Abstract presented at a Reynolds Symposium, Jun. 5, 1984.
Fischler, "Real-Time Microprocessor-Based Analysis of Heartbeat Variability", B.S. Thesis, Massachusetts Institute of Technology (1982).
Fiser et al., Automedica, 2, 143—147 (1978.

(List continued on next page.)

Primary Examiner—Jerry Smith
Assistant Examiner—Kimthanh Tbui
Attorney, Agent, or Firm—Marshall, O'Toole, Gerstein, Murray & Bicknell

[57] ABSTRACT

Malfunctions of the cardiovascular control system may be diagnosed by examination of a patient's heart rate fluctuation power spectra. Particularly indicative of cardiovascular stress are: a level below about 0.1 (beats/min.)$^2$ in the power spectrum of heart rate fluctuations at a frequency between about 0.04 and about 0.10 Hz; a marked increase to above about 10 (beats/min.)$^2$ in a peak in the heart rate fluctuation power spectrum between about 0.04 to 0.10 Hz; and a ratio of the area under a heart rate power spectrum peak at a frequency between about 0.04 and 0.10 Hz to the area under a peak in the respiratory heart rate fluctuation power spectrum centered at the mean respiratory rate about about 0.10 Hz as having an absolute value less than 2.0 for longer than or equal to about one hour or as having an absolute value greater than about 50.

4 Claims, 17 Drawing Sheets

OTHER PUBLICATIONS

Frank, "Analysis of Heart-Rate Variability Using the Radio Shack Color Computer", B.S. Thesis, Massachusetts Institute of Technology (1983).
Gordon et al., *Pediatr. Research*, 18(10) 921–926 (1984).
Jennings et al., *Exp. Aging Research*, 10, 19–23 (1984).
Kuo et al., *Computers in Cardiology*, 347–349, Sep. (1978).
Nygards et al., *Computers in Cardiology*, 393–398, Sep. (1977).
Pagani et al., *Eur. J. Clin. Invest.*, 14, 19 (1984).
Penaz et al., *Physiologia Bohemoslovaca*, 27, 349–357 (1978).
Putman et al., Journal of Clinical Engineering, 5(1), 56–58, Jan.–Mar. (1980).
Raghuveer, "Bispectrum and Multidimensional Power Spectrum Estimation Algorithms based on Parametric Models with Applications to the Analysis of ECG Data," Ph.D. Dissertation, University of Connecticut (1984).
Schick et al., Ann. Biomed. Eng., 6, 154–160 (1978).
Tu, "Time Spectral Analysis of Physiological Signals," Microprocessor System for Real, M.S. Thesis, Massachusetts Institute of Technology (1984).
Wilson et al., *Med. & Biol. Eng. & Comput.*, 20, 293–298 (1982).
Zwiener, *Automedica*, 2, 161–169 (1978).
Zwiener et al., *Automdeica*, 5, 77–90 (1984).

METHODS AND APPARATUS FOR MONITORING CARDIOVASCULAR REGULATION USING HEART RATE POWER SPECTRAL ANALYSIS

BACKGROUND OF THE INVENTION

The present invention relates in general to methods and apparatus for monitoring cardiovascular regulation and in particular to methods and apparatus for heart rate spectral analysis.

Changes in cardiovascular regulation associated with congestive heart failure include attenuation of activity in the parasympathetic division of the autonomic nervous system, enhancement of activity in the sympathetic division of the autonomic nervous system, cardiac catecholamine depletion, down regulation of the beta-receptor system, increased renin-angiotensin system activity, and alteration of baroreceptor function. All of these regulatory changes require either specific clinical manipulations, such as a stress test, a Valsalva maneuver, or the like, and/or invasive maneuvers, such as cardiac biopsy, plasma catecholamine measurement, or the like, in order to determine the extent of regulatory dysfunction and its impact upon the clinical state of the patient and upon prognoses for the patient. These procedures are time consuming, and generally do not permit the formation of a clinical judgment and subsequent action within the timeframe of the course of treatment for critically ill patients in an Intensive Care Unit.

Fluctuations from heartbeat to heartbeat in measured properties of the circulatory system reflect both the presence of a variety of naturally occurring physiological disturbances of the circulatory system homeostasis, and the dynamic response of cardiovascular control systems to these disturbances. For example, the cyclic variation in intrathoracic pressure which accompanies breathing mechanically affects the return of venous blood to the heart and also affects blood pressure in pulmonary vessels and in the aorta. The variation in intrathoracic pressure is also coupled to a cyclic variation in heart rate through a neural mechanism mediated by the central nervous system. Furthermore, the resulting cyclic variation in arterial blood pressure impinges on heart rate through a reflex, known as the baroreceptor reflex, which is mediated by the autonomic nervous system. Disturbances in cardiovascular homeostasis also occur with fluctuations in the resistance of peripheral blood vessels as vascular beds regulate local blood flow to match supply with demand. These fluctuations in peripheral resistance may perturb central blood pressure and through the baroreceptor reflex, may also lead to a compensatory variation in heart rate.

Many types of medical instruments exist for studying heart rate variability. The instantaneous rate-meter is perhaps the earliest such instrument. This meter measures each RR interval through analog or digital circuitry and displays the instantaneous heart rate.

An improvement in the rate-meter is achieved by performing first order statistical evaluation on the RR-intervals. With mini- and micro-computer systems histogram displays of RR-interval differences may be generated along with their mean and standard deviations.

Another technique for heart rate variability analysis involves the study of spectral content of the instantaneous heart rate time series. In one approach to spectral analysis in animals, the computations are done on a computer. Akselrod, et al., *Science*, 213, 220–222 (1981) Hyndman, et al., *Automedica*, 1, 239–252 (1975). Such systems analyze data recorded on magnetic or punched tape. However, not only do these systems introduce additional errors during the recording process, they do not perform in real time. Furthermore, these systems are not multichannel in nature.

A Sparse Discrete Fourier Transform algorithm which may be implemented on a personal computer (CBM 2016) and which may perform on-line monitoring of heart rate variability, based on a low pass filtered cardiac event series is disclosed in Rompelman, et al., *IEEE Trans. Biomed. Engineering*, BME-29, 503–510 (1982). A specialized hardware device also exists for low pass filtering the cardiac event series by a stepwise convolution to create the low pass filtered cardiac event series. Coenen, et al., *Medical and Biological Engineering and Computing*, 15, 423–430 (1977). Nevertheless, these instruments possess a limited band width and a limited frequency resolution capability.

There exists a need for an instrument which provides multi-channel spectral analysis of an instantaneous heart rate and of a respiratory activity time series. There also exists a need for an instrument wherein such calculations are performed in real time at the bedside.

SUMMARY OF THE INVENTION

The present invention provides a method for diagnosis of malfunctions of the cardiovascular control system in a patient. A power spectrum of heart rate fluctuations in the patient is monitored, and a level below 0.1 (beats/min.)$^2$ is identified in the heart rate fluctuation power spectrum at a frequency between 0.04 and 0.10 Hz as indicative of cardiovascular instability or of heart failure.

Another method according to the present invention diagnoses malfunctions of the cardiovascular control system in a patient. A power spectrum of heart rate fluctuations in the patient is monitored, and a marked increase to above about 10 (beats/min.)$^2$ in a peak in the heart rate fluctuation power spectrum is identified at a frequency between 0.04 to 1 Hz as indicative of cardiovascular instability resulting from cardiac tamponade or depleted intravascular volume, or hemorrhage, or chylothorax, or acute hypoxia or acute hypercarbia.

Yet another method according to the present invention diagnoses malfunctions of the cardiovascular control system in a patient. A power spectrum of heart rate fluctuations in a patient is monitored, and a ratio of the area under a peak in the heart rate fluctuation power spectrum at a frequency between about 0.04 and about 0.1 Hz to the area under a respiratory peak in the heart rate fluctuation power spectrum centered at the mean respiratory rate as having an absolute value less than 2.0 as indicative of cardiac instability.

Still another method according to the present invention diagnoses malfunctions of the cardiovascular control system in a patient by monitoring a power spectrum of heart rate fluctuations in the patient and by identifying a ratio of the area under a heart rate power spectrum peak at a frequency between about 0.04 and about 0.1 Hz to the area under a peak in the respiratory heart rate fluctuation power spectrum centered at the mean respiratory rate as having an absolute value greater than or about 50 as indicative of cardiovascular stress.

An apparatus according to the present invention monitors a heart rate power spectrum. Means for converting an analog heart rate signal to a form acceptable to a programmable electronic device are coupled to a programmable electronic device.

DETAILED DESCRIPTION

Figure 1:
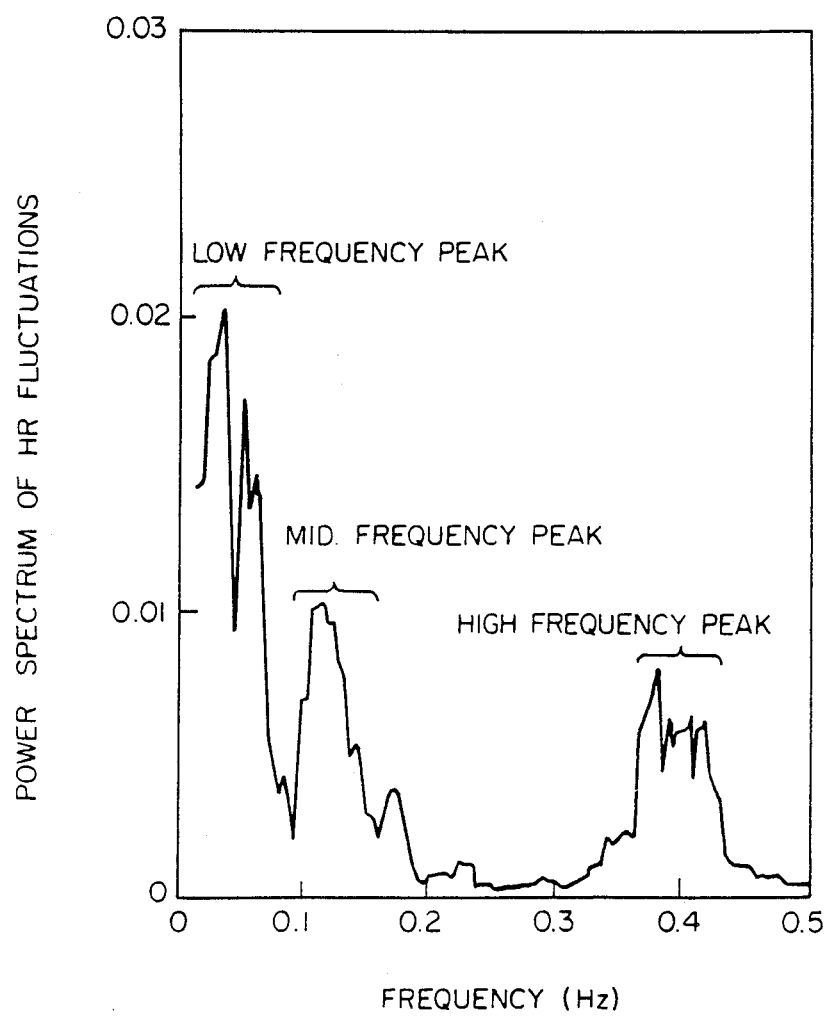
FIG. 1 illustrates low frequency, mid-frequency and high frequency in the power spectrum of heart rate fluctuations in a dog according to the prior art.

Power spectral methods may be used to analyze the frequency content of fluctuations in heart rate and other hemodynamic parameters. Hyndman, et al., *Nature*, 233, 339-341 (1971); Sayers, *Ergonomics*, 16, 17-32 (1973). Short term (i.e., on a time scale of seconds to minutes) fluctuations in these parameters are concentrated in three principal spectral peaks as illustrated for a canine model in FIG. 1. Akselrod, et al., supra. One peak is centered at the respiratory frequency; this peak shifts with changes in the respiratory rate. The second identifiable spectral peak, the mid-frequency peak, occurs typically between 0.1 and 0.15 Hz. The oscillations associated with this second peak occur at 6-9 cycles per minute, a considerably lower frequency than the respiratory frequency, and are related to the frequency response of the baroreceptor reflex. The third peak of the spectrum typically occurs in the frequency band of 0.04 to 0.10 Hz. This low frequency peak is related to thermoregulatory fluctuations in vasomotor tone.

In one approach to the spectral analysis of heart rate, properties of the heart rate fluctuations in the conscious dog may be related to the activity of three cardiovascular control systems—the parasympathetic nervous system, the sympathetic nervous system and the renin-angiotensin system. Akselrod, et al., *Science*, 213, 220-223 (1981). This model is further elaborated in Akselrod, et al., "Hemodynamic Regulation: Investigation by Spectral Analysis" (In Press). Heart rate fluctuations occurring at frequencies above roughly 0.1 Hz are mediated solely by the parasympathetic system. Blockade of the renin-angiotensin system leads to a dramatic increase in the amplitude of the low frequency peak. The effects of an autonomic blockade also exist in humans and changes in body posture alter sympathetic-parasympathetic balance as measured by the heart rate power spectrum. Pomeranz, et al., *Am. J. Physiol.*, 248, H151-H153 (1985).

Figure 2:
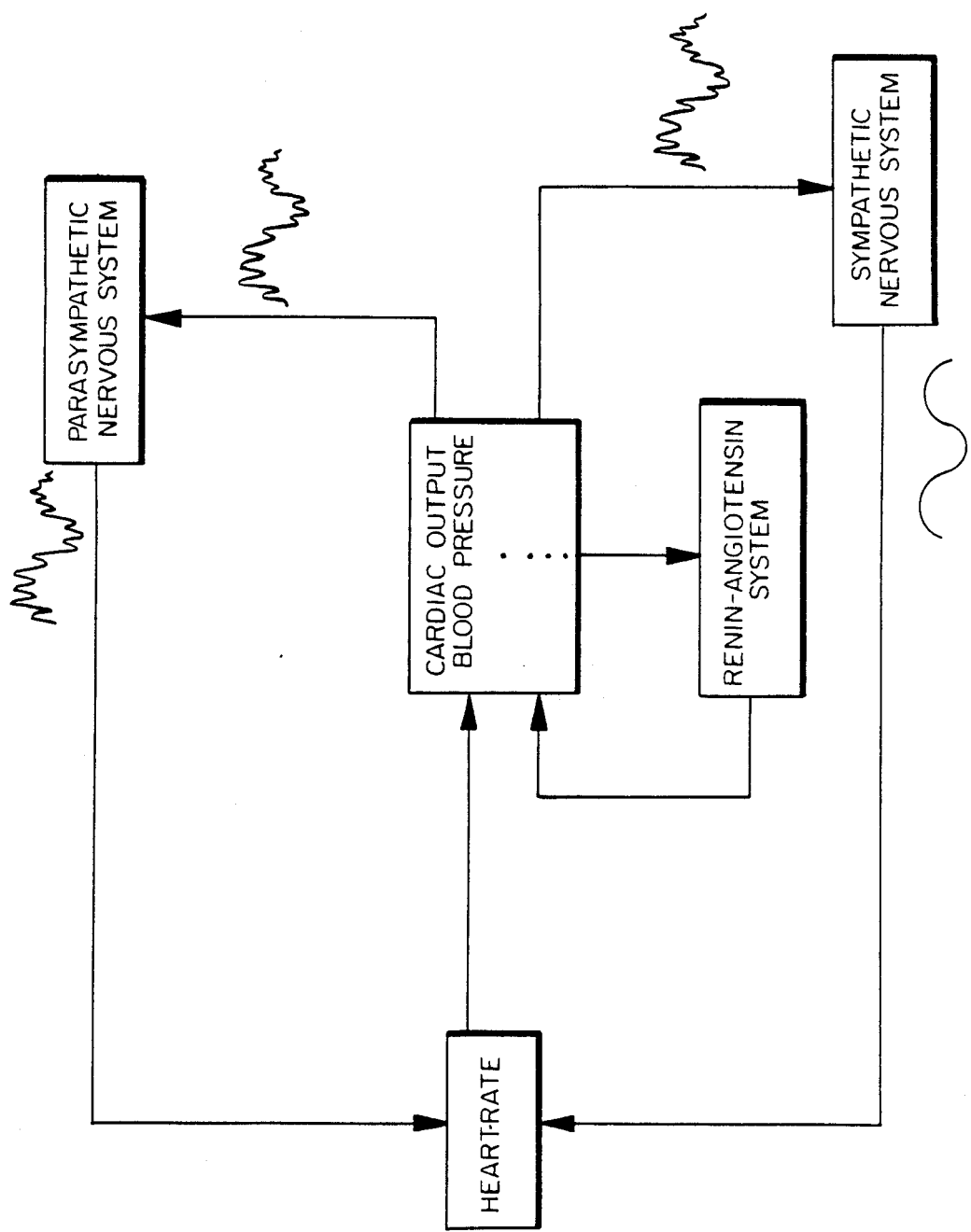
FIG. 2 illustrates aspects of the cardiovascular control system according to the prior art.

A simple model of the short term cardiovascular control system is illustrated in FIG. 2. Akselrod, et al., supra. In this model, heart rate is directly modulated by the sympathetic and parasympathetic nervous systems. Through a variety of receptors both these systems sense, fluctuations in cardiovascular parameters including arterial and venous pressures, vascular volumes, and correlates of blood flow and oxygenation. The parasympathetic system may respond over a wide frequency range while the sympathetic system may only respond at relatively low frequencies below roughly 0.1 Hz.

A hypothesis was proposed in Akselrod, et al., *Science*, 213, 220-223 (1981), that fluctuations in vasomotor tone associated with the low frequency heart rate fluctuations are not solely related to thermoregulation but also reflect local adjustment to resistance in individual beds of blood vessels in order to match local blood flow to local metabolic demand. Such fluctuations in peripheral vasomotor tone lead to fluctuations in central blood pressures which are in turn sensed by pressoreceptors. Stimulation of these pressoreceptors occasions an autonomically mediated baroreceptor reflex, which leads to compensatory fluctuations in heart rate at the corresponding frequency. In addition, the renin-angiotensin hormonal system senses blood pressure fluctuations and, through the elaboration of a substance called angiotensin II, plays the role of the guardian of the overall peripheral vascular resistance. Blockade of the renin-angiotensin system by a converting enzyme inhibitor, may remove this damping influence and may permit increased fluctuations in blood pressure and increased compensatory fluctuations in heart rate in the low frequency regime.

The critically ill infant or child prior to, during, and after cardiac surgery at times exhibits marked changes in heart rate, blood pressure, and peripheral perfusion. These changes may be of no clinical consequence or they may indicate the existence of a major unrecognized pathology whose first outward manifestation may be sudden cardiac arrest. To be able to quantify cardiovascular regulatory reserve permits objective assessment of a patient's cardiovascular stability as well as their response to medical and surgical interventions intended to improve cardiovascular function.

Spectral analysis of tape recorded records of ECG and respiratory activity from patients with complex congenital heart diseases and myocarditis reveals peculiarities in low frequency heart rate fluctuations not seen in studies of healthy children and adults. In particular: (1) low levels of low frequency heart rate fluctuations ar noted for critically ill patients in congestive heart failure, which levels revert to normal after surgical or medical treatment and (2) a marked increase in low frequency heart rate fluctuations is observed in patients with otherwise undetected cardiac tamponade.

A transitional microprocessor-based monitoring instrument, which utilized a Z-80 microprocessor and a S-100 bus, was constructed along with a data acquisition system which interfaced the microprocessor with a Hewlett-Packard 78341 patient monitor A prototype system is described in Jerome C. Tu, "Microprocessor System for Real-Time Spectral Analysis Physiological Signals," Master of Department of Electrical Engineering and Computer Sciences, Science Thesis, Massachusetts Institute of Technology (1984) which is hereby incorporated by reference herein. An electrocardiogram (ECG) was inputed into a the data acquisition system for this prototype system from a patient monitor.

In the data acquisition system the analog voltage signal of the ECG was applied to the input of a variable frequency voltage controlled oscillator in the data acquisition system. A counter coupled to the output of the VCO provided a digital representation of the voltage associated with the ECG peaks. The largest voltage peak, called the R voltage peak and associated in the ECG with ventricular contraction, was used to trigger a clock. Each R peak load the value of the clock into a holding register and restarted the clock. The value of the clock provided a measure of the heart rate as the inverse of the time between beats. (i.e., as the RR internal).

The regular respiratory signal of a patient on a ventilator employed to obtain a respiratory spectrum was similarly obtained through a VCO. The respiratory frequency had to be manually entered to establish a fixed window for computing the power in the heart rate power spectrum in the respiratory peak.

Every 256 seconds the digitized ECG RR intervals were inputed in the microprocessor from the data acquisition system. A smoothed heart rate "tachometer wave form" was created as follows: (1) The instantaneous heart rate time series was computed from the stored RR intervals; (2) A 1024 point time series of the instantaneous heart rate was computed from the stored instantaneous heart rate time series by sampling the latter at 4 Hz; and (3). The mean heart rate computed from the 1024-point time series of instantaneous heart rate was subtracted from the smoothed series resulting in a "tachometer waveform"; The heart rate power spectrum was computed from the heart rate "tachometer waveform" as follows: (1) A 1024-Point Fast Fourier Transform was computed using 1024 points of the tachometer cardiac tachometer waveform; and (2) The heart rate power spectrum was computed by squaring the absolute value of the previously calculated transform.

As new data was inputted into the computer's buffer, the results of the smoothed cardiac tachometer signal, power spectrum and integral of power spectrum were outputted onto a printer. Thus for every 256-second time interval, a spectral representation of the preceding 256 seconds of instantaneous heart rate data was exhibited.

From the above data, the area under the low frequency peak (LFP) between 0.04 and 0.1 Hz and the area under the respiratory frequency peak within a peak width window of 0.2 Hz were determined. Trend graphs of LFP, RFP, and LFP/RFP ratio were created. 256 second data segments were rejected if (1) the patient was not in sinus rhythm, (2) transients and/or artifact were present on the cardiac "tachometer wave form", and (3) the LFP/RFP ratios were greater than 2 standard deviations from the mean for the study period.

The practical problems associated with the prototype monitoring instrument included the extremely tedious calculations required for use of the prototype with free-breathing patients and the large amount of data (as much as 50%, in some instances) which had to be discarded due to presence of motion artifacts. These artifacts resulted from virtually any disturbance of the patient, even one so slight as holding the patient's hand. The prototype system had no capacity to identify or reject artifacts or to examine the data for dropped beats and premature triggers.

Figure 3:
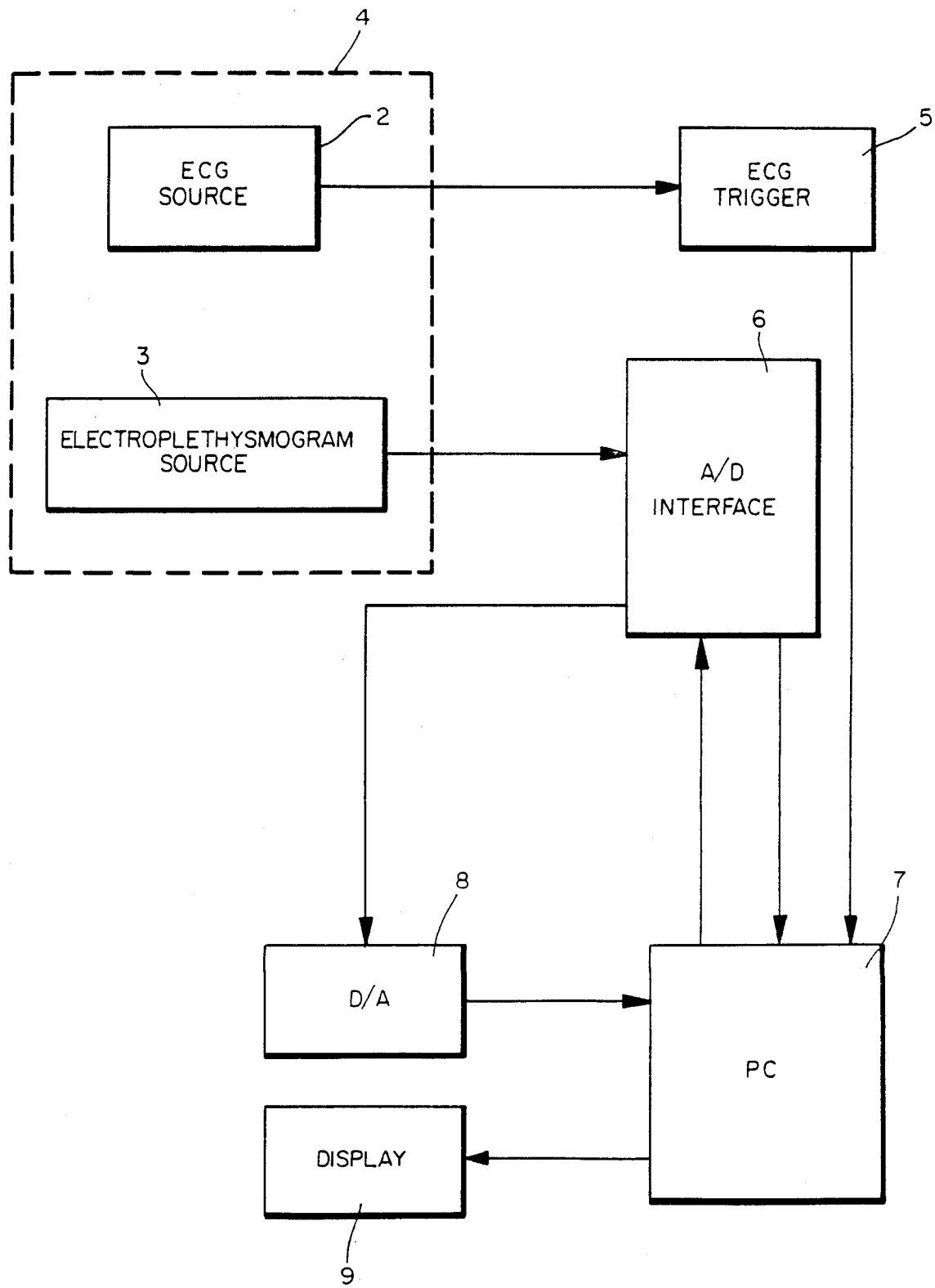
FIG. 3 is a block diagram of apparatus for heart rate fluctuation power spectral analysis according to the present invention.

Upon reviewing clinical studies performed using the prototype, it was discovered that not only were attenuated low frequency heart rate fluctuations associated with a severely compromised regulatory reserve but also that the ratio of the power in the heart rate power spectrum at low frequency to the power at the respiratory frequency provided an even sharper discriminatory index between stable and critically ill patients as illustrated in FIG. 3. In addition it was noted that this ratio was markedly elevated in the setting of moderate to severe congestive heart failure, cardiac tamponade, and prior to the development of malignant ventricular arrthymias.

A low value for LFP/RFP (<2) which is sustained for greater than one hour or a value greater than or about 50 is associated with a clinical course characterized by cardiac arrest and/or profound hypotension. At times this ratio may be the only clinical indicator of cardiovascular instability. The LFP/RFP ratio provides a sensitive and specific index of cardiovascular instability and may provide a clinically important continuous non-invasive probe of cardiovascular stability.

In order to further examine the diagnostic value of the power spectrum of heart rate fluctuations and to overcome the difficulties with the prototype, a multipurpose microcomputer based system including data basing, instantaneous heart rate and respiratory activity spectral monitor was developed using a Hewlett Packard Series 200 Computer and Multiprogrammer as available from Hewlett-Packard. Advantages over the original design include: (1) error correcting routines which correct automatically for motion artifact and missed triggerings of the EKG, thus permitting a substantial increase (>30%) in available data; (2) automated trending of spectral densities along with the instantaneous heart rate and respiratory activity time series; and (3) a data basing program which permits accurate temporal correlation of spectral densities with virtually every clinical intervention, routine ventilatory changes, hemodynamic, fluid monitoring and laboratory results. Software incorporating these advantages is included herein as Appendix A.

In a further improvement, programs and a data acquisition system and programs were developed for use with an IBM PC or compatible personal computer, This improvement is illustrated in FIGS. 3 through 12.

In FIG. 3, a block diagram of apparatus according to the present invention is illustrated. In FIG. 3, a source of an ECG signal 2 and a source of an electroplythsmogram signal 3 are contained within the patient monitor 4. A patient monitor for use with the present invention may be the system 2 infant monitor available from AR-VEE, Incorporated, Battle Creek, Mich. Source 2 is connected to an ECG trigger 5 which is in turn connected to a personal computer 7. Source 3 is connected to an analog to digital interface 6. Interface 6 is connected to analog converter 8 which is connected in turn to a personal computer 7. Personal computer 7 receives input from and provides output to interface 6. Personal computer 7 is connected to a display 9.

Source 2 receives input from pregelled electrodes adhered to the chest wall and thigh of the patient. Source senses respiratory activity through a pair of electrodes by the impedance method. Personal computer 7 and display 9 are available as an IBM and a compatible display available from IBM, Incorporated, Armonk, N.Y. Elements 5, 6 and 8 are described below.

Figure 4:
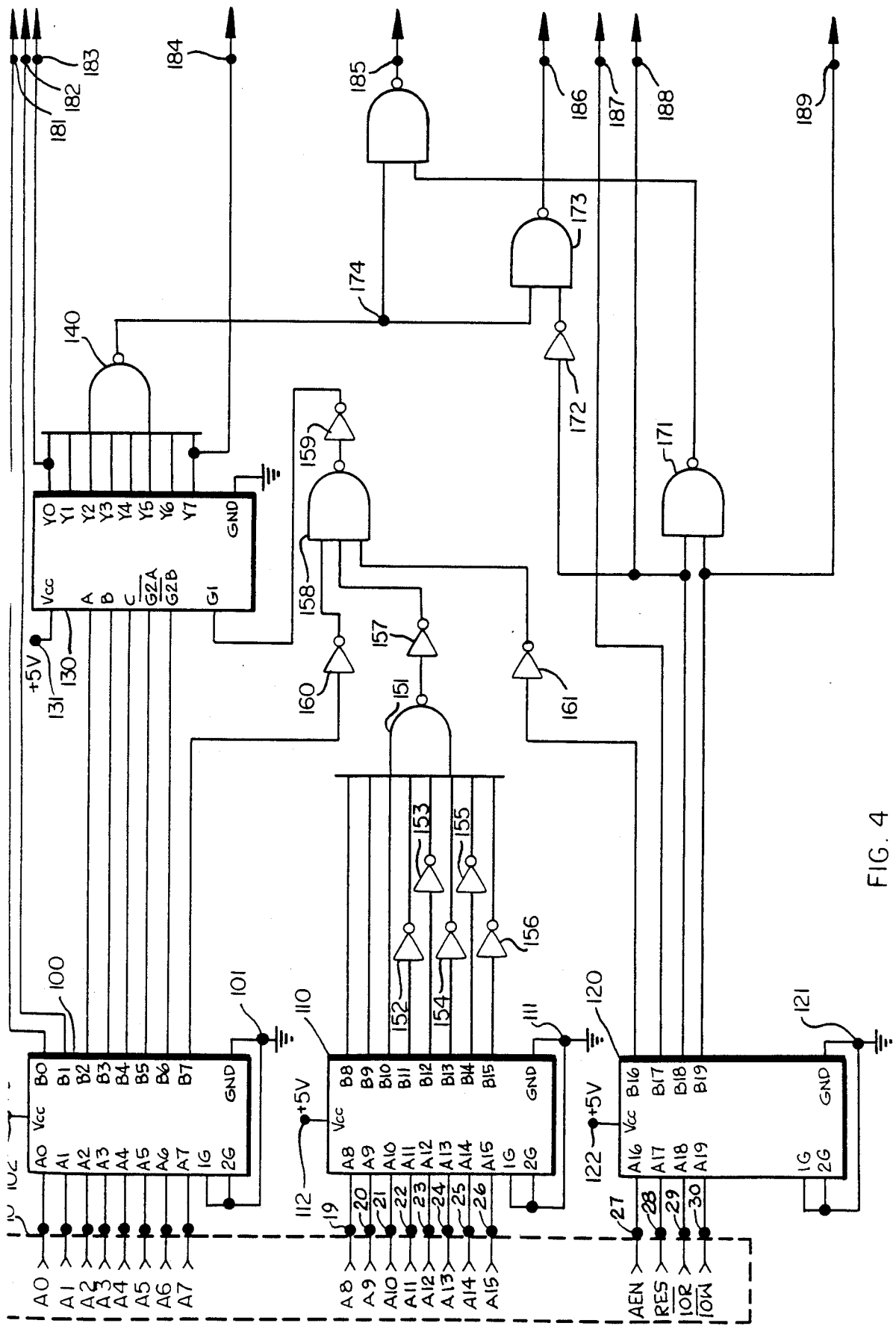
FIG. 4 illustrates address buffers and address decoding a data acquisition device according to the present invention.

In a data acquisition device according to the present invention, address, buffers and address decoding, as illustrated in FIG. 4, receive input from a PC bus 10. Nodes 11, 12, 13, 14, 15, 16, 17, 18, 19, 20, 21, 22, 23, 24, 25 and 26 are respectively connected to address lines A0, A1, A2, A3, A4, A5, A6, A7, A8, A9, A10, A11, A12, A13, A14 and A15 in PC bus 10. A first address buffer 100 has address inputs A0, A1, A2, A3, A4, A5, A6 and A7 which are respectively connected to nodes 11–18. Buffer 100 also has two gate inputs, 1G and 2G, which are connected to ground along with a ground output GND of buffer 100. A power supply input $V_{CC}$ of buffer 100 is connected to a node 102 at a potential of +5 volts.

A second address buffer 110 has address inputs A8, A9, A10, A11, A12, A13, A14 and A15 which are respectively connected to nodes 19–26. Buffer 110 also has two gate inputs, 1G and 2G, which are connected by way of a node 111 to ground. A ground GND output of buffer 110 is also connected to a common potential. Buffer 110 has a power supply input $V_{CC}$ which is connected to a node 112 at a potential of +5 volts.

A status buffer 120 has address inputs A16, A17, A18 and A19 which are respectively connected to nodes 27, 28, 29 and 30. Nodes 27–30 are respectively connected to an address enable line AEN, a reset line RES, an input/output read line IOR and an input/output write line IOW in PC bus 10. Buffer 120 has two gate inputs, 1G and 2G, which are connected by way of a node 121 to ground. A ground output GND of buffer 120 is also connected to ground by way of node 121. A power supply input $V_{CC}$ of buffer 120 is connected to a node 122 at a potential of +5 volts.

According to the present invention, a data acquisition system board which is both reliable and compatible with a personal computer (PC) bus, preferably adheres to the timing requirements and the loading requirements supplied by the PC bus. This means that all connections to the PC bus should be buffered so that the load provided at any input or output of the bus is equivalent to 1 LS TTL load and high speed CMOS integrated circuits are fed for this purpose.

Because there are multiple devices attached to the address bus, address buffers are provided. This is done by buffers 100 and 110. Parts used for buffers 100, 110 and 120 are normally gated, but the gate enables, 1G and 2G, are tied to ground so that the gates are always enabled. Some of the status lines on the PC bus are buffered by a chip 120, in particular: the reset line RES; the read and write lines IOR and IOW respectively, for the input/output (IO) channels; and the address enable AEN.

An address decoder according to the present invention, as illustrated in FIG. 4, includes a three to eight line decoder 130. Decoder 130 has three line inputs A, B and C which are respectively connected to outputs B2, B3 and B4 of buffer 100. Decoder 130 has gate inputs G2A and G2B which are respectively connected to outputs B5 and B6 of buffer 100. A power supply VCC input of decoder 130 is connected to a node 131 at a potential of +5 volts while a ground GND output of decoder 130 is connected to a common potential. Outputs Y0, Y1, Y2, Y3, Y4, Y5, Y6 and Y7 are connected to inputs of a NAND gate 140.

A NAND gate 151 has an input connected to each of outputs B8, B9 and B10 of buffer 110. An output B10 of buffer 110 is connected to an input of an inverter 152 which has an output connected to an input of NAND gate 151. Similarly, outputs B12, B13, B14 and B15 of buffer 110 are respectively connected to an input of each of inverters 153, 154, 155 and 156, each of which has an output connected to an input of NAND gate 151. NAND gate 151 has an output connected to an input of an inverter 157.

A NAND gate 158 has an input connected to an output of inverter 157 and has an output connected to an input of an inverter 159. An inverter 160 has an input connected to an output B7 of buffer 100 and has an output connected to an input of NAND gate 158. Likewise, an inverter 161 has an input connected to an output B16 of buffer 120 and has an output connected to an input of NAND 158. An output of inverter 159 is connected to a gate input G1 of decoder 130.

So that devices on the board are recognized at a particular IO channel address, address decoding is provided. In this particular case, a fixed address location, location hex 700 to 71F (a total of 32 channels), is used. The decoding of the fixed upper bytes in the address is provided by a combination of nine inverting gates, 152, 153, 154, 155, 156, 157, 159, 160 and 161, and NAND gates 151 and 158. These elements, in combination with decoder 140, provide chip enable signals which can be used to select one or another of the functional chips on our board. Each of the eight chip enable signals correspond to a block of four channels. For example, a chip select #0 from output to of decoder 130 corresponds to channels hex 700, 701, 702 and 703.

A logic network for driving a data buffer, as illustrated in FIG. 4, includes a NAND gate 171, an inverter 172 and a NAND gate 173. An output of inverter 172 is connected to a first input of NAND gate 173 while an output of NAND gate 140 is connected by way of a node 174 to a second input of NAND 173 and to a first input of a NAND gate 175. A second input of NAND gate 175 is connected to an output of NAND gate 171.

In addition, a node 181 is connected to an output B0 of buffer 100. A node 182 is connected to an output B1 of buffer 100. Nodes 183 and 184 are respectively connected to output Y0 and output Y7 of decoder 130. Nodes 185 and 186 are respectively connected to an output of NAND gate 175 and an output of NAND gate 173. A node 187 is connected to an output B17 of buffer 120. A node 188 is connected to an output B18 of buffer 120, to a first input of NAND gate 171 and to an input of inverter 172. A node 189 is connected to a second input of NAND 171 and to an output B19 of buffer 120.

Additional chips are used to provide logic which drives a data buffer connected to a data bus. The data bus is bidirectional in order to both transmit data to and from devices on the board. In order that this be accomplished, one must determine at any time whether or not data is either being read from or written to the board. This logic is supplied by NAND gate 171, NAND gate 173, AND gate 175 and inverter 172 which translates the read and write signals for the input/output (IO) channel into an output enable and a transmit enable for a data buffer. The apparatus of FIG. 5 may be used to properly interface a device to the PC bus 10.

Figure 5:
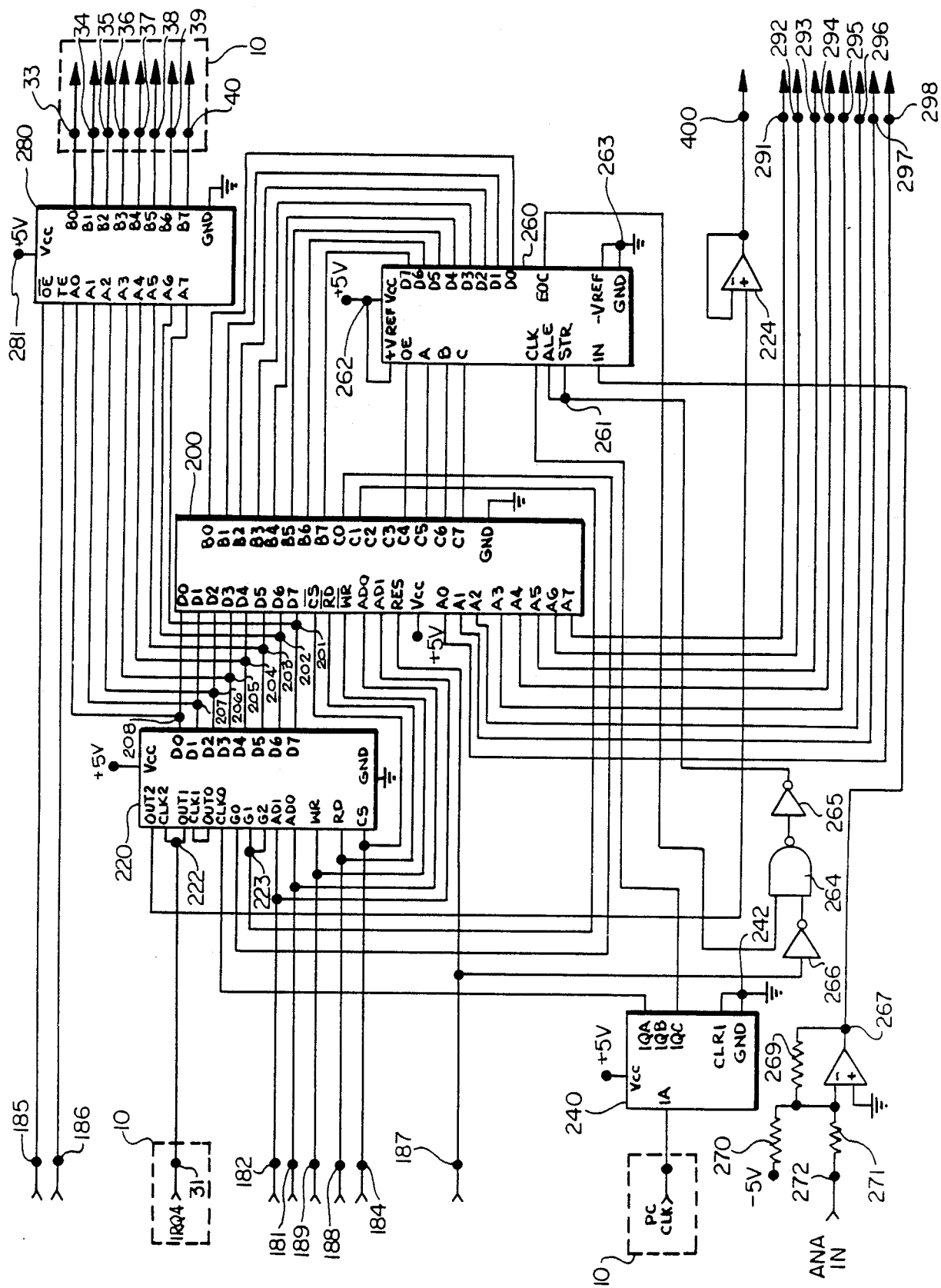
FIG. 5 illustrates components according to the present for interfacing an ECG apparatus with a personal computer according to the present invention.

As illustrated in FIG. 5, components according to the present invention for interfacing an ECG apparatus with a personal computer include a port expander 200. Port expander 200 has four sets of 8 nodes each, the four sets correspond to four ports A, B, C and D. The outputs for port A are A0, A1, A2, A3, A4, A5, A6 and A7. The inputs corresponding to port B are B0, B1, B2, B3, B4, B5, B6 and B7. Outputs corresponding to port C are C0, C1, C2, C3, C4, C5, C6 and C7. A set of outputs corresponding to port D includes D0, D1, D2, D3, D4, D5, D6 and D7. Expander 200 has a chip select input CS connected to node 184. Expander 200 also has a read input RD and a write input WR respectively connected to nodes 188 and 189. Expander 200 has two address inputs, AD0 and AD1 which are respectively connected to nodes 181 and 182. A reset RES input of expander 200 is connected to node 187. Inputs A0, A1, A2, A3, A4, A5, A6, A7 are respectively connected to nodes 291, 292, 293, 294, 295, 296, 297 and 298. Outputs D0-D7 are respectively connected to nodes 208, 207, 206, 205, 204, 203, 202 and 201 which define a data bus. A power supply input $V_{CC}$ of expander 200 is connected to a node 209 at a potential of +5 volts. A ground GND output of expander 200 is connected to a common potential.

Port expander 200 is used to overcome the low speed of the data bus on both A/D converter 260 and a digital analog converter. This permits slowing down the read and write signals inasmuch as they may be provided artificially on port C of expander 200 or as chip select signals from address decoder 130. Port C of expander 200 is a bit addressable register which allows one to individually select or deselect bits without affecting any of the other bits. This is accomplished by sending a one byte command to expander 200. Because expander 200 is given the control function, the address of expander 200 is the highest address in the set of channels. In other words, expander 200 occupies IO channels hex 71C to hex 71F. The ports A, B and C on expander 200 are addresses 71C, 71D and 71E, respectively, and the control register internal for expander is at input/output I/0 channel 71F.

A timer 220 according to the present invention has two address inputs, AD0 and AD1 respectively connected to nodes 181 and 182. Timer 220 also has a read input RD connected to node 188, a write input WR connected to node 189 and a chip select input CS connected to node 184. A first gate input G0 is connected to the C0 of expander 200 while a second gate input G1 and a third gate input G2 are both connected by way of a node 223 to output C1 of expander 200. Timer 220 has three clock inputs CLK0, CLK1 and CLK2, of which CLK1 is connected by way of node 222 to an output OUT0 of timer 220 and input CLK2 is connected to an output OUT1 of timer 221 by way of a node 31. An interrupt request line IRQ4 within PC bus 10 is also connected to node 31.

An output OUT2 is connected to a non-inverting input of an operational amplifier 224, an inverting input and an output of which is connected to a node 400.

A power supply input $V_{CC}$ of timer 220 is connected to a node 221 which at a potential of +5 volts.

Timer 221 has seven outputs D0, D1, D2, D3, D4, D5, D6 and D7 which are respectively connected to nodes 208, 207, 206, 205, 204, 203, 202 and 201. A ground output of timer 220 is connected to a common potential.

Timer 220 includes three 16 bit timers which are addressed at hex locations 704, 705, 706, and 707. In other words, they are provided by chip select 1. The three clocks on timer 220 are connected in series which effectively converts it into a 48 bit counter. However, in the operation of the program, some of the bits in this counter are thrown away because the reset values are less than 65,536. The three clock registers are used in the following way. Counter 0, corresponding to input CLK 0, counts an onboard time base to be discussed later and provides an output which gives the minimum resolution of the heart rate counting. In other words, it provides the counter time base for measuring the heart rate. Counter #1, corresponding to input CLK 1, counts the heart rate counter time base and provides as an output an interrupt at IRQ4. This signal drives the sampling of the respiratory signal at a constant frequency, and is also used to measure interbeat intervals. In the standard data collecting mode, where one is interested in measuring the respiratory signal at 4 hertz intervals, this means that the counter 0 is set to generate output pulses at 11 microsec. intervals and that these pulses are in turn counted by counter 1 to generate 4 hertz pulses which are used to drive data acquisition from the respiratory signal. The last counter register, counter #2, corresponding to input CLK2, is used to count the number of respiratory sampling pulses which have been supplied. This functions as an overflow counter and always has the reset value of 65,536. Thus the counter measuring interbeat intervals effectively overflows only every 65,536 respiratory sampling times, which is far in excess of what would be required to recover dropped beats which occur because the heart rate is not adequately detected.

A counter 240 has an input 1A connected to a clock line PC CLK in PC bus 10 by way of a node 32. Counter 240 has a first output 1QA connected to the CLK0 input of timer 220. Counter 240 has a second output 1QB and has a third output 1QC. A clear input CLR1 of counter 240 and a ground output GND of timer 240 are connected to a common potential by way of a node 242.

A data output buffer 280 has an output enable input OE connected to node 185 and has a transfer enable input TE connected to a node 186. Eight data inputs, A0, A1, A2, A3, A4, A5, A6 and A7, of buffer 280 are respectively connected to nodes 208, 207, 206, 205, 204, 203, 202 and 201. A power supply VCC input of buffer 280 is connected to a source of potential at +5 volts. A ground GND output of buffer 280 is connected to a common potential. Outputs B0, B1, B2, B3, B4, B5, B6 and B7 of buffer 280 are respectively connected to data lines in PC bus 10 by way of nodes 33, 34, 35, 36, 37, 38, 39 and 40.

The time base for this clock system is provided by counter 240. Timer 220 counts only at a rate of 2.6 MHz megahertz which is exceeded by the IBM PC bus clock of 4.77 megahertz. The IBM PC bus clock is divided by 2 using counter 240 and the result used to provide a time base at 2.38 megahertz for timer 220. The 4.77 megahertz clock is also divided by 8 to provide a 596 kilohertz clock which is used to drive an analog to digital (A/D) converter. A/D converter 260 uses this clock signal in order to properly execute the successive approximation scheme to convert analog inputs into digital outputs.

A/D converter 260 has an output enable input OE connected to output C4 of expander 200. A/D converter 260 also has three inputs A, B and C which are respectively connected to outputs C5, C6 and C7 of expander 200. A clock input CLK of A/D converter 260 is connected to the 1QC output of counter 240. An address latch enable ALE and a start input STR of A/D converter 260 are connected to a node 261. A power supply $V_{CC}$ input and a reference voltage $+V_{REF}$ input of A/D converter 260 are connected to a node 262 at a potential of +5 volts. A reference voltage $-V_{REF}$ output and a ground GND output of A/D. converter 260 are connected to a common potential by way of a node 263. A/D converter 260 has seven outputs D0, D1, D2, D3, D4, D5, D6 and D7 which are respectively connected to inputs B0, B1, B2, B3, B4, B5, B6 and B7 of expander 200. In addition, A/D converter 260 has an end of count EOC output connected to a first input of the NAND gate 264, an output of which is connected to an input of an inverter 265. A second input of NAND gate 264 is connected to an output of an inverter 266 which has an input connected to node 187. An output of inverter 265 is connected to node 261.

A/D converter 260 has a signal input IN connected to a node 267. An output of an operational amplifier 268 is connected to node 267 and to a first lead of a resistor 269. A second lead of resistor 269 is connected to a first lead of resistor 270, a second lead of which is connected to a source of potential at −5 volts. The first end of resistor 270 is also connected to an inverting input of amplifier 268 and to a first end of a resistor 271. A non-inverting input of amplifier 268 is tied to ground. A second end of resistor 271 is connected to a node 272 which provides an analog signal input ANA IN for the apparatus according to the present invention.

A/D converter 260 is connected to port B of port expander 200. This A/D has built into it its own 8 channel analog multiplexer which allows the selection of one of eight analog signals to, be converted. The channel select corresponding to inputs A, B and C of converter 260 is connected to port C on bytes 5, 6 and 7.

Because A/D converter 260 operates from 0 to 5 volts, analog input at input IN should be in the range of 0 to 5 volts or an input buffer should be supplied to alter this input range. However, in keeping with general practices for safety and isolation, input IN should always be provided with an analog buffer to provide isolation for both the computer and the instrument being monitored. As illustrated, the input buffer is provided by operational amplifier 268. This amplifier converts a bipolar analog input of plus or minus 5 volts to a single unipolar input of 0 to 5 volts at input IN. This analog input is used to monitor the respiration.

A/D converter 260 is set up in a free running mode such that it continuously does conversions on the analog signal. The end-of-conversion pulse at output EOC is used to generate a start pulse for the A/D so that as soon as an end of conversion occurs it a new conversion is started. This is the reason for the two gates connected between end of conversion output EOC and the start input STR. In order to prevent latchup of the device on power up, the reset line at node 187 is also used to generate a start pulse. This means that the device will always function even after being powered up. Also, in order to update A/D converter 260 as frequently as possible, the address latch enable ALE, which is used to latch in the address value for the channel to be monitored, is re-latched at every start pulse.

Figure 6:
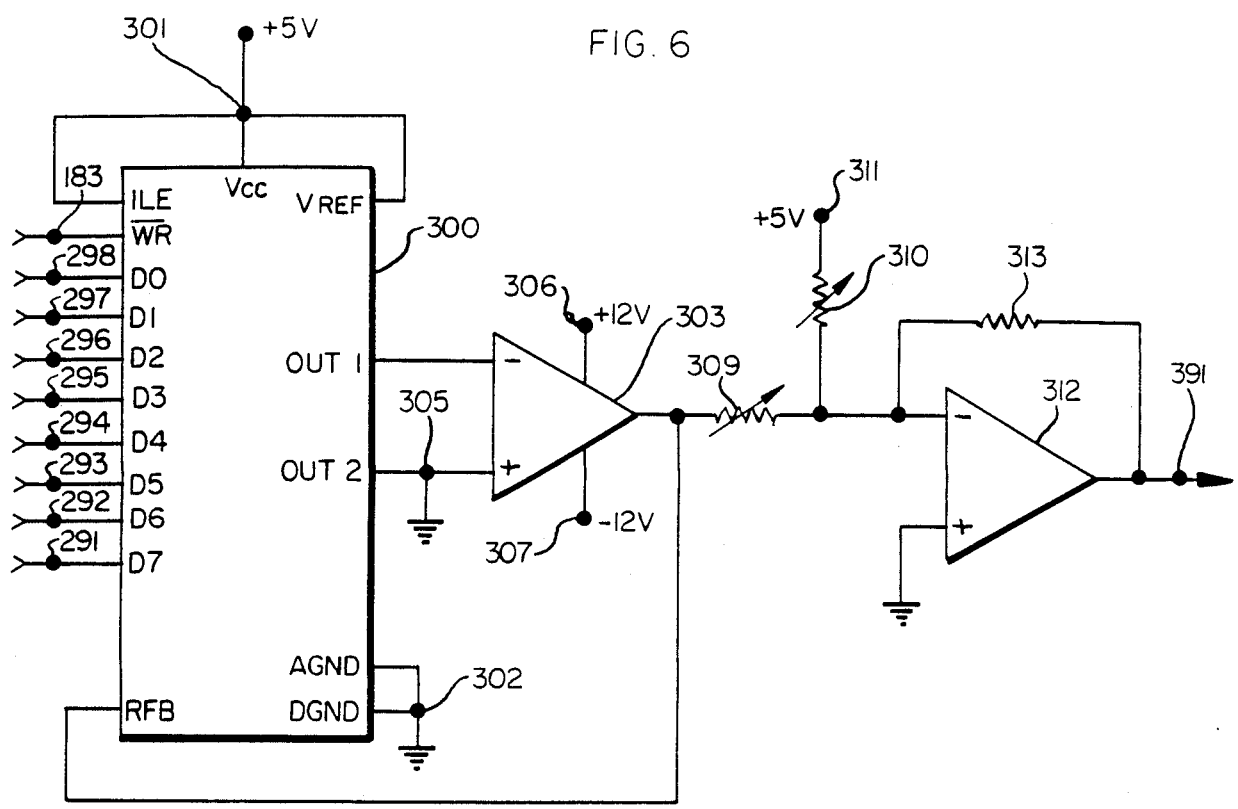
FIG. 6 illustrates a digital to analog converter according to the present invention.

As illustrated in FIG. 6, digital analog (D/A) converter 300 has inputs D0, D1, D2, D3, D4, D5, D6 and D7 which are respectively connected to nodes 298, 297, 296, 295, 294, 293, 292 and 291 as illustrated in FIG. 4. Converter 300 has a write WR input connected to node 183 and has a feedback input RFB. Converter 300 also has a power supply $V_{CC}$ input, a reference voltage $V_{REF}$ input and an input latch enable input ILE all of which are connected to a source of potential at +5 volts by way of a node 301. Converter 300 has an analog ground AGND and a digital ground output DGND, both of which are connected by way of a node 302 to a common potential.

Converter 300 has a first output OUT1 and a second output OUT2 which are respectively connected to an inverting and a non-inverting input of an operational amplifier 303. The non-inverting input of amplifier 303 is also connected to a common potential by way of a node 305. Amplifier 303 has an input connected to a node 306 at a potential of +12 volts and an input connected to a node 307 at a potential of −12 volts. An output of amplifier 303 is connected to a node 308 which is connected to the RFB input of converter 300 and to a first end of a variable resistor 309. A second lead of variable resistor 309 is connected to a first lead of a variable resistor 310, a second lead of which is connected to a node 311 at a potential of +5 volts. The second lead of resistor 309 is also connected to an inverting input of operational amplifier 312 and to a first lead of a resistor 313. A non-inverting input of amplifier 312 is connected to ground. A second lead of resistor 313 is connected to an output of amplifier 312 and to a node 391 which serves as an analog output for the apparatus according to the present invention.

Port A of expander which is at location 71C, is attached to a D/A converter data bus which, includes nodes 291–298. The write latch signal for the D/A converter is provided by chip select #0. In other words, any dummy byte written to any of the addresses 700, 701, 702 or 703 hex will cause a write pulse to be sent to D/A converter 300, thereby latching the data on port A of expander 200 into the D/A converter 300 and allowing an analog signal to be generated corresponding to the digital input. The output of D/A converter 300 chip is in the form of differential currents generated at outputs OUT1 and OUT2. A system having two operational amplifiers is employed to convert these currents to a voltage. Amplifier 303 is a differential current to voltage converter which provides a signal from 0 to 5 volts. Amplifier 312 converts the signal to a bipolar plus or minus 5 volt signal. Feedback control for the current to voltage converter is provided in D/A converter 300 through input RFB so that in actuality three connections are made from the D/A chip to the first operational amplifier. Because the D/A converter is an 8 bit device, this provides 256 voltage levels which are linearly distributed between plus and minus 5 volts. This D/A output may be used to generate calibrating signals or other control signals.

Figure 7:
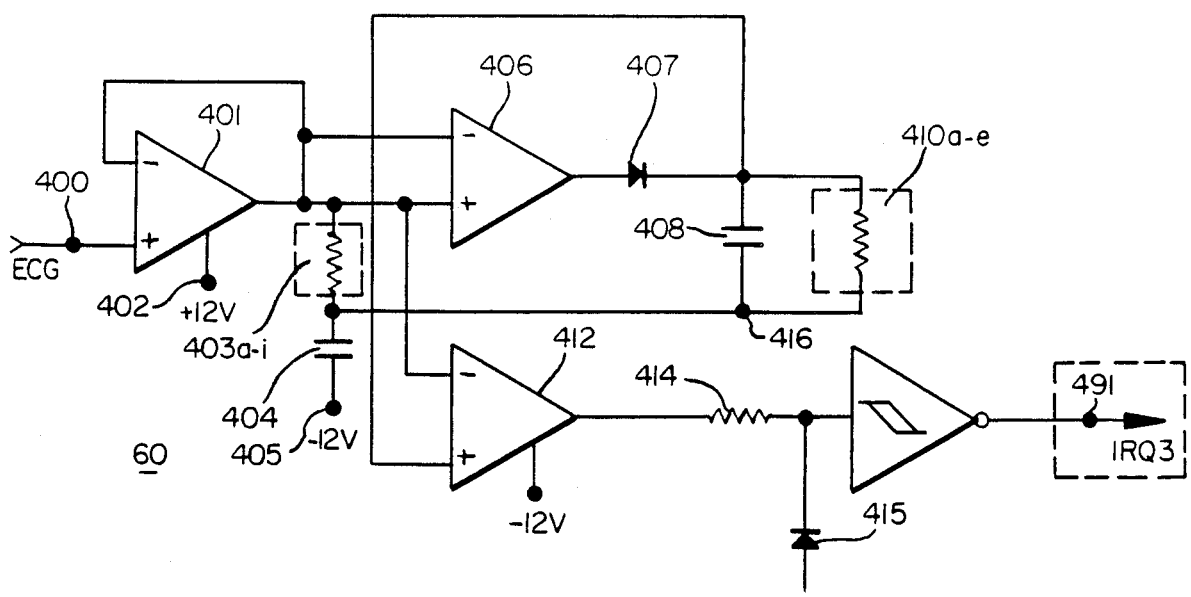
FIG. 7 illustrates a ECG trigger according to the present invention.

As illustrated in FIG. 7, a source of an ECG signal is connected by way of a node 400 to a non-inverting input of an operational amplifier 401 in an ECG trigger 60. An input of amplifier 401 is connected to a node 402 at a potential of plus 12 volts. An inverting input of amplifier 401 is connected to an output of amplifier 401 and to a non-inverting input of an operational amplifier 406. A first lead of each of resistors 403a, 403b, 403c, 403d, 403e, 403f, 403g, 403h and 403i is connected to the output of amplifier 401 while the second lead of resistor 403i is permanently connected and a second lead of one other of resistors 403a through h is connected to a node 410 by a jumper. A first lead of capacitor 404 is connected to node 410 while a second lead of capacitor 404 is connected to a node 405 at a potential of minus 12 volts. An inverting input of amplifier 406 is connected to a cathode of a diode 407, an anode of which is connected to an output of amplifier 406. The cathode of diode 407 is also connected to a first lead of capacitor 408 and a first lead of each of resistors 410a, 410b, 410c, 10i q and 410e, the second lead of resistor 410e is permanently connected and the second lead of one other of which is connected to a node 410 by a jumper 411g. A non-inverting input of an operational amplifier 412 is also connected to the cathode of diode 407 while an inverting input of amplifier 412 is connected to the output of amplifier 406. An input of amplifier 412 is connected to a node 413 at a potential of minus 12 volts. A first lead of resistor 414 is connected to the output of amplifier 412 while a second lead of resistor 414 is connected to a cathode of a diode 415 an anode of which is connected to ground. The cathode of diode 415 is also connected to an input of a Schmitt trigger 416 an output of which is connected to a line designated IRQ3 in PC bus 10 by way of a node 491.

ECG trigger 60 has an input buffer consisting of a non-inverting buffer of an amplifier 401 which isolates the ECG signal from the rest of the board. As illustrated in FIG. 5, the EKG trigger functions in the following manner. The R wave, which is larger than any other signal in the ECG, causes capacitor 408 to charge up to a certain value corresponding to the peak of the R wave. Any values beneath the peak of the R wave will be rejected by amplifier 403 so that no output occurs. Between R waves, the voltage on capacitor 405 decays slowly with a rate given by the RC time constant of capacitor 405 and the resistance across elements 410a-f. The voltage on the capacitor is sent to the inverting input on amplifier 403 and is used as a threshold for the R wave of the EKG. Therefore, as the electrocardiogram is being passed to the non-inverting input of amplifier 406, the only time that the operational amplifier has a positive output is when the EKG signal is larger than the voltage on capacitor 405. Whenever this occurs, capacitor 408 is immediately charged up to the value at the EKG input. In other words, the voltage on capacitor 408 is a sort of envelope on the top of the electrocardiogram, although its decay rate is limited by the RC time constant. Diode 407 insures that the envelope function which is provided by capacitor 408 is the upper envelope and not the lower envelope. The lower envelope is provided by reversing the polarity of diode 407.

The RC network of capacitor 405 and resistors 403a-i provides a low pass filtered ECG. The voltage on capacitor 405 is the baseline for the ECG, which may vary. The array of jumper selected resistors 410a-e allows variation of the time constant of the RC network containing resistors 406a-e and capacitor 408. Thus, this latter network which monitors the ECG envelope is referenced to the ECG baseline present on capacitor 404 permitting accurate tracking of the envelope and therefore better R wave detection. As a further improvement, the jumpers may be replaced with analog switches controlled by the personal computer in order to give the computer control of RC time constant selection.

An output from ECG trigger 60 is generated by connecting amplifier 412 in parallel with peak detector amplifier 406 so that the inputs are reversed. The result is that the output polarity is inverted. Because the amplifiers 401, 406 and 412 are operating from a plus 12 volts to minus 12 volts supply, but the logic levels on the board are only from 0–5 volts, resistor 414 and a diode 415 are used to clamp the output value of the amplifier 412 between 0 and 12 volts. This signal is then passed to a Schmitt trigger 416, which is a single conditioning device. The output of this signal conditioner is finally provided to PC bus 10 in order to drive interrupts at interrupt request 3 (IRQ3) indicating the currents of a R wave. ECG trigger 60 may be modified to allow selection of various decay rates for the envelope and also to provide a floating threshold for the 0 point of the EKG. The ECG triggers if the R wave passes above 0 volts. However, it can be imagined that sometimes the baseline will drift far enough below 0 volts that the R wave does not cross 0 volts and in such a case this trigger would never detect the R wave. This is corrected by connecting the second leads of the charging capacitor 408 and on the selected discharging resistor of 406a-f may be connected to a low pass filter consisting of a capacitor 405 and a selected one of resistors 403a-f (to choose various discharge rates) which low pass filters the electrocardiograms and essentially selects out the baseline. This means that instead of measuring the R wave with respect to 0 volts, the R wave may be measured with respect to the floating baseline of the electrocardiogram. The jumper selected resistor selects an RC time constant much greater than the RR interval. So long as the baseline does not drift faster than one R wave in approximately 10 heart beats, this means that this trigger will successfully detect all R waves. Selecting one of resistors 410a-f allows variation of the RC time constant of elements 408 and 410a-f.

Figure 8:
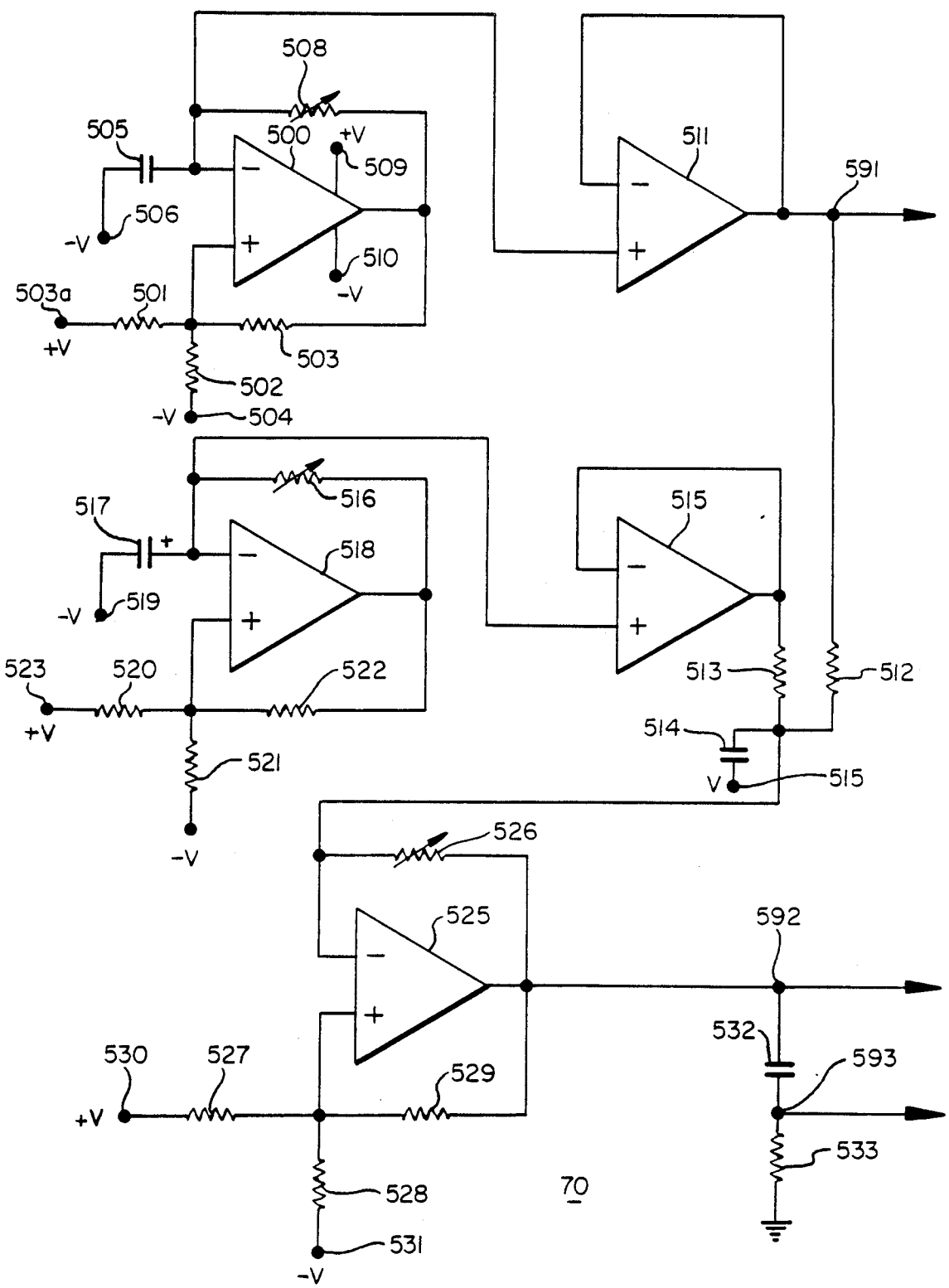
FIG. 8 illustrates a portable calibrator according to the present invention.

As illustrated in FIG. 8, in a portable calibrator 70 according to the present invention, an operational amplifier 500 has a non-inverting input connected to a first lead of each of resistors 501, 502 and 503. A second lead of resistor 501 is connected by way of a node 503a to a positive voltage source while a second lead of resistor 502 is connected by way of a node 504 to a negative voltage source. An inverting input of amplifier 500 is connected to a first lead of a capacitor 505, a second lead of which is connected by way of a node 506 to a negative voltage source. The inverting input of amplifier 505 is also connected to a first lead of a variable resistor 507 and to a first lead of a resistor 508 a second lead of which is connected to an output of amplifier 500. The output of amplifier 500 is also connected to a second lead of resistor 503. Amplifier 500 has an input connected by way of a node 509 to a positive voltage source and by way of a node 510 to a negative voltage source.

A second lead of resistor 507 is connected to a non-inverting input of an amplifier 511, an inverting input of which is connected to an output of amplifier 511 by way of a node 591 which provides an output port for a simulated respiratory frequency.

A first lead of a resistor 512 is connected to node 591 while a second lead of resistor 512 is connected to a first lead of a resistor 513 and to a first lead of a capacitor 514, a second lead of which is connected by way of a node 515 to a negative voltage source. A second lead of resistor 513 is connected to an output of an operational amplifier 514 and to an inverting input of amplifier 515 is connected to a first lead of a resistor 516, to a first lead of a capacitor 517 and to an inverting input of an operational amplifier 518. The second lead of capacitor 517 is connected by way of a node 519 to a negative voltage source. A non-inverting input of amplifier 518 is connected to a first lead of each of resistors 520, 521 and 522. A second lead of resistor 520 is connected by way of a node 523 to a positive voltage source while a second lead of resistor 521 is connected by way of a node 524 to a negative voltage source. A second lead of resistor 522 is connected to an output of amplifier 518 and to a second lead of resistor 516.

An inverting input of an operational amplifier 525 is connected to the first lead of resistor 513 and to a first lead of a variable resistor 526. A non-inverting input of amplifier 525 is connected to a first lead of each of resistors 527, 528 and 529. A second lead of resistor 527 is connected to a node 530 at a positive potential while a second lead of resistor 528 is connected by way of a node 531 to a negative voltage source. A second lead of resistor 529 is connected to a second lead of resistor 526 and to an output of amplifier 525 at a node 592 which provides a square wave output simulating a modulated heart rate pulse. A first lead of a capacitor 532 is connected to node 592 while a second lead of capacitor 532 is connected by way of a node 593 to a first lead of a resistor 533, a second lead of which is connected to ground. Node 593 provides an output port for a spike output simulating the R wave of an EKG.

The source of positive potential for the portable calibrator 70 may be at a voltage between about plus 5 and about plus 18 volts. Similarly, the negative voltage source for portable calibrator 70 may be at a potential of about minus 18 volts to about minus 5 volts.

Portable calibrator 70 provides test signal for the heart rate spectral analysis hardware which, although not of a truly calibrated nature, does allow one to evaluate whether or not the software and hardware is functional. Each of the output signals provided is a triangle wave which represents the respiration and a frequency modulated pulse train representing the heart rate. The modulation of the heart rate is provided at two frequencies which simulate a respiratory modulation and also a low frequency modulation.

The basic circuit of calibrator 70 for providing each pulse train consists of an oscillator having one operational amplifier as typified by the respiratory frequency modulator. A charging capacitor 505 and a variable resistor 507, provide an RC circuit which is charged by the output of the amplifier 500. It is also discharged by the amplifier 500 when the output of the amplifier 500 is low. Progressive cycles of the oscillator consist of charging and discharging the capacitor at the rate prescribed by the RC circuit. The reference level which determines whether or not one is discharging or charging is provided at the non-inverting input of the amplifier 500.

Suppose, for example, that capacitor 505 begins as being completely discharged, then the voltage at the inverting input for the operational amplifier 500 is low. The output of the operational amplifier 500 is therefore high and this means that the input at the non-inverting input is ⅔ the voltage between the negative voltage source V and the positive voltage source V+. Thus the capacitor 505 begins to charge. When the capacitor voltage exceeds the threshold at the non-inverting input of the operational amplifier 500, the output of operational amplifier 500 changes sign and capacitor 505 begins to discharge. However, when the output of the amplifier 500 changes to the negative side, then the threshold voltage at the non-inverting input is changed and now becomes only ⅓ the way from the negative voltage source to the positive voltage source. This means that the voltage on the charging capacitor 505 varies between ⅓ and ⅔ the difference between the negative and the positive voltage source. This determines the range of output on capacitor 505. The voltage at capacitor 505 is buffered by a non-inverting buffer 511 and this provides the respiratory signal at node 591.

An identical oscillator is used to provide low frequency modulation. The difference in the two frequencies is obtained by adjusting the respective variable resistors, 505 and 517, which set the RC time constants. The outputs of these two modulators are fed by resistors 512 and 513 into the charging capacitor 514 for the heart rate.

The heart rate oscillator is similar in design and consists of variable resistor 526 and capacitor 532 which charges and discharges in cycles with the range of voltages on the capacitor ranging between ⅓ the distance from the negative voltage source to the positive voltage source to ⅔ the voltage between the negative voltage source and the positive voltage source. Resistors 512 and 513, which connect the outputs of the low frequency and respiratory frequency modulators to the heart rate modulator, allow a small amount of current to flow into charging capacitor 514 of the heart rate modulator. This alters the charging rate of capacitor 514 and thereby affects the rate at which the heart rate oscillator oscillates. For example, on a positive cycle of the respiratory frequency modulator, the heart rate capacitor is charging more rapidly towards the plus side because more current is being supplied on the plus side of the cycle. Finally, the output of the heart rate modulator is sent through an RC filter comprising capacitor 532 and resistor 533 which converts the square wave output of the heart rate modulator into a spike output which may be sent to an R wave detector. Notice that the spike output includes both positive and negative spikes so that an R detector which depends on a high frequency filtering function may be discharging at twice the heart rate, inasmuch as it may trigger on both positive and negative spikes.

Figure 9A:
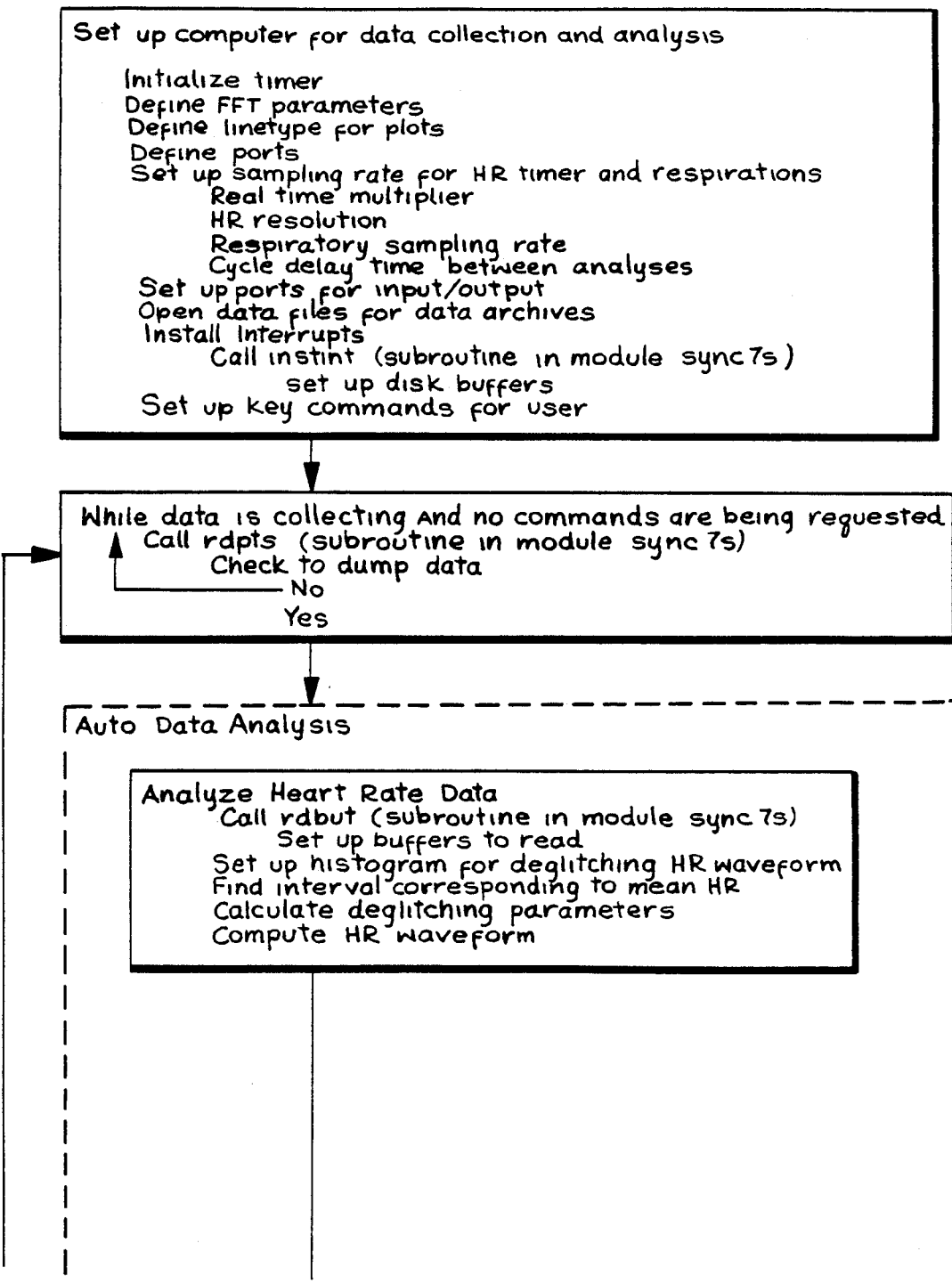
FIG. 9A-B are a flow chart for software applicable to an embodiment of the present invention on a IBM personal computer.
Figure 9B:
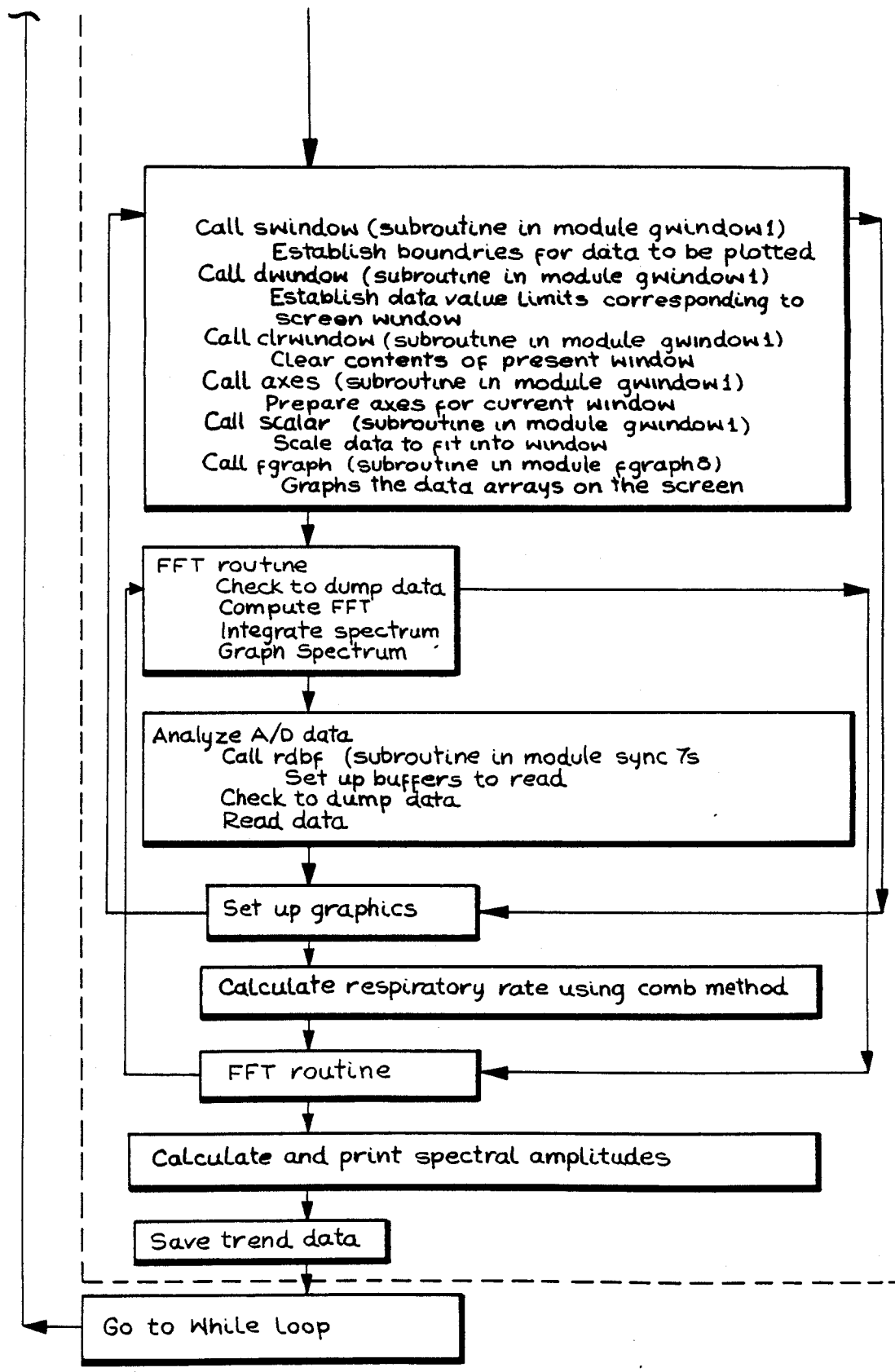
Figure 10:
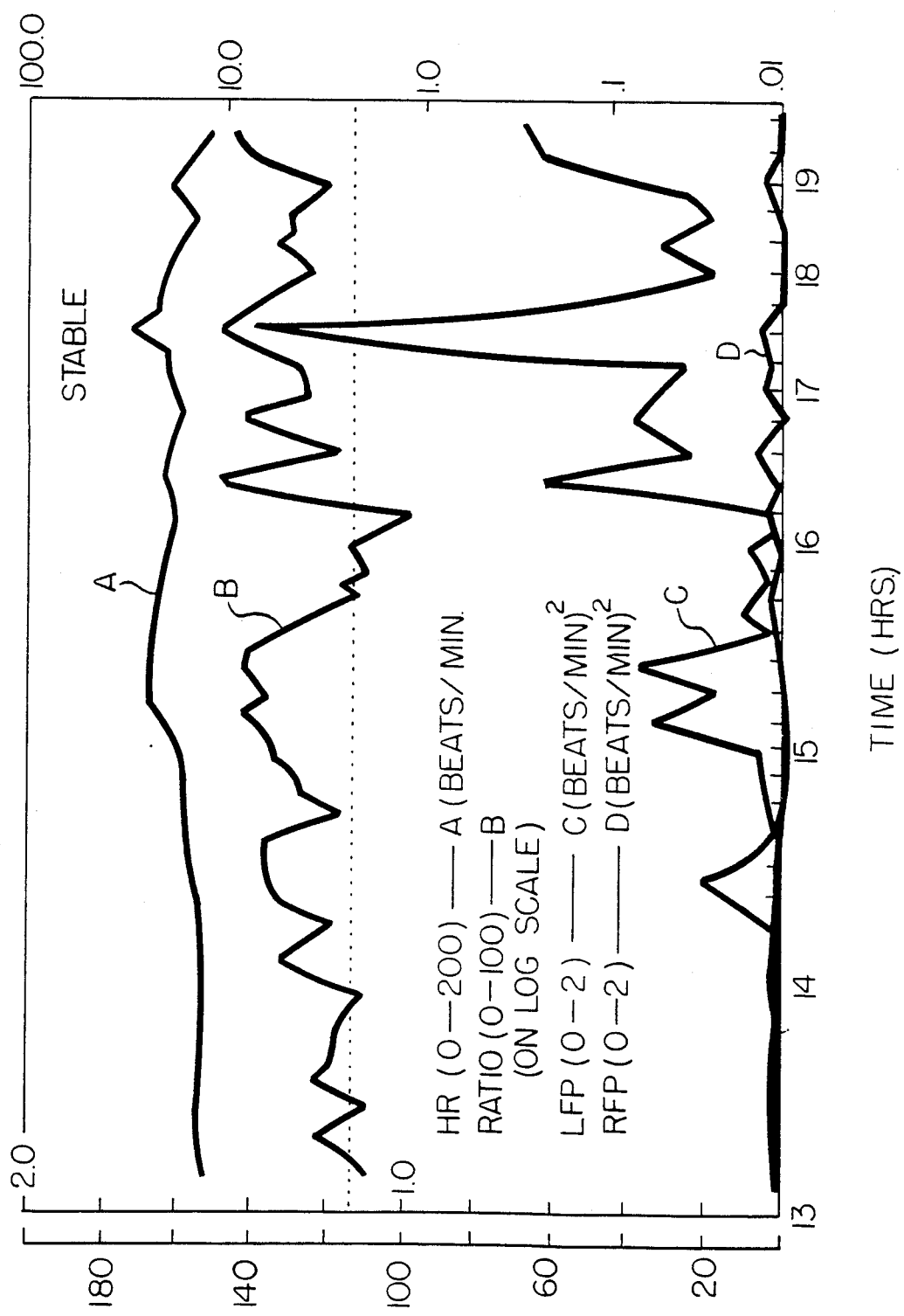
FIG. 10 illustrates a trend for a stable patient according to the present invention.
Figure 11:
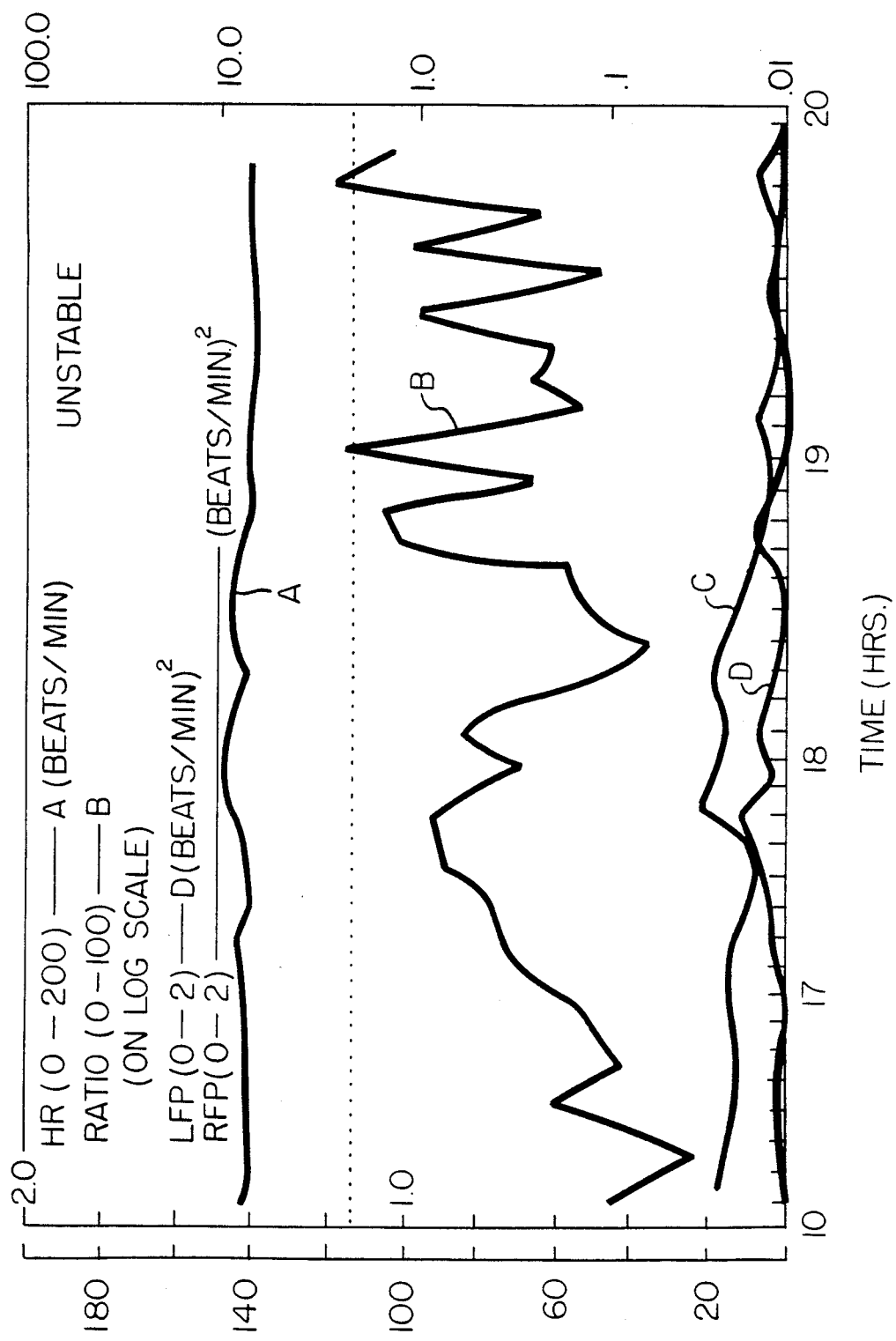
FIG. 11, illustrates a trend display for an unstable patient according to the present invention.

As illustrated by a block diagram in FIG. 9, a block diagram may be constructed for the main program (designated Syncts19) and for sub-routine modules (Sync7s, Gwindow3, and Fgraph8). This block diagram may be used in order to better interpret a complete program for heart rate fluctuation spectral analysis useful on an IBM personal computer, as illustrated in Appendix B. Although programs are provided for a Hewlett-Packard and an IBM computer herein, the software and other aspects of the present invention may be readily modified for use with other mini- and micro-computers.

In the program of Appendix B is a routine for removing artifacts from a detected heart rate provided for by an electrocardiograph machine. This program computes histograms from the heart rate data in order to generate a tachometer waveform. The most common rate on the histogram is selected as the correct rate and other rates are interpreted in light of it. Specifically, in order to correct for a spurious extra trigger, where a first and a second beat are close together while a third beat is spaced at an abnormally long interval, the second beat is discarded if the first beat to second beat interval is less than a predetermined value. The resulting interval between the first and the third beats is divided by an integer in order to provide a more normal interbeat interval. Where a trigger has been missed, so that a first and a second beat are separated by an interval which is approximately a multiple of a normal intrabeat interval, the intrabeat interval is divided by that multiple, most commonly two, in order to provide a more correct interval length. If the slewing rate of the heartbeat samples is outside of an acceptable range of slewing rates determined as a function of a mean variance, and the problem cannot be identified as a missed trigger or as a spurious extra trigger, or if the three previous intervals have been corrected, a determined mean interval, against which all other intervals are judged, is substituted for the inappropriate interval.

The slew rate is calculated on a moving average of the heart rate waveform and corrects for triggers that fall within the parameters of 0.05 Hz (3 beats/min.) per beat and five times the maximum slew. This artifact-correcting routine never slews more than 10 percent of the heart rate waveform.

Within the software of Appendix A is a graphic routine for trending heart rate fluctuation spectral data. The parameters of LFP, RFP, LFP/RFP ratio and heart rate are plotted on a graph over time to show trends in the four parameters. These trends may then be studied in order to examine the effects of various clinical interventions. Values for the parameters heart rate, LFP/RFP ratio, LFP and RFP are stored and may be called up at any point in time through a graphing routine in order to provide a graphic depiction of the course of a patient's condition. This sort of graphic depiction is illustrated for a stable patient in FIG. 10 and for an unstable patient in FIG. 11.

Also present in the program of Appendix B, a routine is provided for the segmentation of data and subsequent reanalysis. In this routine, data from the analog to digital converter 260 is collected continuously into a buffer and is dumped to a disk in blocks of 1,024 numbers (2,048 bytes equals 1,024 words and each block is referred to as a record or EPOCH). The time of heartbeat occurrence as measured by the signal provided by outputs OUT1 and OUT2 of timer 220 are collected continuously into two buffers (hb buffer 1 and hb buffer 2). These times are dumped to the disk in blocks of 1,024 pairs of numbers (1,024 from each buffer which equals 2,048 bytes or 1,024 words each). Because the heart rate is less than the sample rate of A/D converter 260 as required by signal processing, there are fewer heartbeat disk dumps.

In order to properly analyze data, the A/D and heartbeat data must correspond to the same time interval for the purpose of doing correlations. The correspondence may be determined from (1) the record number in a A/D file and (2) the absolute of the times stored in the heartbeat file (time differences used for intrabeat intervals). The instantaneous heart rate signal is generated backwards in time from the heartbeat corresponding to the last A/D sample in the record of interest. This means that if the heart rate signal is analyzed on a frequency scale not corresponding to the respiration data (e.g. respiration sample at 16 Hz but a heart rate analysis at 0 to 4 Hz) then the heart rate waveform extends backwards in time beyond the beginning of the present A/D record. This means that the heart rate waveform overlaps the heart rate waveform corresponding to the previous A/D records.

Overlapping permits lower frequency analysis than would be possible if only data corresponding to the present record were used (as in the prototype apparatus). Also, overlapping leads to the smoothing of parameters and to the subsequent reduction of fluctuating artifacts. In addition, it becomes less critical at what point analysis begins.

Figure 12:
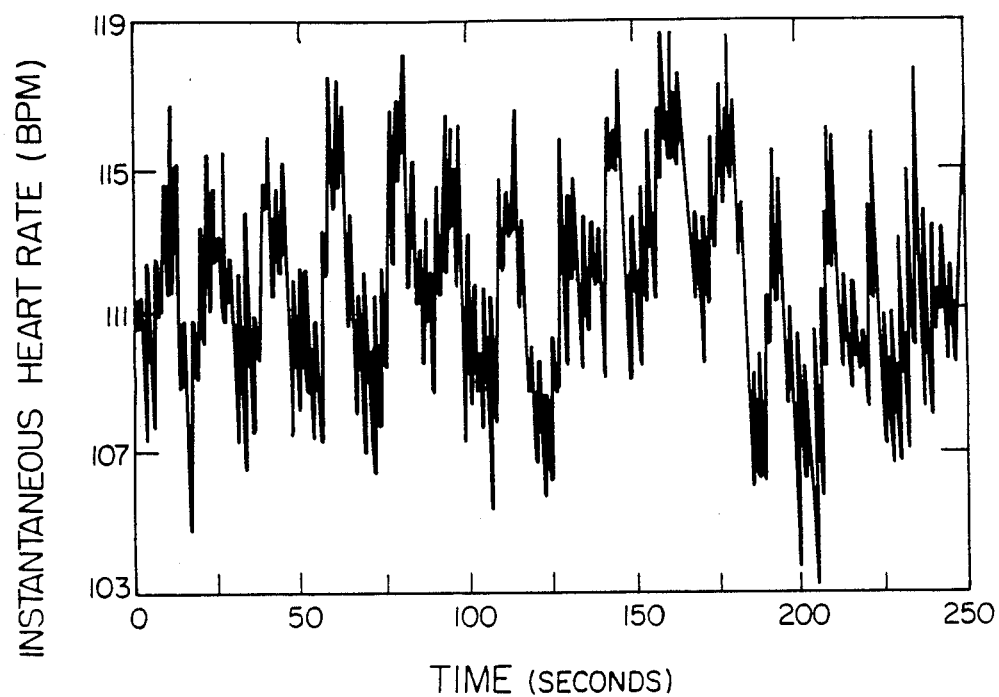
FIG. 12 is an illustration of an instantaneous heart rate according to the present invention.

A calibration program providing a software driven calibrator, which may provide more realistic spectral data than the portable calibrator of FIG. 8, is contained within the program of Appendix A for a Hewlett-Packard micro-computer. FIG. 12 is a program which, although not tested, is believed to provide the same sort of software-driven calibration for an IBM personal computer through the data acquisition system of FIGS. 4 through 7.

In general, outputs OUT0 and OUT1 of timer 220 in FIG. 5 generate a time base used via interrupt request line IRQ4 to clock data from a buffer to D/A converter 300. This buffer contains a respiratory waveform which may be a sign wave or any selected waveform as obtained by changing the contents of the buffer. Output OUT2 of timer 220 generates a heartbeat pulse as its output. In order to work properly, this pulse must be returned to the ECG trigger through node 400 or directly to interrupt request line IRQ3. If the latter course is chosen, however, node 491 must be disconnected from the output of Schmitt trigger 416. By returning the pulse to the ECG trigger, the computer is informed that the timer is through counting the present RR interval and needs a new interval to be loaded into a timer register of timer 220.

Figure 13:
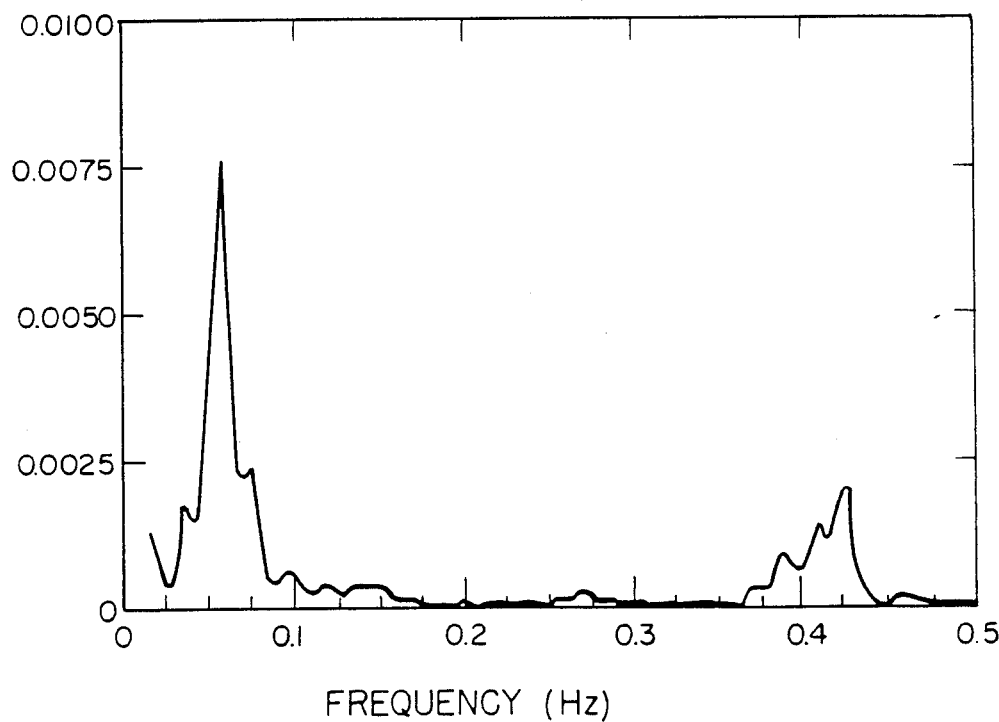
FIG. 13 is an illustration of an instantaneous heart rate fluctuation spectrum of the sort obtainable from apparatus according to the present invention.
Figure 14:
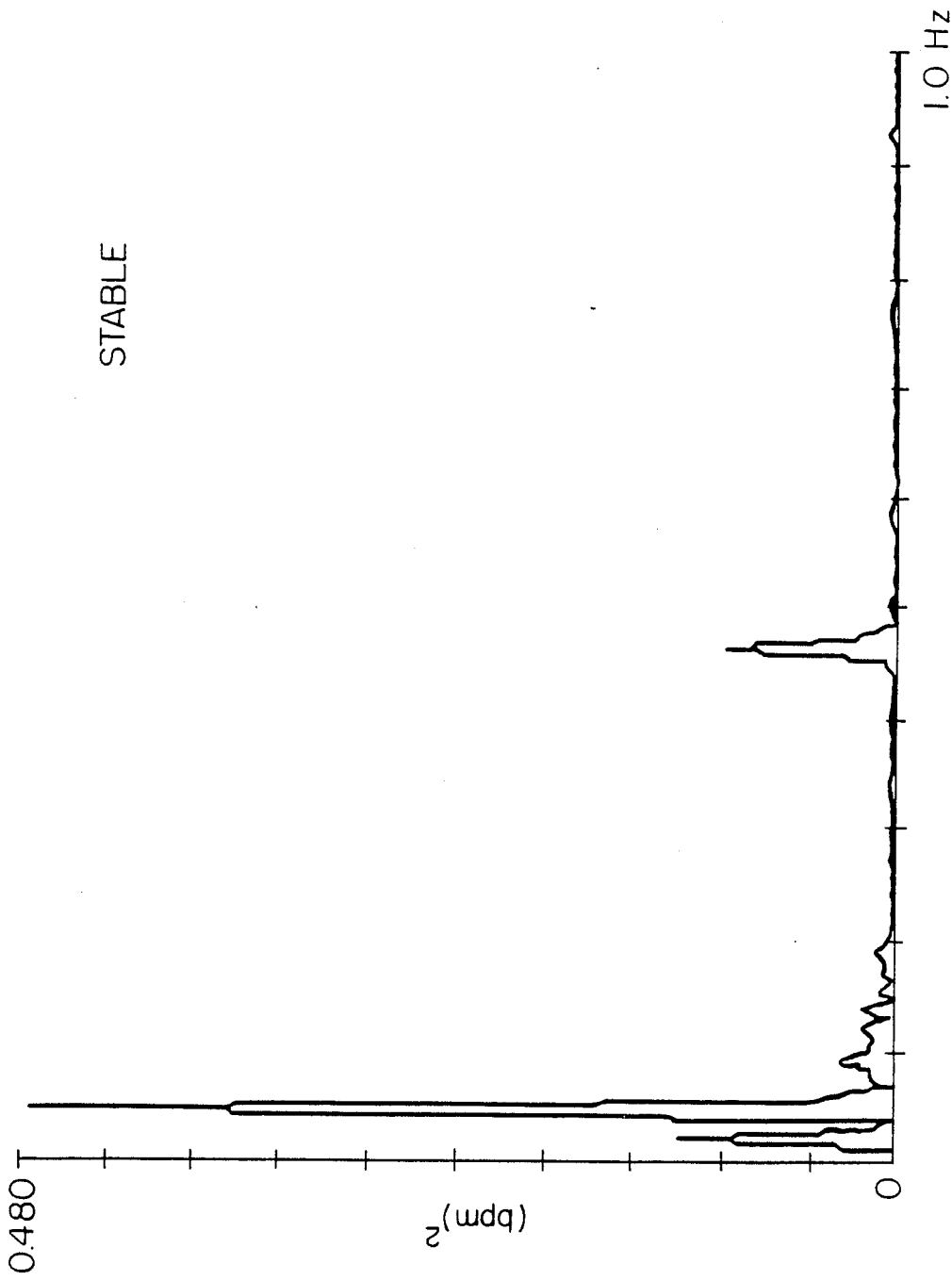
FIG. 14 is a heart rate fluctuation power spectrum according to the present invention of a stable patient.
Figure 15:
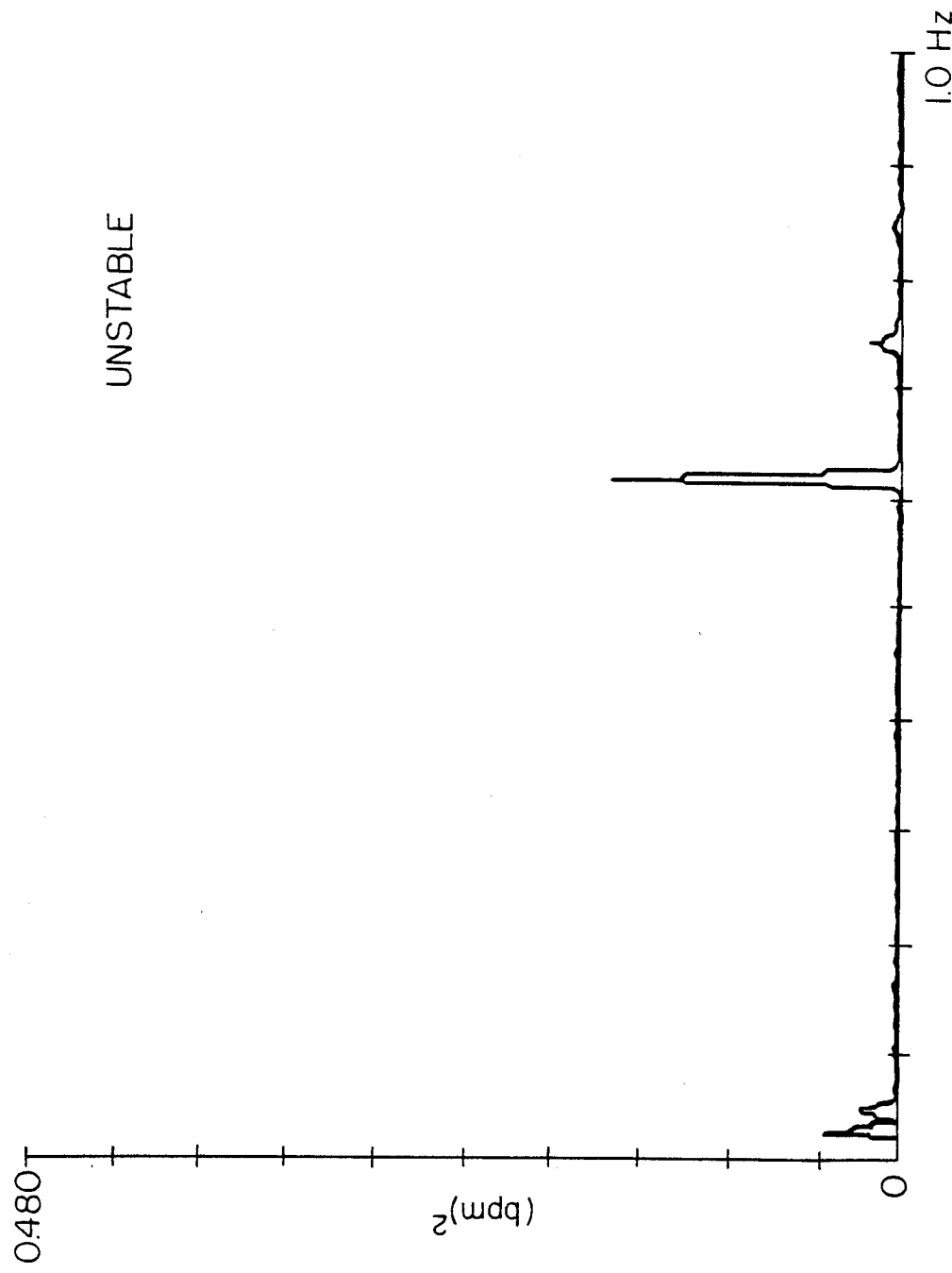
FIG. 15 is a heart rate fluctuation power spectrum according to the invention of an unstable patient.

Through the use of the apparatus according to the present invention, a display of instantaneous heart rate as provided by an electrocardiograph machine, and as illustrated in FIG. 12, may be converted into an instantaneous heart rate fluctuation spectrum as illustrated in FIG. 13. A typical spectrum for a stable patient is illustrated in FIG. 14 while a typical spectrum for an unstable patient is illustrated in FIG. 15.

Example I and Example II relate respectively to diagnosis and to treatment employing the present invention.

Parts suitable for use in construction of the apparatus as illustrated in FIGS. 3 through 8 may include those as listed in Tables I, II, III and IV.

TABLE I

| Element No. | Part No. | Manufacturer, Location |
|---|---|---|
| 100, 110, 120 | 74HC244 | National Semiconductor Santa Clara, California |
| 130 | 74HC138 | National Semiconductor Santa Clara, California |
| 140, 151, 158 | 74HC30 | National Semiconductor Santa Clara, California |
| 152, 153, 154 155, 156, 157 159, 160, 161 172, 265, 266 | 74HC04 | National Semiconductor Santa Clara, California |
| 171, 173, 185 264 | 74HC00 | National Semiconductor Santa Clara, California |
| 200 | 8255A-5 | Intel Corporation Santa Clara, California |
| 220 | 8253-5 | Intel Corporation Santa Clara, California |
| 224 | | |

TABLE I-continued

| Element No. | Part No. | Manufacturer, Location |
|---|---|---|
| 240 | 74HC393 | National Semiconductor Santa Clara, California |
| 260 | ADC0808 | National Semiconductor Santa Clara, California |
| 268, 303, 312 401, 406, 412 500, 511, 515 518, 525 | LM324AN | National Semiconductor Santa Clara, California |
| 280 | 8286 | Intel Corporation Santa Clara, California |
| 300 | DAC0830 | National Semiconductor Santa Clara, California |
| 416 | 74HC14 | National Semiconductor Santa Clara, California |

TABLE II

Diodes

| Element | Part No. |
|---|---|
| 407, 415 | IN4148 |

TABLE III

Resistors

| Element No. | Value (in Ohms) |
|---|---|
| 403i, 410 | 2.2k |
| 269 | 5k |
| 270, 271, 409 | 10k |
| 403h | 15k |
| 403g | 27k |
| 403f | 56k |
| 313 | 82k |
| 309, 310, 501, 502, 503, 520, 521, 522, 527, 528, 529, 533, 403e | 100k (variable) |
| 403d, 410d | 220k |
| 403c, 410c | 560k |
| 508, 516, 526, 403b, 410b | 1 M (variable) |
| 512, 513, 403a, 410a | 2.2 M |

TABLE IV

Capacitors

| Element No. | Value (in microFarads) |
|---|---|
| 405 | 2.2 |
| 404, 505, 517 | 10 |
| 532 | 0.1 |
| 514 | 1 |

EXAMPLE 1

Heart rate spectral analysis was applied to the study of congestive heart failure in infants and children. Congestive heart failure is characterized by a marked alteration in cardiovascular regulation. However, many cardiovascular functions which are normally monitored in cardiac intensive care units (such as: mean heart rate; arterial blood pressure; arterial blood gases; left arterial pressure and right arterial pressure; right atrial, left atrial and pulmonary artery oxygen saturations; the peripheral pulses; peripheral perfusion; and cardiac output) may not clearly indicate a critically unstable cardiovascular condition. The usually-monitored cardiovascular function parameters may be within a normal range immediately before a major cardiovascular crisis, such as hypotension or cardiac arrest, inasmuch as the cardiovascular regulatory system maintains these parameters within a normal range up to the point of system failure.

Twenty-nine infants and children were studied in a cardiac intensive unit. Of the twenty-nine patients, twenty-six have undergone a cardiac surgical procedure. The patients were studied for a minimum of three hours and a maximum of twenty-seven hours, with a mean study time of eight hours. EKG for cases were recorded and analyzed continuously in real time during the study time.

Data for a particular patient was analyzed only if the patient was in sinus rhythm. The patient's clinical course during the period of study was reviewed and, in particular, major events such as cardiac arrest, hemorrhage and profound hypotension were correlated with spectral analysis data. Administration of medication and the mode of ventilation were noted.

Real time heart rate spectral analysis was performed on a dedicated personal computer using a 6809E Motorola Microprocessor-Based System. A data acquisition system interfaced the computer with a patient monitor, available from Hewlett-Packard, Palo Alto, Calif., as Model No. 78341.

The heart rate power spectrum was calculated in continuous 256 second data epochs. A QRS synchronization pulse from the patient monitor was used to determine an RR interval sequence. An instantaneous heart rate signal was computed from RR interval sequence and the magnitude of the signal was set to the reciprocal of the current interbeat interval. The instantaneous heart rate signal was sampled at 4 Hz and the mean heart rate was subtracted from the resulting one thousand twenty-four point time series. A power spectrum was computed by squaring the absolute value of a Fast Fourier Transform of the one thousand twenty-four point time series. Values for low frequency power (LFP) were computed by integrating the spectrum of between 0.04 and 0.1 Hz. Respiratory frequency power (RFP) was computed by integrating the heart rate power spectrum over a 0.2 Hz-wide band centered at the mean respiratory frequency.

Hard copies of the heart rate time series and power spectrum were printed for each 256 second epochs. Trend graphics for the LFP, the RFP, LFP/RFP ratio, mean heart rate and respiratory rate (hereinafter referred to as the study parameters) were constructed by manually entering data in data files and analyzing the entered data by means of a computer.

Mean values for the study parameters were calculated for each period of study. The Mann-Whitney Rank Sum Test was used to determine statistically significant changes in the study parameters in individual patients and to determine differences among groups of patients. When patients were segregated into more than two groups, the Kruskal-Wallis Test, multiple comparison test, and Tukey's HSD were employed to determine statistical significance. P values of less than, 0.05 were considered significant.

It was found that during each three to twenty-four hour period of study the study parameters for a given patient, the LFP, the RFP and the LFP/RFP ratio (hereinafter referred to as the spectral parameters) remain fairly stable.

Based upon the results of this study, the patients were retrospectively divided into three groups. Group I included seventeen stable patients whose median age was one month. The patients in Group I were without major post-operative complications and did not need prolonged inotropic support. The eight patients in Group II suffered cardiac arrest and died. The median age for the members of Group II was one month. In Group III, there was a total of four patients each of whom was critically ill at the time of the study but later recovered. Median age of the members of Group III was one month. Of the four members of Group III, one required re-operation, one had intermittent hypotensive episodes, and two had cardiac arrests from which they were successfully resuscitated.

In order to separate all twenty-nine patients into a group of stable patients (Group A) and a group of critical patients (Group B), data from each patient in Group III was divided into the data collected during the stable period (which applied to three patients) and the data collected during the preceding critical period (which applied to four patients). When handled in this way, Group A included data for twenty patients and Group B included data for twelve patients. Typical heartrate fluctuation power spectra for Group A and B are respectively illustrated in FIGS. 19 and 20.

In addition, studies were performed on three patients who had isolated coarctation of the aorta at three points in time: upon admission for congestive heart failure; during treatment; during post-operative period; and prior to discharge from an intensive care unit. An attempt was made to identify changes in cardiovascular regulatory function of each of these stages.

Patient profiles for Groups I, II and III are respectively provided in Tables V, VI and VII. These profiles include age, diagnosis and operation.

TABLE V

| | PATIENT PROFILE; STABLE POST-OP N = 17 | | | |
|---|---|---|---|---|
| AGE | NO. | DIAGNOSIS | (NO.) | OPERATION |
| <30 DAYS | 9 | TGA,IVS | (3) | ARTERIAL SWITCH |
| | | TGA,VSD,PS | (1) | L-BTS |
| | | HLHS | (1) | STAGE 1 REPAIR |
| | | SV | (1) | L-BTS |
| | | SEV. COAO | (3) | SUBCL.FLAP ANGIO. |
| 1–12 MO. | 5 | TGA,IVS | (1) | ARTERIAL SWITCH |
| | | TGA,VSD,PS | (1) | BTS |
| | | MULT.VSD'S | (1) | VSD PATCH REPAIR |
| | | SUPRA-V. PS | (1) | PA PATCH PLASTY |
| | | DCRV,VSD,COAO | (1) | VSD REPAIR, ANOM. B RESECTion |
| 1–10 YRS. | 2 | PS | (1) | PULM. VALVOTOMY |
| | | TOF | (1) | TOF REPAIR |
| >10 YRS. | 1 | AR,MR | | AVR,MVR |

TABLE VI

| | PATIENT PROFILE; CRITICAL, DIED N = 8 | | | |
|---|---|---|---|---|
| AGE | NO. | DIAGNOSIS | (NO.) | OPERATION |
| <30 DAYS | 4 | HLHS | (3) | NORWOOD PROCEDURE |
| | | SV W/IAA | (1) | GORE-TEX GRAFT |
| 1–12 MO. | 3 | HLHS | (1) | Fontan operation |
| | | DORV,TAPVC, CCAVC | (1) | TAPVC REPAIR, SYS. PULM. SHUNT |
| | | HLHS | (1) | NON-OPERATIVE |
| 6½ YRS. | 1 | T OF S/P REPAIR W/ CHRONIC SEV. CARDIOMYOPATHY, S/P ARREST | | NON-OPERATIVE |

TABLE VII

| | PATIENT PROFILE: CRITICAL, RECOVERED N = 4 | | | |
|---|---|---|---|---|
| AGE | NO. | DIAGNOSIS | (NO.) | OPERATION |
| <30 DAYS | 3 | HLHS,COAO | (1) | NORWOOD PROCEDURE |
| | | HLHS | (2) | NORWOOD PROCEDURE |
| 14 YRS. | 1 | ACUTE MYOCARDITIS, S/P ARREST | | NON-OPERATIVE |

In Tables V, VI and VII: TGA is Transposition of the Great Arteries; IVS is Ventricular Septal Defect; PS is Pulmonic Stenosis; HLHS is Hypoplastic Left Heart Syndrome; SV is Single Ventricle; SEV. is severe; COAO is Coarctation of the Aorta; MULT is multiple; VSD is Ventricular Septal Defect; Supra-V. is Supravalulvar; DCRV is Double Chamber Right Ventricle; TOF is Tetralogy of Fallot; AR is Aortic Regurgitation; MR is Mitral Regurgitation; W/IAA is with Interrupted Aortic Arch; DORV is Double Outlet Right Ventricle; TAPVC is Total Anomalous Pulmonary Venous Connections; CCAVC is Complete Common Atrial Ventricular Canal; S/P is Status Post; L is Left; BTS is Blailock Taussig Shunt; PA is Pulmonary Artery; ANOM. is Anomalous; B is muscle Bundle; PULM is Pulmonary; and SYS is Systemic.

Statistically significant differences were observed in the heart rates spectral parameters between the groups of patients as well as among the individual patients. However, the mean heart rate alone did not distinguish stable from critically ill patients. Both the LFP and the LFP/RFP ratio discriminated between the Group A (stable) patients and the Group B (critical) patients. The LFP/RFP ratio grew out of a statistically significant (p less than symbol 0.00001) discrimination between stable and critical patients. Table VIII presents means of study parameters.

TABLE VIII
MEANS OF STUDY PARAMETERS

| | MEAN | STD. DEV. | STD. ERROR OF MEAN | 99% CONFIDENCE LOWER | UPPER |
|---|---|---|---|---|---|
| GROUP A STABLE | | | | | |
| PARAMETER (BEATS/MIN.) | | | | | |
| LFP | 1.77 | 3.35 | 0.75 | −.37 | 3.91 |
| RFP | 0.28 | 0.70 | 0.16 | −.17 | 0.72 |
| LFP/RFP RATIO | 8.77 | 4.86 | 1.09 | 8.76 | 8.79 |
| HEART RATE | 139 | 19.60 | 4.38 | 139 | 139 |
| GROUP B, CRITICAL | | | | | |
| PARAMETER | | | | | |
| LFP | .05 | .03 | .01 | .02 | .07 |
| RFP | .10 | .09 | .03 | .01 | .18 |
| LFP/RFP RATIO | .83 | .51 | .15 | .83 | .83 |
| HEART RATE | 142 | 24.32 | 7.02 | 142 | 142 |

The discriminate value for the LFP/RFP ratio was two. In Group A, the range of LFP/RFP ratios was 3 to 22 (arithmetic mean 8.77). The range of RFPs was 0.01 to 3.13 (arithmetic mean 0.28) and the range of LFPs was 0.09 to 13.88 (arithmetic mean 1.77). In Group B, the range of LFP/RFP ratios was 0.17 to 1.9 (arithmetic mean 0.83), the ratio of RFPs was 0.02 to 0.32 (arithmetic mean 0.1), and the range of LFPs was 0.01 to 0.1 (arithmetic mean 0.5).

Although the mean value of the LFP/RFP ratio was greater than two for Group I, the ratio for the stable patients fell below two for brief periods. That which distinguishes the stable from the critical patients is the sustained value for greater than or about one hour of the LFP/RFP ratio for the critical group.

Figure 16:
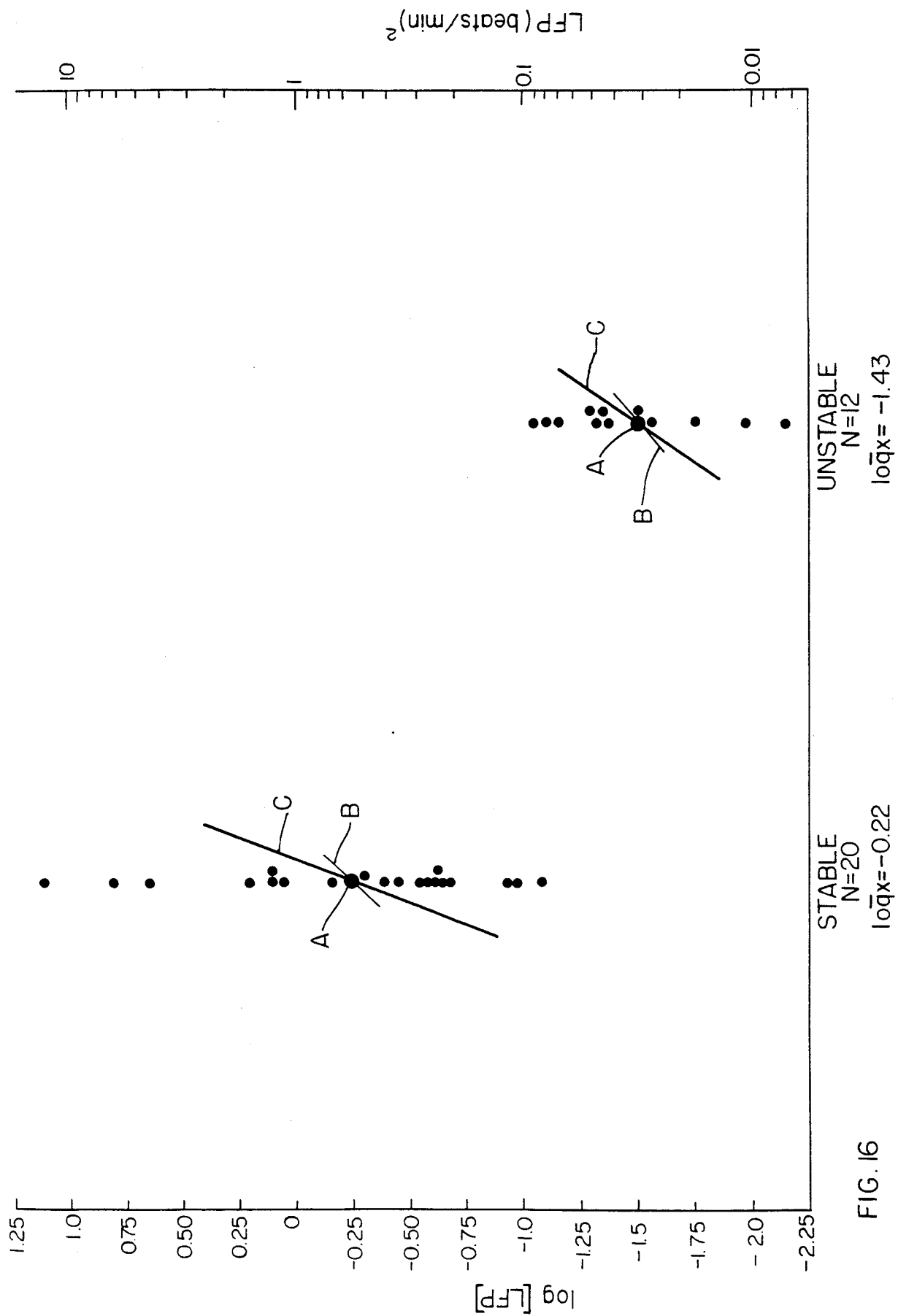
FIG. 16 depicts distributions in LFP data obtained according to the present invention for stable and for unstable patients.
Figure 17:
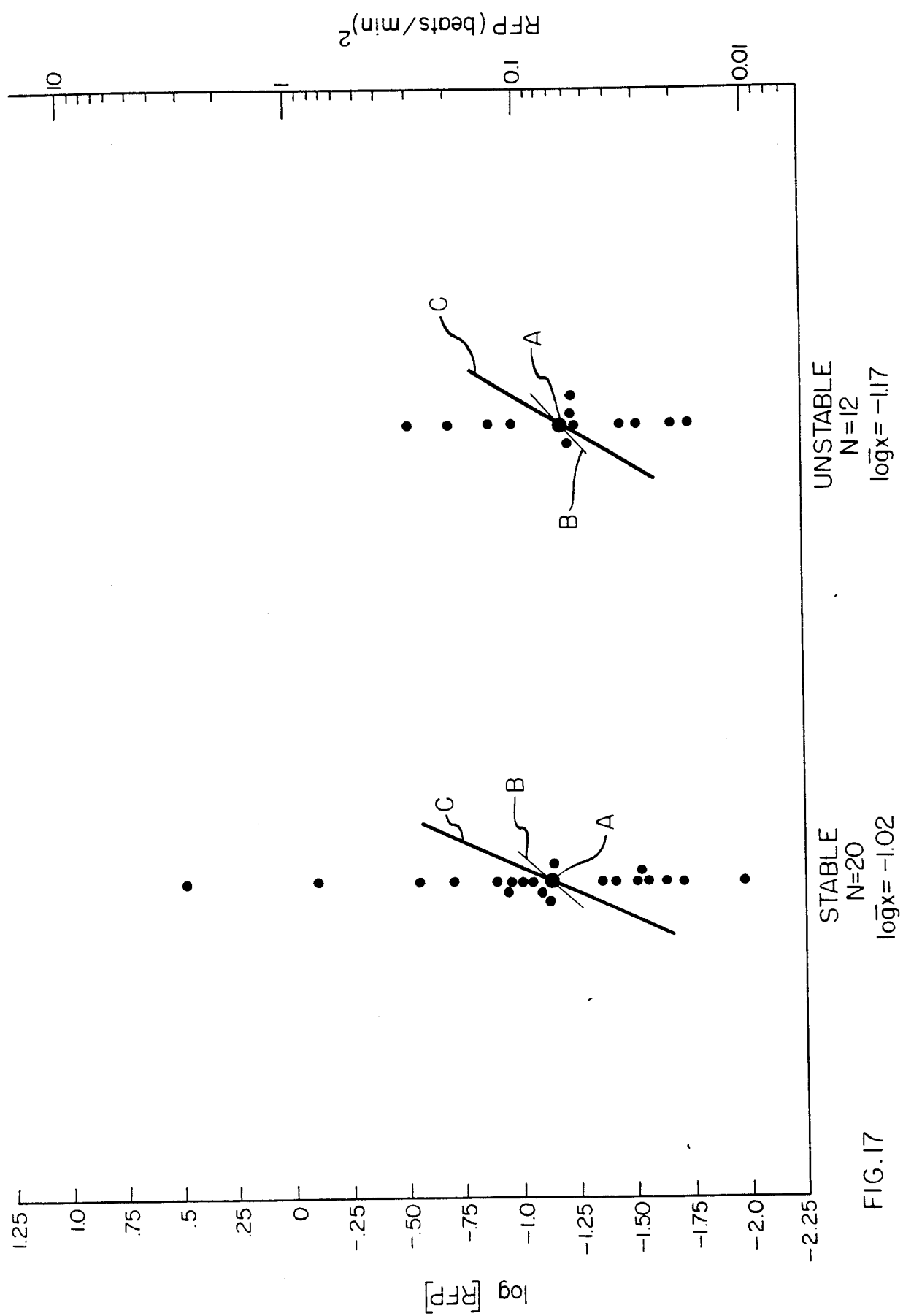
FIG. 17 graphically depicts distributions of RFP data according to the present invention for stable and for unstable patients.
Figure 18:
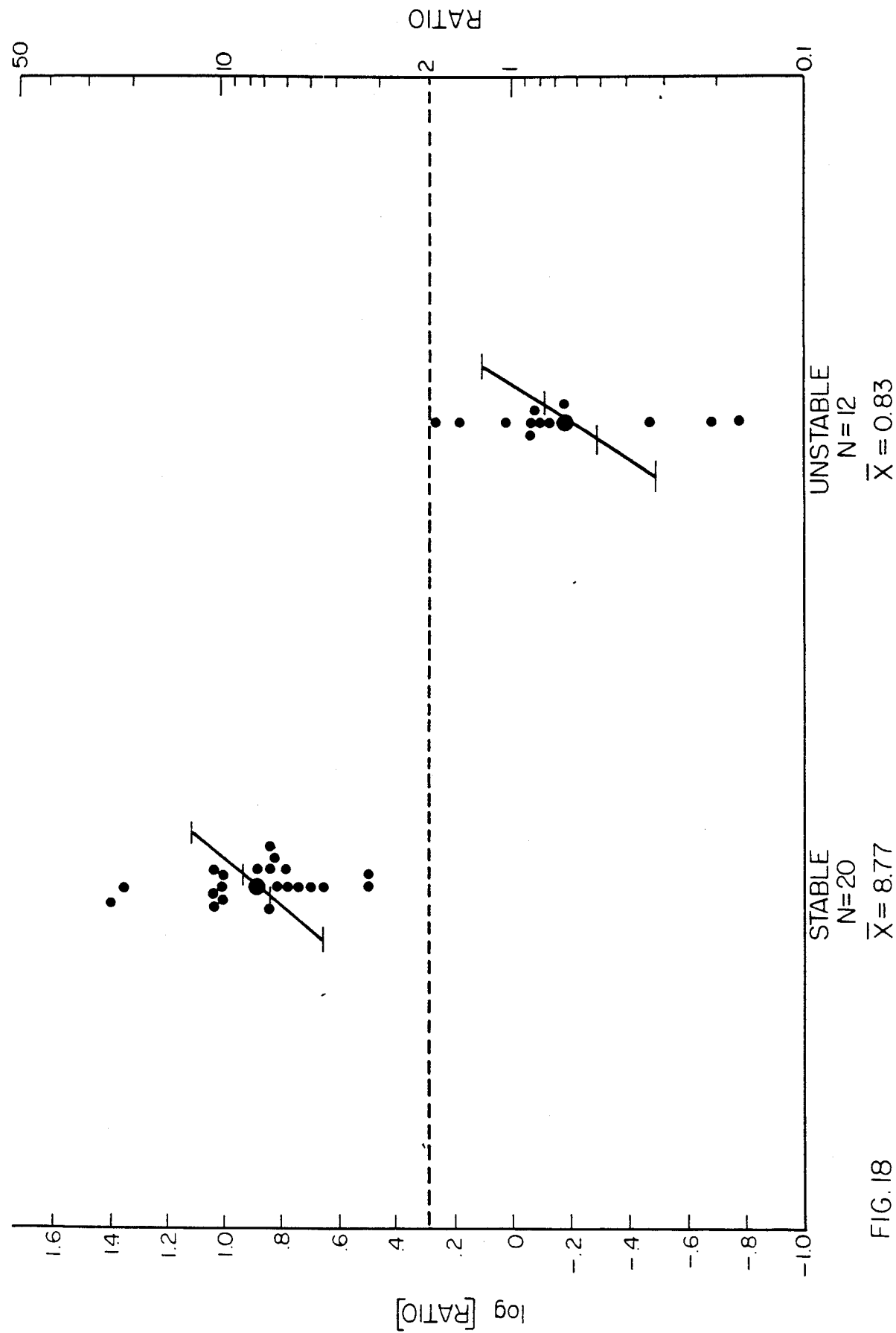
FIG. 18 graphically depicts data for LFP/RFP ratios according to the present invention for stable and for unstable patients.

The results are graphically depicted in FIGS. 16, 17 and 18. In FIGS. 16 and 17, each heavy dot A represents a geometric mean, each light line B indicates the standard error of the geometric mean and each heavy line C represents the standard deviation of the geometric mean. In FIG. 18, each heavy dot A represents an arithmetic mean, each set of slashes B1 and B2 represents the standard error of the arithmetic mean and each set of slashes C1 and C2 represents the standard deviation of the arithmetic mean.

The significance of heart rate spectral analysis for diagnosis of cardiovascular stress and the prediction of fatality is highlighted by the fact that patients with a low LFP/RFP ratio underwent a cardiac arrest even in the presence of otherwise normal vital signs. No patient with a LFP/RFP ratio greater than two experienced a cardiac arrest.

Infusion of pressors, alone or in combination with vasodilators, did not induce a low LFP/RFP ratio.

Four patients in Group III had LFP/RFP ratios less than two during their critical periods. For the three of these four patients who were restudied during their recovery periods, all three had LFP/RFP ratios greater than two.

The mean LFP for Group B [0.05 (Beats per minute)$^2$] was less than the mean LFP for Group A [1.77 beats per minute)$^2$], p<0.0001. There was no significant difference between the mean RFP between the groups.

The initial LFP/RFP ratios for the patients with isolated coarctation of the aorta ranged up to 10 000. The LFP/RFP ratios observed for this group immediate after an operation to correct the condition were within the range for Group A patients. Two patients had LFP/RFP ratios greater than 100 before discharge from the intensive care unit. These ratios were correlated with mild to moderate congestive heart failure.

One of these patients died suddenly at approximately 2½ months after the operation. The other two patients remained alive and well.

Although the LFP/RFP ratio provided the sharpest discrimination between stable and critical patients in these studies, the LFP alone discriminated between Groups A and B, p<0.0001. Neither respiratory frequency peak power nor mean heart rate distinguished between Groups A and B. On the other hand, LFP/RFP ratios and LFP low levels sustained for greater than or about one hour correlate with the course of the conditions of patients who experienced cardiac arrest or severe hypotensive episodes but later recovered.

Although stable patients experienced transient depression of levels of LFP and of the LFP/RFP ratio, depression of these factors for about an hour or more never failed to predict a critical status.

No significant difference was observed between freely ventilating patients and mechanically ventilated patients. Eighteen out the twenty patients in Group A were mechanically ventilated and all twelve of the Group B patients were mechanically ventilated.

All patients in Group B received inotropic support while more than half of the patients in the Group A received at least some inotropic support. The cardiac diagnoses of all of the patients in Group B and for some of the patients in Group A were known to be associated with high mortality. All of the patients in Group B underwent deep hypothermic circulatory arrest during their operations. Of the twenty patients in Group A, nine had extra cardiac surgery (i.e. not involving cardiopulmonary bypass or deep hypothermic circulatory arrest). Three of the patients in Group II did not undergo operations. Therefore, it is not believed that differences in treatment or disease specific pathology alone explained the low values LFP and the low LFP/RFP ratios in Group B patients but that the low values actually reflect a vulnerable circulatory state.

It has also been observed that the value of LFP and of the LFP/RFP ratio increase in moderate to severe heart failure but decreased to subnormal values in end stage myocardial failure. Thus, these two spectral parameters may indicate cardiovascular regulatory effectiveness (cardiovascular regulatory reserve) during the stress of heart failure.

This analysis is consistent with previous physiological studies which indicated that low frequency heart fluctuations may be mediated by both the beta-sympathetic and parasympathetic mechanisms while respiratory fluctuations are exclusively mediated by parasympathetic mechanisms. It is also consistent with this analysis that LFP has been observed to increase during conditions which elicit enhanced sympathetic activity, such as acute hypoxia, postural changes, hemorrhage and aortic constriction. In this light, the LFP/RFP ratio may represent a measure of the balance between beta adrenergic and parasympathetic modulation of cardiac function.

Thus, the increase in LFP and in the LFP/RFP ratio for patients with isolated coarctation of the aorta and moderate heart failure may result from an increased activity from the sympathetic mechanism and a decreased activity of the parasympathetic mechanism. On the other hand, the decreased level of LFP and of the LFP/RFP ratio found in critical patients may be due to non-responsiveness of the sympathetic mechanism. Sympathetic non-responsiveness may be due to myocardial catecholamaine depletion alone or in combination with the observed down regulation of beta receptors from cardiac tissue in the end stage of heart failure.

EXAMPLE II

In patients undergoing operations, shifts in body fluid disposition during surgery may lead to changes in intervascular volume (i.e. a shift of fluid out of a circulatory tree of blood vessels). Accordingly, the availability of the method of diagnosing cardiovascular stress as described in Example I may be used to choose among various protocols for treatment or to justify a radical change in medical or surgical treatment.

For example, by monitoring a patient with the real time heart rate frequency spectral monitor according to the present invention during administration of anesthesia, an anesthesiologist may non-invasively monitor intravascular volume status. Upon observing an increase in the LFP or in the LFP/RFP ratio, the anesthesiologist may increase the amount of fluids administered by way of intravenous injection or may take steps to reverse effects of a particular anesthetic.

It is a particular advantage of the apparatus according to the present invention that heart rate fluctuation spectral analysis may be done in real time. This capability permits correlation of treatment administered with changes in LFP or LFP/RFP ratios.

Although the present invention has been described in terms of preferred embodiments, it is understood that modifications, variations and improvements will occur to those skilled in the art. For example, it will occur to those skilled in the art to employ the present invention for monitoring cardiovascular instability in the following settings in which significant circulatory stress are commonly observed: Labor and Delivery Room; Operating Room; Cardiac Catheterization Laboratory; Neonatal, Pediatric, Adult Medical, Adult Surgical, Cardiothoracic and Neurosurgical Intensive Care Units; Coronary Care Units; Burn Units; and Emergency Rooms.

The present invention may also be used for monitoring cardiovascular instability in the following patients in which adjustments in cardiovascular regulation may provide a central key to understanding the efficiency and efficacy of treatment. Ambulatory patients with known heart disease in which sudden cardiac death is a common association, one example of which would be a patient with a congestive cardiomyopathy who is being treated with vasodialator drugs and for whom the LFP/RFP ratio has changed from a normal baseline level to decreased levels may then subsequently be either admitted to the hospital for adjustment of medications and/or observed and monitored in the physican's office while his vasodialator drug dose is increased. A patient with renal disease (e.g. one who requires dialysis) may exhibit a marked increase in LFP and LFP/RFP ratio secondary to the onset of incipient moderate congestive heart failure would thus be treated by dialysis to relieve a congested circulatory state; a patient with moderate to severe pulmonary disease resulting in hypoxemia and/or hypercarbia who requires bronchodialator and/or supplementary oxygen and/or mechanical ventilation (e.g. a patient who exhibits a marked decrease in LFP/RFP ratio secondary to myocardial failure due to a profound imbalance between myocardial ventricular output and oxygen demand), may be treated by adjustments in bronchodialator drugs, diuretics, and/or ventilator adjustments.

A premature infant of very low birth weight known to be at risk for intraventricular hemorrhage may, for example, develop a slow intracranial bleed associated with an abrupt increase in LFP, which may alert physicians prior to a brisk bleed thus allowing institution of appropriate changes in medical management to limit substantially known risk factors that may predispose to such an event, or may permit recognition of the presence of unsuspected circumstances that contribute to the bleed. In neurologic disease, such as one in which a patient has sustained a major intracerebral event (e.g. neurosurgical evacuation of a space occupying lesion such as a tumor or blood), a patient may, for example, exhibit a markedly attenuated LFP/RFP ratio, secondary to massively increased parasympathetic activity which would markedly increase RFP, at the expense of LFP, but which may or may not be associated with signs of increased intracranial pressure, and which may be treated by, for example, hyperventillation, rapid diuresis, or burr hole placement.

A patient with severe systemic infection may exhibit shock secondary to the infection process may, for example, exhibit an elevated LFP/RFP ratio which may then be subsequently used by the physician in managing the shock state by means of pressor agents and infusion of significant volumes of fluid, thus providing the physician an indication of how effectively he is treating the shocked state above and beyond the traditional measurements such as systemic blood pressure and cardiac output. A patient with hematologic disease associated with anemia, such as Sickle Cell Anemia, exhibits an oscillation in capillary blood flow when severely anemic at the frequency associated with LFP and may exhibit large values for LFP, and for the LFP/RFP ratio may, for example, be treated by blood transfusion which may lead to an expected decrease in LFP, LFP/RFP ratio, and thus enable the physician to monitor by means of heart rate spectral analysis appropriate timing for transfusion therapy. A fetus prior to delivery, may for example, exhibit a marked attenuation in LFP associated with severe fetal distress, and may thus alert the physician to perform an emergency Caesarean section.

One skilled in the art understands that the calibrators according to the present invention may be adjusted to simulate disease states as well as normal conditions. It is also understood that the present invention is not limited to use with patients whose primary disease is of the heart but that modifications may be made for use with such patients.

Lastly, it is clear to one skilled in the art that durations and ranges for levels of LFP and LFP/RFP ratios are conservatively stated herein and that variations from these ranges and durations are contemplated within the scope of the equivalents of the present invention.

Therefore, it is intended that the methods and apparatus according to the present invention to be given the broadest scope allowable for the invention as claimed.

The following appendices are program listings for software useful in implementing the present invention. Specifically: Appendix A illustrates software for an embodiment of the present invention applicable to a Hewlett-Packard microcomputer; Appendix B illustrates software according to the present invention useful for practicing the present invention on an IBM personal computer; and Appendix C is a calibration program designed to implement the software driven calibrator of FIG. 11.

APPENDIX A

```
 5   10  Summary3:!
     20      !This program takes data already collected and allows the data
     30      !to be outputted to a printer
     40      !2 MAY 1985
10   50      !
     60      COM /Trends/ Mean_hr_t(60),Lfa_t(60),Rfa_t(60),Ratio_t(60),T_ptr,Time_nowl,Mean_resp_t(60),Trend_dp
     70      COM /Multi_param/ Start_chan,Stop_chan,Pacing_
15           bits,Pacing_rate,Num_pts,Nu
                m_xfer,Num_xfer_left,Name_len,Scr_file$[28],Scr_file2$[28]
     80      COM /Pressure/ Top1,Top2,Top3,Top4,Bot1,Bot2,Bot3,Bot4
20   90      COM /Editor/ Edit_msg$[80]
     100     COM /Subject/ Sub_name$[25],Hos_num$[15],Id_age$[10],Id_wt$[10],Id_ht$[10
                ],Diag$[30],Opera$[45],Halt_pg,In_file$[6]
     110     COM /Io_chart/ Io_time$(8)[10],Iv_intake(8),Fluid_
25           in(8),In_tot(8),Urine(8
                ),Chest(8),Out_tot(8),Net(8),Io_ptr
     120     COM /Lab_chart/ Lab_
            time$(8)[10],Na(8),K1(8),Cl(8),Hco3(8),Ca(8),Hct(8),G
                luc(8),Dig(8),Pt(8),Ptt(8),Creat(8),Bun(8),Lab_ptr
30   130     COM /Vent_chart/ Vent_
            time$(8)[15],Rate(8),Fio2(8),Pp(8),Peep(8),Tv(8),
                Ie_ratio$(8)[5],Airp(8),Ph(8),Po2(8),
                    Pco2(8),Bgo3(8),Be(8),Vent_ptr
```

```
140    COM /Pres_chart/ Pres_time$(20)[15],Ao_s(20),Ao_
       d(20),Ao_m(20),Pa_s(20),P
       a_d(20),Pa_m(20),La_m(20),Ra_m(20),Pres_
           ptr,Pres_in
150    COM /Heart_index/ Heart_
       time$(15)[15],Ci(15),Pvri(15),Svri(15),Heart_ptr
160    COM /Drugs/ Drug_time$(40)[20],Drug_
       name$(40)[40],Drug_dos$(40)[20],Drug_
           ptr
170    DIM Msg_buffer$[6400] BUFFER
180    DIM Pres_p(20),Io_p(8),Lab_p(8),Vent_p(8),Heart_
           p(5),Drug_p(40)
190    INPUT "enter date on which data was collected
       (ddmmyy) e.g. 22AP85",In_file$
200    Disk1$=":HP8290X,700,1"
210    INPUT "is the trend file named 'trnd'(1) or 'temp_
       trend'(2)?",Ans
220    IF Ans=2 THEN
230        ASSIGN @Trend_file TO "temp_
           trend"&Disk1$;FORMAT OFF
240        ASSIGN @Messages TO "messglog"&Disk1$;FORMAT
           OFF
250        ASSIGN @Hemo_data TO "hemo_
           data"&Disk1$;FORMAT OFF
260        ASSIGN @Io_data TO "io_data"&Disk1$;FORMAT
           OFF
270        ASSIGN @Lab_data TO "lab_data"&Disk1$;FORMAT
           OFF
280        ASSIGN @Vent_data TO "vent_
           data"&Disk1$;FORMAT OFF
290        ASSIGN @Co_data TO "co_data"&Disk1$;FORMAT
           OFF
300        ASSIGN @Drug_data TO "drug_
           data"&Disk1$;FORMAT OFF
310        ASSIGN @Sub_data TO "sub_data"&Disk1$;FORMAT
           OFF
320        ON END @Trend_file GOTO Start
330        FOR I=0 TO 55
340            ENTER @Trend_file;Trans_t(I),Mean_hr_
```

```
                                t(I),Lfa_t(I),Rfa_t(I),Ratio
                                _t(I),Mean_resp_t(I)
            350         NEXT I
            360             T_ptr=I
            370         Num_xfer=T_ptr
            380     ELSE
            390         ASSIGN @Trend_file TO "trnd"&In_
                        file$&Disk1$;FORMAT OFF
            400         ASSIGN @Messages TO "msgs"&In_
                        file$&Disk1$;FORMAT OFF
            410         ASSIGN @Hemo_data TO "hemo"&In_
                        file$&Disk1$;FORMAT OFF
            420         ASSIGN @Io_data TO "io__"&In_
                        file$&Disk1$;FORMAT OFF
            430         ASSIGN @Lab_data TO "lab_"&In_
                        file$&Disk1$;FORMAT OFF
            440         ASSIGN @Vent_data TO "vent"&In_
                        file$&Disk1$;FORMAT OFF
            450         ASSIGN @Co_data TO "co__"&In_
                        file$&Disk1$;FORMAT OFF
            460         ASSIGN @Drug_data TO "drug"&In_
                        file$&Disk1$;FORMAT OFF
            470         ASSIGN @Sub_data TO "sub_"&In_
                        file$&Disk1$;FORMAT OFF
            480         ENTER @Trend_file;Mean_hr_t(*),Lfa_t(*),Rfa_
                        t(*),Ratio_t(*),Mean_resp
                            _t(*),Trans_time(*),T_ptr
            490         Num_xfer=T_ptr
            500     END IF
            510         ASSIGN @Trend_file TO *
            520     ON END @Hemo_data GOTO Hemo1
            530     FOR I=0 TO 20
            540         ENTER @Hemo_data;Pres_time$(I),Ao_s(I),Ao_
                        d(I),Ao_m(I),Pa_s(I),Pa_d(I
                            ),Pa_m(I),La_m(I),Ra_m(I),Pres_p(I)
            550     NEXT I
```

```
560 Hemol:ASSIGN @Hemo_data TO *
570     Pres_ptr=I-1
580     ON END @Io_data GOTO Io1
590     FOR I=0 TO 8
600         ENTER @Io_data;Io_time$(I),Iv_intake(I),Fluid_
              in(I),In_tot(I),Urine(I
              ),Chest(I),Out_tot(I),Net(I),Io_p(I)
610     NEXT I
620 Io1:ASSIGN @Io_data TO *
630     Io_ptr=I-1
640     ON END @Lab_data GOTO Lab1
650     FOR I=0 TO 8
660         ENTER @Lab_data;Lab_
          time$(I),Na(I),Kl(I),Cl(I),Hco3(I),Ca(I),Hct(I),G
          luc(I),Dig(I),Pt(I),Ptt(I),Creat(I),Bun(I),Lab_p(I)
670     NEXT I
680 Lab1:ASSIGN @Lab_data TO *
690     Lab_ptr=I-1
700     ON END @Vent_data GOTO Vent1
710     FOR I=0 TO 8
720         ENTER @Vent_data;Vent_
              time$(I),Rate(I),Fio2(I),Pp(I),Peep(I),Tv(I),
              Ie_ratio$(I),Airp(I),Ph(I),Po2(I),
              Pco2(I),Bgo3(I),Be(I),Vent_p(I)
730     NEXT I
740 Vent1:ASSIGN @Vent_data TO *
750     Vent_ptr=I-1
760     ON END @Co_data GOTO Co1
770     FOR I=0 TO 5
780         ENTER @Co_data;Heart_
              time$(I),Ci(I),Pvri(I),Svri(I),Heart_p(I)
790     NEXT I
800 Co1:ASSIGN @Co_data TO *
810     Heart_ptr=I-1
820     ON END @Drug_data GOTO Drug1
830     FOR I=0 TO 40
```

```
840         ENTER @Drug_data;Drug_time$(I),Drug_
              name$(I),Drug_dos$(I),Drug_p(I)
850     NEXT I
860 Drug1:ASSIGN @Drug_data TO *
870     Drug_ptr=I-1
880        !
890        !
900        !
910     Pacing_rate=250
920     Time_now1=TIMEDATE MOD 86400
930     Out_graph=1
           !....graphics
           dump
940     Trend_dp=2
950     CALL Trend_graph
960     CALL Graph_dump(Out_graph)
970     Trend_dp=1
980     CALL Trend_graph
990     CALL Graph_dump(Out_graph)
1000    !
1010 Chart_dump:!
1020    ENTER @Sub_data;Sub_name$,Hos_num$,Id_age$,Id_
              wt$,Id_ht$,Diag$,Opera$
1030    ASSIGN @Sub_data TO *
1040    Out_graph=2
1050    FOR I=1 TO 5
1060        CALL Chart(I)
1070    CALL Graph_dump(Out_graph)            !....chart dump
1080    NEXT I
1090    !
1100    !
1110 Msg_dump:  !
1120    IF Ans=1 THEN
1130        ASSIGN @Msg_file TO "msgs"&In_
              file$&Disk1$;FORMAT OFF
1140    ELSE
```

```
1150      ASSIGN @Msg_file TO "messglog"&Disk1$;FORMAT
          OFF
1160    END IF
1170    PRINTER IS 701
1180    ASSIGN @Msg_buffer TO BUFFER Msg_buffer$
1190    STATUS @Msg_file,3;Num_rec
1200    STATUS @Msg_file,4;Rec_len
1210    STATUS @Msg_file,7;Eof_rec
1220    STATUS @Msg_file,8;Eof_byte
1230    Num_bytes=(Eof_rec-1)*Rec_len+Eof_byte-1
1240 Read_msg:TRANSFER @Msg_file TO @Msg_buffer;COUNT
     Num_bytes,WAIT
1250    ASSIGN @Msg_file TO *
1260    ASSIGN @Msg_buffer TO *
1270    Cur_ptr=1
1280       PRINT USING Image_wt1;Sub_name$,Hos_num$,In_
           file$
1290 Image_wt1:IMAGE    "Name: ",K,XXXX,"Hosp num:
                       ",K,XXXXX,K
1300       PRINT USING Image_wt2;Id_age$,Id_wt$,Id_
           ht$,Diag$,Opera$
1310 Image_wt2:IMAGE    "Age: ",K,XXXX,"Wt(kg):
           ",K,XXXX,"Ht(cm): ",K,XXXX,"Diag:
           ",K,XXXX,"Op: ",K
1320 Next_msg:!
1330   Beg_msg=POS(Msg_buffer$[4],"Time")+3
1340   IF Beg_msg=3 THEN GOTO Stopper
1350   PRINT Msg_buffer$[1,Beg_msg-1]
1360   Msg_buffer$=Msg_buffer$[Beg_msg]
1370   GOTO Next_msg
1380 Stopper:!PRINTER IS 1
1390   STOP
1400   END
1410      !
1420   !
1430   !This subroutine prints the graphics
```

```
1440  !
1450  !
1460  SUB Trend_graph
1470  !
1480      COM /Trends/ Mean_hr_t(*),Lfa_t(*),Rfa_
            t(*),Ratio_t(*),T_ptr,Time_now
             1,Meas_resp_t(*),Trend_dp,Trans_time(*)
1490      COM /Multi_param/ Start_chan,Stop_chan,Pacing_
            bits,Pacing_rate,Num_pt
             s,Num_xfer,Num_xfer_left,Name_len,Scr_
               file$[28],Scr_
            file2$[28]
1500      COM /Pressure/
            Top1,Top2,Top3,Top4,Bot1,Bot2,Bot3,Bot4
1510      COM /Pres_chart/ Pres_time$(*),Ao_s(*),Ao_
            d(*),Ao_m(*),Pa_s(*),Pa_d(*
            ),Pa_m(*),La_m(*),Ra_m(*),Pres_ptr,Pres_in
1520      DIM First_line(60),Sec_line(60),Third_
            line(60),Fourth_line(60)
1530      IF Trend_dp=1 THEN
1540         MAT First_line= Ao_m
1550         MAT Sec_line= Pa_m
1560         MAT Third_line= La_m
1570         MAT Fourth_line= Ra_m
1580         G_right=INT((Num_xfer*256/60)/15)
1590         Trend_ptr=Pres_ptr
1600         Top1=150
1610         Bot1=0
1620         Top2=75
1630         Bot2=0
1640         Top3=50
1650         Bot3=0
1660         Top4=50
1670         Bot4=0
1680      ELSE
1690         MAT First_line= Mean_hr_t
```

```
1700        MAT Sec_line= Ratio_t
1710        MAT Third_line= Lfa_t
1720        MAT Fourth_line= Rfa_t
1730        G_right=Num_xfer
1740        Trend_ptr=T_ptr
1750        Top1=200
1760        Bot1=0
1770        Top2=2.5
1780        Bot2=-2.5
1790        Top3=10
1800        Bot3=0
1810        Top4=10
1820        Bot4=0
1830     END IF
1840     Block_time=Pacing_rate*1.024/3600.
1850     GINIT
1860     GCLEAR
1870     PRINT CHR$(12)
1880     GRAPHICS ON
1890     Beg_time=Time_now1/3600-Block_time
1900     End_time=Beg_time+Num_xfer*Block_time
1910     Ibeg_time=INT(Beg_time)
1920     IF Ibeg_time<Beg_time THEN Ibeg_time=Ibeg_time+1
1930  !
1940  ! label the time axes
1950  !
1960     VIEWPORT 0,128,45,50
1970     WINDOW Beg_time,End_time,0,1
1980     IF INT(End_time)>Beg_time THEN
1990        LDIR 0
2000        FOR T_label=Ibeg_time TO INT(End_time)
2010           MOVE T_label,.5
2020           LORG 5
2030           CSIZE 4
2040           LABEL T_label
```

```
2050        NEXT T_label
2060      END IF
2070      VIEWPORT 0,128,40,45
2080      WINDOW 0,1,0,1
2090      MOVE .5,0
2100      LORG 4
2110      LABEL "Time (24 hr)"
2120 !
2130 ! draw the axes
2140 !
2150      VIEWPORT 0,128,50,100
2160      WINDOW Beg_time,End_time,0,1
2170      AXES 1/15.,.1,Beg_time,0
2180      WINDOW 1,0,1,0
2190      AXES 0,.25,0,0
2200 !
2210 ! mean heart rate trends
2220 !
2230      WINDOW -1,G_right,Bot1,Top1
2240      MOVE 0,First_line(0)
2250      FOR I=0 TO Trend_ptr-1
2260          DRAW I,First_line(I)
2270      NEXT I
2280 !
2290 ! ratio trends (with a line at ratio=2)
2300 !
2310      WINDOW -1,G_right,Bot2,Top2
2320      LINE TYPE 8,5
2330      IF Trend_dp=2 THEN
2340          MOVE 0,LGT(Sec_line(0))
2350      ELSE
2360          MOVE 0,Sec_line(0)
2370      END IF
2380      FOR I=0 TO Trend_ptr-1
2390          IF Trend_dp=2 THEN
2400              DRAW I,LGT(Sec_line(I))
```

```
2410            ELSE
2420                DRAW I,Sec_line(I)
2430            END IF
2440        NEXT I
2450        IF Trend_dp=2 THEN
2460            LINE TYPE 3,5!..sparsely dotted line at
                        ratio=2
2470            MOVE 0,LGT(2.)
2480            DRAW Trend_ptr-1,LGT(2.)
2490        END IF
2500    !
2510    ! lfa trends
2520    !
2530        WINDOW -1,G_right,Bot3,Top3
2540        LINE TYPE 4,5
2550        MOVE 0,Third_line(0)
2560        FOR I=0 TO Trend_ptr-1
2570            DRAW I,Third_line(I)
2580        NEXT I
2590    !
2600    ! rfa trends
2610    !
2620        WINDOW -1,G_right,Bot4,Top4
2630        LINE TYPE 5,5
2640        MOVE 0,Fourth_line(0)
2650        FOR I=0 TO Trend_ptr-1
2660            DRAW I,Fourth_line(I)
2670        NEXT I
2680    !
2690    ! draw a key for line types
2700    !
2710        VIEWPORT 64,128,0,50
2720        WINDOW 0,1,0,13
2730        IF Trend_dp=2 THEN
2740            PRINT TABXY(1,17);"trend graph"
2750            PRINT TABXY(55,15);"mean hr(0-200)"
```

```
2760            PRINT TABXY(55,16);"ratio(.01-100)"
2770            PRINT TABXY(55,17);"lfa     (0-10)"
2780            PRINT TABXY(55,18);"rfa     (0-10)"
2790         ELSE
2800            PRINT TABXY(1,17);"mean pressure graphs"
2810            PRINT TABXY(50,15);"ao pressure(0-150)"
2820            PRINT TABXY(50,16);"pa pressure(0-75)"
2830            PRINT TABXY(50,17);"la pressure(0-50)"
2840            PRINT TABXY(50,18);"ra pressure(0-50)"
2850         END IF
2860         LINE TYPE 1,5
2870         MOVE .8,11
2880         DRAW 1.,11
2890         LINE TYPE 8,5
2900         MOVE .8,10
2910         DRAW 1.,10
2920         LINE TYPE 4,5
2930         MOVE .8,9
2940         DRAW 1.,9
2950         LINE TYPE 5,5
2960         MOVE .8,8
2970         DRAW 1.,8
2980      SUBEND
2990 !
3000 !
3010 !This subroutine prints the charts
3020 !
3030 !
3040      SUB Chart(Chart_num)
3050         COM /Subject/ Sub_name$,Hos_num$,Id_age$,Id_wt$,Id_ht$,Diag$,Opera$,H
                 alt_pg,In_file$
3060         COM /Io_chart/ Io_time$(*),Iv_intake(*),Fluid_in(*),In_tot(*),Urine(*
                 ),Chest(*),Out_tot(*),Net(*),Io_ptr
3070         COM /Lab_chart/ Lab_
```

```
                time$(*),Na(*),Kl(*),Cl(*),Hco3(*),Ca(*),Hct(*),G
                  luc(*),Dig(*),Pt(*),Ptt(*),Creat(*),Bun(*),Lab_
                  ptr
         3080   COM /Vent_chart/ Vent_
               time$(*),Rate(*),Fio2(*),Pp(*),Peep(*),Tv(*),
               Ie_ratio$(*),Airp(*),Ph(*),Po2(*),Pco2(*),
               Bgo3(*),Be(*),Vent_ptr
         3090   COM /Pres_chart/ Pres_time$(*),Ao_s(*),Ao_
                  d(*),Ao_m(*),Pa_s(*),Pa_d(*
                  ),Pa_m(*),La_m(*),Ra_m(*),Pres_ptr,Pres_in
         3100   COM /Pressure/
                     Top1,Top2,Top3,Top4,Bot1,Bot2,Bot3,Bot4
         3110   COM /Heart_index/ Heart_
                  time$(*),Ci(*),Pvri(*),Svri(*),Heart_ptr
         3120   COM /Drugs/ Drug_time$(*),Drug_name$(*),Drug_
                  dos$(*),Drug_ptr
         3130   Out_graph=2
         3140   Pres_stl=0
         3150   Lab_stl=0
         3160   Io_stl=0
         3170   Vent_stl=0
         3180   Drug_stl=0
         3190   Io_p=Io_ptr
         3200   Lab_p=Lab_ptr
         3210   Vent_p=Vent_ptr
         3220   Pres_p=Pres_ptr
         3230   Heart_p=Heart_ptr
         3240   Drug_p=Drug_ptr
         3250   !
         3260   ! set up identifying subject info
         3270   !
         3280   GRAPHICS OFF
         3290   PRINT CHR$(12)
         3300   PRINT TABXY(1,1);
         3310   PRINT USING Image_wt1;Sub_name$,Hos_num$,In_
                  file$
```

```
3320 Image_wt1:IMAGE    "Name: ",K,XXXX,"Hosp num:
                       ",K,XXXXX,K
3330      PRINT TABXY(1,2);
3340      PRINT USING Image_wt2;Id_age$,Id_wt$,Id_
          ht$,Diag$,Opera$
3350 Image_wt2:IMAGE    "Age: ",K,XXXX,"Wt(kg):
                       ",K,XXXX,"Ht(cm): ",K,XXXX,"Diag:
                       ",K,XXXX,"Op: ",K
3360      !
3370      ! go to appropriate chart
3380      !
3390      ON Chart_num GOTO In_out,Lab_val,Vent_
          val,Pres_val,Drug
3400 In_out:!                          ....intake/output
3410      ! IF Io_ptr>3 THEN Io_stl=2
3420      ! IF Io_ptr>5 THEN
3430      !    DISP "do not input more Intake/Output
          !    data; disc full"
3440      !    WAIT 3
3450      !    SUBEXIT
3460      ! END IF
3470      PRINT TABXY(30,3);"INTAKE/OUTPUT CHART"
3480      PRINT TABXY(1,4);"Intake (cc/hr) "
3490      PRINT TABXY(1,5);"Time"
3500      PRINT TABXY(4,6);"Maint. Fluid"
3510      PRINT TABXY(4,7);"Other Fluids"
3520      PRINT TABXY(1,9);"Total "
3530      PRINT TABXY(1,11);"Output (cc/hr)"
3540      PRINT TABXY(4,12);"Urine"
3550      PRINT TABXY(4,13);"Chest"
3560      PRINT TABXY(1,15);"Total"
3570      PRINT TABXY(1,17);"Net I/O"
3580      Start=25
3590      IF Io_ptr>3 THEN Io_p=3
3600 Io_dp:FOR I=Io_stl TO Io_p
3610         PRINT TABXY(Start,5);Io_time$(I)
```

```
3620        PRINT TABXY(Start,6);Iv_intake(I)
3630        PRINT TABXY(Start,7);Fluid_in(I)
3640        PRINT TABXY(Start,9);In_tot(I)
3650        PRINT TABXY(Start,12);Urine(I)
3660        PRINT TABXY(Start,13);Chest(I)
3670        PRINT TABXY(Start,15);Out_tot(I)
3680        PRINT TABXY(Start,17);Net(I)
3690        Start=Start+10
3700     NEXT I
3710     IF Io_ptr>Io_p THEN
3720        INPUT "more data on next page - do you
            want this dumped to printe
               r? (Y/N)",Ans$
3730        IF Ans$="Y" OR Ans$="y" THEN CALL Graph_
            dump(Out_graph)
3740        Io_stl=4
3750        Io_p=Io_ptr
3760        Start=25
3770        FOR J=5 TO 17
3780           PRINT TABXY(Start,J);"         "
3790        NEXT J
3800        GOTO Io_dp
3810     END IF
3820     GOTO Finish
3830 !
3840 !
3850 Lab_val:!                              ...lab values
3860     !IF Lab_ptr>3 THEN Lab_stl=2
3870     !IF Lab_ptr>5 THEN
3880     !   DISP "do not input any more lab values;
         !     disc full"
3890     !   WAIT 3
3900     !   SUBEXIT
3910     !END IF
3920     PRINT TABXY(30,3);"Lab Values"
3930     PRINT TABXY(10,4);"Time"
```

```
3940      PRINT TABXY(1,6);"Na"
3950      PRINT TABXY(1,7);"K"
3960      PRINT TABXY(1,8);"Cl"
3970      PRINT TABXY(1,9);"HCO3"
3980      PRINT TABXY(1,10);"Ca"
3990      PRINT TABXY(1,11);"Hct"
4000      PRINT TABXY(1,12);"Glucose"
4010      PRINT TABXY(1,13);"Dig level"
4020      PRINT TABXY(1,14);"PT"
4030      PRINT TABXY(1,15);"PTT"
4040      PRINT TABXY(1,16);"Creat"
4050      PRINT TABXY(1,17);"Bun"
4060      Start=15
4070      IF Lab_ptr>3 THEN Lab_p=3
4080 Lab_dp:FOR I=Lab_stl TO Lab_p
4090         PRINT TABXY(Start+10,4);Lab_time$(I)
4100         PRINT TABXY(Start+10,6);Na(I)
4110         PRINT TABXY(Start+10,7);Kl(I)
4120         PRINT TABXY(Start+10,8);Cl(I)
4130         PRINT TABXY(Start+10,9);Hco3(I)
4140         PRINT TABXY(Start+10,10);Ca(I)
4150         PRINT TABXY(Start+10,11);Hct(I)
4160         PRINT TABXY(Start+10,12);Gluc(I)
4170         PRINT TABXY(Start+10,13);Dig(I)
4180         PRINT TABXY(Start+10,14);Pt(I)
4190         PRINT TABXY(Start+10,15);Ptt(I)
4200         PRINT TABXY(Start+10,16);Creat(I)
4210         PRINT TABXY(Start+10,17);Bun(I)
4220         Start=Start+10
4230      NEXT I
4240      IF Lab_ptr>Lab_p THEN
4250         INPUT "more data on next page - do you
                    want this dumped to printe
                    r? (Y/N)",Ans$
4260         IF Ans$="Y" OR Ans$="y" THEN CALL Graph_
                    dump(Out_graph)
```

```
4270            Lab_stl=4
4280            Lab_p=Lab_ptr
4290            Start=15
4300            FOR J=4 TO 17
4310              PRINT TABXY(Start,J);"            "
4320            NEXT J
4330            GOTO Lab_dp
4340          END IF
4350          GOTO Finish
4360 !
4370 !
4380 Vent_val:!                    ....ventilation values
4390     ! IF Vent_ptr>3 THEN Vent_stl=2
4400     ! IF Vent_ptr>5 THEN Vent_stl=4
4410     ! IF Vent_ptr>7 THEN
4420     !     DISP "do not input any more Vent values; disc full"
4430     !     WAIT 3
4440     !     SUBEXIT
4450     ! END IF
4460       PRINT TABXY(30,3);"VENTILATION"
4470       PRINT TABXY(1,4);"Settings            Hour:"
4480       PRINT TABXY(4,5);"Rate"
4490       PRINT TABXY(4,6);"FIO2"
4500       PRINT TABXY(4,7);"Peak Pres"
4510       PRINT TABXY(4,8);"Peep"
4520       PRINT TABXY(4,9);"TV"
4530       PRINT TABXY(4,10);"I:E ratio"
4540       PRINT TABXY(4,11);"Mean air"
4550       PRINT TABXY(1,12);"Blood Gases"
4560       PRINT TABXY(4,13);"ph"
4570       PRINT TABXY(4,14);"pO2"
4580       PRINT TABXY(4,15);"pCO2"
4590       PRINT TABXY(4,16);"HCO3"
4600       PRINT TABXY(4,17);"BE"
4610       Start=15
```

```
4620        IF Vent_ptr>3 THEN Vent_p=3
4630 Vent_dp:FOR I=Vent_stl TO Vent_p
4640            PRINT TABXY(Start+10,4);Vent_time$(I)
4650            PRINT TABXY(Start+10,5);Rate(I)
4660            PRINT TABXY(Start+10,6);Fio2(I)
4670            PRINT TABXY(Start+10,7);Pp(I)
4680            PRINT TABXY(Start+10,8);Peep(I)
4690            PRINT TABXY(Start+10,9);Tv(I)
4700            PRINT TABXY(Start+10,10);Ie_ratio$(I)
4710            PRINT TABXY(Start+10,11);Airp(I)
4720            PRINT TABXY(Start+10,13);Ph(I)
4730            PRINT TABXY(Start+10,14);Po2(I)
4740            PRINT TABXY(Start+10,15);Pco2(I)
4750            PRINT TABXY(Start+10,16);Bgo3(I)
4760            PRINT TABXY(Start+10,17);Be(I)
4770            Start=Start+10
4780        NEXT I
4790        IF Vent_ptr>Vent_p THEN
4800            INPUT "more data on next page - do you want this dumped to printer? (Y/N)",Ans$
4810            IF Ans$="Y" OR Ans$="y" THEN CALL Graph_dump(Out_graph)
4820            Vent_stl=4
4830            Vent_p=Vent_ptr
4840            Start=15
4850            FOR J=4 TO 17
4860                PRINT TABXY(Start,J);"       "
4870            NEXT J
4880            GOTO Vent_dp
4890        END IF
4900        GOTO Finish
4910 !
4920 !
4930 Pres_val:!                               ....pressure values
4940     !IF Pres_ptr>12 THEN Pres_stl=5
```

```
4950        PRINT TABXY(9,3);"Time:"
4960        PRINT TABXY(1,4);"Systemic"
4970        PRINT TABXY(4,5);"systolic"
4980        PRINT TABXY(4,6);"diastolic"
4990        PRINT TABXY(4,7);"mean"
5000        PRINT TABXY(1,8);"Pulmonary"
5010        PRINT TABXY(4,9);"systolic"
5020        PRINT TABXY(4,10);"diastolic"
5030        PRINT TABXY(4,11);"mean"
5040        PRINT TABXY(1,12);"LA mean"
5050        PRINT TABXY(1,13);"RA mean"
5060        PRINT TABXY(9,14);"Time: "
5070        PRINT TABXY(1,15);"C.I."
5080        PRINT TABXY(1,16);"PVRI"
5090        PRINT TABXY(1,17);"SVRI"
5100        Start=15
5110        IF Pres_ptr>12 THEN Pres_p=12
5120 Pres_dp:FOR I=Pres_stl TO Pres_p
5130            PRINT TABXY(Start,3);Pres_time$(I)
5140            PRINT TABXY(Start,5);Ao_s(I)
5150            PRINT TABXY(Start,6);Ao_d(I)
5160            PRINT TABXY(Start,7);Ao_m(I)
5170            PRINT TABXY(Start,9);Pa_s(I)
5180            PRINT TABXY(Start,10);Pa_d(I)
5190            PRINT TABXY(Start,11);Pa_m(I)
5200            PRINT TABXY(Start,12);La_m(I)
5210            PRINT TABXY(Start,13);Ra_m(I)
5220            Start=Start+5
5230        NEXT I
5240        Start=15
5250        FOR I=0 TO Heart_ptr
5260            PRINT TABXY(Start,14);Heart_time$(I)
5270            PRINT TABXY(Start,15);Ci(I)
5280            PRINT TABXY(Start,16);Pvri(I)
5290            PRINT TABXY(Start,17);Svri(I)
5300            Start=Start+5
```

```
5310        NEXT I
5320        IF Pres_ptr>Pres_p THEN
5330            INPUT "more data on next page - do you
                want this dumped to printe
                    r? (Y/N)",Ans$
5340            IF Ans$="Y" OR Ans$="y" THEN CALL Graph_
                dump(Out_graph)
5350            Pres_stl=13
5360            Pres_p=Pres_ptr
5370            Start=15
5380            FOR J=3 TO 13
5390            PRINT TABXY(Start,J);"            "
5400            NEXT J
5410            GOTO Pres_dp
5420        END IF
5430        GOTO Finish
5440 !
5450 !
5460 Drug:!                                    ....hey man, drugs
5470    !IF Drug_ptr>9 THEN Drug_stl=4
5480    ! IF Drug_ptr>14 THEN Drug_stl=9
5490    !IF Drug_ptr>19 THEN Drug_stl=14
5500    !IF Drug_ptr>24 THEN Drug_stl=19
5510    !IF Drug_ptr>29 THEN Drug_stl=24
5520    !IF Drug_ptr>34 THEN Drug_stl=29
5530    !IF Drug_ptr>38 THEN
5540    !    DISP "do not enter more drugs; disc full"
5550    !    WAIT 3
5560    !    SUBEXIT
5570    ! END IF
5580        PRINT TABXY(30,4);"Drug Chart"
5590        PRINT TABXY(1,6);"Name"
5600        PRINT TABXY(30,6);"Dosage"
5610        PRINT TABXY(60,6);"Time"
5620        D_line=7
5630        IF Drug_ptr>9 THEN Drug_p=9
```

```
5640 Drug_dp:FOR I=Drug_stl TO Drug_p
5650          PRINT TABXY(1,D_line);Drug_name$(I)
5660          PRINT TABXY(30,D_line);Drug_dos$(I)
5670          PRINT TABXY(60,D_line);Drug_time$(I)
5680          D_line=D_line+1
5690       NEXT I
5700       IF Drug_ptr>Drug_p THEN
5710          INPUT "more data on next page - do you want this dumped to printer? (Y/N)",Ans$
5720          IF Ans$="Y" OR Ans$="y" THEN CALL Graph_dump(Out_graph)
5730          Drug_stl=Drug_stl+10
5740          Drug_p=Drug_p+10
5750          D_line=7
5760          FOR J=7 TO 17
5770             PRINT TABXY(1,J);"         "
5780          NEXT J
5790          GOTO Drug_dp
5800       END IF
5810 Finish: !
5820    SUBEND
5830 !
5840 !
5850 !
5860    SUB Graph_dump(A)
5870 Graph_dump:INPUT "do you want a hard copy? <Y/N>",Ans$
5880       IF Ans$="Y" OR Ans$="y" THEN
5890          IF A=1 THEN
5900             DUMP GRAPHICS #701
5910             PRINTER IS 701
5911             PRINT CHR$(12)
5920             GRAPHICS OFF
5930          ELSE
5940             DUMP ALPHA #701
5950             PRINTER IS 701
5960             PRINT CHR$(12)
5970          END IF
```

```
5980         END IF
5990         PRINTER IS 1
6000     SUBEND

10 Hrsa3:!THIS IS A PROGRAM TO SET UP THE HIGH SPEED A/D     !SYSTEM
20       ! AND CONTINUOUSLY OBTAIN INFORMATION
30       !
40       !
50       !..........................................
60       !
70       ! LAST REVISION: 30 April 1985
80       !
90       !..........................................

100      !
110      !
120      ! > FULL SET OF DECLARATIONS FOR THE HPIB BUS
                EXTENDED TALK ADDRESSES
130      !
140      !
150 Assignments:   !
160      ASSIGN @Multi TO 723
170      ASSIGN @Input_para TO 72301
180      ASSIGN @Input_intr TO 72302
190      ASSIGN @Input_ext TO 72303
200      ASSIGN @Read_format TO 72304
210      ASSIGN @Memory_input TO 72305
220      ASSIGN @Read_val TO 72306
230      ASSIGN @Read_status TO 72308
240      ASSIGN @Output_intr TO 72309
250      ASSIGN @Hpib_srq_status TO 72310
260      ASSIGN @Err_status_1st TO 72311
270      ASSIGN @Int_addr TO 72312
280      ASSIGN @Busy_instr TO 72313
290      ASSIGN @Read_clock TO 72314
300      !
310      !
```

```
320    !................................................
330    !
340    ! SET UP INTERRUPT/ERROR HANDLERS
350    ! SET UP COMMON STORAGE/ARRAY STORAGE
360    !................................................

370    !
380    !
390    COM /Intr_7/ Int_flag,Status_bytes(5)
400    COM /Flags/ Atod_done,Scanner_done,Memory1_
       done,Memory2_done,Timer_done,Counter_done,
           Memory3_done,Memory4_done
410    COM /Io_arrays/ Counters(3),Counters2(3),Time_
       base$[7]
420    COM /Multi_param/ Start_chan,Stop_chan,Pacing_
       bits,Pacing_rate,Num_pts,Nu m_xfer,Num_xfer_
           left,Name_len,Scr_file$[28],Scr_
       file2$[28]
430    COM /Hr_sig/ Num_pulses,Last_pulse,First_blk_
       flg,Last_time,Num_hr_sig,Max_hr_pts,Avg_
           hr,Rollover,Hr_smooth
440    COM /Plot_par/ Plotbox,Boxcar_flg,Log_
           plotflg,Freq_limit,Resp_search,Pct_thresh
450    COM /Graphs/
       Hrdata(512),Hrspec(512),Respspec(512),Bpspec(512)
460    COM /Vitaldata/ Rfa,Lfa,Peakratio,Meas_resp,Next_
       time
470    COM /Messagecom/ Message$(10)[80],@Messages
480    COM /Trends/ Mean_hr_t(60),Lfa_t(60),Rfa_
       t(60),Ratio_t(60),T_ptr,Time_now 1,Meas_resp_
           t(60),Trend_dp
490    COM /Pressure/
       Top1,Top2,Top3,Top4,Bot1,Bot2,Bot3,Bot4
500    COM /Editor/ Edit_msg$[80]
510    COM /Subject/ Sub_name$[25],Hos_num$[15],Id_
       age$[10],Id_wt$[10],Id_ht$[10 ],Diag$[30],
```

```
                        Opera$[45],Halt_pg
        520     COM /Io_chart/ Io_time$(8)[10],Iv_intake(8),Fluid_
                    in(8),In_tot(8),Urine(8 ),Chest(8),Out_
                        tot(8),Net(8),Io_ptr
 5      530     COM /Lab_chart/ Lab_time$(8)[10],Na(8),Kl(8),
                        Cl(8),Hco3(8),Ca(8),Hct(8),G luc(8),
                        Dig(8),Pt(8),Ptt(8),Creat(8),Bun(8),Lab_ptr
        540     COM /Vent_chart/ Vent_
                    time$(8)[15],Rate(8),Fio2(8),Pp(8),Peep(8),Tv(8),
10                  Ie_ratio$(8)[10],Airp(8),Ph(8),Po2(8),
                    Pco2(8),Bgo3(8),Be(8),Vent_ptr
        550     COM /Pres_chart/ Pres_time$(20)[15],Ao_s(20),Ao_
                    d(20),Ao_m(20),Pa_s(20),Pa_d(20),Pa_m(20),
                    La_m(20),Ra_m(20),Pres_ptr,Pres_in
15      560     COM /Heart_index/ Heart_
                    time$(15)[15],Ci(15),Pvri(15),Svri(15),Heart_ptr
        570     COM /Drugs/ Drug_time$(40)[20],Drug_
                    name$(40)[40],Drug_dos$(40)[20],Drug_ptr
        590     DIM Io$(5,15)[30],Io_msg$(5,15)[80]
20      600     DIM Msg_pad$(10)[80]
        610     DIM Msg_buffer$[80] BUFFER
        620     ASSIGN @Msg_buffer TO BUFFER Msg_buffer$
        630     Log_plotflg=0
        640     Freq_limit=1.
25      650     Resp_search=.1
        660     Pct_thresh=.2
        670     Scr_file$="?"
        680     Halt_pg=0
        690     Message$(0)="messages in "
30      700     Message$(1)="I/O chart "
        710     Message$(2)="lab values"
        720     Message$(3)="hemodynamics"
        730     Message$(4)="Trends Display"
        740     Message$(5)="messages out"
35      750     Message$(6)="STOP PROGRAM"
        760     Message$(7)="ventilation"
```

```
770    Message$(8)="drugs"
780    Message$(9)="B.P. Display"
790    Msg_pad_ptr=0
800    P_ptr=0
810    !
820    ! Set up common/array storage for waveform
           analysis
830    !
840    !........................................
850    !
860    ! Set up common/array storage for waveform
           analysis
870    !........................................

880    !
890    COM /Directory/ Dir$[160],@Printer
900    COM /Wf1/ Printer,Plotter,String$[40]
910    COM /Wf2/ Signal(1089),Number_pnts,Type,Sampling_
           period
920    COM /Wf3/ Segment_size,Overlap,Num_segments,Pnts_
           used,Fft_size
930    COM /Wf5/ Refn(63),Refd(63),Refno,Refdo,Refgain
940    COM /Autoparam/ Up_down,Up_delay,Dn_delay
950    COM /Vars/ Ffthrvar,Fftrespvar
960    !
970    DISP "loading subroutines"
980    LOADSUB ALL FROM "multi_subs"
990    LOADSUB ALL FROM "hr_siggen8"
1000   LOADSUB ALL FROM "automaxsb2"
1010   LOADSUB ALL FROM "fft_anal6"
1020   DISP "load data disks and press CONTINUE"
1030   PAUSE
1040   !
1050   !........................................
1060   ! The HP 9826/9836 flexible disk (5-1/4") has the
       ! following structure
```

```
                             75                          76
1070    ! 2 sides, 33 tracks/side, 16 sectors/track, 256
        ! bytes/sector
1080    !   1 track =    4096 bytes =   16 sectors
1090    !   1 side  = 135168 bytes =  528 sectors
1100    !   1 disk  = 270336 bytes = 1056 sectors
1110    !   1 disk  = 135168 words = 132K words
1120    !...............................................

1130    !
1140    !
1150      INTEGER Hpib_buffer1(2048) BUFFER
1160      INTEGER Hpib_buffer2(2048) BUFFER
1170      DIM Hr_signal(1024) BUFFER
1180      Read_ptr1=0
1190      Read_ptr2=0
1200    !
1210    !
1220    !...........................................
1230    ! CLEAR MULTIPROGRAMMER
1240    !...............................................

1250    !
1260    !
1270      ON INTR 7 CALL Hpib_intr
1280    Begin:CALL Multi_clear
1290    !
1300    !
1310    !...........................................
1320    ! LOAD SUPPLEMENTAL INSTRUCTION SET ("MR")
1330    ! usage: "MR,<card addr>,<# words>,<read ptr>,<mode>T"
1340    !         <mode= 1-FIFO, 4-recirculating>
1350    !...........................................

1360    !
1370    !
```

```
1380    DISP "DOWNLOADING MR INSTRUCTION"
1390    CALL Xfer("MR")
1400    !
1410    !
1420    !..........................................
1430    ! SET UP CARDS FOR DATA COLLECTION
1440    !..........................................

1450    !
1460    !
1470 Selections:DISP "SETUP DATA COLLECTION"
1480    OUTPUT @Multi;"CY,3T"!CYCLE SCAN/PACER CARD TO
        SET DEFINITE STATE
1490    !
1500    !
1510    ! NOW SET UP THE SCAN CARD PARAMETERS (DEFAULT
        ! VALUES)
1520    !       START CHANNEL (3.0) -  0
1530    !        STOP CHANNEL (3.1) -  1
1540    !             PACING (3.2) - 40 USEC
1550    !        SEQN'L SCAN (3.3) - XXXX XXXX XXX1 (  1)
1560    !       INTN'L PACING (3.3) - XXXX XXXX X1XX (  4)
1570    !       MSEC TIMEBASE (3.3) - XXX1 XXXX XXXX (256)
1580    !
1590    CALL Get_param
1600    ASSIGN @Messages TO
        "messglog:HP8290X,700,1";FORMAT OFF
1610    ASSIGN @Temp_trend TO "temp_
        trend:HP8290X,700,1";FORMAT OFF
1620    ASSIGN @Hemo_data TO "hemo_
        data:HP8290X,700,1";FORMAT OFF
1630    ASSIGN @Io_data TO "io_data:HP8290X,700,1";FORMAT
        OFF
1640    ASSIGN @Lab_data TO "lab_
        data:HP8290X,700,1";FORMAT OFF
1650    ASSIGN @Vent_data TO "vent_
```

```
        data:HP8290X,700,1";FORMAT OFF
1660    ASSIGN @Co_data TO "co_data:HP8290X,700,1";FORMAT
        OFF
1670    ASSIGN @Drug_data TO "drug_
        data:HP8290X,700,1";FORMAT OFF
1680    IF Num_pts=0 THEN GOTO Begin
1690    Read_ptr1=0
1700    !
1710    !
1720    ! SET FIFO MODE AND CLEAR POINTERS IN MEMORY
1730    !
1740    !
1750 Setup_scan:DISP " NUMBER OF POINTS=";Num_pts
1760    OUTPUT @Multi;"WF,3.0",Start_chan,"3.1",Stop_
        chan,"3.3",Pacing_bits,"3.2"
            ,Pacing_rate,"T"
1770    OUTPUT @Multi;"CC,6T"
1780    OUTPUT @Multi;"WF,5.1,1,T" ! memory set to FIFO
        input mode
1790    OUTPUT @Multi;"AC,3,5,6T"  ! cards are armed to
        supply interrupts
1800    OUTPUT @Multi;"RV,6.0,6.1,6.2,6.3T" ! checking
        control registers
1810    ENTER @Read_val;Counters(*)
1820    Read_ptr1=0
1830    Read_ptr2=0
1840    !
1850    ! setup the counter card to count
1860    !
1870 Setup_counter:OUTPUT @Multi;"CC,10,11,12,13T"
1880    OUTPUT @Multi;"AC,10,12,13T" !_counter not armed
1890    OUTPUT @Multi;"CY,11T"
1900    !
1910    ! setup the pacer card to generate a clock with
        period 32 Usec
1920    !      (one half period is 16 Usec)
```

```
1930 !          (corresponds to 31.25KHz)
1940 !
1950 Setup_clock:OUTPUT @Multi;"WF10.2,1T"
1960    OUTPUT @Multi;"WF10,16U T"
1970    CALL Completer("setup completed")
1980 !
1990 !
2000 ! START THE PACERS BY CYCLING IN PARALLEL
2010 !
2020    OUTPUT @Multi;"GPT"
2030    CALL Init_flags
2040    ENABLE INTR 7;2
2050    OUTPUT @Multi;"CY,3,10T"
2060    OUTPUT @Multi;"GST"
2070    Start_pacing=TIMEDATE
2080    CALL Completer("PACING STARTED")
2090    Block_time=Pacing_rate*1.024
2100    Next_time=TIMEDATE+INT(Block_time)
2110    First_blk_flg=1
2120    Num_msgs=0
2130    Message_line=0
2140    Msg_dp_request=0
2150    Resp_dpflg=0
2160    Max_hr_pts=1024
2170    Last_time=0
2180    Trend_dp=0
2190    Hemo_dp=0
2200    Top1=0
2210    Top2=0
2220    Top3=0
2230    Top4=0
2240    Bot1=0
2250    Bot2=0
2260    Bot3=0
2270    Bot4=0
2280 !
```

```
2290    Io$(1,1)="Time - hh:mm(hh=1 to 24)"
2300    Io$(1,2)="Maint. fluids"
2310    Io$(1,3)="other fluids"
2320    Io$(1,4)="urine output"
2330    Io$(1,5)="chest output"
2340    Io$(2,1)="Time - hh:mm"
2350    Io$(2,2)="Na"
2360    Io$(2,3)="K"
2370    Io$(2,4)="Cl"
2380    Io$(2,5)="HCO3"
2390    Io$(2,6)="Ca"
2400    Io$(2,7)="Hct"
2410    Io$(2,8)="Glucose"
2420    Io$(2,9)="Dig level"
2430    Io$(2,10)="PT"
2440    Io$(2,11)="PTT"
2450    Io$(2,12)="Creat"
2460    Io$(2,13)="Bun"
2470    Io$(3,1)="Time - hh:mm(hh=1 to 24)"
2480    Io$(3,2)="Resp rate"
2490    Io$(3,3)="FIO2"
2500    Io$(3,4)="Peak pres"
2510    Io$(3,5)="peep"
2520    Io$(3,6)="TV"
2530    Io$(3,7)="I:E"
2540    Io$(3,8)="mean airway"
2550    Io$(3,9)="ph"
2560    Io$(3,10)="pO2"
2570    Io$(3,11)="pCO2"
2580    Io$(3,12)="HCO3"
2590    Io$(3,13)="BE"
2600    Io$(4,1)="Time - hh:mm(hh=1 to 24)"
2610    Io$(4,2)="ao/s"
2620    Io$(4,3)="ao/d"
2630    Io$(4,4)="ao/m"
2640    Io$(4,5)="pa/s"
```

```
2650    Io$(4,6)="pa/d"
2660    Io$(4,7)="pa/m"
2670    Io$(4,8)="la/m"
2680    Io$(4,9)="ra/m"
2690    Io$(4,10)="Time - hh:mm(hh=1 to 24)"
2700    Io$(4,11)="C.I."
2710    Io$(4,12)="pvri"
2720    Io$(4,13)="svri"
2730    Io$(5,1)="name"
2740    Io$(5,2)="dosage"
2750    Io$(5,3)="Time - hh:mm:ss(hh=1 to 24)"
2760    Io_ptr=0
2770    Lab_ptr=0
2780    Vent_ptr=0
2790    Pres_ptr=0
2800    Heart_ptr=0
2810    Drug_ptr=0
2820    Io_in=0
2830    Lab_in=0
2840    Vent_in=0
2850    Pres_in=0
2860    Heart_in=0
2870    Drug_in=0
2880    Fst=1
2890    Fix_val=0
2900    !
2910    ! Read data continuously and write to the disk continuously until enough
2920    ! enough data has been obtained
2930    !
2940    !
2950 Reading:  !
2960    !
2970    ! set up the A/D buffers and disk files
2980    !
2990    ASSIGN @Memory_input TO 72305;FORMAT OFF
```

```
3000    ASSIGN @In_buffer TO BUFFER Hpib_buffer1(*)
3010    ASSIGN @Out_buffer TO Scr_file$;FORMAT OFF
3020    !
3030    ! set up the counter memory buffers and files
3040    !
3050    ASSIGN @Memory_input2 TO 72305;FORMAT OFF
3060    ASSIGN @In_buffer2 TO BUFFER Hpib_buffer2(*)
3070    ASSIGN @Out_buffer2 TO Scr_file2$;FORMAT OFF
3080    !
3090    Data_lockout=0
3100    !
3110    Time_now=TIMEDATE
3120    Date_now$=DATE$(TIMEDATE)
3130    Time_now1=Time_now MOD 86400
3140    !
3150 Blk_xfer:!
3160    CONTROL @In_buffer,3;1
        ! Reset fill pointer for buffer
3170    CONTROL @In_buffer,4;0
        ! Reset current number of bytes in buffer
3180    CONTROL @In_buffer,5;1    ! Reset empty pointer
        for buffer
3190    !
3200    ! write an 8 byte sequence to disk as a header for
        ! the transfer
3210    !
3220    CALL Xfheader(@Out_buffer,Num_pts,"R")
3230    !
3240    ! read A/D buffer into memory (hpib_buffer1) in 32
          segments
3250    ! if possible
3260    !
3270    IF FRACT(Num_pts/32.)=0 THEN
3280        Num_rdseg=32
3290        Num_rdpts=Num_pts/32
3300    ELSE
```

```
3310        Num_rdseg=1
3320        Num_rdpts=Num_pts
3330    END IF
3340  !
3350  ! reading segments here. segmenting allows disk
      access between segments
3360  !
3370    FOR Rdseg=1 TO Num_rdseg
3380        OUTPUT @Multi;"MR,5",Num_rdpts,Read_
      ptr1,"1T"! FIFO mode
3390        ON EOT @Memory_input GOTO Next_rdseg
3400        TRANSFER @Memory_input TO @In_buffer;COUNT
            Num_rdpts*2,CONT
3410        PRINT TABXY(1,18);
3420        PRINT USING Image_wtl;Num_xfer-Num_xfer_
            left+1,Num_xfer,TIME$(Next_time),
            Rdseg,Num_rdseg
3430 Image_wtl:IMAGE    "Next xfer(",K,"/",K,"): ",K,"
     seg=",K,"/",K
3440 Waiter1:DISP "Now: ";TIME$(TIMEDATE);"
     ";DATE$(TIMEDATE)
3450        IF Next_time-TIMEDATE<12 THEN
3460            OFF KEY
3470            OFF KBD
3480            OFF KNOB
3490            GOTO Waiter1
3500        END IF
3510        ON KEY 0 LABEL Message$(0) GOSUB Key0
3520        ON KEY 1 LABEL Message$(1) GOSUB Key1
3530        ON KEY 2 LABEL Message$(2) GOSUB Key2
3540        ON KEY 3 LABEL Message$(3) GOSUB Key3
3550        ON KEY 4 LABEL Message$(4) GOSUB Key4
3560        ON KEY 5 LABEL Message$(5) GOSUB Key5
3570        ON KEY 6 LABEL Message$(6) GOSUB Key6
3580        ON KEY 7 LABEL Message$(7) GOSUB Key7
3590        ON KEY 8 LABEL Message$(8) GOSUB Key8
```

```
3600        ON KEY 9 LABEL Messages(9) GOSUB Key9
3610        ON KBD GOTO Control_chars
3620        IF Msg_dp_request=2 THEN
3630            ON KNOB .05 GOSUB Move_msgs
3640        ELSE
3650            OFF KNOB
3660        END IF
3670        STATUS @In_buffer,10;In_xfer_stat
3680        IF In_xfer_stat<64 THEN GOTO Next_rdseg
3690        IF Msg_dp_request=3 THEN
3700            CALL Msg_dump(Message_chart$(*),Message_
                 line,Msg_dp_request)
3710        END IF
3720        GOTO Waiter1
3730 Control_chars:!
3740        Kbd_hold$=KBD$
3741        IF POS(Kbd_hold$,CHR$(6))<>0 THEN
              !..change lfa disp.range
3742            Lfa_top=Lfa_top+2.5
3750        IF POS(Kbd_hold$,CHR$(6))<>0 THEN
              !..change spectra disp.freq.range
3760            IF Freq_limit=1. THEN
3770                Freq_limit=2.
3780            ELSE
3790                Freq_limit=1.
3800            END IF
3810            Resp_search=.1
              !..reset resp search point each time
3820            DISP "Spectra displayed to";Freq_
                 limit;"Hz"
3830            WAIT 2
3840        END IF
3850        IF POS(Kbd_hold$,CHR$(8))<>0 THEN   !..help:
              display commands
3860            CALL Disp_ctrls
3870        END IF
```

```
3880            IF POS(Kbd_hold$,CHR$(16))<>0 THEN
       !..change peak search threshold
3890                Pct_thresh=Pct_thresh+.2
3900                IF Pct_thresh>.8 THEN Pct_thresh=.2
3910                DISP "resp peak search threshold=";Pct_
                    thresh;"%"
3920                WAIT 1
3930            END IF
3940            IF POS(Kbd_hold$,CHR$(18))<>0 THEN
       !..display respiration time series
3950                IF Resp_dpflg=0 THEN
3960                    Resp_dpflg=1
3970                    DISP "resp series plot w/hr series"
3980                    WAIT 2
3990                ELSE
4000                    Resp_dpflg=0
4010                    DISP "cancel resp series plot"
4020                    WAIT 2
4030                END IF
4040            END IF
4050            IF POS(Kbd_hold$,CHR$(19))<>0 THEN
       !..change respiration peak search
4060                Resp_search=Resp_search+.1
4070                IF Resp_search>Freq_limit-.1 THEN Resp_
                    search=.1
4080                DISP "resp peak search starts at";Resp_
                    search;"Hz"
4090                WAIT 1
4100            END IF
4110            GOTO Waiter1
4120 Next_rdseg:!
4130 !
4140 ! storing messages from soft keys if any
4150 !
4160            IF Msg_pad_ptr>0 THEN
4170                Num_msgs=Num_msgs+Msg_pad_ptr
```

```
4180        FOR I=0 TO Msg_pad_ptr-1
4190            Msg_buffer$=Msg_pad$(I)
4200            Len_message=LEN(Msg_buffer$)
4210            CONTROL @Msg_buffer,4;Len_
                message       !....number of bytes
4220            CONTROL @Msg_buffer,5;1
        !..empty pointer to beginning
4230            TRANSFER @Msg_buffer TO
                @Messages;COUNT Len_message,CONT
4240        NEXT I
4250        IF Msg_dp_request>=2 THEN
4260            DEALLOCATE Message_chart$(*)
4270            Msg_dp_request=0
4280        END IF
4290        OFF KNOB
4300        Msg_pad_ptr=0
4310    END IF
4320    IF Msg_dp_request=1 THEN
4330        Message_line=0
4340        ALLOCATE Message_chart$(17)[640]
4350        CALL Msg_dump(Message_chart$(*),Message_
                line,Msg_dp_request)
4360        IF Msg_dp_request=0 THEN
        !...no messages
                yet
4370            DEALLOCATE Message_chart$(*)
4380        END IF
4390    END IF
4400 !
4410 ! get read pointer for next segment
4420 !
4430    OUTPUT @Multi;"RV,6.0T"
        !  checking current read pointer
4440    ENTER @Read_val;Read_ptr1
4450 NEXT Rdseg
4460 !
```

```
4470  ! store A/D buffer on complete data file (also
        save pointers for heart rate)
4480  !
4490  !
4500 Resume1:OFF EOT @Memory_input
4510   OFF KEY
4520   OFF KBD
4530   OFF KNOB
4540   IF Msg_dp_request>=2 THEN
4550       DEALLOCATE Message_chart$(*)
4560       Msg_dp_request=0
4570   END IF
4580   IF Trend_dp=1 OR Trend_dp=2 THEN DEALLOCATE
        Spectra(*)
4590   Next_time=Next_time+INT(Block_time)
4600   ON EOT @Out_buffer GOTO Resume2
4610   OUTPUT @Multi;"RV,13.0,13.1,13.2,13.3T"
        ! checking control registers
4620   ENTER @Read_val;Counters2(*)
4630   Read_ptr2=Counters2(0)
4640   Num_pulses=Counters2(1)
4650   TRANSFER @In_buffer TO @Out_buffer;COUNT Num_
        pts*2,CONT
4660 Waiter2:DISP TIME$(TIMEDATE),DATE$(TIMEDATE)
4670   GOTO Waiter2
4680  !
4690  !
4700  !
4710  !
4720 Resume2:OFF EOT @Out_buffer
4730   Num_xfer_left=Num_xfer_left-1
4740    OUTPUT @Multi;"MR,12",Num_pulses,Read_
        ptr2,"1T"          ! FIFO mode
4750    CONTROL @In_buffer2,3;1
        ! Reset fill pointer for buffer
4760    CONTROL @In_buffer2,4;0
```

```
             ! Reset current number of bytes in buffer
     4770    CONTROL @In_buffer2,5;1
             ! Reset empty pointer for buffer
     4780    !
     4790    ! write an 8 byte sequence to disk as a header for
             ! the transfer
     4800    !
     4810    CALL Xfheader(@Out_buffer2,Num_pulses,"H")
     4820    !
     4830    ! read multiprogrammer into computer memory (hpib_
             buffer)
     4840    !
     4850    ON EOT @Memory_input2 GOTO Resume4
     4860    TRANSFER @Memory_input2 TO @In_buffer2;COUNT Num_
             pulses*2,CONT
     4870 Waiter4:DISP TIME$(TIMEDATE),DATE$(TIMEDATE)
     4880    GOTO Waiter4
     4890    !
     4900    ! store computer memory on complete data file
     4910    !
     4920 Resume4:OFF EOT @Memory_input2
     4930    ON EOT @Out_buffer2 GOTO Resume5
     4940    TRANSFER @In_buffer2 TO @Out_buffer2;COUNT Num_
             pulses*2,CONT
     4950 Waiter5:DISP TIME$(TIMEDATE),DATE$(TIMEDATE)
     4960    GOTO Waiter5
     4970    !
     4980 Resume5:OFF EOT @Out_buffer2
     4990    CALL Hr_sig_gen(Hpib_buffer2(*),Hr_signal(*))
     5000    !

5010    !
     5020 Resume6:!
     5030    OUTPUT @Multi;"RV,6.0,6.1,6.2,6.3T"
             ! checking control registers
```

```
5040    ENTER @Read_val;Counters(*)
5050    Read_ptrl=Counters(0)
5060    IF Counters(1)=4095 THEN ! Data lockout probably
            occurred
5070        PRINT "DATA LOCKOUT!! TIME RECORD NOT
                    CONTINUOUS!!"
5080        PRINT "ABORTING CURRENT DATA COLLECTION."
5090        Data_lockout=1
5100        Num_xfer_left=0
5110    END IF
5120    OUTPUT 2;CHR$(255)&CHR$(75);
      ! Clear CRT of text
5130    GINIT
5140    PLOTTER IS 3,"INTERNAL"
5150    GRAPHICS ON
5160    Xscale=8
5170    Hr_max=MAX(Hr_signal(*))
5180    Hr_min=MIN(Hr_signal(*))
5190    VIEWPORT 0,64,50,100
5200    WINDOW 0,1,0,1
5210    AXES .1,.1,0,0
5220    CSIZE 4
5230    Hr_signal(1024)=0
5240    Hr_sigsum=SUM(Hr_signal)
5250    Mean_hr=INT((Hr_sigsum/1024+Avg_hr))
5260    Hr_bias=Hr_sigsum/1024
5270    LDIR 0
5280    LORG 3
5290    MOVE .2,.9
5300    LABEL "HR data    hr=";Mean_hr
5310    CSIZE 4
5320    MOVE .05,1
5330    LORG 3
5340    LABEL "250 bpm"
5350    WINDOW 1,0,1,0
5360    AXES 0,0,0,0
```

```
5370    IF Hr_dispflg=1 THEN
5380        WINDOW 0,1024,Hr_min,Hr_max
5390    ELSE
5400        Low_window=INT(-Avg_hr)
5410        High_window=Low_window+250.
5420        WINDOW 0,1024,Low_window,High_window
5430    END IF
5440    FOR I=0 TO 1023
5450        PLOT I,Hr_signal(I)
5460    NEXT I
5470    !
5480    ! display respirations time series also
5490    !
5500    IF Resp_dpflg=1 THEN
5510        Max_resp=MAX(Hpib_buffer1(*))
5520        Min_resp=MIN(Hpib_buffer1(*))
5530        IF Mean_hr>100 THEN
5540            VIEWPORT 0,64,50,65
5550        ELSE
5560            VIEWPORT 0,64,75,90
5570        END IF
5580        WINDOW 0,1023,Min_resp,Max_resp
5590        MOVE 0,Hpib_buffer1(0)
5600        FOR I=1 TO 1023
5610            PLOT I,Hpib_buffer1(I)
5620        NEXT I
5630    ELSE
5640        Resp_dpflg=0
5650    END IF
5660    !
5670    ! now process heart rate data with waveform
             analysis package
5680    ! make sure the hr_signal has zero mean
5690    !
5700    FOR I=0 TO 1023
5710        Signal(I)=Hr_signal(I)-Hr_bias
```

```
5720    NEXT I
5730    Plotbox=2
5740    DISP "HR fft in process"
5750    CALL Wf_analyzer(Pacing_rate)
5760    !
5770    ! now process respiration data with waveform
          analysis package
5780    !
5790    MAT Signal= (0)
5800    FOR I=0 TO 1023
5810        Signal(I)=Hpib_buffer1(I)
5820    NEXT I
5830    Signal_avg=SUM(Signal)/1024.
5840    MAT Signal= Signal-(Signal_avg)
5850    Plotbox=4
5860    DISP "RESP fft in process"
5870    CALL Wf_analyzer(Pacing_rate)
5880    Trend_dp=0 !..trend graph not displayed
5890    !
5900    ! waveform analysis completed, compile trends and
          store in temporary file
5910    !
5920    Mean_hr_t(T_ptr)=Mean_hr
5930    Lfa_t(T_ptr)=Lfa
5940    Rfa_t(T_ptr)=Rfa
5950    Ratio_t(T_ptr)=Peakratio
5960    Meas_resp_t(T_ptr)=Meas_resp
5961    Trans_time(T_ptr)=Xfer_time
5970    T_ptr=T_ptr+1
5980    OUTPUT @Temp_trend;T_ptr-1,Mean_
          hr,Lfa,Rfa,Peakratio,Meas_resp,Xfer_time
5990    IF Pres_in=1 THEN
6000        Pr=Pres_ptr-1
6010        OUTPUT @Hemo_data;Pres_time$(Pr),Ao_s(Pr),Ao_
              d(Pr),Ao_m(Pr),Pa_s(Pr),
                Pa_d(Pr),Pa_m(Pr),La_m(Pr),Ra_m(Pr),Pr
```

```
6020        Pres_in=0
6030    END IF
6040    IF Io_in=1 THEN
6050        Io=Io_ptr-1
6060        OUTPUT @Io_data;Io_time$(Io),Iv_
            intake(Io),Fluid_in(Io),In_tot(Io),Ur
            ine(Io),Chest(Io),Out_tot(Io),Net(Io),Io
6070        Io_in=0
6080    END IF
6090    IF Lab_in=1 THEN
6100        L=Lab_ptr-1
6110        OUTPUT @Lab_data;Lab_
time$(L),Na(L),K1(L),Cl(L),Hco3(L),Ca(L),Hct(L),
Gluc(L),Dig(L),Pt(L),Ptt(L),Creat(L),Bun(L),L
6120        Lab_in=0
6130    END IF
6140    IF Heart_in=1 THEN
6150        H=Heart_ptr-1
6160        OUTPUT @Co_data;Heart_
            time$(H),Ci(H),Pvri(H),Svri(H),H
6170        Heart_in=0
6180    END IF
6190    IF Vent_in=1 THEN
6200        V=Vent_ptr-1
6210        OUTPUT @Vent_data;Vent_
            time$(V),Rate(V),Fio2(V),Pp(V),Peep(V),Tv(V),
            Ie_ratio$(V),Airp(V),Ph(V),Po2(V),Pco2(V),
            Bgo3(V),Be(V),V
6220        Vent_in=0
6230    END IF
6240    IF Drug_in=1 THEN
6250        D=Drug_ptr-1
6260        OUTPUT @Drug_data;Drug_time$(D),Drug_
            name$(D),Drug_dos$(D),D
6270        Drug_in=0
6280    END IF
```

```
6290  !
6300  ! continue with data collection
6310  !
6320  IF Num_xfer_left<=0 THEN
6330     Halt_pg=1
6340     GOTO Eo_blk_xfer
6350  ELSE
6360     DISP Num_xfer_left;"transfers remaining"
6370     WAIT 3
6380     GOTO Blk_xfer
6390  END IF
6400 Eo_blk_xfer:End_time=TIMEDATE
6410    Delta_time=End_time-Start_time
6420    !
6430    OUTPUT @Multi;"WF,3.2,0T"
6440    Stop_pacing=TIMEDATE
6450 !
6460 Aborter:!
6470    ASSIGN @In_buffer TO *
6480    ASSIGN @In_buffer2 TO *
6490    ASSIGN @Out_buffer TO *
6500    ASSIGN @Out_buffer2 TO *
6510    ASSIGN @Messages TO *
6520    ASSIGN @Temp_trend TO *
6530    ASSIGN @Hemo_data TO *
6540    ASSIGN @Io_data TO *
6550    ASSIGN @Lab_data TO *
6560    ASSIGN @Vent_data TO *
6570    ASSIGN @Co_data TO *
6580    ASSIGN @Drug_data TO *
6590    OUTPUT @Multi;"CC,3,5,6,10,11,12,13T"
6600    OUTPUT @Multi;"CC,5T"
6610    CALL Completer("READY TO RESTART")
6620    CALL Pauser
6630    GRAPHICS OFF
6640    CALL Get_param
```

```
6650    ASSIGN @Messages TO
            "messglog:HP8290X,700,1";FORMAT OFF
6660    IF Num_pts=0 THEN GOTO Begin
6670    GOTO Setup_scan
6680 Diag:OUTPUT 723;"RV,3.0,3.3T"
6690    ENTER 72306;C,C0
6700    PRINT "CURRENT/START CHANNEL";C,C0
6710    OUTPUT 723;"RV,6.0,6.1,6.2,6.3T"
        ! checking control registers
6720    ENTER 72306;Counters(*)
6730    PRINT "COUNTERS=";Counters(*)
6740    STOP
6750 Purger:!
6760    GRAPHICS OFF
6770    DELSUB Hpib_intr TO END
6780    PURGE "AOK:HP8290X,700,1"
6790    PURGE "hrAOK:HP8290X,700,1"
6800    PURGE "messglog:HP8290X,700,1"
6810    PURGE "temp_trend:HP8290X,700,1"
6820    PURGE "hemo_data:HP8290X,700,1"
6830    PURGE "co_data:HP8290X,700,1"
6840    PURGE "vent_data:HP8290X,700,1"
6850    PURGE "lab_data:HP8290X,700,1"
6860    PURGE "drug_data:HP8290X,700,1"
6870    PURGE "io_data:HP8290X,700,1"
6871    PURGE "sub_data:HP8290X,700,1"
6880    STOP
6890 !
6900 ! definitions for keys
6910 !
6920 Move_msgs:! knob is processed here
6930    IF Msg_dp_request<>2 THEN RETURN
6940    Message_line=Message_line+KNOBX
6950    IF Message_line>Num_msgs-3 THEN Message_line=Num_msgs-3
6960    IF Message_line<0 THEN Message_line=0
```

```
6970   Msg_dp_request=3
6980   RETURN
6990   !
7000   !
7010 Key0:Key_id=0
7020   Edit_msg$=""
7030   CALL Editor
7040 Key_msg:Msg_pad$(Msg_pad_
       ptr)="Time:"&TIME$(TIMEDATE)&" "&Edit_msg$
7050   Msg_pad_ptr=Msg_pad_ptr+1
7060   DISP "only";10-Msg_pad_ptr;"more messages during
       this segment"
7070   PRINT TABXY(1,18);"
                                    "
7080   PRINT TABXY(1,18);Edit_msg$
7090   WAIT 3
7100   PRINT TABXY(1,18);"
                                    "
7110   PRINT TABXY(1,18);"Next transfer: ";TIME$(Next_
       time)
7120   GOTO Keyend
7130   !
7140   !
7150   !
7160 Key1:Chart_num=1
       !...input/output charting
7170   IF Next_time-TIMEDATE<45 THEN
7180       DISP "not enough time to enter data; wait for
           next xfer"
7190       WAIT 2
7200       GOTO Keyend
7210   END IF
7220   GRAPHICS OFF
7230   PRINT CHR$(12)
7240   Num_var=5
7250   IF Io_in=1 THEN
```

```
7260      DISP "data in for this xfer; chart displayed"
7270      WAIT 2
7280      Io_ptr=Io_ptr-1
7290      CALL Chart(Chart_num)
7300      Io_ptr=Io_ptr+1
7310      GOTO Keyend
7320    ELSE
7330      INPUT "Input values=1 or display chart=2?",Inp
7340      IF Inp=1 THEN
7350          IF Io_ptr>5 THEN
7360              DISP "Do not enter more I/O data; disc full"
7370              WAIT 3
7380              GOTO Keyend
7390          ELSE
7400              GOTO I_o
7410          END IF
7420      ELSE
7430          CALL Chart(Chart_num)
7440          GOTO Keyend
7450      END IF
7460    END IF
7470 Data1:!
7480    Io_time$(Io_ptr)=Io_msg$(Chart_num,1)
7490    Iv_intake(Io_ptr)=FNLval(Io_msg$(Chart_num,2))
7500    IF Iv_intake(Io_ptr)=9999.999 THEN
7510        Ionum=2
7520        Fix_val=1
7530        GOTO Data_edit
7540    END IF
7550    Fluid_in(Io_ptr)=FNLval(Io_msg$(Chart_num,3))
7560    IF Fluid_in(Io_ptr)=9999.999 THEN
7570        Ionum=3
7580        Fix_val=1
7590        GOTO Data_edit
```

```
7600    END IF
7610    Urine(Io_ptr)=FNLval(Io_msg$(Chart_num,4))
7620    IF Urine(Io_ptr)=9999.999 THEN
7630        Ionum=4
7640        Fix_val=1
7650        GOTO Data_edit
7660    END IF
7670    Chest(Io_ptr)=FNLval(Io_msg$(Chart_num,5))
7680    IF Chest(Io_ptr)=9999.999 THEN
7690        Ionum=5
7700        Fix_val=1
7710        GOTO Data_edit
7720    END IF
7730    In_tot(Io_ptr)=Iv_intake(Io_ptr)+Fluid_in(Io_ptr)
7740    Out_tot(Io_ptr)=Urine(Io_ptr)+Chest(Io_ptr)
7750    Net(Io_ptr)=In_tot(Io_ptr)-Out_tot(Io_ptr)
7760    CALL Chart(Chart_num)
7770    Io_ptr=Io_ptr+1
7780    Io_in=1
7790    Fix_val=0
7800    GOTO Keyend
7810    !
7820    !
7830 Key2:Chart_num=2
        !...ventilation charting
7840    GRAPHICS OFF
7850    PRINT CHR$(12)
7860    IF Next_time-TIMEDATE<45 THEN
7870        DISP "not enough time to enter data; wait for next xfer"
7880        WAIT 2
7890        GOTO Keyend
7900    END IF
7910    Num_var=13
7920    IF Lab_in=1 THEN
7930        DISP "data in for this xfer; chart displayed"
```

```
7940      WAIT 2
7950      Lab_ptr=Lab_ptr-1
7960      CALL Chart(Chart_num)
7970      Lab_ptr=Lab_ptr+1
7980      GOTO Keyend
7990   ELSE
8000      INPUT "Input values=1 or display chart=2?",Inp
8010      IF Inp=1 THEN
8020         IF Lab_ptr>7 THEN
8030            DISP "Do not enter more Lab data; disc full"
8040            WAIT 3
8050            GOTO Keyend
8060         ELSE
8070            GOTO I_o
8080         END IF
8090      ELSE
8100         CALL Chart(Chart_num)
8110         GOTO Keyend
8120      END IF
8130   END IF
8140 Data2:!
8150   Lab_time$(Lab_ptr)=Io_msg$(Chart_num,1)
8160   Na(Lab_ptr)=FNLval(Io_msg$(Chart_num,2))
8170   IF Na(Lab_ptr)=9999.999 THEN
8180      Ionum=2
8190      Fix_val=1
8200      GOTO Data_edit
8210   END IF
8220   K1(Lab_ptr)=FNLval(Io_msg$(Chart_num,3))
8230   IF K1(Lab_ptr)=9999.999 THEN
8240      Ionum=3
8250      Fix_val=1
8260      GOTO Data_edit
8270   END IF
```

```
8280    Cl(Lab_ptr)=FNLval(Io_msg$(Chart_num,4))
8290    IF Cl(Lab_ptr)=9999.999 THEN
8300        Ionum=4
8310        Fix_val=1
8320        GOTO Data_edit
8330    END IF
8340    Hco3(Lab_ptr)=FNLval(Io_msg$(Chart_num,5))
8350    IF Hco3(Lab_ptr)=9999.999 THEN
8360        Ionum=5
8370        Fix_val=1
8380        GOTO Data_edit
8390    END IF
8400    Ca(Lab_ptr)=FNLval(Io_msg$(Chart_num,6))
8410    IF Ca(Lab_ptr)=9999.999 THEN
8420        Ionum=6
8430        Fix_val=1
8440        GOTO Data_edit
8450    END IF
8460    Hct(Lab_ptr)=FNLval(Io_msg$(Chart_num,7))
8470    IF Hct(Lab_ptr)=9999.999 THEN
8480        Ionum=7
8490        Fix_val=1
8500        GOTO Data_edit
8510    END IF
8520    Gluc(Lab_ptr)=FNLval(Io_msg$(Chart_num,8))
8530    IF Gluc(Lab_ptr)=9999.999 THEN
8540        Ionum=8
8550        Fix_val=1
8560        GOTO Data_edit
8570    END IF
8580    Dig(Lab_ptr)=FNLval(Io_msg$(Chart_num,9))
8590    IF Dig(Lab_ptr)=9999.999 THEN
8600        Ionum=9
8610        Fix_val=1
8620        GOTO Data_edit
8630    END IF
```

```
8640        Pt(Lab_ptr)=FNLval(Io_msg$(Chart_num,10))
8650        IF Pt(Lab_ptr)=9999.999 THEN
8660            Ionum=10
8670            Fix_val=1
8680            GOTO Data_edit
8690        END IF
8700        Ptt(Lab_ptr)=FNLval(Io_msg$(Chart_num,11))
8710        IF Ptt(Lab_ptr)=9999.999 THEN
8720            Ionum=11
8730            Fix_val=1
8740            GOTO Data_edit
8750        END IF
8760        Creat(Lab_ptr)=FNLval(Io_msg$(Chart_num,12))
8770        IF Creat(Lab_ptr)=9999.999 THEN
8780            Ionum=12
8790            Fix_val=1
8800            GOTO Data_edit
8810        END IF
8820        Bun(Lab_ptr)=FNLval(Io_msg$(Chart_num,13))
8830        IF Bun(Lab_ptr)=9999.999 THEN
8840            Ionum=13
8850            Fix_val=1
8860            GOTO Data_edit
8870        END IF
8880        CALL Chart(Chart_num)
8890        Lab_ptr=Lab_ptr+1
8900        Lab_in=1
8910        Fix_val=0
8920        GOTO Keyend
8930        !
8940        !
8950 Key3:Chart_num=4
            !...hemodynamic graphics
8960        IF Next_time-TIMEDATE<45 THEN
8970            DISP "not enough time to enter data; wait for
                next xfer"
```

```
8980      WAIT 2
8990      GOTO Keyend
9000   END IF

9010   GRAPHICS OFF
9020   PRINT CHR$(12)
9030   INPUT "Blood pressures(1) or cardiac indices(2)?",Bp
9040   IF Bp=1 THEN
9050      Num_var=9
9060   ELSE
9070      Fst=10
9080      Num_var=13
9090   END IF
9100   IF Pres_in=1 AND Bp=1 THEN
9110      DISP "data in for this xfer; chart displayed"
9120      WAIT 2
9130      Pres_ptr=Pres_ptr-1
9140      IF Heart_in=1 THEN Heart_ptr=Heart_ptr-1
9150      CALL Chart(Chart_num)
9160      IF Heart_in=1 THEN Heart_ptr=Heart_ptr+1
9170      Pres_ptr=Pres_ptr+1
9180      GOTO Keyend
9190   ELSE
9200      IF Heart_in=1 AND Bp=2 THEN
9210         DISP "data in for this xfer; chart displayed"
9220         WAIT 2
9230         IF Pres_in=1 THEN Pres_ptr=Pres_ptr-1
9240         Heart_ptr=Heart_ptr-1
9250         CALL Chart(Chart_num)
9260         Heart_ptr=Heart_ptr+1
9270         IF Pres_in=1 THEN Pres_ptr=Pres_ptr-1
9280         GOTO Keyend
9290      ELSE
```

```
9300        INPUT "Input values=1 or display
            chart=2?",Inp
9310        IF Inp=1 THEN
9320            IF Bp=1 AND Pres_ptr>17 THEN
9330                DISP "Do not enter more Pressure
                    data; disc full"
9340                WAIT 3
9350                GOTO Keyend
9360            ELSE
9370                GOTO I_o
9380            END IF
9390        ELSE
9400            IF Heart_in=1 THEN Heart_ptr=Heart_
                ptr-1
9410            IF Pres_in=1 THEN Pres_ptr=Pres_ptr-1
9420            CALL Chart(Chart_num)
9430            IF Heart_in=1 THEN Heart_ptr=Heart_
                ptr+1
9440            IF Pres_in=1 THEN Pres_ptr=Pres_ptr+1
9450            GOTO Keyend
9460        END IF
9470    END IF
9480 END IF
9490 Data4:!
9500    IF Bp=1 THEN
9510        Pres_time$(Pres_ptr)=Io_msg$(Chart_num,1)
9520        Ao_s(Pres_ptr)=FNLval(Io_msg$(Chart_num,2))
9530        IF Ao_s(Pres_ptr)=9999.999 THEN
9540            Ionum=2
9550            Fix_val=1
9560            GOTO Data_edit
9570        END IF
9580        Ao_d(Pres_ptr)=FNLval(Io_msg$(Chart_num,3))
9590        IF Ao_d(Pres_ptr)=9999.999 THEN
9600            Ionum=3
9610            Fix_val=1
```

```
9620            GOTO Data_edit
9630          END IF
9640          Ao_m(Pres_ptr)=FNLval(Io_msg$(Chart_num,4))
9650          IF Ao_m(Pres_ptr)=9999.999 THEN
9660            Ionum=4
9670            Fix_val=1
9680            GOTO Data_edit
9690          END IF
9700          Pa_s(Pres_ptr)=FNLval(Io_msg$(Chart_num,5))
9710          IF Pa_s(Pres_ptr)=9999.999 THEN
9720            Ionum=5
9730            Fix_val=1
9740            GOTO Data_edit
9750          END IF
9760          Pa_d(Pres_ptr)=FNLval(Io_msg$(Chart_num,6))
9770          IF Pa_d(Pres_ptr)=9999.999 THEN
9780            Ionum=6
9790            Fix_val=1
9800            GOTO Data_edit
9810          END IF
9820          Pa_m(Pres_ptr)=FNLval(Io_msg$(Chart_num,7))
9830          IF Pa_m(Pres_ptr)=9999.999 THEN
9840            Ionum=7
9850            Fix_val=1
9860            GOTO Data_edit
9870          END IF
9880          La_m(Pres_ptr)=FNLval(Io_msg$(Chart_num,8))
9890          IF La_m(Pres_ptr)=9999.999 THEN
9900            Ionum=8
9910            Fix_val=1
9920            GOTO Data_edit
9930          END IF
9940          Ra_m(Pres_ptr)=FNLval(Io_msg$(Chart_num,9))
9950          IF Ra_m(Pres_ptr)=9999.999 THEN
9960            Ionum=9
9970            Fix_val=1
```

```
9980          GOTO Data_edit
9990        END IF
10000       IF Heart_in=1 THEN Heart_ptr=Heart_ptr-1
10010       CALL Chart(Chart_num)
10020       IF Heart_in=1 THEN Heart_ptr=Heart_ptr+1
10030       Pres_ptr=Pres_ptr+1
10040       Pres_in=1
10050       Fix_val=0
10060       GOTO Keyend
10070     ELSE
10080       Heart_time$(Heart_ptr)=Io_msg$(Chart_num,10)
10090       Ci(Heart_ptr)=FNLval(Io_msg$(Chart_num,11))
10100       IF Ci(Heart_ptr)=9999.999 THEN
10110          Ionum=11
10120          Fix_val=1
10130          GOTO Data_edit
10140       END IF
10150       Pvri(Heart_ptr)=FNLval(Io_msg$(Chart_num,12))
10160       IF Pvri(Heart_ptr)=9999.999 THEN
10170          Ionum=12
10180          Fix_val=1
10190          GOTO Data_edit
10200       END IF
10210       Svri(Heart_ptr)=FNLval(Io_msg$(Chart_num,13))
10220       IF Svri(Heart_ptr)=9999.999 THEN
10230          Ionum=13
10240          Fix_val=1
10250          GOTO Data_edit
10260       END IF
10270       IF Pres_in=1 THEN Pres_ptr=Pres_ptr-1
10280       CALL Chart(Chart_num)
10290       IF Pres_in=1 THEN Pres_ptr=Pres_ptr+1
10300       Heart_ptr=Heart_ptr+1
10310       Heart_in=1
10320       Fst=1
10330       Fix_val=0
```

```
10340     END IF
10350     GOTO Keyend
10360     !
10370     !
10380 Key4:Key_id=4
10390     IF Trend_dp=0 THEN
10400         ALLOCATE INTEGER Spectra(7499)
10410         GSTORE Spectra(*)
10420         Trend_dp=2
10430         Top1=200
10440         Top2=2.5
10450         Bot2=-2.5
10460         Top3=10
10470         Top4=10
10480         CALL Trend_graph
10490     ELSE
10500         IF Trend_dp=2 THEN
10510             GRAPHICS ON
10520             GLOAD Spectra(*)
10530             DEALLOCATE Spectra(*)
10540             CALL Offgraph
10550             Trend_dp=0
10560         ELSE
10570             Trend_dp=2
10580             Top1=200
10590             Top2=2.5
10600             Bot2=-2.5
10610             Top3=10
10620             Top4=10
10630             CALL Trend_graph
10640         END IF
10650     END IF
10660     GOTO Keyend
10670     !
10680     !
10690 Key5:Key_id=5
```

```
                !...display message file
       10700   IF Msg_dp_request<2 THEN
       10710       DISP "messages will be recalled soon"
       10720       Msg_dp_request=1
       10730       WAIT 1
       10740   ELSE
       10750       Msg_dp_request=3
       10760   END IF
       10770   GOTO Keyend
       10780   !
       10790   !
       10800   Key6:Key_id=6                    !..premature program
                                                  termination
       10810   DISP "To halt program hit KEY 6 again (within 10
                 sec)"
       10820   ON TIME (TIMEDATE+10) MOD 86400,4 GOTO Keyend
       10830   ON KEY 6,3 GOTO Halter
       10840   Cancel_wait:GOTO Cancel_wait
       10850   Halter:Num_xfer_left=1
       10860   Halt_pg=1
       10870   GOTO Key_msg
       10880   !
       10890   !
       10900   Key7:Chart_num=3
       10910   IF Next_time-TIMEDATE<45 THEN
       10920       DISP "not enough time to enter data; wait for
                    next xfer"
       10930       WAIT 2
       10940       GOTO Keyend
       10950   END IF
       10960   GRAPHICS OFF
       10970   PRINT CHR$(12)
       10980   Num_var=13
       10990   IF Vent_in=1 THEN
       11000       DISP "data in for this xfer; chart displayed"
       11010       WAIT 2
```

```
11020        Vent_ptr=Vent_ptr-1
11030        CALL Chart(Chart_num)
11040        Vent_ptr=Vent_ptr+1
11050        GOTO Keyend
11060    ELSE
11070        INPUT "Input values=1 or display chart=2?",Inp
11080        IF Inp=1 THEN
11090            IF Vent_ptr>7 THEN
11100                DISP "Do not enter more Vent data; disc full"
11110                WAIT 3
11120                GOTO Keyend
11130            ELSE
11140                GOTO I_o
11150            END IF
11160        ELSE
11170            CALL Chart(Chart_num)
11180            GOTO Keyend
11190        END IF
11200    END IF
11210 Data3:!
11220    Vent_time$(Vent_ptr)=Io_msg$(Chart_num,1)
11230    Rate(Vent_ptr)=FNLval(Io_msg$(Chart_num,2))
11240    IF Rate(Vent_ptr)=9999.999 THEN
11250        Ionum=2
11260        Fix_val=1
11270        GOTO Data_edit
11280    END IF
11290    Fio2(Vent_ptr)=FNLval(Io_msg$(Chart_num,3))
11300    IF Fio2(Vent_ptr)=9999.999 THEN
11310        Ionum=3
11320        Fix_val=1
11330        GOTO Data_edit
11340    END IF
11350    Pp(Vent_ptr)=FNLval(Io_msg$(Chart_num,4))
```

```
11360    IF Pp(Vent_ptr)=9999.999 THEN
11370        Ionum=4
11380        Fix_val=1
11390        GOTO Data_edit
11400    END IF
11410    Peep(Vent_ptr)=FNLval(Io_msg$(Chart_num,5))
11420    IF Peep(Vent_ptr)=9999.999 THEN
11430        Ionum=5
11440        Fix_val=1
11450        GOTO Data_edit
11460    END IF
11470    Tv(Vent_ptr)=FNLval(Io_msg$(Chart_num,6))
11480    IF Tv(Vent_ptr)=9999.999 THEN
11490        Ionum=6
11500        Fix_val=1
11510        GOTO Data_edit
11520    END IF
11530    Ie_ratio$(Vent_ptr)=Io_msg$(Chart_num,7)
11540    Airp(Vent_ptr)=FNLval(Io_msg$(Chart_num,8))
11550    IF Airp(Vent_ptr)=9999.999 THEN
11560        Ionum=8
11570        Fix_val=1
11580        GOTO Data_edit
11590    END IF
11600    Ph(Vent_ptr)=FNLval(Io_msg$(Chart_num,9))
11610    IF Ph(Vent_ptr)=9999.999 THEN
11620        Ionum=9
11630        Fix_val=1
11640        GOTO Data_edit
11650    END IF
11660    Po2(Vent_ptr)=FNLval(Io_msg$(Chart_num,10))
11670    IF Po2(Vent_ptr)=9999.999 THEN
11680        Ionum=10
11690        Fix_val=1
11700        GOTO Data_edit
11710    END IF
```

```
11720  Pco2(Vent_ptr)=FNLval(Io_msg$(Chart_num,11))
11730  IF Pco2(Vent_ptr)=9999.999 THEN
11740     Ionum=11
11750     Fix_val=1
11760     GOTO Data_edit
11770  END IF
11780  Bgo3(Vent_ptr)=FNLval(Io_msg$(Chart_num,12))
11790  IF Bgo3(Vent_ptr)=9999.999 THEN
11800     Ionum=12
11810     Fix_val=1
11820     GOTO Data_edit
11830  END IF
11840  Be(Vent_ptr)=FNLval(Io_msg$(Chart_num,13))
11850  IF Be(Vent_ptr)=9999.999 THEN
11860     Ionum=13
11870     Fix_val=1
11880     GOTO Data_edit
11890  END IF
11900  CALL Chart(Chart_num)
11910  Vent_ptr=Vent_ptr+1
11920  Vent_in=1
11930  Fix_val=0
11940  GOTO Keyend
11950  !
11960  !
11970  Key8:Chart_num=5
11980  IF Next_time-TIMEDATE<45 THEN
11990     DISP "not enough time to enter data; wait for next xfer"
12000     WAIT 2
12010     GOTO Keyend
12020  END IF
12030  GRAPHICS OFF
12040  PRINT CHR$(12)
12050  Num_var=3
12060  IF Drug_in=1 THEN
```

```
12070      DISP "data in for this xfer; chart displayed"
12080      WAIT 2
12090      Drug_ptr=Drug_ptr-1
12100      CALL Chart(Chart_num)
12110      Drug_ptr=Drug_ptr+1
12120      GOTO Keyend
12130    ELSE
12140      INPUT "Input values=1 or display chart=2?",Inp
12150      IF Inp=1 THEN
12160         IF Drug_ptr>38 THEN
12170            DISP "Do not enter more Drug data; disc full"
12180            WAIT 3
12190            GOTO Keyend
12200         ELSE
12210            GOTO I_o
12220         END IF
12230      ELSE
12240         CALL Chart(Chart_num)
12250         GOTO Keyend
12260      END IF
12270    END IF
12280 Data5:!
12290    Drug_time$(Drug_ptr)=Io_msg$(Chart_num,3)
12300    Drug_name$(Drug_ptr)=Io_msg$(Chart_num,1)
12310    Drug_dos$(Drug_ptr)=Io_msg$(Chart_num,2)
12320    CALL Chart(Chart_num)
12330    Drug_ptr=Drug_ptr+1
12340    Drug_in=1
12350    GOTO Keyend
12360 !
12370 !
12380 Key9:Key_id=9
12390 Bp_graph: !
12400    IF Next_time-TIMEDATE<12 THEN GOTO Waiter1
12410    IF Trend_dp=0 THEN
12420       Trend_dp=1
```

```
12430      Top1=150
12440      Top2=75
12450      Bot2=0
12460      Top3=50
12470      Top4=50
12480      ALLOCATE INTEGER Spectra(7499)
12490      GSTORE Spectra(*)
12500      CALL Trend_graph
12510    ELSE
12520      IF Trend_dp=1 THEN
12530        GRAPHICS ON
12540        GLOAD Spectra(*)
12550        DEALLOCATE Spectra(*)
12560        CALL Offgraph
12570        Trend_dp=0
12580      ELSE
12590        Trend_dp=1
12600        Top1=150
12610        Top2=75
12620        Bot2=0
12630        Top3=50
12640        Top4=50
12650        CALL Trend_graph
12660      END IF
12670    END IF
12680    GOTO Keyend
12690    !
12700    !
12710 I_o:!
12720    IF TIMEDATE>Next_time-20 THEN
12730      DISP "not enough time to enter data; wait for next xfer"
12740      WAIT 2
12750      GOTO Keyend
12760    END IF
12770    PRINT TABXY(1,1);"enter values"
12780    FOR I=Fst TO Num_var
12790      PRINT TABXY(1,17);"          "
```

```
12800        PRINT TABXY(1,17);Io$(Chart_num,I)
12810        Edit_msg$=""
12820        CALL Editor
12830        Io_msg$(Chart_num,I)=Edit_msg$
12840        PRINT TABXY(1,I+2);Io$(Chart_num,I);"=";Io_
             msg$(Chart_num,I)
12850   NEXT I
12860   PRINT TABXY(1,17);"                    "
12870   PRINT TABXY(1,18);"                    "
12880!
12890!....editing the data
12900!
12910 Io_fix:DISP "Do you want to edit I/O
values?                         (Y/N)"
12920   ENTER 2;Ans$
12930   DISP "                                "
12940   IF Ans$="Y" OR Ans$="y" THEN
12950        IF TIMEDATE>Next_time-15 THEN
12960            DISP "not enough time; data not stored;
                 retry next xfer"
12970            GOTO Keyend
12980        END IF
12990        ON Chart_num GOTO Value,Lab,Vent,Pres,Drug
13000 Value:DISP "which value? 1=time, 2=maint. fluid,
                 3=other fluids, 4=urine, 5=chest"
13010        ENTER 2;Ionum
13020        IF Ionum<1 OR Ionum>5 THEN GOTO Value
13030        GOTO Data_edit
13040 Lab: DISP "which value?
        1=time,2=Na,3=K,4=Cl,5=HCO3,6=Ca,7=Hct,8=Gluc,9=Di
        g,10=PT,11=PTT,12=Creat,13=Bun"
13050        ENTER 2;Ionum
13060        IF Ionum<1 OR Ionum>13 THEN GOTO Lab
13070        GOTO Data_edit
13080 Vent:PRINT TABXY(1,17);"which value?
             1=time,2=rate,3=FIO2,4=PP,5=peep,6=TV,
             7=I:E,8=airway"
13090        PRINT TABXY(1,18);
```

```
                  "9=ph,10=pO2,11=pCO2,12=HCO3,13=Be"
       13100      ENTER 2;Ionum
       13110      IF Ionum<1 OR Ionum>13 THEN GOTO Vent
       13120      GOTO Data_edit
       13130 Pres:IF Bp=1 THEN
       13140         PRINT TABXY(1,17);"which value? 1=pres
                         time,2=ao/s,3=ao/d,4=ao/m,
                         5=pa/s,6=pa/d,7=pa/m,8=la,9=ra"
       13150      ELSE
       13160         PRINT TABXY(1,18);"which value? 10=heart
                         time,11=c.i.,12=pvri,13=svri"
       13170      END IF
       13180      ENTER 2;Ionum
       13190      IF Ionum<1 OR Ionum>13 THEN GOTO Pres
       13200      GOTO Data_edit
       13210 Drug:DISP "which value? 1=name,2=dosage,3=time"
       13220      ENTER 2;Ionum
       13230      IF Ionum<1 OR Ionum>10 THEN GOTO Drug
       13240      GOTO Data_edit
       13250 Data_edit:!
       13260      IF TIMEDATE>Next_time-15 THEN
       13270         DISP "not enough time; data not stored;
                         retry next xfer"
       13280         WAIT 2
       13290         GOTO Keyend
       13300      END IF
       13310      C_num=Chart_num
       13320      R_num=2
       13330      IF Fix_val=1 THEN
       13340         PRINT TABXY(1,17);"Error on input; enter
                         value again"
       13350         PRINT TABXY(1,18);Io$(C_num,Ionum)
       13360      END IF
       13370      PRINT TABXY(1,18);Io_msg$(C_num,Ionum)
       13380      Edit_msg$=Io_msg$(C_num,Ionum)
       13390      CALL Editor
       13400      Io_msg$(C_num,Ionum)=Edit_msg$
       13410      PRINT TABXY(1,Ionum+R_num);"              "
```

```
13420      PRINT TABXY(1,Ionum+R_num);Io$(C_
           num,Ionum);"=";Edit_msg$
13430      PRINT TABXY(1,17);"                    "
13440      PRINT TABXY(1,18);"                    "
13460      GOTO Io_fix
13470   ELSE
13480      ON Chart_num GOTO
              Data1,Data2,Data3,Data4,Data5
13490   END IF
13500 Keyend:OFF TIME
13510   OFF KBD
13520   RETURN
13530   END
13540 !
13550 !
13560 !
13570 !
13580 !
13590 SUB Pauser
13600    DISP "press CONTINUE to continue"
13610    PAUSE
13620    DISP
13630 SUBEND
13640 !
13650 !
13660 !
13670 !
13680 !
13690 SUB Get_param
13700    COM /Multi_param/ Start_chan,Stop_chan,Pacing_
         bits,Pacing_rate,Num_pt
         s,Num_xfer,Num_xfer_left,Name_len,Scr_
            file$[28],Scr_
         file2$[28]
13710    COM /Messagecom/ Message$(10)[80],@Messages
13720    COM /Trends/ Mean_hr_t(*),Lfa_t(*),Rfa_
         t(*),Ratio_t(*),T_ptr,Time_now
         1,Meas_resp_t(*),Trend_dp
```

```
13730      COM /Vitaldata/ Rfa,Lfa,Peakratio,Meas_
           resp,Next_time
13740      COM /Pressure/
           Top1,Top2,Top3,Top4,Bot1,Bot2,Bot3,Bot4
13750      COM /Pres_chart/ Pres_time$(*),Ao_s(*),Ao_
           d(*),Ao_m(*),Pa_s(*),Pa_d(*
           ),Pa_m(*),La_m(*),Ra_m(*),Pres_ptr,Pres_in
13760      COM /Subject/ Sub_name$[25],Hos_num$[15],Id_
           age$[10],Id_wt$[10],Id_ht
           $[10],Diag$[30],Opera$[45],Halt_pg
13770      COM /Io_chart/ Io_time$(*),Iv_intake(*),Fluid_
           in(*),In_tot(*),Urine(*
           ),Chest(*),Out_tot(*),Net(*),Io_ptr
13780      COM /Lab_chart/ Lab_
           time$(*),Na(*),K1(*),Cl(*),Hco3(*),
              Ca(*),Hct(*),Gluc(*),Dig(*),Pt(*),
              Ptt(*),Creat(*),Bun(*),Lab_ptr
13790      COM /Vent_chart/ Vent_
           time$(*),Rate(*),Fio2(*),Pp(*),Peep(*),Tv(*),Ie
           _ratio$(*),Airp(*),Ph(*),Po2(*),Pco2(*),
           Bgo3(*),Be(*),Vent_ptr
13800      COM /Heart_index/ Heart_
           time$(*),Ci(*),Pvri(*),Svri(*),Heart_ptr
13810      COM /Drugs/ Drug_time$(*),Drug_name$(*),Drug_
           dos$(*),Drug_ptr
13820      DIM Mo$[24]
13830      Mo$="JAFBMRAPMYJNJLAUSPOCNODC"
13840 !    INTEGER Id_buffer(255) BUFFER
13850      Disk_name$=":HP8290X,700,1"
13860      IF Halt_pg=1 THEN GOTO Purger_get!.....quit
           program
13870 !
13880 ! change soft key messages
13890 !
13900 Oldmsg:PRINT CHR$(12)
13910      PRINT "These are the current soft key
           messages:"
13920      FOR I=0 TO 9
```

```
13930          PRINT "KEY";I;":";Message$(I)
13940      NEXT I
14100      DISP "Press cont when ready to continue"
14110      PAUSE
14120 !
14130      INPUT "Enter subject name, 10 chars (Doe if
           unknown)",Sub_name$
14140      Sub_name$=Sub_name$[1,10]
14150      INPUT "Enter hospital number, 8 chars (00 if
           unknown):",Hos_num$
14160      Hos_num$=Hos_num$[1,8]
14170      INPUT "Enter subject age(00 if unknown):",Id_
           age$
14180      INPUT "Enter subject weight,kg (00 if
           unknown):",Id_wt$
14190      INPUT "Enter subject height,cm (00 if
           unknown):",Id_ht$
14200      INPUT "Enter diagnosis, 10 chars (Unk if
           unknown):",Diag$
14210      Diag$=Diag$[1,10]
14220      INPUT "Enter operation, 15 chars (Unk if
           unknown):",Opera$
14230      Opera$=Opera$[1,15]
14240 !
14250 Ch_sel:!
14260      Start_chan=0
14270      Stop_chan=0
14280 !
14290      Pacing_bits=0
14300 Pacing_sel:!
14310      Base$="M"
14320      Pacing_bits=261
14330 !
14340      Base$=Base$&"SEC"
14350 !
14360 !
14370 ! FINDOUT BLOCKSIZE FOR DATA TRANSFER
14380 !
```

```
15  14390        Num_xfer=55
    14400!
    14410! since new data is to be taken, zero the trend
           graphs (120 pts=8hrs)
    14420!
20  14430        MAT Mean_hr_t= (0)
    14440        MAT Rfa_t= (0)
    14450        MAT Lfa_t= (0)
    14460        MAT Ratio_t= (0)
    14470        MAT Meas_resp_t= (0)
25  14471        MAT Trans_time= (0)
    14480        T_ptr=0
    14490        MAT Pres_time$= ("")
    14500        MAT Ao_s= (0)
    14510        MAT Ao_d= (0)
30  14520        MAT Ao_m= (0)
    14530        MAT Pa_s= (0)
    14540        MAT Pa_d= (0)
    14550        MAT Pa_m= (0)
    14560        MAT La_m= (0)
35  14570        MAT Ra_m= (0)
    14580        MAT Io_time$= ("")
    14590        MAT Iv_intake= (0)
    14600        MAT Fluid_in= (0)
    14610        MAT In_tot= (0)
    14620        MAT Urine= (0)
 5  14630        MAT Chest= (0)
    14640        MAT Out_tot= (0)
    14650        MAT Net= (0)
    14660        MAT Lab_time$= ("")
    14670        MAT Na= (0)
10  14680        MAT K1= (0)
    14690        MAT Cl= (0)
    14700        MAT Hco3= (0)
    14710        MAT Ca= (0)
    14720        MAT Hct= (0)
15  14730        MAT Gluc= (0)
    14740        MAT Dig= (0)
```

```
14750     MAT Pt= (0)
14760     MAT Ptt= (0)
14770     MAT Creat= (0)
14780     MAT Bun= (0)
14790     MAT Vent_time$= ("")
14800     MAT Rate= (0)
14810     MAT Fio2= (0)
14820     MAT Pp= (0)
14830     MAT Peep= (0)
14840     MAT Tv= (0)
14850     MAT Ie_ratio$= ("")
14860     MAT Airp= (0)
14870     MAT Ph= (0)
14880     MAT Po2= (0)
14890     MAT Pco2= (0)
14900     MAT Bgo3= (0)
14910     MAT Be= (0)
14920     MAT Heart_time$= ("")
14930     MAT Ci= (0)
14940     MAT Pvri= (0)
14950     MAT Svri= (0)
14960     MAT Drug_time$= ("")
14970     MAT Drug_name$= ("")
14980     MAT Drug_dos$= ("")
14990     Pres_ptr=0
15000     Trend_ptr=0

15010     Ratio_t(0)=1 !..prevent trend graph errors on startup
15020     Rfa=0
15030     Lfa=0
15040     Meas_resp=0
15050     Peakratio=1
15060     !
15070     !
15080     Pacing_rate=250
15090     Num_pts=1024*Num_xfer
```

```
15100      Num_header=256+8*Num_xfer
15110      IF Scr_file$="?" THEN GOTO Skipl
15120 Purger_get:DISP "PURGE FILE?"
15130      ENTER 2;Resp$
15140      IF Resp$="Y" OR Resp$="YES" THEN
15150          PURGE Scr_file$
15160          PURGE Scr_file2$
15170          PURGE "messglog:HP8290X,700,1"
15180          PURGE "temp_trend:HP8290X,700,1"
15190          PURGE "hemo_data:HP8290X,700,1"
15200          PURGE "io_data:HP8290X,700,1"
15210          PURGE "drug_data:HP8290X,700,1"
15220          PURGE "lab_data:HP8290X,700,1"
15230          PURGE "co_data:HP8290X,700,1"
15231          PURGE "sub_data:HP8290X,700,1"
15240      ELSE
15250!
15260! the data files are named according to the date
15270! in the following format:
15280!     xxxxmmddyy
15290! where
15300!     xxxx - resp,hr__,msgs,errs,trnd
15310!     dd   - day
15320!     mm   - month
                 (JA,FB,MR,AP,MY,JN,JL,AU,SP,OC,NO,DC)
15330!     yy   - year
15340          Date_now$=DATE$(TIMEDATE)
15350          Month_now=FNMonth(Date_now$)*2-1
15360          Mm$=Mo$[Month_now;2]
15370          Id_field$=Date_now$[1;2]&Mm$&Date_now$[10;2]
15380! new name for respiratory file: respddmmyy
15390          RENAME Scr_file$ TO "resp"&Id_field$&Disk_name$
15400! new name for heart rate file: hr__ddmmyy
15410          RENAME Scr_file2$ TO "hr__"&Id_field$&Disk_name$
15420! new name for message log: msgsddmmyy
```

```
15430           RENAME "messglog:HP8290X,700,1" TO
                "msgs"&Id_field$&Disk_name$
15440!  new name for hemo data: dataddmmyy
15450           RENAME "hemo_data:HP8290X,700,1" TO
                "hemo"&Id_field$&Disk_name$
15460!  new name for io data
15470           RENAME "io_data:HP8290X,700,1" TO "io_
                "&Id_field$&Disk_name$
15480!  new name for lab data
15490           RENAME "lab_data:HP8290X,700,1" TO "lab_
                "&Id_field$&Disk_name$
15500!  new name for vent data
15510           RENAME "vent_data:HP8290X,700,1" TO
                "vent"&Id_field$&Disk_name$
15520!  new name for co data
15530           RENAME "co_data:HP8290X,700,1" TO "co_
                "&Id_field$&Disk_name$
15540!  new name for drug data
15550           RENAME "drug_data:HP8290X,700,1" TO
                "drug"&Id_field$&Disk_name$
15551!  new name for subject data
15552           RENAME "sub_data:HP8290X,700,1" TO "sub_
                "&Id_field$&Disk_name$
15560!  name for trend summary file: trndddmmyy
15570           PURGE "temp_trend:HP8290X,700,1"
15580           CREATE BDAT "trnd"&Id_field$&Disk_
                name$,19,256
15590           ASSIGN @Trend_file TO "trnd"&Id_
                field$&Disk_name$;FORMAT OFF
15600           OUTPUT @Trend_file;Mean_hr_t(*),Lfa_
                t(*),Rfa_t(*),Ratio_t(*),Meas
                _resp_t(*),Trans_time(*),T_ptr
15610           ASSIGN @Trend_file TO *
15620       END IF
15630       IF Halt_pg=1 THEN     !..terminate program
15640           DISP "PROGRAM COMPLETED"
15650           STOP
15660       END IF
```

```
15670 Skipl:DISP
15680      Scr_file$="AOK"&Disk_name$
15690      Num_rec=-INT(-(Num_pts+Num_header)/128.)
15700      Scr_file2$="hr"&Scr_file$
15710      CREATE BDAT Scr_file$,Num_rec,256
15720      CREATE BDAT Scr_file2$,Num_rec,256
15730      CREATE BDAT "messglog:HP8290X,700,1",20,640
15740      CREATE BDAT "temp_trend"&Disk_name$,19,256
15750      CREATE BDAT "hemo_data"&Disk_name$,10,256
15760      CREATE BDAT "io_data"&Disk_name$,10,256
15770      CREATE BDAT "lab_data"&Disk_name$,10,256
15780      CREATE BDAT "vent_data"&Disk_name$,10,256
15790      CREATE BDAT "co_data"&Disk_name$,10,256
15800      CREATE BDAT "drug_data"&Disk_name$,10,256
15801      CREATE BDAT "sub_data"&Disk_name$,1,256
15802      ASSIGN @Sub_data TO "sub_data"&Disk_name$;FORMAT OFF
15803      OUTPUT @Sub_data;Sub_name$,Hos_num$,Id_age$,Id_wt$,Id_ht$,Diag$,Opera$
15804      ASSIGN @Sub_data TO *
15810      Halt_pg=0
15820      Num_pts=1024
15830      PRINT Num_pts*Num_xfer;"points will be transferred in";Num_xfer;"blocks of";Num_pts;"points"
15840      !
15850      Num_xfer_left=Num_xfer
15860 SUBEND
15870 !
15880 !
15890 !
15900 !
15910 DEF FNMonth(Date_now$)
15920      Month$=Date_now$[4;3]
15930      Month=0
15940      IF Month$="Jan" THEN Month=1
15950      IF Month$="Feb" THEN Month=2
15960      IF Month$="Mar" THEN Month=3
```

```
15970    IF Month$="Apr" THEN Month=4
15980    IF Month$="May" THEN Month=5
15990    IF Month$="Jun" THEN Month=6
16000    IF Month$="Jul" THEN Month=7
16010    IF Month$="Aug" THEN Month=8
16020    IF Month$="Sep" THEN Month=9
16030    IF Month$="Oct" THEN Month=10
16040    IF Month$="Nov" THEN Month=11
16050    IF Month$="Dec" THEN Month=12
16060    RETURN Month
16070 FNEND
16080 !
16090 !
16100 !
16110 !
16120 !
16130 SUB Xfheader(@Disk,Num_bytes,File_id$)
16140    INTEGER Xheader(7) BUFFER
16150    Xheader(0)=(TIMEDATE MOD 86400)/60
16160    Xheader(1)=Num_bytes
16170    Xheader(2)=NUM(File_id$[1;1])
16180    Xheader(3)=0
16190    Xheader(4)=0
16200    Xheader(5)=0
16210    Xheader(6)=0
16220    Xheader(7)=0
16230    ASSIGN @Xheader TO BUFFER Xheader(*)
16240    CONTROL @Xheader,5;1   ! Reset empty pointer for buffer
16250    CONTROL @Xheader,4;16  ! Reset current number of bytes in buffer
16260    TRANSFER @Xheader TO @Disk;COUNT 16,WAIT
16270    ASSIGN @Xheader TO *
16280 SUBEND
16290 !
16300 !
16310 !
16320 !
```

```
16330  !
16340  !
16350  SUB Trend_graph
16360  !
16370      COM /Trends/ Mean_hr_t(*),Lfa_t(*),Rfa_t(*),Ratio_t(*),T_ptr,Time_now1,Meas_resp_t(*),Trend_dp,Trans_time(*),Lfa_top,Rfa_top
16380      COM /Multi_param/ Start_chan,Stop_chan,Pacing_bits,Pacing_rate,Num_pts,Num_xfer,Num_xfer_left,Name_len,Scr_file$[28],Scr_file2$[28]
16390      COM /Pressure/ Top1,Top2,Top3,Top4,Bot1,Bot2,Bot3,Bot4
16400      COM /Pres_chart/ Pres_time$(*),Ao_s(*),Ao_d(*),Ao_m(*),Pa_s(*),Pa_d(*),Pa_m(*),La_m(*),Ra_m(*),Pres_ptr,Pres_in
16410      DIM First_line(60),Sec_line(60),Third_line(60),Fourth_line(60)
16420      IF Trend_dp=1 THEN
16430          MAT First_line= Ao_m
16440          MAT Sec_line= Pa_m
16450          MAT Third_line= La_m
16460          MAT Fourth_line= Ra_m
16470          G_right=INT((Num_xfer*256/60)/15)
16480  !       IF Pres_in=0 THEN !    Trend_ptr=Pres_ptr+1
16490  !           Trend_ptr=Pres_ptr+1
16500  !       ELSE
16510          Trend_ptr=Pres_ptr
16520  !       END IF
16530      ELSE
16540          MAT First_line= Mean_hr_t
16550          MAT Sec_line= Ratio_t
16560          MAT Third_line= Lfa_t
16570          MAT Fourth_line= Rfa_t
16580          G_right=Num_xfer
```

```
16590          Trend_ptr=T_ptr
16600        END IF
16610        Block_time=Pacing_rate*1.024/3600.
16620        GINIT
16630        GCLEAR
16640        PRINT CHR$(12)
16650        GRAPHICS ON
16660        Beg_time=Time_now1/3600-Block_time
16670        End_time=Beg_time+Num_xfer*Block_time
16680        Ibeg_time=INT(Beg_time)
16690        IF Ibeg_time<Beg_time THEN Ibeg_time=Ibeg_
             time+1
16700 !
16710 ! label the time axes
16720 !
16730        VIEWPORT 0,128,45,50
16740        WINDOW Beg_time,End_time,0,1
16750        IF INT(End_time)>Beg_time THEN
16760            LDIR 0
16770            FOR T_label=Ibeg_time TO INT(End_time)
16780                MOVE T_label,.5
16790                LORG 5
16800                CSIZE 4
16810                LABEL T_label
16820            NEXT T_label
16830        END IF
16840        VIEWPORT 0,128,40,45
16850        WINDOW 0,1,0,1
16860        MOVE .5,0
16870        LORG 4
16880        LABEL "Time (24 hr)"
16890 !
16900 ! draw the axes
16910 !
16920        VIEWPORT 0,128,50,100
16930        WINDOW Beg_time,End_time,0,1
16940        AXES 1/15.,.1,Beg_time,0
16950        WINDOW 1,0,1,0
```

```
16960        AXES 0,.25,0,0
16970!
16980! mean heart rate trends
16990!
17000        WINDOW -1,G_right,Bot1,Top1
17010        MOVE 0,First_line(0)
17020        FOR I=0 TO Trend_ptr-1
17030            DRAW I,First_line(I)
17040        NEXT I
17050!
17060! ratio trends (with a line at ratio=2)
17070!
17080        WINDOW -1,G_right,Bot2,Top2
17090        LINE TYPE 8,5
17100        IF Trend_dp=2 THEN
17110            MOVE 0,LGT(Sec_line(0))
17120        ELSE
17130            MOVE 0,Sec_line(0)
17140        END IF
17150        FOR I=0 TO Trend_ptr-1
17160            IF Trend_dp=2 THEN
17170                DRAW I,LGT(Sec_line(I))
17180            ELSE
17190                DRAW I,Sec_line(I)
17200            END IF
17210        NEXT I
17220        IF Trend_dp=2 THEN
17230            LINE TYPE 3,5!..sparsely dotted line at ratio=2
17240            MOVE 0,LGT(2.)
17250            DRAW Trend_ptr-1,LGT(2.)
17260        END IF
17270!
17280! lfa trends
17290!
17300        WINDOW -1,G_right,Bot3,Top3
17310        LINE TYPE 4,5
17320        MOVE 0,Third_line(0)
```

```
       17330        FOR I=0 TO Trend_ptr-1
       17340            DRAW I,Third_line(I)
35     17350        NEXT I
       17360!
       17370! rfa trends
       17380!
       17390        WINDOW -1,G_right,Bot4,Top4
       17400        LINE TYPE 5,5
 5     17410        MOVE 0,Fourth_line(0)
       17420        FOR I=0 TO Trend_ptr-1
       17430            DRAW I,Fourth_line(I)
       17440        NEXT I
       17450!
10     17460! draw a key for line types
       17470!
       17480        VIEWPORT 64,128,0,50
       17490        WINDOW 0,1,0,13
       17500        IF Trend_dp=2 THEN
15     17510            PRINT TABXY(1,17);"trend graph"
       17520            PRINT TABXY(55,15);"mean hr(0-200)"
       17530            PRINT TABXY(55,16);"ratio(.01-100)"
       17540            PRINT TABXY(55,17);"lfa     (0-10)"
       17550            PRINT TABXY(55,18);"rfa     (0-10)"
20     17560        ELSE
       17570            PRINT TABXY(1,17);"mean pressure graphs"
       17580            PRINT TABXY(50,15);"ao pressure(0-150)"
       17590            PRINT TABXY(50,16);"pa pressure(0-75)"
       17600            PRINT TABXY(50,17);"la pressure(0-50)"
25     17610            PRINT TABXY(50,18);"ra pressure(0-50)"
       17620        END IF
       17630        LINE TYPE 1,5
       17640        MOVE .8,11
       17650        DRAW 1.,11
30     17660        LINE TYPE 8,5
       17670        MOVE .8,10
       17680        DRAW 1.,10
       17690        LINE TYPE 4,5
       17700        MOVE .8,9
```

```
17710       DRAW 1.,9
17720       LINE TYPE 5,5
17730       MOVE .8,8
17740       DRAW 1.,8
17750   SUBEND
17760!
17770!
17780!
17790!
17800!
17810   SUB Msg_dump(Message_chart$(*),Message_line,Flg)
17820       COM /Messagecom/ Message$(10)[80],@Messages
17830       DIM Msg_buffer$[1280] BUFFER
17840       IF Flg>=2 THEN GOTO Chart_filled
17850       ASSIGN @Msg_buffer TO BUFFER Msg_buffer$;FORMAT OFF
17860       STATUS @Messages,3;Num_rec
17870       STATUS @Messages,4;Rec_len
17880       STATUS @Messages,5;Cur_rec
17890       STATUS @Messages,6;Cur_byte
17900       IF Cur_rec<=1 AND Cur_byte<=1 THEN !.. no messages yet
17910           Flg=0
17920           DISP "no messages yet"
17930           WAIT 2
17940           SUBEXIT
17950       END IF
17960       Flg=2
17970       CONTROL @Messages,5;1
17980       CONTROL @Messages,6;1
17990       FOR Rec=1 TO Cur_rec-1
18000 Read_msg:TRANSFER @Messages TO @Msg_buffer;COUNT Rec_len,WAIT
18010           Message_chart$(Rec-1)=Msg_buffer$[1;Rec_len]
18020           CONTROL @Msg_buffer,4;0
18030           CONTROL @Msg_buffer,5;1
18040       NEXT Rec
```

```
18050      IF Cur_byte>1 THEN
18060          TRANSFER @Messages TO @Msg_buffer;COUNT
               Cur_byte-1,WAIT
18070          Message_chart$(Cur_rec-1)=Msg_
               buffer$[1;Cur_byte-1]
18080      END IF
18090      ASSIGN @Msg_buffer TO *
18100 Reset_msg_file:!
18110      CONTROL @Messages,5;Cur_rec
18120      CONTROL @Messages,6;Cur_byte
18130 Chart_filled:!
18140      STATUS @Messages,5;Cur_rec
18150      STATUS @Messages,6;Cur_byte
18160      Flg=2
18170      Cur_msg_ptr=0
18180      Chart_line=1
18190      Msg_buffer$=Message_chart$(0)
18200      Last_msg=Message_line+17
18210      Clear$=CHR$(255)&CHR$(75)
18220      OUTPUT 2;Clear$
18230      GRAPHICS OFF
18240 Next_msg:!
18250      Beg_msg=POS(Msg_buffer$[4],"Time")+3
18260      IF Beg_msg=3 THEN GOTO Next_chart_line
18270      Cur_msg_ptr=Cur_msg_ptr+1
18280      IF Cur_msg_ptr>Message_line THEN
18290          Tab_line=Cur_msg_ptr-Message_line
18300          PRINT TABXY(1,Tab_line);"         "
18310          PRINT TABXY(1,Tab_line);Msg_buffer$[1,Beg_
               msg-1]
18320      END IF
18330      Msg_buffer$=Msg_buffer$[Beg_msg]
18340      IF Cur_msg_ptr=Last_msg THEN Subend_msg
18350      GOTO Next_msg
18360 Next_chart_line:IF Chart_line<Cur_rec THEN
18370          Msg_buffer$=Msg_buffer$&Message_
               chart$(Chart_line)
18380          Chart_line=Chart_line+1
```

```
18390          GOTO Next_msg
18400      END IF
18410 Stopper:PRINT Msg_buffer$
18420 Subend_msg:PRINT
18430   SUBEND
18440 !
18450 !
18460 !
18470 !
18480 !
18490   SUB Disp_ctrls
18500       DISP "f̂ - freq range adjust (1 or 2 Hz)"
18510       WAIT 2
18520       DISP "ĥ - help: display these controls"
18530       WAIT 2
18540       DISP "p̂ - peak threshold adjust (+20%)"
18550       WAIT 2
18560       DISP "r̂ - resp time series display"
18570       WAIT 2
18580       DISP "ŝ - search for resp peak (+.1 Hz)"
18590       WAIT 2
18600   SUBEND
18610 !
18620 !
18630 !
18640   SUB Offgraph
18650       COM /Vitaldata/ Rfa,Lfa,Peakratio,Meas_
                resp,Next_time
18660       PRINT CHR$(12)
18670       PRINT TABXY(1,14);"RR=";PROUND(Meas_resp,-
                2);"Hz"
18680       PRINT TABXY(1,15);"lfa=";Lfa
18690       PRINT TABXY(1,16);"rfa=";Rfa
18700       PRINT TABXY(1,17);"ratio=";Peakratio
18710       PRINT TABXY(1,18);"next transfer:
                ";TIME$(Next_time)
18720   SUBEND
18730       !
```

```
18740        !
18750        ! This subroutine edits the data
18760        !
18770        !
18780   SUB Editor
18790        COM /Editor/ Edit_msg$[80]
18800        COM /Vitaldata/ Rfa,Lfa,Peakratio,Meas_
             resp,Next_time
18810 Key_in:!
18820        PRINT TABXY(1,18);"                          "
18830        PRINT TABXY(1,18);Edit_msg$
18840        IF TIMEDATE>Next_time-15 THEN GOTO Keyend
18850        ON TIME (TIMEDATE+10) MOD 86400,3 GOTO Keyend
18860        DISP "type message"
18870        GRAPHICS OFF
18880        ON KBD,2 GOTO Next_char
18890 Key_wait:GOTO Key_wait
18900 Next_char:Key$=KBD$
18910        ON TIME (TIMEDATE+10) MOD 86400,3 GOTO Keyend
18920        IF NUM(Key$)=255 THEN
18930            IF NUM(Key$[2])=69 THEN GOTO End_key
18940            IF NUM(Key$[2])=66 THEN !..backspacing
18950                New_msg_len=LEN(Edit_msg$)-1
18960                IF New_msg_len<=0 THEN New_msg_len=0
18970                Edit_msg$=Edit_msg$[1;New_msg_len]
18980            END IF
18990            IF NUM(Key$[2])=35 THEN !..clear line
19000                Edit_msg$=""
19010            END IF
19020        ELSE
19030            IF LEN(Edit_msg$)<66 THEN !..can add
                 ! characters
19040                Edit_msg$=Edit_msg$&Key$
19050            ELSE
19060                BEEP
19070            END IF
19080        END IF
19090        PRINT TABXY(1,18);"                          "
```

```
19100        PRINT TABXY(1,18);Edit_msg$
19110        GOTO Key_wait
19120 Keyend: !
19130 End_key:OFF KBD
19140        OFF TIME
19150   SUBEND
19160 !
19170 !
19180 !
19190   SUB Chart(Chart_num)
19200        COM /Subject/ Sub_name$,Hos_num$,Id_age$,Id_
             wt$,Id_ht$,Diag$,Opera$,Halt_pg
19210        COM /Io_chart/ Io_time$(*),Iv_intake(*),Fluid_
             in(*),In_tot(*),Urine(*),Chest(*),Out_
             tot(*),Net(*),Io_ptr
19220        COM /Lab_chart/ Lab_
        time$(*),Na(*),K1(*),Cl(*),Hco3(*),Ca(*),Hct(*),G
        luc(*),Dig(*),Pt(*),Ptt(*),Creat(*),Bun(*),Lab_
             ptr
19230        COM /Vent_chart/ Vent_
             time$(*),Rate(*),Fio2(*),Pp(*),Peep(*),Tv(*),
             Ie_ratio$(*),Airp(*),Ph(*),Po2(*),Pco2(*),
             Bgo3(*),Be(*),Vent_ptr
19240        COM /Pres_chart/ Pres_time$(*),Ao_s(*),Ao_
             d(*),Ao_m(*),Pa_s(*),Pa_d(*
             ),Pa_m(*),La_m(*),Ra_m(*),Pres_ptr,Pres_in
19250        COM /Pressure/
             Top1,Top2,Top3,Top4,Bot1,Bot2,Bot3,Bot4
19260        COM /Heart_index/ Heart_
             time$(*),Ci(*),Pvri(*),Svri(*),Heart_ptr
19270        COM /Drugs/ Drug_time$(*),Drug_name$(*),Drug_
             dos$(*),Drug_ptr
19280        Pres_stl=0
19290        Lab_stl=0
19300        Io_stl=0
19310        Vent_stl=0
19320        Drug_stl=0
19330        !
```

```
19340        ! set up identifying subject info
19350        !
19360        PRINT CHR$(12)
19370        PRINT TABXY(1,1);
19380        PRINT USING Image_wt1;Sub_name$,Hos_
             num$,TIME$(TIMEDATE),DATE$(TIMEDATE)
19390 Image_wt1:IMAGE   "Name: ",K,XXXX,"Hosp num:
             ",K,XXXXX,K,XXXXX,K
19400        PRINT TABXY(1,2);
19410        PRINT USING Image_wt2;Id_age$,Id_wt$,Id_
             ht$,Diag$,Opera$
19420 Image_wt2:IMAGE   "Age: ",K,XXXX,"Wt(kg):
             ",K,XXXX,"Ht(cm): ",K,XXXX,"Diag
               : ",K,XXXX,"Op: ",K
19430        !
19440        ! go to appropriate chart
19450        !
19460        ON Chart_num GOTO In_out,Lab_val,Vent_
             val,Pres_val,Drug
19470 In_out:!                              ....intake/output
19480        IF Io_ptr>3 THEN Io_st1=2
19490        IF Io_ptr>5 THEN
19500            DISP "do not input more Intake/Output
                 data; disc full"
19510            WAIT 3
19520            SUBEXIT
19530        END IF
19540        PRINT TABXY(30,3);"INTAKE/OUTPUT CHART"
19550        PRINT TABXY(1,4);"Intake (cc/hr) "
19560        PRINT TABXY(1,5);"Time"
19570        PRINT TABXY(4,6);"Maint. Fluid"
19580        PRINT TABXY(4,7);"Other Fluids"
19590        PRINT TABXY(1,9);"Total "
19600        PRINT TABXY(1,11);"Output (cc/hr)"
19610        PRINT TABXY(4,12);"Urine"
19620        PRINT TABXY(4,13);"Chest"
19630        PRINT TABXY(1,15);"Total"
19640        PRINT TABXY(1,17);"Net I/O"
```

```
19650      Start=25
19660      FOR I=Io_stl TO Io_ptr
19670          PRINT TABXY(Start,5);Io_time$(I)
19680          PRINT TABXY(Start,6);Iv_intake(I)
19690          PRINT TABXY(Start,7);Fluid_in(I)
19700          PRINT TABXY(Start,9);In_tot(I)
19710          PRINT TABXY(Start,12);Urine(I)
19720          PRINT TABXY(Start,13);Chest(I)
19730          PRINT TABXY(Start,15);Out_tot(I)
19740          PRINT TABXY(Start,17);Net(I)
19750          Start=Start+10
19760      NEXT I
19770      GOTO Finish
19780 !
19790 !
19800 Lab_val:!         ...lab values
19810      IF Lab_ptr>3 THEN Lab_stl=2
19820      IF Lab_ptr>7 THEN
19830          DISP "do not input any more lab values;
                   disc full"
19840          WAIT 3
19850          SUBEXIT
19860      END IF
19870      PRINT TABXY(30,3);"Lab Values"
19880      PRINT TABXY(10,4);"Time"
19890      PRINT TABXY(1,6);"Na"
19900      PRINT TABXY(1,7);"K"
19910      PRINT TABXY(1,8);"Cl"
19920      PRINT TABXY(1,9);"HCO3"
19930      PRINT TABXY(1,10);"Ca"
19940      PRINT TABXY(1,11);"Hct"
19950      PRINT TABXY(1,12);"Glucose"
19960      PRINT TABXY(1,13);"Dig level"
19970      PRINT TABXY(1,14);"PT"
19980      PRINT TABXY(1,15);"PTT"
19990      PRINT TABXY(1,16);"Creat"
20000      PRINT TABXY(1,17);"Bun"
```

```
20010      Start=15
20020      FOR I=Lab_st1 TO Lab_ptr
20030          PRINT TABXY(Start+10,4);Lab_time$(I)
20040          PRINT TABXY(Start+10,6);Na(I)
20050          PRINT TABXY(Start+10,7);K1(I)
20060          PRINT TABXY(Start+10,8);Cl(I)
20070          PRINT TABXY(Start+10,9);Hco3(I)
20080          PRINT TABXY(Start+10,10);Ca(I)
20090          PRINT TABXY(Start+10,11);Hct(I)
20100          PRINT TABXY(Start+10,12);Gluc(I)
20110          PRINT TABXY(Start+10,13);Dig(I)
20120          PRINT TABXY(Start+10,14);Pt(I)
20130          PRINT TABXY(Start+10,15);Ptt(I)
20140          PRINT TABXY(Start+10,16);Creat(I)
20150          PRINT TABXY(Start+10,17);Bun(I)
20160          Start=Start+10
20170      NEXT I
20180      GOTO Finish
20190!
20200!
20210 Vent_val:!                    ....ventilation values
20220      IF Vent_ptr>3 THEN Vent_st1=2
20230      IF Vent_ptr>5 THEN Vent_st1=4
20240      IF Vent_ptr>7 THEN
20250          DISP "do not input any more Vent values; disc full"
20260          WAIT 3
20270          SUBEXIT
20280      END IF
20290      PRINT TABXY(30,3);"VENTILATION"
20300      PRINT TABXY(1,4);"Settings          Hour:"
20310      PRINT TABXY(4,5);"Rate"
20320      PRINT TABXY(4,6);"FIO2"
20330      PRINT TABXY(4,7);"Peak Pres"
20340      PRINT TABXY(4,8);"Peep"
20350      PRINT TABXY(4,9);"TV"
20360      PRINT TABXY(4,10);"I:E ratio"
20370      PRINT TABXY(4,11);"Mean air"
```

```
20380      PRINT TABXY(1,12);"Blood Gases"
20390      PRINT TABXY(4,13);"ph"
20400      PRINT TABXY(4,14);"pO2"
20410      PRINT TABXY(4,15);"pCO2"
20420      PRINT TABXY(4,16);"HCO3"
20430      PRINT TABXY(4,17);"BE"
20440      Start=15
20450      FOR I=Vent_stl TO Vent_ptr
20460           PRINT TABXY(Start+10,4);Vent_time$(I)
20470           PRINT TABXY(Start+10,5);Rate(I)
20480           PRINT TABXY(Start+10,6);Fio2(I)
20490           PRINT TABXY(Start+10,7);Pp(I)
20500           PRINT TABXY(Start+10,8);Peep(I)
20510           PRINT TABXY(Start+10,9);Tv(I)
20520           PRINT TABXY(Start+10,10);Ie_ratio$(I)
20530           PRINT TABXY(Start+10,11);Airp(I)
20540           PRINT TABXY(Start+10,13);Ph(I)
20550           PRINT TABXY(Start+10,14);Po2(I)
20560           PRINT TABXY(Start+10,15);Pco2(I)
20570           PRINT TABXY(Start+10,16);Bgo3(I)
20580           PRINT TABXY(Start+10,17);Be(I)
20590           Start=Start+10
20600      NEXT I
20610      GOTO Finish
20620 !
20630 !
20640 Pres_val:!                    ....pressure values
20650      IF Pres_ptr>12 THEN Pres_stl=5
20660      IF Pres_ptr>17 THEN
20670           DISP "Do not input any more pressures;
                disc full"
20680           WAIT 3
20690           SUBEXIT
20700      END IF
20710      PRINT TABXY(9,3);"Time:"
20720      PRINT TABXY(1,4);"Systemic"
20730      PRINT TABXY(4,5);"systolic"
20740      PRINT TABXY(4,6);"diastolic"
```

```
20750        PRINT TABXY(4,7);"mean"
20760        PRINT TABXY(1,8);"Pulmonary"
20770        PRINT TABXY(4,9);"systolic"
20780        PRINT TABXY(4,10);"diastolic"
20790        PRINT TABXY(4,11);"mean"
20800        PRINT TABXY(1,12);"LA mean"
20810        PRINT TABXY(1,13);"RA mean"
20820        PRINT TABXY(9,14);"Time: "
20830        PRINT TABXY(1,15);"C.I."
20840        PRINT TABXY(1,16);"PVRI"
20850        PRINT TABXY(1,17);"SVRI"
20860        Start=15
20870        FOR I=Pres_stl TO Pres_ptr
20880            PRINT TABXY(Start,3);Pres_time$(I)
20890            PRINT TABXY(Start,5);Ao_s(I)
20900            PRINT TABXY(Start,6);Ao_d(I)
20910            PRINT TABXY(Start,7);Ao_m(I)
20920            PRINT TABXY(Start,9);Pa_s(I)
20930            PRINT TABXY(Start,10);Pa_d(I)
20940            PRINT TABXY(Start,11);Pa_m(I)
20950            PRINT TABXY(Start,12);La_m(I)
20960            PRINT TABXY(Start,13);Ra_m(I)
20970            Start=Start+5
20980        NEXT I
20990        Start=15
21000        FOR I=0 TO Heart_ptr
21010            PRINT TABXY(Start,14);Heart_time$(I)
21020            PRINT TABXY(Start,15);Ci(I)
21030            PRINT TABXY(Start,16);Pvri(I)
21040            PRINT TABXY(Start,17);Svri(I)
21050            Start=Start+5
21060        NEXT I
21070        GOTO Finish
21080!
21090!
21100 Drug:!                              ....hey man, drugs
21110        IF Drug_ptr>9 THEN Drug_stl=4
21120        IF Drug_ptr>14 THEN Drug_stl=9
```

```
21130      IF Drug_ptr>19 THEN Drug_stl=14
21140      IF Drug_ptr>24 THEN Drug_stl=19
21150      IF Drug_ptr>29 THEN Drug_stl=24
21160      IF Drug_ptr>34 THEN Drug_stl=29
21170      IF Drug_ptr>38 THEN
21180          DISP "do not enter more drugs; disc full"
21190          WAIT 3
21200          SUBEXIT
21210      END IF
21220      PRINT TABXY(30,4);"Drug Chart"
21230      PRINT TABXY(1,6);"Name"
21240      PRINT TABXY(30,6);"Dosage"
21250      PRINT TABXY(60,6);"Time"
21260      D_line=7
21270      FOR I=Drug_stl TO Drug_ptr
21280          PRINT TABXY(1,D_line);Drug_name$(I)
21290          PRINT TABXY(30,D_line);Drug_dos$(I)
21300          PRINT TABXY(60,D_line);Drug_time$(I)
21310          D_line=D_line+1
21320      NEXT I
21330 Finish: !
21340   SUBEND
21350   !
21360   !
21370   DEF FNLval(Lnum$)
21380      Numval=VAL("9"&Lnum$)
21390      If Num val=9 THEN
21400      Rval=9999.999
21410      RETURN Rval
21420      ELSE
21430      Numval=VAL(Lnum$)
21440      RETURN Numval
21450      END IF
21460      FNEND
10 Teaser7:!This program reviews data taken by sgrape
20      ! and allows all the graphs to be printed (when
30      ! its done)
40      !
```

```
50    !......................................................
60    !
70    ! LAST REVISION: 1 May  1985
80    !......................................................

90    !
100   !
110   !......................................................
120   !
130   ! SET UP ERROR HANDLERS
140   ! SET UP COMMON STORAGE/ARRAY STORAGE
150   !......................................................

160   !
170   !
171       COM /Vars/ Ffthrvar,Fftrespvar
180       COM /Intr_7/ Int_flag,Status_bytes(5)
190       COM /Flags/ Atod_done,Scanner_done,Memory1_
              done,Memory2_done,Timer_done,Counter_done,
                Memory3_done,Memory4_done
200       COM /Io_arrays/ Counters(3),Counters2(3),Time_
              base$[7]
210       COM /Multi_param/ Start_chan,Stop_chan,Pacing_
              bits,Pacing_rate,Num_pts,Num_xfer,
                Num_xfer_left,Name_len,Scr_file$[28],Scr_
                    file2$[28]
220       COM /Hr_sig/ Num_pulses,Last_pulse,First_blk_
              flg,Last_time,Num_hr_sig,Max
                _hr_pts,Avg_hr,Rollover,Hr_smooth
230       COM /Hr_stats/ Hr_histo(128),Histo_min,Histo_
              max,Num_fudge,Num_histo_pnts
                ,@Err_log
240       COM /Plot_par/ Plotbox,Boxcar_flg,Log_
              plotflg,Freq_limit,Resp_search,Pct_thresh
250       COM /Graphs/
              Hrdata(512),Hrspec(512),Respspec(512),Bpspec(512)
260       COM /Vitaldata/ Rfa,Lfa,Peakratio,Meas_resp,Next_
              time
```

```
270   COM /Idfield/ Id_field$[18]
280   COM /Messagecom/ Message$(10)[80],@Messages
290   COM /Trends/ Mean_hr_t(60),Lfa_t(60),Rfa_
      t(60),Ratio_t(60),T_ptr,Time_now
        1,Meas_resp_t(60)
300   DIM Msg_pad$(20)[80],Edit_msg$[80]
310   DIM Msg_buffer$[80] BUFFER
320   ASSIGN @Msg_buffer TO BUFFER Msg_buffer$
330   Log_plotflg=0
340   Freq_limit=1.
350   Resp_search=.1
360   Pct_thresh=.2
370   Scr_file$="?"
380   !
390   ! Set up common/array storage for waveform
        analysis
400   !
410   !........................................
420   !
430   ! Set up common/array storage for waveform
      ! analysis
440   !........................................

450   !
460   COM /Directory/ Dir$[160],@Printer
470   COM /Wf1/ Printer,Plotter,String$[40]
480   COM /Wf2/ Signal(8257),Number_pnts,Type,Sampling_
      period
490   COM /Wf3/ Segment_size,Overlap,Num_segments,Pnts_
      used,Fft_size
500   COM /Wf5/ Refn(63),Refd(63),Refno,Refdo,Refgain
510   COM /Autoparam/ Up_down,Up_delay,Dn_delay
520   COM /Fftcom/ INTEGER Bitrev(512),Sincos(512)
530   !
540   DISP "loading subroutines"
550   LOADSUB ALL FROM "hr_siggen8"
560   LOADSUB ALL FROM "automaxsb2"
570   LOADSUB ALL FROM "fft_anal6"
```

```
580    DISP "load data disks and press CONTINUE"
590    PAUSE
600    !
610    !..............................................
620    ! The HP 9826/9836 flexible disk (5-1/4") has the
         following structure
630    ! 2 sides, 33 tracks/side, 16 sectors/track, 256
         bytes/sector
640    !   1 track =    4096 bytes =    16 sectors
650    !   1 side  =  135168 bytes =   528 sectors
660    !   1 disk  =  270336 bytes =  1056 sectors
670    !   1 disk  =  135168 words =  132K words
680    !..............................................

690    !
700    !
710    INTEGER Hpib_buffer1(2048) BUFFER
720    INTEGER Hpib_buffer2(2048) BUFFER
730    DIM Hr_signal(1024) BUFFER
740    Read_ptr1=0
750    Read_ptr2=0
760 Begin: !
770 Selections: !
780    !
790    !
800    ! NOW SET UP THE SCAN CARD PARAMETERS (DEFAULT
       ! VALUES)
810    !       START CHANNEL (3.0) -  0
820    !        STOP CHANNEL (3.1) -  1
830    !             PACING (3.2) - 40 USEC
840    !        SEQN'L SCAN (3.3) - XXXX XXXX XXX1 (  1)
850    !      INTN'L PACING (3.3) - XXXX XXXX X1XX (  4)
860    !      MSEC TIMEBASE (3.3) - XXX1 XXXX XXXX (256)
870    !
880    CALL Get_param
890    !
900    ! set up the bit reverse index
910    !
```

```
920    Npair=Num_pts/2
930    K=0
940    FOR J=1 TO Npair-1
950        I=2
960        Ndivi=Npair/I
970        IF K<Ndivi THEN 1010
980        K=K-Ndivi
990        I=I+I
1000       GOTO 960
1010       K=K+Ndivi
1020       Bitrev(J+1)=K+1
1030   NEXT J
1040 !
1050 ! set up the sin/cosine table
1060 !
1070   Angl=ATN(1)*8/Npair
1080   FOR J=0 TO Npair-1
1090       Sincos(J)=SIN(Angl*J)
1100   NEXT J
1110 !
1120 ! set up other data  paths
1130 !
1140 ! ASSIGN @Err_log TO "errs"&Id_
            field$&":HP8290X,700,1";FORMAT OFF
1150 ! ASSIGN @Messages TO "msgs"&Id_
            field$&":HP8290X,700,1";FORMAT OFF
1160 ! ASSIGN @Temp_trend TO "trnd"&Id_
            field$&":HP8290X,700,1";FORMAT OFF
1170   IF Num_pts=0 THEN GOTO Begin
1180   Read_ptr1=0
1190 Setup_scan:DISP " NUMBER OF POINTS=";Num_pts
1200   Read_ptr1=0
1210   Read_ptr2=0
1220 Setup_counter:!
1230 Setup_clock:!
1240   Block_time=Pacing_rate*1.024
1250   First_blk_flg=1
1260   Num_msgs=0
```

```
1270    Message_line=0
1280    Msg_dp_request=0
1290    Resp_dpflg=0
1300    Max_hr_pts=1024
1310    Last_time=0
1320 !
1330 ! setup control parameters
1340 !
1350 Defaultset:!
1360    INPUT "use default settings?",Resp$
1370    IF Resp$="N" THEN Frqlimset
1380    Freq_limit=2.
1390    Pct_thresh=.2
1400    Resp_dpflg=1
1410    Resp_search=.2
1420    Hcdopyflg=0
1430    PRINT "Spectra displayed to";Freq_limit;"Hz"
1440    PRINT "resp peak search threshold=";Pct_thresh
1450    PRINT "resp series plot w/hr series"
1460    PRINT "resp peak search starts at";Resp_search;"Hz"
1470    PRINT "no hard copy will be printed"
1480    INPUT "is this ok?",Resp$
1490    IF Resp$<>"Y" THEN Defaultset
1500    GOTO Skipset
1510 Frqlimset:!
1520    INPUT "frequency limit?",Freq_limit   !..change spectra disp.freq.range
1530    IF Freq_limit<>1. THEN Freq_limit=2.
1540    PRINT "Spectra displayed to";Freq_limit;"Hz"
1550    INPUT "is this ok?",Resp$
1560    IF Resp$<>"Y" THEN Frqlimset
1570 Searchset:!
1580    INPUT "resp peak threshold?",Pct_thresh !..change peak search threshold
1590    IF Pct_thresh>.8 THEN Pct_thresh=.2
1600    PRINT "resp peak search threshold=";Pct_thresh
1610    INPUT "is this ok?",Resp$
```

```
1620     IF Resp$<>"Y" THEN Searchset
1630 Respdpset:!
1640     INPUT "display resp time series?",Resp$
             !..display respiration time series
1650     IF Resp$<>"N" THEN
1660         Resp_dpflg=1
1670         PRINT "resp series plot w/hr series"
1680     ELSE
1690         Resp_dpflg=0
1700         PRINT "cancel resp series plot"
1710     END IF
1720     INPUT "is this ok?",Resp$
1730     IF Resp$<>"Y" THEN Respdpset
1740 Resppkset: !
1750     INPUT "start for resp peak search?",Resp_
         search     !..change respiration
                         peak search
1760     IF Resp_search>Freq_limit-.1 THEN Resp_search=.1
1770     PRINT "resp peak search starts at";Resp_
         search;"Hz"
1780     INPUT "is this ok?",Resp$
1790     IF Resp$<>"Y" THEN Resppkset
1800 Hdcopyset: !
1810     INPUT "print hardcopy?",Resp$
1820     IF Resp$="N" THEN
1830         Hdcopyflg=0
1840         PRINT "no hard copy will be printed"
1850     ELSE
1860         Hdcopyflg=1
1870         PRINT "hard copy will be printed"
1880     END IF
1890     INPUT "is this ok?",Resp$
1900     IF Resp$<>"Y" THEN Hdcopyset
1910 Skipset:  !
1920     !
1930     ! Read data continuously
1940     !
1950     ! Set up the memory buffers and disk files
```

```
1960 !
1970 Reading:  !
1980   ASSIGN @In_buffer TO BUFFER Hpib_buffer1(*)
1990   ASSIGN @Diskbuffer TO Scr_file$;FORMAT OFF
2000   ASSIGN @In_buffer2 TO BUFFER Hpib_buffer2(*)
2010   ASSIGN @Diskbuffer2 TO Scr_file2$;FORMAT OFF
2020   !
2030   Data_lockout=0
2040 !
2050 ! generate id fields to identify data files
2060 !..........................................
2070 ! the first 256 bytes of the file are reserved for identification
2080 !
2090 ! the reserved data are:
2100 !     byte   1 - 72 ("H") or 82 ("R"): hr or resp_file
2110 !     byte   2 - year (at beginnig of expt.)
2120 !     byte   3 - month
2130 !     byte   4 - day
2140 !     byte   5 - hour
2150 !     byte   6 - minute
2160 !     byte   7 - collecting program date (0-365)
2170 !     byte   8 - collecting program year (1984-?)
2180 !     byte   9-16: unused
2190 !     byte   17 - pacing rate (0-32768)
2200 !     byte   18 - pacing rate units(77 ="M" or 85 ="U")
2210 !     byte   19 - number of transfers
2220 !     byte   20 - number of point/transfer (=1024)
2230 !     byte   21 - number of A/D channels used (=1)
2240 !     byte   22-256 : unassigned
2250 !
2260 !     the remainder of the file is data
2270 !     each transfer is preceded by an identifying string of 8 bytes
2280 !     byte 1 - time of day (timedate mod 86400)/60
2290 !     byte 2 - number of points in next transfer
```

```
2300 !      byte 3 - H/R (check to make sure this is the
            right file)
2310 !................................................
2320 !
2330 ! INTEGER Id_buffer(255) BUFFER
2340   Time_now=TIMEDATE
2350 ! Id_buffer(0)=72                     !..Heart rate file
2360   Date_now$=DATE$(TIMEDATE)
2370 ! Day_now=VAL(Date_now$)
2380 ! Year_now=VAL(Date_now$[8;4])
2390 ! Month_now=FNMonth(Date_now$)
2400 ! Id_buffer(1)=Year_now                !..year
2410 ! Id_buffer(2)=Month_now               !..month
2420 ! Id_buffer(3)=Day_now                 !..day
2430   Time_now1=Time_now MOD 86400
2440 ! Id_buffer(4)=Time_now1/3600          !..hour
2450 ! Id_buffer(5)=(Time_now1 MOD 3600)/60 !..min
2460 ! Id_buffer(6)=348                     !..pgm date
2470 ! Id_buffer(7)=1984                    !..pgm year
2480 ! Id_buffer(16)=Pacing_rate
2490 ! Id_buffer(17)=77                     !..MSEC
2500 ! Id_buffer(18)=Num_xfer
2510 ! Id_buffer(19)=1024                   !..num_pts
2520 ! Id_buffer(20)=1                      !..# channels
2530 !
2540 !
2550 ! read id field for heart rate file
2560 !
2570 ! ASSIGN @Id_buffer TO BUFFER Id_buffer(*)
2580 ! TRANSFER @Diskbuffer2 TO @Id_buffer;COUNT
     ! 256,WAIT
2590 ! ASSIGN @Id_buffer TO *
2600 !
2610 ! read id field for respiratory file
2620 !
2630 ! Id_buffer(0)=82                     !..Resp file
2640 ! ASSIGN @Id_buffer TO BUFFER Id_buffer(*)
2650 ! TRANSFER @Diskbuffer TO @Id_buffer;COUNT 256,WAIT
```

```
2660 ! ASSIGN @Id_buffer TO *
2670 !
2680 !
2690 !
2700 ! begin transferring data from the A/D buffer
2710 !
2720 Blk_xfer:!
2730    CONTROL @In_buffer,3;1
        ! Reset fill pointer for buffer
2740    CONTROL @In_buffer,4;0
        ! Reset current number of bytes in buffer
2750    CONTROL @In_buffer,5;1
        ! Reset empty pointer for buffer
2760 !
2770 ! read an 8 byte sequence to disk as a header for
     ! the transfer
2780 !
2790    CALL Rdheader(@Diskbuffer,Num_pts,"R")
2800 !
2810    Num_rdpts=Num_pts
2820    TRANSFER @Diskbuffer TO @In_buffer;COUNT Num_rdpts*2,CONT
2830    PRINT TABXY(1,18);
2840    PRINT USING Image_wt1;Num_xfer-Num_xfer_left+1,Num_xfer,TIME$(Next_time),
        Rdseg,Num_rdseg
2850 Image_wt1:IMAGE   "Next xfer(",K,"/",K,"): ",K,"    seg=",K,"/",K
2860 !
2870 ! store A/D buffer on complete data file (also
     !        save pointers for heart rate)
2880 !
2890 !
2900 Resume1:!
2910    Next_time=Next_time+INT(Block_time)
2920 !
2930 !
2940 !
```

```
2950 Resume2:!
2960    Num_xfer_left=Num_xfer_left-1
2970    CONTROL @In_buffer2,3;1
        ! Reset fill pointer for buffer
2980    CONTROL @In_buffer2,4;0
        ! Reset current number of bytes in buffer
2990    CONTROL @In_buffer2,5;1
        ! Reset empty pointer for buffer
3000    !
3010    ! read an 8 byte sequence to disk as a header for
        ! the transfer
3020    !
3030    CALL Rdheader(@Diskbuffer2,Num_pulses,"H")
3040    TRANSFER @Diskbuffer2 TO @In_buffer2;COUNT Num_
        pulses*2,WAIT
3050    !
3060 Resume5:!
3070    Histo_max=8000
3080    Histo_min=-8000
3090    CALL Hr_sig_gen(Hpib_buffer2(*),Hr_signal(*))
3100    !
3110    !
3120 Resume6:!
3130    OUTPUT 2;CHR$(255)&CHR$(75);
        ! Clear CRT of text
3140    GINIT
3150    PLOTTER IS 3,"INTERNAL"
3160    GRAPHICS ON
3170    Xscale=8
3180    Hr_max=MAX(Hr_signal(*))
3190    Hr_min=MIN(Hr_signal(*))
3200    VIEWPORT 0,64,50,100
3210    WINDOW 0,1,0,1
3220    AXES .1,.1,0,0
3230    CSIZE 4
3240    Hr_signal(1024)=0
3250    Hr_sigsum=SUM(Hr_signal)
3260    Mean_hr=INT((Hr_sigsum/1024+Avg_hr))
```

```
3270    LDIR 0
3280    LORG 3
3290    MOVE .2,.9
3300    LABEL "HR data    hr=";Mean_hr
3310    CSIZE 4
3320    MOVE .05,1
3330    LORG 3
3340    LABEL "250 bpm"
3350    WINDOW 1,0,1,0
3360    AXES 0,0,0,0
3370    IF Hr_dispflg=1 THEN
3380        WINDOW 0,1024,Hr_min,Hr_max
3390    ELSE
3400        Low_window=INT(-Avg_hr)
3410        High_window=Low_window+250.
3420        WINDOW 0,1024,Low_window,High_window
3430    END IF
3440    FOR I=0 TO 1023
3450        PLOT I,Hr_signal(I)
3460    NEXT I
3470    !CALL Pauser
3480    IF Fftskpflg=1 THEN GOTO Skip_fft
3490    !
3500    ! display respirations time series also
3510    !
3520    IF Resp_dpflg=1 THEN
3530        Max_resp=MAX(Hpib_buffer1(*))
3540        Min_resp=MIN(Hpib_buffer1(*))
3550        IF Mean_hr>100 THEN
3560            VIEWPORT 0,64,50,65
3570        ELSE
3580            VIEWPORT 0,64,75,90
3590        END IF
3600        WINDOW 0,1023,Min_resp,Max_resp
3610        MOVE 0,Hpib_buffer1(0)
3620        FOR I=1 TO 1023
3630            PLOT I,Hpib_buffer1(I)
3640        NEXT I
```

```
      3650   ELSE
      3660       Resp_dpflg=0
      3670   END IF
30    3680   !
      3690   ! now process heart rate data with waveform
             analysis package
      3700   ! make sure the hr_signal has zero mean
      3710   !
35    3711   MAT Signal= (0)
      3720   Hr_bias=Hr_sigsum/1024
      3730   FOR I=0 TO 1023
      3740       Signal(I)=Hr_signal(I)-Hr_bias
      3750   NEXT I
      3751   Hr_var=DOT(Signal,Signal)/1024
 5    3760   Plotbox=2
      3770   DISP "HR fft in process"
      3780   CALL Wf_analyzer(Pacing_rate)
      3790   !
      3800   ! now process respiration data with waveform
10           analysis package
      3810   !
      3820   MAT Signal= (0)
      3830   FOR I=0 TO 1023
      3840       Signal(I)=Hpib_buffer1(I)
15    3850   NEXT I
      3860   Signal_avg=SUM(Signal)/1024.
      3870   MAT Signal= Signal-(Signal_avg)
      3880   Plotbox=4
      3881   Respvar=DOT(Signal,Signal)/1024
20    3890   DISP "RESP fft in process"
      3900   CALL Wf_analyzer(Pacing_rate)
      3901   PRINT "hr_var,respvar";Hr_var;Respvar
      3902   PRINT "fft vars: ";Ffthrvar,Fftrespvar
      3910   Trend_dp=0 !..trend graph not displayed
25    3920   !
      3930   ! waveform analysis completed, compile trends and
             store in temporary file
      3940   !
```

```
3950      Mean_hr_t(T_ptr)=Mean_hr
3960      Lfa_t(T_ptr)=Lfa
3970      Rfa_t(T_ptr)=Rfa
3980      Ratio_t(T_ptr)=Peakratio
3990      Meas_resp_t(T_ptr)=Meas_resp
4000      T_ptr=T_ptr+1
4010      IF Hdcopyflg=1 THEN
4011          DUMP DEVICE IS 701
4020          DUMP GRAPHICS
4030          PRINTER IS 701
4040          PRINT "hr=";Mean_hr
4050          PRINT "lfa=";Lfa
4060          PRINT "rfa=";Rfa
4070          PRINT "ratio";Peakratio
4080          PRINT "RR";Meas_resp
4090          PRINT "transfer#";T_ptr
4091          PRINT "hr_var,respvar";Hr_var;Respvar
4092          PRINT "fft vars: ";Ffthrvar,Fftrespvar
4100          PRINTER IS 1
4110      END IF
4120  !
4130  ! continue with data collection
4140  !
4150 Skip_fft: !
4160      IF Num_xfer_left<=0 THEN
4170          GOTO Eo_blk_xfer
4180      ELSE
4190          DISP Num_xfer_left;"transfers remaining"
4200          WAIT 3
4210          GOTO Blk_xfer
4220      END IF
4230 Eo_blk_xfer:End_time=TIMEDATE
4240      Delta_time=End_time-Start_time
4250  !
4260      Stop_pacing=TIMEDATE
4270  !
4280 Aborter:!
4290      ASSIGN @In_buffer TO *
```

```
4300  ASSIGN @In_buffer2 TO *
4310  ASSIGN @Diskbuffer TO *
4320  ASSIGN @Diskbuffer2 TO *
4330 ! ASSIGN @Err_log TO *
4340 ! ASSIGN @Messages TO *
4350 ! ASSIGN @Temp_trend TO *
4360  CALL Pauser
4370  GRAPHICS OFF
4380  CALL Get_param
4390 ! ASSIGN @Err_log TO "errs"&Id_
      field$&":HP8290X,700,1";FORMAT OFF
4400 ! ASSIGN @Messages TO "msgs"&Id_
      field$&":HP8290X,700,1";FORMAT OFF
4410  IF Num_pts=0 THEN GOTO Begin
4420  GOTO Setup_scan
4430  END
4440  !
4450  !
4460  !
4470  !
4480  !
4490  SUB Pauser
4500     DISP "press CONTINUE to continue"
4510     PAUSE
4520     DISP
4530  SUBEND
4540  !
4550  !
4560  !
4570  !
4580  !
4590  SUB Get_param
4600     COM /Multi_param/ Start_chan,Stop_chan,Pacing_
         bits,Pacing_rate,Num_pt
         s,Num_xfer,Num_xfer_left,Name_len,Scr_
         file$[28],Scr_
         file2$[28]
4610     COM /Trends/ Mean_hr_t(*),Lfa_t(*),Rfa_
         t(*),Ratio_t(*),T_ptr,Time_now
```

```
             1,Meas_resp_t(*)
    4620     COM /Vitaldata/ Rfa,Lfa,Peakratio,Meas_
             resp,Next_time
    4630     COM /Idfield/ Id_field$
    4640     DIM Mo$[24]
    4650     Mo$="JAFBMRAPMYJNJLAUSPOCNODC"
    4660     INTEGER Id_buffer(255) BUFFER
    4670     Disk_name$=":HP8290X,700,1"
    4680 Oldmsg:PRINT CHR$(12)
    4690 !
    4700 !
    4710 Ch_sel:!
    4720     Start_chan=0
    4730     Stop_chan=0
    4740 !
    4750     Pacing_bits=0
    4760 Pacing_sel:!
    4770     Base$="M"
    4780     Pacing_bits=261
    4790 !
    4800     Base$=Base$&"SEC"
    4810 !
    4820 !
    4830 ! FINDOUT BLOCKSIZE FOR DATA TRANSFER
    4840 !
    4850 Get_xfer:DISP "Enter number of transfers: (0 -
             change scan, <0 - quit)"
    4860     OUTPUT 2;55;
    4870     ENTER 2;Num_xfer
    4880     IF Num_xfer<0 THEN      !..terminate program
    4890         INPUT "to lose trend data type
                 'lose'",Response$
    4900         IF Response$<>"lose" THEN
    4910             CREATE BDAT
                     "teasertrnd:HP8290X,700,1",19,256
    4920             ASSIGN @Trndfile TO
                     "teasertrnd:HP8290X,700,1";FORMAT OFF
    4930             OUTPUT @Trndfile;Mean_hr_t(*),Lfa_
                     t(*),Rfa_t(*),Ratio_t(*),Me
```

```
                              as_resp_t(*),T_ptr
4940                ASSIGN @Trndfile TO *
4950             END IF
4960             DISP "PROGRAM COMPLETED"
4970             STOP
4980          END IF
4990          IF Num_xfer=0 THEN
5000             Num_pts=0
5010             SUBEXIT
5020          END IF
5030 !
5040 ! since new data is to be taken, zero the trend
     graphs (120 pts=8hrs)
5050 !
5060          MAT Mean_hr_t= (0)
5070          MAT Rfa_t= (0)
5080          MAT Lfa_t= (0)
5090          MAT Ratio_t= (0)
5100          MAT Meas_resp_t= (0)
5110          T_ptr=0
5120          Ratio_t(0)=1 !..prevent trend graph errors on
               startup
5130          Rfa=0
5140          Lfa=0
5150          Meas_resp=0
5160          Peakratio=1
5170 !
5180 Intvl_sel:DISP "ENTER PACING RATE (IN
     ";Base$[1,4];"):"
5190          OUTPUT 2;250;
5200          ENTER 2;Pacing_rate
5210          IF Pacing_rate<0 OR Pacing_rate>65535 THEN
               GOTO Intvl_sel
5220 !
5230          Num_pts=1024*Num_xfer
5240          Num_header=256+8*Num_xfer
```

```
5250      INPUT "type in date on which data was
          taken",Datdate$
5251      INPUT "is trend file named 'trnd' (1) or
          'temp_trend' (2)?",File_nm
5260      Datdate$=DATE$(DATE(Datdate$))
5270 !
5280 ! the data files are named according to the date
5290 ! in the following format:
5300 !     xxxxmmddyy
5310 ! where
5320 !     xxxx - resp,hr__,msgs,errs,trnd
5330 !     dd   - day
5340 !     mm   - month
             (JA,FB,MR,AP,MY,JN,JL,AU,SP,OC,NO,DC)
5350 !     yy   - year
5360      Month_now=FNMonth(Datdate$)*2-1
5370      Mm$=Mo$[Month_now;2]
5380      Id_field$=Datdate$[1;2]&Mm$&Datdate$[10;2]
5390 ! new name for respiratory file: respddmmyy
5391 IF File_nm=1 THEN
5400      Scr_file$="resp"&Id_field$&Disk_name$
5410 ! new name for heart rate file: hr__ddmmyy
5420      Scr_file2$="hr__"&Id_field$&Disk_name$
5421      ELSE
5422          Scr_file$="AOK"&Disk_name$
5423          Scr_file2$="hrAOK"&Disk_name$
5424      END IF
5430 ! new name for errorlog: errsddmmyy
5440 ! new name for message log: msgsddmmyy
5450 ! name for trend summary file: trndddmmyy
5460      Num_rec=-INT(-(Num_pts+Num_header)/128.)
5470      Num_pts=1024
5480      PRINT Num_pts*Num_xfer;"points were
          transferred in";Num_xfer;"blocks
          of";Num_pts;"points"
5490 !
```

```
5500        Num_xfer_left=Num_xfer
5510    SUBEND
5520    !
5530    !
5540    !
5550    !
5560    DEF FNMonth(Date_now$)
5570        Month$=Date_now$[4;3]
5580        Month=0
5590        IF Month$="Jan" THEN Month=1
5600        IF Month$="Feb" THEN Month=2
5610        IF Month$="Mar" THEN Month=3
5620        IF Month$="Apr" THEN Month=4
5630        IF Month$="May" THEN Month=5
5640        IF Month$="Jun" THEN Month=6
5650        IF Month$="Jul" THEN Month=7
5660        IF Month$="Aug" THEN Month=8
5670        IF Month$="Sep" THEN Month=9
5680        IF Month$="Oct" THEN Month=10
5690        IF Month$="Nov" THEN Month=11
5700        IF Month$="Dec" THEN Month=12
5710        RETURN Month
5720    FNEND
5730    !
5740    !
5750    !
5760    !
5770    !
5780    SUB Rdheader(@Disk,Num_bytes,File_id$)
5790        INTEGER Xheader(7) BUFFER
5800        ASSIGN @Xheader TO BUFFER Xheader(*)
5810        TRANSFER @Disk TO @Xheader;COUNT 16,WAIT
5820        ASSIGN @Xheader TO *
5830        Num_bytes=Xheader(1)
5840        File_id$=CHR$(Xheader(2))
5850    SUBEND
```

```
5860  !
5870  !
5880  !
5890  !
5900  !
5910  !
5920     SUB Trend_graph
5930  !
5940        COM /Trends/ Mean_hr_t(*),Lfa_t(*),Rfa_
            t(*),Ratio_t(*),T_ptr,Time_now
              1,Meas_resp_t(*)
5950        COM /Multi_param/ Start_chan,Stop_chan,Pacing_
            bits,Pacing_rate,Num_pt
            s,Num_xfer,Num_xfer_left,Name_len,Scr_
               file$[28],Scr_
            file2$[28]
5960        Block_time=Pacing_rate*1.024/3600.
5970        GINIT
5980        GCLEAR
5990        PRINT CHR$(12)
6000        GRAPHICS ON
6010        PRINT TABXY(1,18);"trend graph"
6020        Beg_time=Time_now1/3600-Block_time
6030        End_time=Beg_time+Num_xfer*Block_time
6040        Ibeg_time=INT(Beg_time)
6050        IF Ibeg_time<Beg_time THEN Ibeg_time=Ibeg_
            time+1
6060  !
6070  ! label the time axes
6080  !
6090        VIEWPORT 0,128,45,50
6100        WINDOW Beg_time,End_time,0,1
6110        IF INT(End_time)>Beg_time THEN
6120           LDIR 0
6130           FOR T_label=Ibeg_time TO INT(End_time)
6140              MOVE T_label,.5
```

```
6150            LORG 5
6160            CSIZE 4
6170            LABEL T_label
6180         NEXT T_label
6190      END IF
6200      VIEWPORT 0,128,40,45
6210      WINDOW 0,1,0,1
6220      MOVE .5,0
6230      LORG 4
6240      LABEL "Time (24 hr)"
6250 !
6260 ! draw the axes
6270 !
6280      VIEWPORT 0,128,50,100
6290      WINDOW Beg_time,End_time,0,1
6300      AXES 1/15.,.1,Beg_time,0
6310      WINDOW 1,0,1,0
6320      AXES 0,.25,0,0
6330 !
6340 ! mean heart rate trends
6350 !
6360      WINDOW -1,Num_xfer,0,200.
6370      MOVE 0,Mean_hr_t(0)
6380      FOR I=0 TO T_ptr-1
6390         DRAW I,Mean_hr_t(I)
6400      NEXT I
6410 !
6420 ! lfa trends
6430 !
6440      WINDOW -1,Num_xfer,0,10.
6450      LINE TYPE 4,5
6460      MOVE 0,Lfa_t(0)
6470      FOR I=0 TO T_ptr-1
6480         DRAW I,Lfa_t(I)
6490      NEXT I
6500 !
```

```
6510 ! rfa trends
6520 !
6530         WINDOW -1,Num_xfer,0,10.
6540         LINE TYPE 5,5
6550         MOVE 0,Rfa_t(0)
6560         FOR I=0 TO T_ptr-1
6570             DRAW I,Rfa_t(I)
6580         NEXT I
6590 !
6600 ! ratio trends (with a line at ratio=2)
6610 !
6620         WINDOW -1,Num_xfer,-2.5,2.5
6630         LINE TYPE 8,5
6640         MOVE 0,LGT(Ratio_t(0))
6650         FOR I=0 TO T_ptr-1
6660             DRAW I,LGT(Ratio_t(I))
6670         NEXT I
6680         LINE TYPE 3,5 !..sparsely dotted line at ratio=2
6690         MOVE 0,LGT(2.)
6700         DRAW T_ptr-1,LGT(2.)
6710 !
6720 ! respiration trends
6730 !
6740         WINDOW -1,Num_xfer,0,200
6750         LINE TYPE 5,10
6760         MOVE 0,Meas_resp_t(0)
6770         FOR I=0 TO T_ptr-1
6780             DRAW I,Meas_resp_t(I)
6790         NEXT I
6800 !
6810 ! draw a key for line types
6820 !
6830         VIEWPORT 64,128,0,50
6840         WINDOW 0,1,0,13
6850         PRINT TABXY(55,15);"mean hr(0-200)"
6860         PRINT TABXY(55,16);"lfa    (0-10)"
6870         PRINT TABXY(55,17);"rfa    (0-10)"
6880         PRINT TABXY(55,18);"ratio(.01-100)"
```

```
6890        LINE TYPE 1,5
6900        MOVE .8,11
6910        DRAW 1.,11
6920        LINE TYPE 4,5
6930        MOVE .8,10
6940        DRAW 1.,10
6950        LINE TYPE 5,5
6960        MOVE .8,9
6970        DRAW 1.,9
6980        LINE TYPE 8,5
6990        MOVE .8,8
7000        DRAW 1.,8
7010        LINE TYPE 1,5
7020    SUBEND
```

```
' CALIB - program to calibrate instruments using
    board#1
' last revision: 4 April 1985 defint a-y         ' only z denotes a real number
dim buffer(12800)
hrbpm=0
zfqlow=0.
zfqres=0.
zlfa=0.
zrfa=0.
cls 'define ports on 8253
timer0=&h720
timer1=&h721
timer2=&h722
con8253=&h723
```

```
        ' set timer modes to 16 bit square wave rate
            generators
        out con8253,&h36
        out con8253,&h76
        out con8253,&hB6

'for testing set timer 0 to 100Hz timebase
'2.38MHz/23864: 23864=93*256+56
'set timer 0 to 1280Hz timebase
'(2.38MHz/1864) (1864=7*256+72)
'set timer 1 as a 1Hz clock at startup
'(gives a heart rate signal at
'60bpm) 'set timer 2 as a flip flop
        out timer0,56
        out timer0,93
        out timer0,72
        out timer0,7
        out timer1,0
        out timer1,5
        hrbpm=60
        out timer2,2
        out timer2,0

' turn the gates on using the 8255 at bits 0,1,2
on portc
        porta=&H700
        portb=&H708
        portc=&H710
        con8255=&H718

' first set all 8255 ports to output, then set
portc to 0FFH
        out con8255,128
        out portc,&H0FF
```

```
        ' first print out the present value of the
interrupt vectors
        locate 4,1
30      gosub 10000

' install the interrupt with a dummy buffer and
            print vectors
35      reseter=256
        call wrbuffer(reseter)
        reseter=128
        call wrbuffer(reseter)
        call instint
        locate 5,1
5       gosub 10000

' now go through required startup subroutines
        gosub 90                ' set up breathing
10  signal
        gosub 70                ' set up heart rate
variations
        gosub 50                ' put some information
on screen
15      gosub 80                ' turn D/A on
        locate 1,1
        print "commands: h(rvar),i(nt
on),q(uit),r(beats),b(reath),c(ounts)"

20

' wait until user hits a key
        savekey$=""
40      while
len(savekey$)=0:savekey$=savekey$+inkey$:wend
25      if savekey$="r" then gosub 50    'print heart
    beats
        if savekey$="q" then goto 9996   'quit
        if savekey$="c" then gosub 60    'print timers
        if savekey$="h" then gosub 70    'set up heart
```

```
30      rate
                ' variations
                if savekey$="i" then gosub 80    'unmask
        interrupts
                if savekey$="b" then gosub 90    'set up
35      breathing signal
                savekey$=""
                goto 40

'print present value of heartbeats 5       50      locate 7,1
                call rdbeat(n)
                print "present heart beats are: ";n;time$
                return 10
                ' print present value of counters
        60      out control,0              'latch timer0
                tlow0=inp(timer0)
                thigh0=inp(timer0)
15              out control,&h40           'latch timer1
                tlow1=inp(timer1)
                thigh1=inp(timer1)
                out control,&h80           'latch timer2
                tlow2=inp(timer2)
20              thigh2=inp(timer2)
                locate 8,1
                print "timer0: ";tlow0+thigh0*16;tab(20);"
        timer1:
                ";tlow1+thigh1*16;
25              print tab(40);"timer2: ";tlow2+thigh2*16
                return 30              ' set up the heart rate variations
                '       respiratory frequency is given by
```

```
                                1280Hz/buffer
                     '          length
                     '          low frequency is 1280Hz/low frequency
35        divider
                     '
          70         if numval<=0 then beep:print "setup analog
     buffer
                        first":return
          71         locate 17,1
 5                   print "present lfa,rfa(bpm)= ";zlfa,zrfa,"at
     freqs(Hz):
                        ";zfqlow,zfqres
                     input "lfa,rfa,low freq: ",zlfan,zrfan,zfqlown
                     if zlfan>30. then beep:goto 71 else zlfa=zlfan
10                   if zrfan>30. then beep:goto 71 else zrfa=zrfan
                     if zfqlown<.02 or zfrlown>zfqres then beep:goto
     71 else
                        zfqlow=zfqlown
                     locate 21,1
15                   print "mean heart rate(bpm)= ";hrbpm
          72         locate 22,1
                     input "new mean heart rate(bpm): ",newhrbpm
                     if newhrbpm>150 or newhrbpm<30 then beep:goto 72
     else
20                   hrbpm=newhrbpm
                             'clear screen after input
                     locate 17,1
                     print space$(72)
                     print space$(72)
25                   print space$(72)
                     print space$(72)
                     print space$(72)

30                   ' now compute values for hrsetup subroutine
                     meandiv=76800#/hrbpm     '1280*60 ticks/min gives
                        ticks/beat
                     rfascal=76800#/(hrbpm-zrfa)-76800#/(hrbpm+zrfa)
```

```
                    ' rfascal is the total excursion
                    of
                    ' respiration
lfascal=76800#/(hrbpm-zlfa)-76800#/(hrbpm+zlfa)
                    ' lfascal is the total excursion
                                 of low frequency
lowdiv=meandiv-(rfascal+lfascal)/2# tbaserst=1280#/zfqlow
locate 17,1
print "tbaserst,rfascal,lfascal,lowdiv:
     ";tbaserst;rfascal;lfascal;
print lowdiv
call hrsetup(tbaserst,rfascal,lfascal,lowdiv)

return

' print out interrupt controller parameters
80        locate 10,1
          mask=inp(&h21)
          if (mask mod 16)<8 then mask=mask+8 else mask=mask-8
          out &h21,mask
          mask=inp(&h21)
          print "8259 IMR(interrupt mask regsiter)=
";mask;"
                  =";hex$(mask)
          return ' this subroutine will change the analog buffer
90        locate 12,1
          input "enter breathing rate (bpm): ",brate
          if brate>75 or brate<7 then beep:goto 90
          zfqres=brate/60#
          numval=76800#/brate
```

```
            ztincr=8*ATN(1#)/numval
            locate 12,40
            color 31:print "calculating respiratory
  signal...":color 7
            call exstint          ' turn off interrupts
                                    while resetting buffer
            reseter=256
            call wrbuffer(reseter)
            for itime=0 to numval
                ztnow=ztnow+ztincr
                analogval=127*(1#+SIN(ztnow))
                call wrbuffer(analogval)
            next itime
            call instint
            locate 12,40
            print "respiratory signal active now      "
            return ' exstall the interrupt and print vector
    9996    cls
            locate 4,1
            gosub 10000
            call exstint
            locate 5,1
            gosub 10000
            locate 21,1
    9999    stop ' subroutine to print out the interrupt vectors 10000   def seg=0
            print "IRQ3 @0B*4H: ";hex$(peek(&h2C));"
                ";hex$(peek(&h2D));" ";
```

```
        print hex$(peek(&h2E));" ";hex$(peek(&h2F));tab(40);
        print "IRQ4 @0C*4H: ";hex$(peek(&h30));" ";hex$(peek(&h31));" ";
        print hex$(peek(&h32));" ";hex$(peek(&h33))
        return end
                        page    66,80
; bdzint.asm - an assembler routine to handle interrupts
;               from IRQ3
; Last revision:  1 April 1985
;
;

;---------------------------------;
                ; 8088 interrupt location         ;
                ;---------------------------------;

abs0            segment at 0    ;absolute memory segment
                                ;allows placement of
                                ;interrupt address
                                ;future timebase
                                ; interrupt handler
                                ; resides at int 0B
IRQ3_int        dw      2 dup(?);offset value is a word org     0CH*4   ;heart beat interrupt
                                ;handler resides at int
                                ; 0C
IRQ4_int        dw      2 dup(?);offset value is a word abs0            ends            ;

;---------------------------------;
                ; int_buffer: area to save DOS    ;
                ;       dummy interrupt ptr       ;
                ;---------------------------------;
```

```
        int_buffer      segment            ;data segment containing
                                           ;user interrupt buffer
        save_int        dw       4 dup(?)  ;offset for two DOS
                                           ;interrupts saved
                                           ;to be restored using
                                           ;exstint int_buffer      ends               ;

;---------------------------;
                        ; working storage for       ;
                        ; time base interrupts      ;
                        ;---------------------------;

dseg_tbase      segment            ;data segment for timebase
                                           ; interrupt
        heartbeats      dw       ?         ;keep track of heart beats
                                           ; here (for debugging)
        base_rate       dw       ?         ;lowest divisor for heart
                                           ; rate
        lfa_scal        db       ?         ;low frequency modulation
        rfa_scal        db       ?         ;high frequency modulation
        tbase_ctr       dw       ?         ;counter for timebase
                                           ; interrupt
                                           ;(use for low frequency
                                           ;  generation)
        tbase_rst       dw       ?         ;reset value for tbase_ctr
                                           ; used to set low frequency
        tbase_ptr       dw       ?         ;pointer to present analog
                                           ; value
        tbase_len       dw       ?         ;length of analog data buffer
        tbase_buffer    db    2800dup(?)   ;buffer for A/D values
        dseg_tbase      ends               ;
```

```
                    ;-----------------------------------;
                    ; setup structures to allow access to;
                    ; arguments pased by BASIC           ;
                    ;-----------------------------------;

; subroutine rdbeat(BASIC_beats)
    frame_rd    struc           ;define the stack
                                ;structure for passing
                                ;arguments to BASIC
    savebp1     dw      ?       ;caller's base pointer
    saveret1    dd      ?       ;return offset and
                                ;segment pushed by BASIC
    BASIC_beats dw      ?       ;place to return heart
                                ;beats to BASIC
    frame_rd    ends ;subroutine wrbuffer (analog)
    frame_wr    struc   ;define the stack structure
                        ;   for passing
                        ;arguments from BASIC to
                        ;   analog buffer
    savebp2     dw      ?       ;caller's base pointer
    saveret2    dd      ?       ;return offset and segment
                                ;   pushed by BASIC
    analog      dw      ?       ;place to receive analog value
                                ;   from BASIC
    frame_wr    ends ;subroutine hrsetup(B_lreset,
                    ;   Brfa_scal,Blfa_scal,Bbase_
                    ;   rate)
    frame_hr    struc   ;define the stack structure for
                        ;   passing
                        ;arguments from BASIC to heart
                        ;   rate controls
```

```
        savebp3     dw      ?       ;caller's base pointer
        saveret3    dd      ?       ;return offset and segment pushed
                                    ;   by BASIC
        Bbase_rate  dw      ?       ;BASIC's lowest divider for heart
                                    ;   rate
        Blfa_scal   dw      ?       ;BASIC's low frequency scaler
                                    ;   (amplitude)
        Brfa_scal   dw      ?       ;BASIC's high frequency scaler
                                    ;   (amplitude)
        B_lreset    dw      ?       ;BASIC's low frequency timer
                                    ;   reset value
        frame_hr    ends ;..........code segment begins here cseg_calibs     segment 'code'
        basic_dgroup    group   data,stack,const,heap,memory
                                        ;defining link to BASIC
        porta           equ     0700H   ;port definitions for
                                        ;8255 port expander
        portb           equ     0708H   ;these addresses are
                                        ;decoded on the homemade
        portc           equ     0710H   ;board
        control         equ     0718H   ;control word in the
                                        ;8255
        timer0          equ     0720H   ;8253 timer0 register
        timer1          equ     0721H   ;8253 timer1 register
        timer2          equ     0722H   ;8253 timer2 register
        con8253         equ     0723H   ;8253 control register ;-------------------------------------------------;
        ; timebase interrupt handler (not accessible to;
        ; BASIC)                                          ;
        ;-------------------------------------------------;
                            ;this routine reads the A/D every timer0
```

```
                                ;tick
                                ;with the next point in the analog
                                ;buffer tbase_int       proc    far     ;this procedure is not
                                        ;made public
                        assume  cs:cseg_sync,ds:dseg_
                           base,es:nothing,ss:nothing
                        push    ax      ;save registers used
                                        ;during interrupt
                        push    bx      ;
                        push    dx      ;
                        push    ds      ;

mov     ax,dseg_base    ;set up segment
                                                ;register for data area
                        mov     ds,ax           ;

;..........increment counter used for
                                    ;low frequency generation
                        dec     tbase_ctr       ;decrement
                                                ;interrupt counter
                        jnz     ctr_ok          ;if not zero then
                                                ;continue
                        mov     ax,tbase_rst    ;else reload reset
                                                ;value
                        mov     tbase_ctr,ax    ;
                        ctr_ok:
                                ;..........get analog value from
                                 ;buffer and send to DAC mov     bx,tbase_ptr    ;get pointer to
```

```
                                        ;analog data
            dec    bx                   ;
            mov    al,tbase_buffer[bx]  ;get analog
                                        ;value mov    dx,porta             ;send analog value
                                        ;to DAC
            out    dx,al                ;

mov    dx,control           ;toggle the write
                                        ;latch for the DAC
            mov    al,6                 ;by using direct
                                        ;bit reset
            out    dx,al                ;and
            inc    al                   ;reset commands
            out    dx,al                ;

dec    tbase_ptr            ;point to next
                                        ;value
            jnz    tbase_eoi            ;if zero, reset
                                        ;pointer
            mov    ax,tbase_len         ;reset with buffer
                                        ;length
            mov    tbase_ptr,ax         ;

;..........acknowledge interrupt to
            ;             8259A
tbase_eoi:  mov    al,20H               ;send EOI to 8259A
            out    20H,al               ;

pop    ds                   ;restore registers which
                                        ;were used
            pop    dx                   ;
            pop    bx                   ;
            pop    ax                   ;
            iret                        ;return to place where
```

;interrupt occurred

```
        debugmsg1       db      'this is the end of the time
                                 base interrupt' tbase_int       endp
```

```
;----------------------------------------;
; heart beat interrupt handler (not accessible ;
; to BASIC)                               ;
;----------------------------------------;

;this routine updates the timer1 rate generator
;every heart beat with the divider necessary to
;generate the next heart beat
;
;the respiratory modulation is given by a scaler
;   (0-255)
;times the present value of the respiratory
;   signal.
;the low frequency modulation is given by scaler
;   (0-255)
;times a value selected from the respiratory
;   buffer.
;the value selected is the
;   (tbase_ctr/tbase_rst)*buffer_length
;element hbeat_int       proc    far     ;this procedure is not
                                        ;made public
                        assume  cs:cseg_calibs,ds:dseg_tbase
                        assume  es:nothing,ss:nothing
```

```
        push    ax              ;save registers during
                                ;interrupt
        push    bx              ;
        push    cx              ;
        push    dx              ;
        push    ds              ;

mov     ax,dseg_tbase   ;set up segment
                                ;register for data area
        mov     ds,ax           ;

inc     heartbeats      ;increment heart
                                ;    beat counter ;........calculate low frequency modulation
;          (the tbase buffer is used as a trig
;             table here)
        mov     ax,tbase_ctr    ;get number of 1280Hz
                                ;pulses
        dec     ax              ;
        mul     tbase_len       ;scale by length of
                                ;  respiratory
                                ;  buffer
        div     tbase_rst       ;divided by reset
                                ;value to get
                                    pointer
        mov     bx,ax           ;to low frequency
                                ;  modulation
        mov     al,tbase_buffer[bx]   ;get sinusoidal
                                ;         modulation
        mul     lfa_scal        ;and scale
                                ;   appropriately
        mov     cx,ax           ;cx accumulate
                                ;divider for 1280Hz
                                    clock
```

```
;........calculate respiratory modulation
    mov    bx,tbase_ptr       ;get present
                              ;respiration signal
    mov    al,tbase_buffer[bx]   ;from buffer
    mul    rfa_scal           ;scale with rfa scaler
    add    cx,ax              ;and add to cx add    cx,base_rate       ;finally add base rate
                              ;to get
                              ;  value for
                              ;timer1 (heart rate
                              ;generator on
                              ;   8253)

;........send new divider to 8253 timer
    mov    al,76H             ;set timer 1 to square
                              ;  wave
                              ;  generator
    mov    dx,con8253         ;
    out    dx,al              ;

mov    dx,timer1          ;send divider to
                              ;time1
    mov    al,cl              ;low byte first
    out    dx,al              ;
    mov    al,ch              ;high byte next
    out    dx,al              ;

;..........acknowledge interrupt to
;             8259A
    mov    al,20H   ;send EOI to 8259A
    out    20H,al   ;

pop    ds                 ;restore registers and
    pop    dx                 ;
    pop    cx                 ;
```

```
                        pop     bx      ;
                        pop     ax      ;
                        iret            ;return to place where
                                        ;interrupt occurred debugmsg2       db      'this is the end of the heart
                                 beat interrupt' hbeat_int       endp

;------------------------------------------------;
                ; subroutine instint (install_interrupts)        ;
                ;------------------------------------------------;

instint         proc    far
                        public  instint
                        ;public symbol allows external references
                        ;es,ds used to access interrupt and must
                        ; be restored movsw
                        ;uses (ds:si)(es:di) addr
                        assume  cs:cseg_calibs,ss:basic_
                            dgroup,ds:basic_dgroup
                        assume  es:int_buffer ;..........save registers
                        push    ds      ;save ds register on the
                                        ;   stack
                        push    es      ;save es register on the
                                        ;   stack push    bp      ;save BASIC base pointer
                                        ;     for return to BASIC
                        mov     bp,sp   ;point stack pointer at
```

```
                        ;frame reference to
                        ;address of BASIC analog
                        ;data buffer push    ax      ;save additional
                        ;registers
        push    si      ;
        push    di      ;

;set up the segment registers as assumed mov     ax,int_buffer   ;
        ;es points to buffer area to save
        ;DOS dummy interrupt vector
        mov     es,ax           ;
        mov     ax,0            ;ds points to
                                ;abs0 (interrupt table)
        mov     ds,ax           ;
        assume  ds:abs0         ;

;setup access to interrupt vectors
        lea     di,save_int     ;load offset of
                                ;save_int in es,di
        lea     si,IRQ3_int     ;load offset of
                                ;IRQ3_int in ds,si
        movsw                   ;save DOS dummy
                                ;interrupt vectors to be
        movsw                   ;restored later
        movsw                   ;now saving IRQ4
        movsw                   ;

;install the DAC timebase (IRQ3)
        mov     IRQ3_int+2,cseg_calibs
        mov     IRQ3_int,offset tbase_int;
                        ;interrupt handler now
```

;install the heart beat (IRQ4) interrupt handler now
                mov     IRQ4_int+2,cseg_calibs;
                mov     IRQ4_int,offset hbeat_int;

;..........return to BASIC pop     di      ;restore additional
                                 registers
                pop     si      ;
                pop     ax      ;

pop     bp      ;restore BASIC's base
                                ;pointer and
                pop     es      ;segment registers
                                 before returning
                pop     ds      ;
                ret     0       ;delete 0 parameters (0
                                ;bytes) from the stack
                                ;and return to the
                                ;calling routine debugmsg3   db      'this is the end of the
                        interrupt installation' instint     endp

;----------------------------------------;
                ; subroutine exstint (exstall_           ;
                ; interrupts)                            ;
                ;----------------------------------------;

```
exstint     proc    far
            public  exstint ;public symbol allows
                            ;external references
            assume  cs:cseg_calibs,ss:basic_dgroup
            assume  ds:int_buffer,es:abs0
            ;es,ds used to access interrupt
            ;vectors and must be restored
            ;movsw uses (ds:si)(es:di) addr ;..........save registers push    ds      ;save ds register on the
                            ;   stack
            push    es      ;save es register on the
                            ;   stack
            push    bp      ;save BASIC base pointer
                            ;   for return to BASIC
            mov     bp,sp   ;point stack pointer at
                            ;   frame reference to
                            ;access arguments passed
                            ;   by BASIC (none here)

push    ax      ;save additional
                            ;registers
            push    si      ;
            push    di      ;
                            ;set up the segment
                            ;   registers as assumed
            mov     ax,0            ;es points to
                            ;abs0 (interrupt table)
            mov     es,ax           ;
            mov     ax,int_buffer   ;ds points to
                            ;buffer area to save
            mov     ds,ax           ;DOS dummy
                            ;interrupt vector
```

```
                ;setup access to interrupt vectors
        lea     di,IRQ3_int     ;load offset of
                                ;IRQ3_int in es,di
        lea     si,save_int     ;load offset of
                                ;save_int in ds,si
        movsw                   ;restore DOS
                        ;dummy interrupt vectors
        movsw                   ;for IRQ3
        movsw                   ;and IRQ4
        movsw                   ;

;..........return to BASIC pop     di      ;restore additional
                        ;  registers
        pop     si      ;
        pop     ax      ;

pop     bp      ;restore BASIC's base
        pop     es      ;pointer and segment
        pop     ds      ;registers before
                        ;returning
        ret     0       ;delete 0 parameters (0
                        ;bytes) from the stack
                        ;and return to the
                        ;calling routine debugmsg4       db      'this is the end of the
                        interrupt exstallation' exstint         endp
```

```
;----------------------------------;
; subroutine rdbeat (read_heart_beats  ;
;----------------------------------;

rdbeat          proc    far
                public  rdbeat          ;public symbol allows
                                        ;external references
                assume  cs:cseg_calibs,es:dseg_tbase
                assume  ds:basic_dgroup,ss:basic_dgroup ;..........save registers push    bp              ;save BASIC base pointer
                                        ;for return to BASIC
                mov     bp,sp           ;point stack pointer at
                                        ;frame reference to
                                        ;access arguments passed
                                        ;by BASIC (one here)

push    ax              ;save additional
                                        ;registers
                push    es              ;
                push    di              ;

mov     ax,dseg_tbase   ;set up segment
                                        ;register for data area
                mov     es,ax           ;

mov     ax,heartbeats           ;get
                                        ;beats from local memory
                mov     di,[bp].BASIC_beats     ;
                mov     [di],ax                 ;send
```

;beats to BASIC

;..........return to BASIC

```
        pop     di      ;restore additional
                        ; registers
        pop     es      ;
        pop     ax      ;

pop     bp      ;restore BASIC's base
                        ;pointer,
        ret     2       ;delete 2 parameters (4
                        ;bytes) from the stack
                        ;and return to the
                        ;calling routine debugmsg5       db      'this is the end of the heart
                        beat read routine' rdbeat  endp

;----------------------------------------;
; subroutine wrbuffer(analog)            ;
;----------------------------------------;

wrbuffer        proc    far
                public wrbuffer    ;public symbol allows
                                   ;external references
                assume cs:cseg_calibs,es:dseg_tbase
                assume ds:basic_dgroup,ss:basic_dgroup ;..........save registers
```

```
        push    bp              ;save BASIC base pointer
                                ;for return to BASIC
        mov     bp,sp           ;point stack pointer at
                                ;frame reference to
                                ;access arguments passed
                                ;by BASIC (one here)

push    ax              ;save additional
                                ;registers
        push    bx              ;
        push    es              ;
        push    si              ;
        mov     ax,dseg_tbase   ;set up segment
                                ;register for data area
        mov     es,ax           ;

mov     si,[bp].analog  ;get analog value
                                ;from BASIC
        mov     ax,[si]         ;
        test    ah,0FFH         ;if upper byte is
                                ;zero
        jz      new_buff        ;then install a
                                ; new point in
                                ;   the buffer
        mov     tbase_len,0     ;otherwise reset
                                ;the buffer
        mov     tbase_ptr,1     ;
        jmp     wr_ret          ;

mov     bx,tbase_len    ;get present
                                ;pointer and
                                ;use it
        mov     tbase_buffer[bx],al  ;to store
                                     ;  buffer value
        inc     tbase_len       ;point to next
                                ;buffer value
```

```
                        ;..........return to BASIC pop     si          ;restore additional
                                ;registers
wr_ret:     pop     es          ;wr_ret:
            pop     bx          ;
            pop     ax          ;

pop     bp          ;restore BASIC's base
                                ;pointer,
            ret     2           ;delete 1 parameters (2
                                ;bytes) from the stack
                                ;and return to the
                                ;calling routine debugmsg6   db          'this is the end of the buffer
                         write routine' wrbuffer    endp

;------------------------------------------------------;
; subroutine hrsetup(B_lreset,Brfa_scal,Blfa_scal,     ;
; Bbase_rate)                                          ;
;------------------------------------------------------;

proc    far
            public  hrsetup     ;public symbol allows
                                    external references
            assume  cs:cseg_calibs,es:dseg_tbase
            assume  ds:basic_dgroup,ss:basic_dgroup ;............save registers
```

```
        push    bp              ;save BASIC base
                                ;pointer for return
                                ;to BASIC
        mov     bp,sp           ;point stack pointer
                                ;at frame
                                ;reference to
                                ;access arguments
                                ;passed by BASIC
                                ;(one here)

push    ax              ;save additional
                                ;registers
        push    es              ;
        push    si              ;

mov     ax,dseg_tbase   ;set up segment
                                ;register for
                                ;data area
        mov     es,ax           ;

mov     si,[bp].Bbase_rate  ;get lowest
                                    ;divisor for heart
        mov     ax,[si]         ;rate from BASIC
        mov     base_rate,ax    ;and save in local
                                ;      data
                                ;      segment mov     si,[bp],Blfa_sacl   ;get low freq
                                    ;     modulation
                                    ;     scale
        mov     ax,[si]         ;         from BASIC
        mov     lfa_scal,al     ;and save LSbyte in
                                ;local data
                                ;    segment
```

```
                mov     si,[bp].Brfa_scal   ;get high freq
                                            ;   modulation scale
                mov     ax,[si]             ;from BASIC
                mov     rfa_scal,al         ;and save
                                            ;LSbyte in local data
                                            ;segment
                mov     si,[bp].B_lreset    ;get low freq
                                            ;   timer reset value
                mov     ax,[si]             ;from BASIC
                mov     tbase_rst,ax        ;and save in
                                            ;   local data segment ;..........return to BASIC pop     si                  ;restore additional
                                            ;registers
                pop     es                  ;
                pop     ax                  ;

pop     bp                  ;restore BASIC's base
                                            ;pointer,
                ret     8                   ;delete 4 parameters (8
                                            ;  bytes) from the stack
                                            ;and return to the
                                            ;   calling routine debugmsg 7  db      'this is the end of the heart rate
                        setup routine' hrsetup     endp cseg_calibs ends end
```

APPENDIX B

```
                      1985 - Makoto R. Arai
                      Laura E. McAlpine, and
                           Daivd Gordon ' SYNCTS19 - program to test synchrounous data
    '             acquisition and also
    '             test asynchronous processing using
    '             board#2
    '             addition: asynchronous data
    '             archiving (poll driven)
    '             reviewing old data
    ' last revision:  15 May 1985
    '
    ' REQUIRED SUBROUTINES: <MODULE>
    '
    '       instint(fdbuf1ptr,fdbuf2ptr,fdbuf3ptr)
    '         <SYNC7S>
    '       exstint                         <SYNC7S>
    '       rdbeat(heart,sync)              <SYNC7S>
    '       rdbuf(dataptr,bufferno)         <SYNC7S>
    '       rdptrs(adrd,hbrd,adflag,hbflag) <SYNC7S>
    '
    '       swindow(xmins,xmaxs,ymins,ymaxs)
    '         <GWINDOW3>
    '       dwindow(xmind,xmaxd,ymind,ymaxd)
    '         <GWINDOW3>
    '       clrwindw                        <GWINDOW3>
    '       axes                            <GWINDOW3>
    '       scaler(dataptr,gdataptr,numval)
    '         <GWINDOW3>
    '
    '       fgraph(dataptr,numval,xnow,linemask)
    '         <FGRAPH8>
    '              [for scaled graphs, use
```

```
'                    xnow=xmins,
'                    numval=numvalg=xmaxs-xmins+1,
'                    and gdataptr]
'         dumpgr    [to dump graphics]         <DUMPGR>
' defint a-y        ' only z denotes a real number
          defdbl z
          dim zreal(514),zrimag(514),zdata(1025)
          dim ydata(1025),ydatag(1025)
          dim hb1(1025),hb2(1025),zhr(1025)
          dim zspec.hb.real(512),zspec.hb.imag(512)
          dim sresetval(5),resprstval(5)
          dim linetype(3),histogram(100)
          def fnzmag(z1,z2)=z1*z1+z2*z2
          def fnzcoher(zr1,zi1,zr2,zi2)=fnzmag
             (zr1*zr2+zi1*zi2,zi1*zr2-zr1*zi2)

' initialize timer reset values
      1   sval=27 : for i=1 to 5 sresetval(i)=sval :
             sval=sval+sval : next i
      2   sval=1381 : for i=0 to 3 : resprstval(i)=sval :
             sval=sval+sval : next i
      3   resprstval(4)=sval ' define fft parameters
      4   fftsize=1024 : npair=fftsize/2 :
             znpair=cdbl(npair) : .lpower=9

5   for i=0 to 514 : zreal(i)=0# : zrimag(i)=0# :
             next i datacycle=0
```

```
           ' flag for automatic fft: when non-zero,
           '   marks stage of data
           '    processing (semi asynchronous)
         cyclewait=0
5          ' define linetype for plots
           linetype(0)=&HFFFF
           linetype(1)=&HAAAA
           linetype(2)=&HCCCC
           linetype(3)=&HFAFA
10         req.cls=0
           sounder=1

'define ports on 8253
15         timer0=&h704
           timer1=&h705
           timer2=&h706
           con8253=&h707

20

'define ports on 8255
           porta=&H71C
           portb=&H71D
           portc=&H71E
25         con8255=&H71F ' set up sampling rate for heart rate timer and
           '    respirations
30         gosub 100

' first set 8255 ports A,C to output, port B to
35         '   input
           ' turn the gates on using the 8255 at bits 0,1,2
```

```
'       on portc
' by setting portc to 1FH
' this also selects channel 0 for the A/D
out con8255,130
out portc,&H1F ' now go through required startup subroutines to
'    set up data archives
     open "R",1,"resp.dat",2048
     open "R",2,"hb1.dat",2048
     open "R",3,"hb2.dat",2048
     open "R",10,"trends.dat",128

31   field #1,2048 as analog$
     field #2,2048 as fdhb1$
     field #3,2048 as fdhb2$
     field #10,128 as trends$ fdflag=0
     fdrecord=1
     record1no=0 : record2no=0 : record3no=0 :
       record10no=0
     adflag1st=0 : hbflag1st=0
     fdbuf1ptr=varptr(#1)+188         ' set up
         'pointers to disk buffers
     fdbuf2ptr=varptr(#2)+188
     fdbuf3ptr=varptr(#3)+188

'..........field definitions for
           '              trend data file
     field #10,8 as hr$,8 as rr$,8 as rcf$,8
         as lfa$,8 as rfa$,8 as coher$
     field #10,48 as dummy1$,8 as ratio$,8
         as cratio$,8 as hrintegral$
```

```
        field #10,72 as dummy2$,8 as respintegral$,8
          as timestamp$
        field #10,120 as dummy3$,2 as hbrecord$,2
          as adrecord$
5       field #10,124 as dummy4$,2 as hbeat$,2
          as samplrate$ ' first print out the present value of the
10      '    interrupt vectors
        locate 23,1 : gosub 20000
        gosub 19000

15      ' make sure interrupts are off before installing
        '    handlers
        mask=inp(&h21) : mask=mask or 24 : out &h21,mask ' install the interrupts
20      call instint(fdbuf1ptr,fdbuf2ptr,fdbuf3ptr)
        locate 24,1 : gosub 20000
        gosub 19000

25      ' turn interrupts back on
        mask=inp(&h21) : mask=mask and &h0e7 : out
          &h21,mask 30  40  locate 1,1 : gosub 20000
        print "commands: c(ounts), f(ft), g(raph),
            i(in on), q(uit), r(beats)";
        print "s(tore), x(cls), #(samples);

35      ' wait until user hits a key
    41  savekey$=""
```

```
            while len(savekey$)=0 and datacycle<=0
                savekey$=savekey$+inkey$:gosub 30000:locate
                    24,70:print time$;:wend 5           while datacycle=1
                fdrecord=record1no : fdflag=1
                                        'set up future A/D analysis
                analrec.ad=record1no : analrec.hr=record2no+1
                if req.cls=1 then cls : req.cls=0
10                  'clear screen if needed gosub 950   '......analyze heart rate
            42          hrspecsum#=zspectsum*2#

15      gosub 900     '.........analyze A/D data (from floppy
            43          respspecsum#=zspectsum*2# gosub 15000
                '                   calculate spectral amplitudes
20              gosub 16000
                                                save trend data datacycle=cyclewait : wend
                'end auto data analysis cycle
25

49
30              if savekey$="c" then gosub 60
                ' print timer counts
                if savekey$="f" then gosub 900
                ' fft A/D buffer contents
                if savekey$="F" then gosub 950
35              ' fft heart rate buffer contents
                if savekey$="g" then gosub 12700
```

```
           ' graph current A/D buffer
           if savekey$="G" then gosub 12710
           ' graph current heart rate buffer
           if savekey$="h" then gosub 90
           ' (no) plot histogram
           if savekey$="p" then gosub 91
           ' (no) print trends
           if savekey$="i" then gosub 80
           ' unmask interrupt 3
           if savekey$="I" then gosub 81
           'unmask interrupt 4
           if savekey$="q" then goto 9996
           ' quit
           if savekey$="r" then gosub 50
           ' print heart beats
           if savekey$="S" then gosub 800
           ' analyze data in disk file (set fdflag)
           if savekey$="t" then gosub 16500
           ' print out the trends
           if savekey$="x" then cls        'clear screen
           if savekey$="#" then gosub 100
           ' reset sampling rate
           if savekey$="?" then gosub 700   'help
           savekey$=""

goto 41

'print present value of heartbeats 50     locate 24,1 : gosub 20000
           call rdbeat(heart,sync)
           print "heart beats: ";heart,"sync pulses:
              ";sync;time$;
           return
```

```
     ' print present value of counters
60   out con8253,0             'latch timer0
     tlow0=inp(timer0)
     thigh0=inp(timer0)
     out con8253,&h40          'latch timer1
     tlow1=inp(timer1)
     thigh1=inp(timer1)
     out con8253,&h80          'latch timer2
     tlow2=inp(timer2)
     thigh2=inp(timer2)
     locate 24,1 : gosub 20000
     print "timer0: ";tlow0+thigh0*256;tab(20);"
         timer1: ";tlow1+thigh1*256;
61   print tab(40);"timer2: ";tlow2+thigh2*256#;
     return ' print out interrupt controller parameters:
     ' entry point for IRQ3
80   mask=inp(&h21) : mask=mask xor 8 : out &h21,mask
     goto 82
     ' entry point for IRQ4
81   mask=inp(&h21) : mask=mask xor 16 : out
         &h21,mask
82   mask=inp(&h21)
     locate 24,1 : gosub 20000
     print "8259 IMR(interrupt mask regsiter)=
         ";mask;" =";hex$(mask);
     return ' (re)set sampling rates
     ' set timer0 to 16 bit square wave rate
```

```
                    ' generator mode
                    ' set timers 1,2 to 16 bit rate generator mode
         100        out con8253,&h36
                    out con8253,&h74
                    out con8253,&hB4

'..........set real time multiplier
         105        locate 23,1 : gosub 20000
                    input "real time multiplier: ",rt.mult
                    rt.multqual=0
                    if rt.mult=1 then rt.multqual=1
                    if rt.mult=2 then rt.multqual=2
                    if rt.mult=4 then rt.multqual=3
                    if rt.mult=8 then rt.multqual=4
                    if rt.multqual<>0 then goto 110
                    beep : goto 105

' get heart rate resolution desired to reset
                    ' timer0 reset value
         110        locate 1,1 : gosub 20000
                    input "heart rate resolution: (11,23,45,91,181
                        usec) ",hrresol ' check heart rate resolution validity
                    hrqual=0
                    if hrresol=11 then hrqual=1
                    if hrresol=23 then hrqual=2
                    if hrresol=45 then hrqual=3
                    if hrresol=91 then hrqual=4
                    if hrresol=181 then hrqual=5
                    if hrqual<>0 then sreset=sresetval(hrqual) :
                        goto 120
                    beep : goto 110
                    ' invalid heart rate resolution
```

```
            sreset=27           'set timer 0 to 88384Hz
                                'timebase (11.3 usec res
                                '(2.38MHz/27)(max resp
                                'samples then 64Hz)

sreset=54           'set timer 0 to 44192Hz
                                'timebase (22.6 usec res
                                '(2.38MHz/54)(max resp
                                'samples then 32Hz)

sreset=108          'set timer 0 to 22096Hz
                                'timebase (45.3 usec res
                                '(2.38MHz/108)(max resp
                                'samples then 16Hz)

sreset=216          'set timer 0 to 11048Hz
                                'timebase (90.5 usec res
                                '(2.38MHz/216)(max resp
                                'samples then 8Hz)

sreset=432          'set timer 0 to 5524Hz
                                 timebase (181 usec res
                                ' (2.38MHz/432)(max resp
                                 samples then 4Hz)

'..........set respiratory sampling rate
        120   locate 2,1 : gosub 20000
              print "respiratory sampling rate: ( 4";
              twopwr=4 : for i=hrqual+rt.multqual to 5 :
              twopwr=twopwr+twopwr
                  print using ",##";twopwr; : next i : print "
                      Hz) ";
              input respsampl
```

```
' check respiratory sampling rate validity
respqual=0 : respsampl.eff=respsampl*rt.mult
if respsampl=4 then respqual=1
if respsampl=8 then respqual=2
if respsampl=16 then respqual=3
if respsampl=32 then respqual=4
if respsampl=64 then respqual=5
if respqual=0 or respqual+hrqual+rt.multqual>7
    then beep : goto 120 resprst=resprstval(7-hrqual-respqual-
    rt.multqual)

'..........set cycle delay time between
          '              analyses
130  locate 3,1 : gosub 20000
     input "waiting time between cycles: ",dropcycle
     if dropcycle<0 or dropcycle>5 then beep : goto
        130
     cyclewait=0-dropcycle out timer0,(sreset mod 256)
     ' system timebase generated here out
     '     timer0,(sreset\256)

out timer1,(resprst mod 256)
     ' timer 1 counts timebase and outputs out
     '     timer1,(resprst\256)
     ' the respiratory sampling rate out timer2,0
     ' set timer 2 as an overflow counter for the
     '     out timer2,0
     ' number of overflows (65536 counts)
```

```
200    timer2over#=65536#
       ' overflow value for timer2
201    zlover=resprst              ' reset count for timer1
202    zlfreq=14318180#/6#/sreset
       ' timer1 input clock frequency
203    zhrsampler=zlover/zlfreq
       ' timer1 output=sampling interval
204    segment.time=fftsize*zhrsampler
205    zlfreq.real=zlfreq/rt.mult
       ' real time used to calculate HR
206    zhrsampler.real=zlover/zlfreq.real '..........respiratory peak search
       '                   parameters
210    minrespfrq#=.2#
       ' start at frequency (in pixels)
211    minresp=minrespfrq#/respsampl*1024
212    combwidth#=.032#
       use comb tooth width (in pixels)
213    combpix=combwidth#/respsampl*1024
214    if combpix<=0 then combpix=0

'..........low frequency
                    peak/integration parameters
220    pixel.04=cint(40.96#/fftsampl)+1
       ' pixel for .04Hz
221    pixel.10=cint(102.4#/fftsampl)+1
       ' pixel for .10Hz
222    fft.expansion=respsampl/fftsampl if datacycle=0 then datacycle=-1
       if recordlno=0 then return
       ' on startup don't delay
       ' exclude the current data segment
       ' from analysis since changes in
       ' sampling rate will introduce glitches
```

```
        return

' set floppy disk flag (fdflag) to analyze data
        ' stored on floppy (resp)
800     fdflag=1
        locate 23,1 : gosub 20000 : input "record
            number: ",fdrecord
        if fdrecord>=1 and fdrecord<=record1no then
            gosub 12700 : return
        locate 24,1 : gosub 20000 : beep : print
            "invalid record number";
        return ' set up data for fft here
        ' get analog data from the A/D
900     gosub 12700      ' get analog data and plot
901     for i=1 to fftsize : zdata(i)=ydata(i) : next i
902     locate 23,1 : gosub 20000 : print "A/D buffer is
            transformed";

xmins=330 : xmaxs=630 : ymins=102 : ymaxs=167
        call swindow(xmins,xmaxs,ymins,ymaxs)

glabel=3         ' plot label is "resp spect"
        gosub 10000      ' fft
        return ' get heart rate data for fft
950     locate 23,1 : gosub 20000 : print "heart rate is
            transformed";
951     gosub 12710      ' get hr function and plot it
```

```
952     for i=1 to fftsize : zdata(i)=zhr(i) : next i 953     xmins=330 : xmaxs=630 : ymins=28 : ymaxs=93
954     call swindow(xmins,xmaxs,ymins,ymaxs)

955     glabel=4          ' plot label is "hr spect"
956     gosub 10000       ' fft ' save spectrum in spec.hr buffers
960     for i=0 to 512
961        zspec.hb.real(i)= zreal(i) :
              zspec.hb.imag(i)=zrimag(i)
962        next i return ' exstall the interrupt and print vector
9996    cls
                 ' make sure interrupts are off before
                   removing handlers
        mask=inp(&h21) : mask=mask or 24 : out &h21,mask ' remove interrupt handlers
        screen 0 locate 4,1
        gosub 19000
        call exstint
        locate 5,1
        gosub 19000
        locate 21,1
```

```
        ' close files after storing last bit of data
        bufferno=0
        call rdbuf(fdbuf1ptr,bufferno)
        put #1,record1no+1
        bufferno=1
        call rdbuf(fdbuf2ptr,bufferno)
        put #2,record2no+1
        bufferno=2
        call rdbuf(fdbuf3ptr,bufferno)
        put #3,record3no+1 close #1,#2,#3,#10

' and quit
9999    stop

' FFT ROUTINE
        '
        ' set up the data
        '
10000   zreal(0)=0#
10001   zrimag(0)=0#
10002   zreal(npair+1)=0#
10003   zrimag(npair+1)=0#

' compute mean value of array
10004   zmean=0#
10005   for i=1 to fftsize : zmean=zmean+zdata(i)
            : next i
10006   zmean=zmean/1024#
```

```
10007   for k=1 to npair : j=k+k-1 : zreal(k)=zdata
        (j)-zmean
10008   zrimag(k)=zdata(j+1)-zmean : next k 10009   ' locate 24,1 : gosub 20000
10010   ' print "arrays initialized at
        ' ";time$;space$(20);

'
        ' fft routine <fftandift> begins here
        '
10011   ' locate 24,1 : print "entering fft routine at
        ' ";time$;space$(20);
10012   k=0
10013   for j=1 to npair-1 : i=2
10014     ndivi=npair/i
10015     if k<ndivi then 10017
10016        k=k-ndivi : i=i+i : goto 10014
10017     k=k+ndivi
10018     if k<=j then 10025
10019        za=zreal(j+1)
10020        zreal(j+1)=zreal(k+1)
10021        zreal(k+1)=za
10022        za=zrimag(j+1)
10023        zrimag(j+1)=zrimag(k+1)
10024        zrimag(k+1)=za
10025   next j
10026   ' locate 24,1:print "bit reversal completed at
        ' ";time$;space$(20);

10030   g=1 : zp=1#
10031   for i=1 to lpower : gosub 30000
        'check if disk requires service
10032   'locate 24,1:print "entering stage ";g;" at
```

```
10033    ' time ";time$;space$(20);
10033    if i=1 then zsign=-1# else zsign=1#
10034    zc=1# : ze=0#
10035    zq2=(1#-zp)/2# : if zq2<=0# then zq=0# : else
            zq=sqr(zq2)
10036    zp2=(1#+zp)/2# : if zp2<=0# then zp=0# : else
            zp=zsign*sqr(zp2)
10037    itwog=g+g 10040    for r=1 to g
10041       for j=r to npair step itwog
              k=j+g : if k>npair then print "kjg
                 over>> ";k;j;g
10042          za=zc*zreal(k)+ze*zrimag(k)
10043          zb=ze*zreal(k)-zc*zrimag(k)
10044          zreal(k) =zreal(j) -za
10045          zrimag(k)=zrimag(j)+zb
10046          zreal(j) =zreal(j) +za
10047          zrimag(j)=zrimag(j)-zb
10048       next j
10049       za=ze*zp+zc*zq
10050       zc=zc*zp-ze*zq
10051       ze=za
10052    next r
10053    g=itwog
10054 next i
10055 'locate 24,1:print "entering final stage at
            ";time$;space$(20);
10056 gosub 30000
      ' check if disk requires service 10060 za=4#*atn(1#)/znpair
10061 zp=cos(za)
10062 zq=sin(za)
10063 za=zreal(1)
10064 zreal(1)=za+zrimag(1)
```

```
10065    zrimag(1)=za-zrimag(1)
10066    zreal(1)=zreal(1)/2#
10067    zrimag(1)=zrimag(1)/2#
10068    zc=1# : ze=0#

10070    j=2
10071    while j<npair/2
10072       za=ze*zp+zc*zq
10073       zc=zc*zp-ze*zq
10074       ze=za
10075       k=npair-j+2
10076       za=zreal(j)+zreal(k)
10077       zb=(zrimag(j)+zrimag(k))*zc-(zreal(j)-
               zreal(k))*ze
10078       zu=zrimag(j)-zrimag(k)
10079       zv=(zrimag(j)+zrimag(k))*ze+(zreal(j)-
               zreal(k))*zc
10080       zreal(j)=(za+zb)/2#
10081       zrimag(j)=(zu-zv)/2#
10082       zreal(k)=(za-zb)/2#
10083       zrimag(k)=-(zu+zv)/2#
10084    j=j+1 : wend
10085    zrimag(npair/2+1)=-zrimag(npair/2+1)

10090    for j=2 to npair
10091       zreal(j)=zreal(j)/znpair/2#
10092       zrimag(j)=zrimag(j)/znpair/2#
10093    next j
10094    zreal(1)=zreal(1)/znpair
10095    zrimag(1)=zrimag(1)/znpair '
         ' fft routine now completed
         '
10100    locate 24,1:print "fft completed
             ";time$;space$(20);
```

```
        '...integrate spectrum
        '    sum up the spectrum noting that only the
        '     first npair elements of
        '    the fft are valid
        '    (npair+1 to fftsize are complex conjugates
        '     of 1 to npair and are
        '      not calculated)
10101   zspectsum=0#
10102   zsummax=0#
10103   ipeak=-1
10104   for i=1 to npair
10105     zadd=fnzmag(zreal(i),zrimag(i))
10106     zspectsum=zspectsum+zadd
10107     if zadd<=zsummax then 10110
10108        zsummax=zadd
10109        ipeak=i
10110   next i '
        ' graphing routine for fft spectra
        '
10111   'locate 1,1 : gosub 20000
10113   'print "total spectral weight
        '    <variance>:";zspectsum*2#;
10114   'locate 2,1 : gosub 20000
10115   'print "peak weight : ";zsummax;" peak
        '     frequency= ";
10116   'print (ipeak-1#)/fftsize*respsampl;

10117   gosub 12730
        ' fgraph of spectrum
10118   return
```

```
'---------------------------------'
' UTILITIY ROUTINES HERE          '
'---------------------------------'

' graphing routine: gets data from A/D buffer
'   and displays graph
12700   glabel=1
        numpts=fftsize
        indata=0
        ' local flag
        '   indicating data is read while indata=0 and
        '     fdflag=0
            dataptr=varptr(ydata(1))
            bufferno=0              'read A/D buffer
            call rdbuf(dataptr,bufferno)
            indata=1
            wend while indata=0 and fdflag=1
            gosub 30000
        ' check file buffer to see if service is
        '   required
            get #1,fdrecord
            for i=1 to 1024 :
            ydata(i)=cvi(mid$(analog$,i+i-1,2)) : next i
            indata=1
            wend xmins=10 : xmaxs=310 : ymins=102 : ymaxs=167
        call swindow(xmins,xmaxs,ymins,ymaxs)

xmind=0 : xmaxd=300 : ymind=0 : ymaxd=255
        call dwindow(xmind,xmaxd,ymind,ymaxd)
```

```
                 ' max A/D value is 255
                 call clrwindw
                 call axes
                 goto 12770

' entry point for plot of heart rate function
        12710    screen 2              ' get heart rate function
        12711    glabel=2
        12712    numpts=fftsize
        12713    gosub 13000
        12714    ibeg=adrd+2
        12715    for i=1 to fftsize : if ibeg=i then
                      ibeg=ibeg+fftsize
        12716       ydata(i)=cint(zhr(ibeg-i)) : next i xmins=10 : xmaxs=310 : ymins=28 : ymaxs=93
                 call swindow(xmins,xmaxs,ymins,ymaxs)

xmind=0 : xmaxd=300 : ymind=0 : ymaxd=250
                 call dwindow(xmind,xmaxd,ymind,ymaxd)
                 ' max hr is 250 bpm goto 12770

' entry point for plotting spectra (screen
                 '   windows already setup)
        12730    zgain=250#/zsummax
        12731    for i=1 to npair
        12732       ydata(i)=cint(zgain*fnzmag
                      (zreal(i),zrimag(i))) +1
        12733    next i
        12734    numpts=npair ' max spectral element (scaled to 250)
```

```
                    xmind=0 : xmaxd=300 : ymind=0 : ymaxd=255
                    call dwindow(xmind,xmaxd,ymind,ymaxd)

12770       call clrwindw
                    call axes 12780       dataptr=varptr(ydata(1))
                    gdataptr=varptr(ydatag(1))
                    call scaler(dataptr,gdataptr,numpts)
                    'correctly selects screen width ' entry point for plot of ydatag(i)
        12790       x=xmins
                    numvalg=xmaxs-xmins+1
                    linemask=&hffff
                    gdataptr=varptr(ydatag(1))
                    call fgraph(gdataptr,numvalg,x,linemask)

' graph labels printed here
                    on glabel goto 12800,12810,12820,12830
                    return   'invalid label ' respirations in time domain
        12800       if fdflag=1 then locate 14,30 : print
                        "rec#";fdrecord : fdflag=0
                    return ' heart rate in time domain
        12810       locate 5,3
                    print using "HR= ### bpm";cint(zavghr)
                    return ' respiratory spectrum
        12820       locate 14,63 :          print " Resp Spect ";
                    locate 15,63 : print using " (0-
                        ##Hz)";respsampl\2
```

```
             gosub 14000
             ' respiratory rate from spectrum by comb method
             locate 14,3
             ' print respiratory rate with time tracing
             print using "RR=### bpm
                 (rcf=#.###)";cint(respfreq#*60),respcombfrac#
             return ' heart rate spectrum
    12830    locate 4,63 :       print " HR Spect ";
             locate 5,63 : print using " (0-##Hz)";fftsampl\2
             return 'heart rate functions:
             '    read times from memory
             '      convert to heart rate function
             '      FFT resulting buffer
             '      display the spectral amplitudes 13000    call rdptrs(adrd,hbrd,adflag,hbflag)
    13002    if record2no=0 then startup=1 else startup=0 '
                 startup is special 13003    hbptr1=varptr(hb1(1))
    13004    bufferno=1
             'read heart beat buffer 1 (least sig. cts
    13005    call rdbuf(hbptr1,bufferno)
    13006    locate 24,1 : gosub 20000
    13007    print "hbrd= ";hbrd; : anal.beat=hbrd 13008    hbptr2=varptr(hb2(1))
    13009    bufferno=2
             'read heart beat buffer 2 (most sig. cts
    13010    call rdbuf(hbptr2,bufferno)
```

```
13011   for i=0 to 100 : histogram(i)=0 : next i
        'initialize histogram for deglitching (.4-40Hz)
13012   histomax#=zlfreq.real*2.5#
13013   histoscal#=zlfreq.real/40#

' compute time differences for entire hb array
        ' and save in zdata
        ' from the top down
        ' zdata will contain the latest hr intervals,
        ' with the latest in
        ' (hbrd) and older intervals for decreasing
        ' array index
        ' since the timers are decrementing,
        ' lstbeat<thisbeat
        ' (lstbeat is later, therefore smaller)
        ' this relation fails whenever there is a carry
        ' over (timer overflow)
        ' note: timer1 overflows exactly fftsize times
        ' during one data segment
13020   lstbeat#=hb1(hbrd) : lstover#=hb2(hbrd)
13022   hbnow=hbrd-1
13023   if hbnow<=0 then hbnow=fftsize
13024   if startup=1 and hbnow=fftsize then return ' no
            data yet 13025   numint=1
                ' valid intervals only (1 less than
                ' buffer size
13026   while numint<fftsize
13027       thisbeat#=hb1(hbnow)
                ' check for overflow of overflow counter
13028       thisover#=hb2(hbnow)
13029       if hb2(hbnow)<cint(lstover#) then
                lstover#=lstover#-timer2over#
13030       hbnow=hbnow-1
```

```
13031        if hbnow=0 then hbnow=fftsize
13032        if hbnow=fftsize and startup=1 then goto
                13048
13033        zdatnow=thisbeat#-1stbeat#+overdif#*zlover
13034           if zdatnow>=0 then goto 13047 '?error 13040        if zdatnow>histomax# then goto 13044
13041        index=cint(zdatnow/histoscal#)
13042        histogram(index=histogram(index)+1
13043        goto 13045
             'keep histogram of intervals (.2-20Hz:
             '   give 10% resolution @2Hz) extended
             '      data lapses
13044            histogram(100)=histogram(100)+1
             ' extended data lapses 13045        zdata(numint)=zdatnow : numint=numint+1
13046        1stbeat#=thisbeat# : 1stover#=thisover#
13047        wend
13048   numint=numint-1

'..........find the interval
             '           corresponding to mean heart rate
             '             1) find largest peak in
             '                .5-4Hz (2 pixels wide)
             '             2) calculate corrected
             '                mean interval
             '             3) calculate corrected
             '                interval variance
             '             4) set slewing
             '                parameters for HR
             '                generation 13050   1stint=histogram(4) : hpeak=0 : hpeak.ht=0
13051   for i=3 to 40 : thisint=histogram(i)
13052       if (thisint+1stint)>hpeak.ht then
```

```
                     hpeak.ht=thisint+lstint : hpeak=i
     13053           lstint=thisint : next i
     13054      approx.avg#=(hpeak-0.5#)*histoscal#

5    13060      zhistsum=0# : zhistsum2=0#
     13061      for i=1 to numint :
                     index=cint(zdata(i)/approx.avg#)
     13062           if index<=0 then index=1
     13063           zhistsum=zhistsum+zdata(i)/index : next i
10   13064      avgint#=zhistsum/numint 13070      for i=1 to numint : index=cint(zdata(i)/avgint#)
     13071           if index<=0 then index=1
     13072           zdif=zdata(i)/index-avgint# :
15                        zhistsum2=zhistsum2+zdif*zdif
     13073           next i
     13074      histvar#=zhistsum2/numint ' calculate deglitching parameters
20   13081      varslew#=31.4#*sqr(histvar#)/respsampl
                '5x max slew (1Hz rfa) slew at least .05Hz
                '    (3bpm)/beat infslew has infimum of slew
                '         maxima
     13082      min.maxslew#=.05
25   13083      infslew#=1#/(1#/avgint#-
                     min.maxslew#/zlfreq.real)-avgint#
     13084      if maxslew#<infslew# then maxslew#=infslew#
     13085      supslew#=avgint#/5#
                'never slew more than 20% HR
30   13086      if maxslew#>supslew# then maxslew#=supslew#
     13087      locate 1,1 : gosub 20000 ': print "maxslew:
                     ";maxslew#

' compute heart rate waveform next
35   13100      ztime=0#
                ' time for present heart rate signal
```

```
                ' pointer in zdata to present beat number
                ' of beats accepted
      13101     intnow=1
      13102     beatno=1 :
      13103     while zdata(intnow)<=0
      13104         intnow=intnow+1 : if intnow>numint then goto
                        13140 : wend
      13105     zintlst=avgint# : zdropper=avgint# :
                    zintnow=zdata(intnow)
      13106     znext=zintnow/zlfreq.real
                ' time of previous heart beat deglitch first
                '    beat present heart rate keep statistics for
                '       deglitching sampling rate determined by
                '          timers
      13107     avgnow#=avgint# : gosub 13500
      13108     zhrnow=60#*zlfreq.real/zintnow
      13109     zsum=zhrnow
      13110     zsum2=zhrnow*zhrnow
      13111     zincr=zhrsampler.real
      13120     numsig=1
                ' point to heart rate function 13121     while numsig<=fftsize and ztime<=znext
      13122         zhr(numsig)=zhrnow : numsig=numsig+1 :
                    ztime=ztime+zincr
      13123         wend:zintlst=zintnow
      13124     if numsig=fftsize+1 then goto 13142
      13125         intnow=intnow+1 : if intnow>numint then goto
                        13140
      13126         zintnow=zdata(intnow) : if zintnow<=0 then
                        goto 13125
      13127         znext=znext+zintnow/zlfreq.real : gosub
                        13500          ' deglitcher
      13128         zhrnow=60#*zlfreq.real/zintnow
      13129         zsum=zsum+zhrnow : zsum2=zsum2+zhrnow*zhrnow
                        : beatno=beatno+1
```

```
13130        goto 13121

13140   zavghr=zsum/beatno
        ' averaged over number of beats
13141   while numsig<=fftsize : zhr(numsig)=zavghr :
            numsig=numsig+1 : wend
13142   zavghr=zsum/beatno 13400   locate 24,13 : print "  avg hr(bpm): ";zavghr;

' zhr now has heart rate function
13401   print " ...heart rate function computed";

return

' deglitching of three types employed here:
        '       correction of premature triggers (not
        '       yet)
        '       correction of dropped beats (not yet)
        '       slew rate limiting of final output (a
        '       crude bandlimiter)
13500   if abs(zintnow-zintlst)<maxslew# then return
        'check for dropped beats
13501   numdrop=cint(zintnow/avgnow#) : if numdrop<=0
            then goto 13510
13502   if abs(zintlst-zintnow/numdrop)>maxslew# then
            1350#
13503   zintnow=zintnow/numdrop : sound 1200,sounder :
            return                            'dropped beat
13504   if numdrop>1 then goto 13520 else goto 13510

' check for premature trigger (note:
                '       premature trigger assump-
                '       -tion remains in effect
                '       only for glitched time
                '       (if added portion is an
```

```
                              '       acceptable beat,
                              '       (that's how it's used;
                              '       otherwise slew rate
                              '       (limiter extends '            assumption to added portion
        13510          if abs(zintnow+zdata(intnow+1)_
                          zintlst)>maxslew# then 13520
        13511          zintnow=zintnow+zdata(intnow+1)
                      ' assume premature trigger here
        13512          sound 1400,sounder : return ' slew rate limiter
        13520      sound 600,sounder : zintnow=zintlstr return ' calculating the respiratory rate using the
                   '       comb method
                   ' [spectrum in ydata(*)]
                   '       start at frequency :    minrespfrq#
                   '            (in pixels):       minresp
                   '       use comb tooth width:   combwidth#
                   '            (in pixels):       combpix 14000    maxcomb#=0# : respcomb=0 : combstep=combpix\2+1
                 ' for loop shifts comb beginning to different
                 ' frequencies
        14001    for comb=minresp to npair step combstep
        14002        curcomb#=0# : harmbeg=comb-combstep+2
        14003        lastbeg=harmbeg+9*comb : if lastbeg>npair
                         then lastbeg=npair ' while loop adds up 10 teeth
```

```
                        ' (harmonics) in the comb
        14004       while harmbeg<=lastbeg
        14005           toothptr=harmbeg
        14006           lstooth=harmbeg+combpix : if
                            lstooth>npair then lstooth=npair ' this while loop adds one tooth's
                        ' contribution to comb
        14007           while toothptr<=lstooth
        14008               curcomb#=curcomb#+ydata(toothptr)
        14009               toothptr=toothptr+1
        14010           wend
        14011           harmbeg=harmbeg+comb
        14012       wend
        14013       if curcomb#>maxcomb# then maxcomb#=curcomb# :
                        respcomb=comb
        14014   next comb 14050   locate 3,1 : gosub 20000 : print "respiratory
                    comb fraction: ";
        14051   curcomb#=0# : for i=1 to npair :
                    curcomb#=curcomb#+ydata(i) : next i
        14052   respcombfrac#=maxcomb#/curcomb# : print using
                    "#.###";respcombfrac#;

' respcomb now has respiratory frequency or a
                ' subharmonic
                ' to decide which is the first harmonic look at
                ' weight in each tooth
                ' of the comb; a higher harmonic comb must
                ' contribute at least double
                ' amplitude to be designated as the fundamental
                ' (4xspectral weight)

14100   maxtooth#=0 : resptooth=0 : harmbeg=respcomb+1-
                    combpix
```

```
14101   lastbeg=harmbeg+9*respcomb : if lastbeg>npair
            then lastbeg=npair 14102   while harmbeg<=lastbeg
14103       toothptr=harmbeg : curtooth#=0#
14104       lstooth=harmbeg+combpix+combpix
14105       if lstooth>npair then lstooth=npair ' add up one widened tooth
14110       while toothptr<=lstooth
14111           curtooth#=curtooth#+ydata(toothptr)
                    : toothptr=toothptr+1
14112       wend
            ' compare to previous teeth
14120       if curtooth#<4*maxtooth# then goto 14130
14121           maxtooth#=curtooth# :
                    resptooth=harmbeg 14130       harmbeg=harmbeg+respcomb
14131   wend ' compute respiratory frequency as peak
        ' average
14200   toothptr=resptooth : respfreq#=0#
14201   lstooth=toothptr+combpix+combpix
14202   if lstooth>npair then lstooth=npair ' average frequency over fundamental
        ' peak
14210   while toothptr<=lstooth
14211       respfreq#=respfreq#+ydata(toothptr)
                *cdbl(toothptr-1)
14212       toothptr=toothptr+1
14213   wend
14214   respfreq#=respfreq#/maxtooth#/1024#*respsampl
```

```
14220   resp.lopixel=cint((respfreq#-
            .06#)/respsampl*1024#)+1
        ' integration limits
14221   resp.hipixel=cint((respfreq#+.06#)
            /respsampl*1024#)+1 return

' spectral amplitude calculations
15000   lfa#=0# : rfa#=0# : coherence#=0#
15001   for i=pixel.04 to pixel.10
15002       lfa#=lfa#+fnzmag(zspec.hb.real(i),
                zspec.hb.imag(i))
15003       next i
15004   lfa#=lfa#+lfa#

15010   for i=resp.lopixel to resp.hipixel
15011       rfa#=rfa#+fnzmag(zspec.hb.real(i),
                zspec.hb.imag(i))
15012       next i
15013   rfa#=rfa#+rfa#

15020   for i=1 to 512
15021       coherence#=coherence#+fnzcoher
                (zreal(i),zrimag(i),_
                    zspec.hb.real(i),
                    zspec.hb.imag(i))
15022       next i
15023   coherence#=coherence#/zspectsum 15030   ratio#=lfa#/rfa#
15031   cratio#=lfa#/coherence#

15040   locate 6,60 : print using   "lfa: ##.###";lfa#;
```

```
15041    locate 7,60 : print using   "rfa: ##.###
                                  (##.###)";rfa#,coherence#;
15042    locate 8,58 : print using "ratio: ##.###
                                  (##.###)";ratio#,cratio#;
         return ' storing trend data on floppy disk (file #10)
16000    lset hr$=mkd$(zavghr)
16001    lset rr$=mkd$(respfreq#)
16002    lset rcf$=mkd$(respcombfrac#)
16003    lset lfa$=mkd$(lfa#)
16004    lset rfa$=mkd$(rfa#)
16005    lset coher$=mkd$(coherence#)
16006    lset ratio$=mkd$(ratio#)
16007    lset cratio$=mkd$(cratio#)
16008    lset hrintegral$=mkd$(hrspecsum#)
16009    lset respintegral$=mkd$(respspecsum#)
16010    lset timestamp$=time$
16011    lset hbrecord$=mki$(analrec.hr)
16012    lset adrecord$=mki$(analrec.ad)
16013    lset hbeat$=mki$(anal.beat)
16014    lset samplrate$=mki$(respsampl)

record10no=record10no+1 : put #10,record10no return

' reading trend data from floppy disk (file #10)
16500    if record10no<=1 then return
16501    cls 16510    xmins=10 : xmaxs=310 : ymins=2: ymaxs=197 :
```

```
               numvalg=xmaxs-xmins+1
     16511   call swindow(xmins,xmaxs,ymins,ymaxs)

16512   call clrwindw
     16513   call axes 16520   numpts=record10no
     16521   lfa.beg=record10no
     16522   rfa.beg=2*record10no
     16523   ratio.beg=3*record10no
     16524   lastydata=4*record10no
     16525   ln10#=log(10#)
     16526   xscale#=numvalg/record10no ' get trend information from the disk file
     16530   for temprec=1 to record10no
     16531      get #10,temprec
     16532      ydata(temprec)=197-.78#*cvd(hr$)
     16533      ydata(temprec+lfa.beg)=197-19.5*cvd(lfa$)
     16534      ydata(temprec+rfa.beg)=197-19.5*cvd(rfa$)
     16535      ydata(temprec+ratio.beg)=100-
                    log(cvd(ratio$))/ln10#*45#
     16536   next temprec 16537   for i=1 to lastydata : if ydata(i)<ymins then
                 ydata(i)=ymins
     16538       if ydata(i)>ymaxs then ydata(i)=ymaxs :
                    next i ' plot trends here
     16540   for trend=0 to 3 : trendoff=trend*record10no
     16542      gctr=1 : ydatalst=ydata(1) :
                    ydatag(1)=ydatalst
     16543      for temprec=2 to record10no :
                    gctrmax=temprec*xscale#
     16544         gdif=gctrmax-gctr : if gdif<=0 then goto
```

```
16545      ydatadif=ydata(temprec+trendoff)-
               ydatalst : part=0
16546      while gctr<gctrmax : gctr=gctr+1 :
               part=part+1
16547          ydatag(gctr)=ydatalst+
               (part/gdif)*ydatadif : wend
16548      ydatalst=ydata(temprec+trendoff)
16550      next temprec
16551    linemask=linetype(trend) : x=xmins
16552    gdataptr=varptr(ydatag(1)) : numvalg=xmaxs-
             xmins+1
16553    call fgraph(gdataptr,numvalg,x,linemask)
16554  next trend 16560  locate 2,42 : print "HR (0-250 bpm)";
16561  locate 3,42 : print "lfa (0-10 bpm^2)";
16562  locate 4,42 : print "rfa (0-10 bpm^2)";
16563  locate 5,42 : print "ratio (.01-100)";

16600  req.cls=1 return

' subroutine to print out the interrupt vectors 19000  def seg=0
       print "IRQ3 @0B*4H: ";hex$(peek(&h2C));
       '  "";hex$(peek(&h2D));" ";
       print hex$(peek(&h2E));
       '  "";hex$(peek(&h2F));tab(40);
       print "IRQ4 @0C*4H: ";hex$(peek(&h30));
       '  "";hex$(peek(&h31));" ";
```

```
                print hex$(peek(&h32));" ";hex$(peek(&h33));
                return ' routine to clear the present line
20000   csnow=csrlin:locate csnow,1:print
        return ' check pointers to see if any disk files need
        ' to be written
30000   call rdptrs(adwr,hbwr,adflag,hbflag)
30001   if adflag=adflaglst and hbflag=hbflaglst then
                return 30010   while adflag>record1no+1 : beep : locate 23,1 :
                print "data #1 loss";
30011           record1no=adflag-1 : wend
30020   while hbflag>record2no+1 : beep : locate 23,1 :
                print "data #2 loss";
30021           record2no=hbflag-1 : wend
30030   while hbflag>record3no+1 : beep : locate 23,1 :
                print "data #3 loss";
30031           record3no=hbflag-1 : wend 30040   if adflag<record1no+1 then goto 30050
30041       record1no=adflag : put #1,adflag
30042       if datacycle<=0 then datacycle=datacycle+1
            'if not processing, begin
30050   if hbflag=record2no+1 then record2no=hbflag :
            put #2,hbflag
30060   if hbflag=record3no+1 then record3no=hbflag :
            put #3,hbflag locate 3,1 : gosub 20000 : print "current file
        records: ";adflag; print " (#1) ";hbflag;"
```

```
                    (#2)";
            adflaglst=adflag : hbflaglst=hbflag return end page    66,80
    ; sync7s.asm - an assembler routine to handle interrupts
    ;               from IRQ4 and collect
    ;               synchronous data from the A/D (board 2
    ;               configuration assumed)
    ;               The routine checks A/D readings for
    ;               output validity
    ;               Data is loaded by interrupts into both a
    ;               processing buffer and
    ;               a disk file I/O buffer to allow quick
    ;               archival; an overflow
    ;               flag signals when a disk file buffer
    ;               should be stored and
    ;               also indicates whether the disk buffer
    ;               was corrupted.
    ;               To acknowledge storage of a disk buffer
    ;               one must reset the
    ;               overflow flag using <ackfdio>
    ; Last revision:  3 May 1985
    ;
    ;

;--------------------------------;
                    ; 8088 interrupt location        ;
                    ;--------------------------------;

abs0            segment at 0    ;absolute memory segment
                                    ;allows placement of
                                    ;interrupt address
                    org     0BH*4   ;future heart beat
                                    interrupt handler resides
    IRQ3_int        dw      2 dup(?);at int 0B
```

```
                org     0CH*4       ;8253 timebase interrupt
                                    ;handler resides
IRQ4_int        dw      2 dup(?);at int 0C
abs0            ends                ;

;----------------------------------;
; int_buffer: area to save DOS     ;
;       dummy interrupt ptrs       ;
;----------------------------------;

int_buffer      segment             ;data segment containing
                                    ;user interrupt buffer save_int        dw      4 dup(?);offset for two DOS
                                    ;interrupts saved
                                    ;to be restored using
                                    ;exstint int_buffer      ends                ;

;----------------------------;
; working storage for        ;
; interrupts                 ;
;----------------------------;

dseg_sync       segment             ;data segment for
                                    ;interrupts ;..........declare all variables public
                ;          for use by other
                ;          assembly level routines
                public ad_buffer,ad_rd,ad_wr,sync_ctr
                public hb_buffer1,hb_buffer2,hb_rd,hb_
``` wr,heartbeats

; .........timebase local storage and
;            buffer

```
ad_buffer    db    1024 dup(?)  ;buffer for A/D
                                ; values
ad_rd        dw    ?            ;read indicator for A/D
                                ;disk buffer
ad_wr        dw    ?            ;write pointer for A/D
                                ;buffer (incrementing)
sync_ctr     dw    ?            ;counter for timebase
                                ;interrupt (overflows)
```

; .........heart beat local storage and
;            buffer
;          note:for main clock
;               14.318 180 MHz (osc)
;          system clock
;               4.772 727 MHz (clock)
;          8253 clock
;               2.386 363 MHz (ck8253)
;                   (ck8253 /    432)
;                 5.524 KHz    (hb.clk)
;               (ck8253 /596592)  4 Hz
;                                (respck)
;          hb.clk = 1381*respck
;          sync.ctr overflow =
;               16384 sec (4:33:04)

```
hb_buffer1   dw    1024 dup(?)  ;heart beat time
                                ; stamps for previous 1024
hb_buffer2   dw    1024 dup(?)  ;beats (2 words:
                                ; hb.clk,sync.ctr)
hb_rd        dw    ?            ;read indicator for
                                ;heart beat disk buffers
hb_wr        dw    ?            ;write pointer
```

```
                                        ;(incrementing) for hb_buffer heartbeats      dw      ?       ;keep track of number of
                                        ;beats processed ;..........pointers to disk file buffers fd1ptr          label   dword   ;pointer to floppy disk
                                            file #1 buffer
        fd1ptroff       dw      ?       ; (offset)
        fd1ptrseg       dw      ?       ; (segment)

fd2ptr          label   dword   ;pointer to floppy disk
                                            file #2 buffer
        fd2ptroff       dw      ?       ; (offset)
        fd2ptrseg       dw      ?       ; (segment)

fd3ptr          label   dword   ;pointer to floppy disk
                                            file #3 buffer
        fd3ptroff       dw      ?       ; (offset)
        fd3ptrseg       dw      ?       ; (segment)

dseg_sync       ends            ;

;-----------------------------------;
                        ; setup structures to allow access to;
                        ; arguments pased by BASIC           ;
                        ;-----------------------------------;

; subroutine
                        ; instint(fil1ptr,fil2ptr,fil3ptr)
        frame_rd        struc           ;define the stack
                                        ;structure for passing
                                        ;arguments to BASIC
        savebp0         dw      ?       ;caller's base pointer
```

```
        saveret0        dd      ?       ;return offset and
                                        ;segment pushed by BASIC
        B_fil3ptr       dw      ?       ;offset of file #3 disk
                                        ;buffer
10      B_fil2ptr       dw      ?       ;offset of file #2 disk
                                        ;buffer
        B_fil1ptr       dw      ?       ;offset of file #1 disk
                                         buffer
        frame_rd        ends
15
                        ; subroutine rdbeat(BASIC_beats,BASIC_
                        ; syncs)
        frame_rd        struc           ;define the stack
                                        ;structure for passing
20                                      ;arguments to BASIC
        savebp1         dw      ?       ;caller's base pointer
        saveret1        dd      ?       ;return offset and
                                        ;segment pushed by BASIC
        BASIC_syncs     dw      ?       ;place to return sync
25                                      ;pulses to BASIC
        BASIC_beats     dw      ?       ;place to return heart
                                        ;beats to BASIC
        frame_rd        ends 30                      ; subroutine rdbuf (BASIC_ptr,whichbuff)
        frame_rdbuf     struc           ;define the stack
                                        ;structure for passing
                                        ;arguments to BASIC
        savebp2         dw      ?       ;caller's base pointer
35      saveret2        dd      ?       ;return offset and
                                        ;segment pushed by BASIC
        whichbuff       dw      ?       ;place to select which
                                        ;buffer to read
        BASIC_ptr       dw      ?       ;place to get pointer to
                                        ;BASIC data array
5       frame_rdbuf     ends ; subroutine rdptrs
```

```
                                ;(adwr,hbwr,adflag,hbflag)
        frame_rdptrs    struc           ;define the stack
                                        ;structure for passing
                                        ;arguments to BASIC
        savebp3         dw      ?       ;caller's base pointer
        saveret3        dd      ?       ;return offset and
                                        ;segment pushed by BASIC
        hbflag          dw      ?       ;flag indicating disk
                                        ;file #1,#2 buffers full
        adflag          dw      ?       ;flag indicating disk
                                        ;file #1 buffer is full
        BASIC_hbwr      dw      ?       ;write pointer for heart
                                        ;beat buffer
        BASIC_adwr      dw      ?       ;write pointer for ad
                                        ;buffer
        frame_rdptrs    ends ;..........code segment begins here cseg_sync       segment 'code'
        basic_dgroup    group   data,stack,const,heap,memory
                                        ;defining link to BASIC
        porta           equ     071CH   ;port definitions for
                                        ;8255 port expander
        portb           equ     071DH   ;these addresses are
                                        ;decoded on the homemade
        portc           equ     071EH   ;board
        control         equ     071FH   ;control word in the
                                        ;8255
        timer0          equ     0704H   ;8253 timer0 register
        timer1          equ     0705H   ;8253 timer1 register
        timer2          equ     0706H   ;8253 timer2 register
        con8253         equ     0707H   ;8253 control register

;------------------------------------------------;
```

; timebase interrupt handler (not accessible to;
; BASIC)                                       ;
;----------------------------------------------;
                ;this routine reads the A/D every timer1
                ;tick
                ;and stores the point in the analog
                ;buffer tbase_int       proc    far     ;this procedure is not
                                ;made public
                assume  cs:cseg_sync,ds:dseg_
                sync,es:nothing,ss:nothing
                push    ax      ;save registers used
                                ;during interrupt
                push    bx      ;
                push    cx      ;
                push    dx      ;
                push    si      ;
                push    di      ;
                push    ds      ;
                push    es      ;

mov     ax,dseg_sync    ;set up segment
                                        ;register for data area
                mov     ds,ax           ;
                ;.........increment counters/ decrement
                ;         pointers
                inc     sync_ctr        ;increment
                                        ;interrupt counter
                mov     cx,20           ;allow up to 20
                                        ;rereads of A/D ;.........get analog value from A/D and
                ;         send to buffer
                mov     dx,portb        ;get analog
                                        ;value from A/D
                in      al,dx           ;

```
                mov     bx,ad_wr        ;and put analog
                                        ;data pointer in bx
retry:          mov     ad_buffer[bx],al
                ;save analog value in ad_buffer chk_adc:        in      al,dx           ;reread adc and
                                        ;check if previous
                cmp     ad_buffer[bx],al ;value agrees
                je      adc_ok          ;if value is the
                                        ;same we're done
                loop    retry           ;retry if retry
                                        ;counter is not depleted
                                        ;failure returns
                                        ;last value read adc_ok:         inc     ad_wr           ;increment write
                                        ;pointer
                cmp     ad_wr,1023      ;see if write
                                        pointer<=1023
                jle     tbase_eoi       ;if pointer is
                                        ;in range then finish
    int
                ;.........reset local ptr and load disk
                ;          buffer for file #1 xor     ah,ah           ;zero ah as
                                        ;upper byte of A/D reading
                mov     cx,1024         ;load counter
                                        ;for 1024 repetitions
                lea     si,ad_buffer    ;load local
                                        ;buffer address
                les     di,fd1ptr       ;load pointer to
                                        ;disk file #1 buffer
fd1lp:          lodsb                   ;repeat moves
                                        ;1024 times (ds:si->es:di)
                stosw                   ;converting
                                        ;bytes to words
```

```
                loop    fdllp           ;
                mov     ad_wr,cx        ;reset write
                                        ;pointer (wrap around)
                inc     ad_rd           ;increment read
                                        ;request for disk ;..........acknowledge interrupt to
                ;          8259A
tbase_eoi:      mov     al,20H          ;send EOI to 8259A
                out     20H,al          ;

pop     es              ;restore registers which
                                        ;were used
                pop     ds              ;
                pop     di              ;
                pop     si              ;
                pop     dx              ;
                pop     cx              ;
                pop     bx              ;
                pop     ax              ;
                iret                    ;return to place where
                                        ;interrupt occurred debugmsg1       db      'this is the end of the time
                        base interrupt' tbase_int       endp

;----------------------------------------;
                ; heart beat interrupt handler (not accessible ;
                ; to BASIC)                              ;
                ;----------------------------------------;
                ;this routine reads the local system
                ;timers
                ;every heart beat and stores the time in
```

```
                    ;the heart beat buffer for use in
                    ;spectral analysis
                    ;

hbeat_int   proc    far     ;this procedure is not
                            ;made public
            assume  cs:cseg_sync,ds:dseg_sync
            assume  es:nothing,ss:nothing push    ax      ;save registers during
                            ;interrupt
            push    bx      ;
            push    cx      ;
            push    dx      ;
            push    si      ;
            push    di      ;
            push    ds      ;
            push    es      ;

mov     ax,dseg_sync    ;set up segment
                                    ;register for data area
            mov     ds,ax           ;

inc     heartbeats      ;increment heart
                                    ;   beat counter ;..........read counters and store
            ;          result in hb_buffer
            mov     dx,con8253      ;prepare to read
                                    ;hbl.clk from timer1
            mov     al,40H          ;by latching
                                    ;counts in timer1
            out     dx,al           ;

mov     dx,timer1       ;prepare to read
                                    ;the latched value
```

```
        in      al,dx           ;from the timer
                                ;(low byte first)
        mov     ah,al           ;save low byte
                                ;in ah
        in      al,dx           ;(high byte
                                ;last)
        xchg    al,ah           ;get the bytes'
                                ;order right mov     bx,hb_wr        ;get write
                                ;pointer for hb_buffer
        add     bx,bx           ;double to
                                ;point to a word
        mov     hb_buffer1[bx],ax   ;and store
                                ;hb1.clk counts ;........read overflow counter from
;           timer2
        mov     dx,con8253      ;prepare to read
                                ;hb2.clk from timer2
        mov     al,80H          ;by latching
                                ;counts in timer2
        out     dx,al           ;

mov     dx,timer2       ;prepare to read
                                ;the latched value
        in      al,dx           ;from the timer
                                ;(low byte first)
        mov     ah,al           ;save low byte
                                ;in ah
        in      al,dx           ;(high byte
                                ;last)
        xchg    al,ah           ;get the bytes'
                                ;order right in ax
        mov     hb_buffer2[bx],ax   ;store
                                result in hb2.clk buffer
```

```
                ;........increment write pointer and
                ;           check for buffer overflow
        inc     hb_wr               ;increment write
                                    ;pointer
        cmp     hb_wr,1023          ;if hb_wr<=1023
        jle     hb_eoi              ;then finish up ;..........reset local ptr/load disk
                ;           buffers for files #2,#3
                ;           (routine takes about 15-20
                ;           msec to fill disk buffer)
        mov     cx,1024             ;load counter
                                    ;for 1024 repetitions
        lea     si,hb_buffer1       ;load local
                                    ;buffer address
        les     di,fd2ptr           ;load pointer to
                                    ;disk file #2 buffer
fd21p:  movsw                       ;repeat moves
                                    ;1024 times (ds:si->es:di)
        loop    fd21p               ;
        mov     cx,1024             ;load counter
                                    ;for 1024 repetitions
        lea     si,hb_buffer2       ;load local
                                    ;buffer address
        les     di,fd3ptr           ;load pointer to
                                    ;disk file #3 buffer
fd31p:  movsw                       ;repeat moves
                                    ;1024 times (ds:si->es:di)
        loop    fd31p               ;
        mov     hb_wr,cx            ;reset write
                                    ;pointer (wrap around)
        inc     hb_rd               ;increment read
                                    ;request ;..........acknowledge interrupt to
                ;           8259A
hb_eoi: mov     al,20H      ;send EOI to 8259A
        out     20H,al      ;
```

```
                pop     es      ;restore registers and
                pop     ds      ;
                pop     di      ;
                pop     si      ;
                pop     dx      ;
                pop     cx      ;
                pop     bx      ;
                pop     ax      ;
                iret            ;return to place where
                                ;interrupt occurred
    debugmsg2   db      'this is the end of the heart
                        beat interrupt' hbeat_int   endp

;---------------------------------------------;
; subroutine instint [install_interrupts]     ;
; (fillptr,fil2ptr,fil3ptr)                   ;
;---------------------------------------------;

instint     proc    far
                public  instint
                ;public symbol allows external references
                ;es,ds vectors and must be restored movsw
                ;uses (ds:si)(es:di) addr
                assume  cs:cseg_sync,ss:basic_
                        dgroup,ds:basic_dgroup
                assume  es:basic_dgroup
                used to access interrupt ;..........save registers push    bp      ;save BASIC base pointer
                                ;   for return to BASIC
                mov     bp,sp   ;point stack pointer at
```

```
                        ;frame reference to
                        ;address of BASIC analog
                        ;data buffer push    ax      ;save additional
                        ;registers
        push    si      ;
        push    di      ;
        push    ds      ;
        push    es      ;
        pushf           ;and flags ;set up the segment
                        ;registers
        mov     ax,dseg_sync    ;set up access
                        ;to floopy disk data ptrs
        mov     es,ax           ;
        assume  es:dseg_sync    ;

;..........put disk file pointers into
;          local memory
        mov     di,[bp].B_fil1ptr       ;get
                        pointers from BASIC
        mov     ax,[di]                 ;and
;               save in dseg_sync areas
        mov     fd1ptroff,ax            ;

mov     di,[bp].B_fil2ptr       ;
        mov     ax,[di]                 ;
        mov     fd2ptroff,ax            ;

mov     di,[bp].B_fil3ptr       ;
        mov     ax,[di]                 ;
        mov     fd3ptroff,ax            ;

mov     ax,ds           ;put segment
                                ;registers into
```

```
        mov     fd1ptrseg,ax        ;pointers
        mov     fd2ptrseg,ax        ;
        mov     fd3ptrseg,ax        ;

;set up the segment
                                    ;registers
        mov     ax,int_buffer
;es points to buffer area to save
        mov     es,ax               ;DOS dummy
                                    ;interrupt vector
        assume es:int_buffer        ;
        mov     ax,0                ;ds points to
                                    ;abs0 (interrupt table)
        mov     ds,ax               ;
        assume ds:abs0              ;

;setup access to
                                    ;interrupt vectors
        lea     di,save_int         ;load offset of
                                    ;save_int in es,di
        lea     si,IRQ3_int         ;load offset of
                                    ;IRQ3_int in ds,si
        cld                         ;clear direction
                                    ;flag to increment ptrs
        movsw                       ;save DOS dummy
                                    ;interrupt vectors to be
        movsw                       ;restored later
        movsw                       ;now saving IRQ4
        movsw                       ;

mov     IRQ3_int+2,cseg_sync    ;install
                                        ;the heart beat (IRQ3)
        mov     IRQ3_int,offset hbeat_int
                                    ;interrupt handler now
        mov     IRQ4_int+2,cseg_sync    ;install
                                        ;the DAC timebase (IRQ4
```

```
            mov     IRQ4_int,offset tbase_int
                                    ;interrupt handler now ;..........initialization of buffer
            control variables mov     ax,dseg_sync    ;setup data
                                    ;segment for initialization
            mov     ds,ax           ;
            assume  ds:dseg_sync    ;ds segment
                                    ;register now redefined xor     ax,ax           ;zero ax
                                    ;register to initialize
            mov     heartbeats,ax   ;counters
            mov     sync_ctr,ax     ;
            mov     ad_wr,ax        ;initialize
                                    ;read/write pointers to top
            mov     hb_wr,ax        ;of buffer
            mov     ad_rd,ax        ;
            mov     hb_rd,ax        ;

;..........return to BASIC popf                    ;restore flags
            pop     es              ;restore additional
                                    ; registers
            pop     ds              ;
            pop     di              ;
            pop     si              ;
            pop     ax              ;

pop     bp              ;restore BASIC's base
                                    ;pointer and
            ret     6               ;delete 3 parameters (6
                                    ;bytes) from the stack
                                    ;and return to the
```

```
                                            ;calling routine debugmsg3       db      'this is the end of the
                            interrupt installation' instint         endp

;----------------------------------;
                    ; subroutine exstint (exstall_     ;
                    ; interrupts)                      ;
                    ;----------------------------------;

exstint         proc    far
                    public  exstint ;public symbol allows
                                    ;external references
                    assume  cs:cseg_sync,ss:basic_dgroup
                    assume  ds:int_buffer,es:abs0
                    ;es,ds used to access interrupt
                    ;vectors and must be restored
                    ;movsw uses (ds:si)(es:di) addr ;..........save registers push    bp      ;save BASIC base pointer
                                    ;    for return to BASIC
                    mov     bp,sp   ;point stack pointer at
                                    ;    frame reference to
                                    ;access arguments passed
                                    ;    by BASIC (none here)

push    ax      ;save additional
                                    ;registers
                    push    si      ;
                    push    di      ;
```

```
        push    ds              ;
        push    es              ;
        pushf                   ;and flags ;set up the segment
                                ;registers as assumed
        mov     ax,0            ;es points to
                                ;abs0 (interrupt table)
        mov     es,ax           ;
        mov     ax,int_buffer   ;ds points to
                                ;buffer area to save
        mov     ds,ax           ;DOS dummy
                                ;interrupt vector ;setup access to
                                ;interrupt vectors
        lea     di,IRQ3_int     ;load offset of
                                ;IRQ3_int in es,di
        lea     si,save_int     ;load offset of
                                ;save_int in ds,si
        cld                     ;clear direction
                                ;flag to increment ptrs
        movsw                   ;restore DOS
                                ;dummy interrupt vectors
        movsw                   ;for IRQ3
        movsw                   ;and IRQ4
        movsw                   ;

;..........return to BASIC popf            ;restore flags
        pop     es      ;restore additional
                        ;registers
        pop     ds      ;
        pop     di      ;
        pop     si      ;
        pop     ax      ;
```

```
            pop     bp          ;restore BASIC's base
                                ;pointer and
            ret     0           ;delete 0 parameters (0
                                ;bytes) from the stack
                                ;and return to the
                                ;calling routine debugmsg4   db      'this is the end of the
                    interrupt exstallation' exstint     endp

;--------------------------------------;
; subroutine rdbeat (heartbeats,sync_   ;
; pulses)                               ;
;--------------------------------------;

rdbeat      proc    far
            public  rdbeat      ;public symbol allows
            external references
            assume  cs:cseg_sync,es:dseg_sync
            assume  ds:basic_dgroup,ss:basic_dgroup ;..........save registers
            push    bp          ;save BASIC base poin
                                ;ter for return to BASIC
            mov     bp,sp       ;point stack pointer at
                                ;frame reference to
                                ;access arguments passed
                                ;by BASIC (one here)
```

```
            push    ax              ;save additional
                                    ; registers
            push    di              ;
            push    es              ;

mov     ax,dseg_sync    ;set up segment
                                    ; register for data area
            mov     es,ax           ;

mov     ax,heartbeats           ;get
                                            ;beats from local memory
            mov     di,[bp].BASIC_beats     ;
            mov     [di],ax                 ;send
                                            ;beats to BASIC mov     ax,sync_ctr             ;get
                                            ;sync pulses from local
            mov     di,[bp].BASIC_syncs     ;memory
            mov     [di],ax                 ;send
                                            ;sync pulses to BASIC ;..........return to BASIC pop     es              ;restore additional
                                    ; registers
            pop     di              ;
            pop     ax              ;
            pop     bp              ;restore BASIC's base
                                    ;pointer,
            ret     4               ;delete 2 parameters (4
                                    ;bytes) from the stack
                                    ;and return to the
                                    ;calling routine debugmsg5   db              'this is the end of the heart
                            beat read routine'
``` rdbeat   endp

```
;-----------------------------------;
; subroutine rdbuf (BASIC_           ;
; ptr,whichbuff)                     ;
;-----------------------------------;
                ;this routine dumps a buffer
                ;from the
                ;assembly routine data area to a
                ;BASIC array
                ;pointed to by BASIC_ptr;
                ;whichbuff selects
                ;the assembler buffer to be
                ;dumped.
                ;choices of buffer are:
                ;   0 - ad_buffer      (bytes)
                ;   1 - hb_buffer1     (words)
                ;   2 - hb_buffer2     (words)

rdbuf           proc    far
                public rdbuf    ;public symbol allows
                                ;external references
                assume cs:cseg_sync,es:basic_dgroup
                assume ds:basic_dgroup,ss:basic_dgroup
                ;..........save registers push    bp      ;save BASIC base pointer
                                ;for return to BASIC
                mov     bp,sp   ;point stack pointer at
                                ;frame reference to
                                ;access arguments passed
                                ;by BASIC (one here)

push    ax      ;save additional
                                ;registers
                push    cx      ;
                push    si      ;
```

```
            push    di          ;
            push    ds          ;
            push    es          ;
            pushf               ;and flags ;.........get pointers from BASIC
            mov     di,[bp].whichbuff       ;get
                                ;buffer choice from BASIC
            mov     ax,[di]                 ;

mov     di,[bp].BASIC_ptr
    ;get pointer to BASIC's data area
            mov     di,[di]         ;and put pointer
                                    ;into di ;.........set up extra segment register
    ;           and counter
            mov     cx,dseg_sync    ;set up segment
                                    register for data area
            mov     ds,cx           ;
            assume  ds:dseg_sync
            mov     cx,1024         ;load counter
                                    ;with number of objects ;.........select buffer here and place
    ;           pointer in si
            or      ax,ax           ;compare
                                    ;selector with 0
            jz      rd_adbuf
    ;if zero (select =0) read ad_buffer
            dec     ax              ;decrement to
                                    ;see if select was 1
            jz      rd_hbbufl
    ;if zero (select =1) read hb_bufferl
            dec     ax              ;decrement to
```

```
                        ;see if select was 2
            jz      rd_hbbuf2
                    ;if zero (select =2) read hb_buffer2
            jmp     rdbuf_end
                    ;not a valid buffer, so return to BASIC rd_adbuf:   lea     si,ad_buffer    ;point source
                                    ;index to ad_buffer
            jmp     move_dta_byte   ;

rd_hbbuf1:  lea     si,hb_buffer1   ;point source
                                    ;index to hb_buffer1
            jmp     move_dta_word   ;

rd_hbbuf2:  lea     si,hb_buffer2   ;point source
                                    ;index to hb_buffer2
            jmp     move_dta_word   ;

;..........move byte data from local
            ;          storage to BASIC array
move_dta_byte: xor   ah,ah   ;zero upper byte of ax cld             ;clear direction flag to
                            ;increment si,di by 2
byt_lp:     lodsb           ;move data bytes from
                            ;local storage (ds:si)
            stosw           ;and store as a word in
                            ;BASIC's area (es:di)
            loop    byt_lp  ;
            jmp     rdbuf_end ;finished ;..........move word data from local
            ;          storage to BASIC array
move_dta_word: cld          ;clear direction flag to
                            ;increment si,di by 2
wd_lp:      movsw           ;get data word from
                            ;local storage (ds:si)
```

```
                    loop    wd_lp       ;and store as a word in
                                        ;BASIC's area (es:di)

;..........return to BASIC rdbuf_end:  popf                ;restore flags
                    pop     es          ;restore additional
                                        ;registers
                    pop     ds          ;
                    pop     di          ;
                    pop     si          ;
                    pop     cx          ;
                    pop     ax          ;

pop     bp          ;restore BASIC's base
                                        ;pointer,
                    ret     4           ;delete 2 parameters (4
                                        ;bytes) from the stack
                                        ;and return to the
                                        ;calling routine debugmsg6   db      'this is the end of the buffer
                             read routine' rdbuf       endp

;------------------------------------------------;
        ; subroutine rdptrs (BASIC_adwr,BASIC_            ;
        ; hbwr,adflag,hbflag)                             ;
        ;------------------------------------------------;
                            ;this routine returns pointers
                            ;appropriate
                            ;arrays returned to BASIC through rdbuf
                            ;this means the pointers are subtracted
                            ;from 1025
                            ;since the buffers have decrementing
```

```
                        ;pointers
                        ;whereas the BASIC data has incrementing
25                      ;pointers
                        ;the flags indicate whether or not the
                        ;respective
                        ;disk file buffers have been filled and
                        ;therefore require
30                      ;service (eg, a BASIC PUT command to
                        ;store the buffer on disk)

rdptrs          proc    far
                        public rdptrs    ;public symbol allows
35                                       ;external references
                        assume cs:cseg_sync,es:dseg_sync
``` assume ds:basic_dgroup,ss:basic_dgroup

;..........save registers

```
        push    bp              ;save BASIC base pointer
                                ;for return to BASIC
        mov     bp,sp           ;point stack pointer at
                                ;frame reference to
                                ;access arguments passed
                                ;by BASIC (one here)

push    ax              ;save additional
                                ;registers
        push    di              ;
        push    es              ;

mov     ax,dseg_sync    ;set up segment
                                ;register for data area
        mov     es,ax           ;

mov     ax,ad_wr        ;get write
                                ;pointer for A/D buffer
        mov     di,[bp].BASIC_adwr      ;and send
                                        ;to BASIC
        mov     [di],ax         ;

mov     ax,hb_wr                ;get
                                ;write pointer for heart
        mov     di,[bp].BASIC_hbwr      ;beat
                                ;buffer and send to BASIC
        mov     [di],ax         ;

mov     ax,ad_rd                ;get
                                ;disk file flag for A/D
        mov     di,[bp].adflag          ;buffer
                                        ;and send to BASIC
```

```
            mov     [di],ax                 ;

mov     ax,hb_rd                ;get
                                            ;disk file flag for heart
            mov     di,[bp].hbflag          ;beat
                                            ;buffers and send to BASIC
            mov     [di],ax                 ;

;..........return to BASIC pop     es          ;restore additional
                                ;registers
            pop     di          ;
            pop     ax          ;

pop     bp          ;restore BASIC's base
                                ;pointer,
            ret     8           ;delete 4 parameters (8
                                ;bytes) from the stack
                                ;and return to the
                                ;calling routine debugmsg7   db      'this is the end of the pointer
                    read routine' rdptrs  endp cseg_sync       ends
                end
; module gwindow1.asm - a collection of routines useful
;                       for preparing data
;                       for the fast graphics routine.
;
;       subroutines:
;
;               dwindow(xmin,xmax,ymin,ymax) - establish
;               data value limits corresponding to
```

```
;                       screen window.
;
;               swindow(xmin,xmax,ymin,ymax) - establish
;                 screen boundaries for data to be
;                 plotted.
;
;               clrwindw - clear contents of present
;                   window
;
;               axes - prepare axes for current window
;                               (no tick marks yet)
;                   (first version: only draws a box
;                     around window)
;
;               scaler(indata_ptr,outdata_ptr,numval) -
;                 scale data to fit into window requires
;                               correct initialization
;                                       using dwindow
;                                       and swindow
;                   (first version: only scales y-
;                       coordinate with dwindow)
;                   (           x coordinate
;                         scaled by numval)
;                   (           maximum y-value
;                         is plotted)
;
;
;------------------------------------------------------------
;
;               arguments passed by BASIC
;
;
;       indata_ptr      - offset of BASIC array
;                           containing y-coordinates of
;                             points to be plotted
;       outdata_ptr     - offset of BASIC array
;                         containing scaled y-coordinates
;       numval          - number of values to plot
```

;
;------------------------------------------------------

;..........screen memory definition

```
screen_memory   segment at 0B800H
even_pixels     db      8000 dup(?)     ;pixels with
                                        ;even y-coordinates
                org     2000H           ;beginning of
                                        ;high screen memory
odd_pixels      db      8000 dup(?)     ;pixels with odd
                                        ;y-coordinates
screen_memory   ends
```

;..........local memory definitions

```
dseg_wind       segment                 ;valid default values
                                        ;present at startup xmin_s          dw      0               ;minimum screen ordinate
                                        ;for window
xmax_s          dw      639             ;maximum screen ordinate
                                        ;for window
ymin_s          dw      0               ;minimum screen abscissa
                                        ;for window
ymax_s          dw      199             ;maximum screen abscissa
                                        ;for window
xmin_d          dw      0               ;minimum data ordinate
                                        ;for window
xmax_d          dw      16384           ;maximum data ordinate
                                        ;for window
ymin_d          dw      0               ;minimum data abscissa
                                        ;for window
ymax_d          dw      16384           ;maximum data abscissa
                                        ;for window
```

```
    ulh_cor         dw      0        ;offset for upper left
                                     ;hand corner of screen
    urh_cor         dw      79       ;offset for upper right
                                     ;hand corner of screen
    llh_cor         dw      3EF0H    ;offset for lower left
                                     ;hand corner of screen
    lrh_cor         dw      3F3FH    ;offset for lower right
                                     ;hand corner of screen outptr          dw      ?        ;pointer to output array
                                     ;in BASIC (must be
                                     ;at least as large as
                                     ;input array)
    rndoff          dw      ?        ;roundoff correction (if
                                     ;fraction>.5 round up)
    numvalt         dw      ?        ;save number of points
                                     ;in input array for xpass
    bx_last         dw      ?        ;save pointer during x-
                                     ;scaling to allow
                                     ;use of largest y per x
                                     ;pixel
    dseg_wind       ends ;----------------------------------------------------;
; define structures for passing arguments from       ;
; BASIC                                              ;
;----------------------------------------------------;

; subroutines
                    ;     dwindow/swindow(xmin,xmax,ymin,ymax)
    frame_lim       struc            ;define structure
    savebpl         dw      ?        ;caller's base pointer
    saveretl        dd      ?        ;return offset and
                                     ;segment pushed by BASIC
    ymax            dw      ?        ;maximum abscissa
```

```
                                    ;(screen or data coordinate)
        ymin            dw      ?   ;minimum abscissa
                                    ;(screen or data coordinate)
        xmax            dw      ?   ;maximum ordinate
                                    ;(screen or data coordinate)
        xmin            dw      ?   ;minimum ordinate
                                    ;(screen or data coordinate)
        frame_lim       ends ; subroutine scaler(indata_ptr,outdata_
                        ; ptr,numval)
        frame_scl       struc       ;define structure
        savebp2         dw      ?   ;caller's base pointer
        saveret2        dd      ?   ;return offset and
                                    ;segment pushed by BASIC
        numval          dw      ?   ;number of values in
                                    ;BASIC's data array
        outdata_ptr     dw      ?   ;scaled values are
                                    ;passed to a BASIC
                                    ;array pointed to by
                                    ;this pointer(for fgraph)
        indata_ptr      dw      ?   ;values to be graphed
                                    ;are passed from a BASIC
                                    ;array pointed to by
                                    ;this pointer.
        frame_scl       ends ;..........subroutines' code begins here cseg_gr segment 'code'
        dgroup  group   data,stack,const,heap;memory
                ;defining link to BASIC
```

```
;----------------------------------------;
; subroutine dwindow(xmin,xmax,ymin,ymax) ;
;----------------------------------------;
                ;subroutine to establish data value
                ;limits
                ;corresponding to screen window.

dwindow     proc    far
                public  dwindow
                ;public symbols allow external references
                assume  cs:cseg_gr,ds:dgroup
                ;BASIC defines regs
                assume  ss:dgroup,es:dseg_wind push    bp              ;save base pointer for the
                                ;return to BASIC
        mov     bp,sp           ;point stack pointer at frame
                                ;structure ;..........save additional registers and
                ;          set up extra data seg
        push    ax      ;
        push    di      ;
        push    es      ;

mov     ax,dseg_wind    ;set up extra data
                                ;segment as assumed
        mov     es,ax           ;

;....get specifications for window from
                ;    BASIC and store locally mov     di,[bp].ymax    ;
        mov     ax,[di]         ;
        mov     ymax_d,ax       ;
```

```
            mov     di,[bp].ymin    ;
            mov     ax,[di]         ;
            mov     ymin_d,ax       ;

mov     di,[bp].xmax    ;
            mov     ax,[di]         ;
            mov     xmax_d,ax       ;

mov     di,[bp].xmin    ;
            mov     ax,[di]         ;
            mov     xmin_d,ax       ;

;..........restore all registers which
            ;          were corrupted
            pop     es              ;
            pop     di              ;
            pop     ax              ;
            pop     bp              ;restore BASIC base
                                    ;pointer before returning
            ret     8               ;delete 4 parameter
                                    ;addresses (8 bytes) from
                                    ;stack and return to
                                    ;calling routine
    dwindow endp ;------------------------------------------------;
            ; subroutine swindow(xmin,xmax,ymin,ymax)        ;
            ;------------------------------------------------;
            ;subroutine to establish absolute screen
            ;coordinate limits
            ;corresponding to screen window.

swindow         proc    far
                    public  swindow ;public symbols allow
                    external references
                    assume  cs:cseg_gr,ss:dgroup
```

```
                    ;BASIC defines regs
                    assume  ds:dseg_wind,es:dgroup push    bp          ;save base pointer for the
                            ;return to BASIC
        mov     bp,sp       ;point stack pointer at frame
                            ;structure ;..........save additional registers and
                ;          set up extra data seg
        push    ax      ;
        push    cx      ;
        push    dx      ;
        push    di      ;
        push    ds      ;

mov     ax,dseg_wind    ;set up extra data
                                ;segment as assumed
        mov     ds,ax           ;

;....get specifications for window from
                ;    BASIC and store locally
                ;........first y coordinate ranges
        mov     di,es:[bp].ymax ;
        mov     ax,es:[di]              ;
        cmp     ax,199          ;make sure ymax_s <=199
        jg      y_bad           ;use default value if
                                ;value sent is bad
        mov     ymax_s,ax       ;

mov     di,es:[bp].ymin ;
        mov     ax,es:[di]              ;
        mov     ymin_s,ax       ;

;..........y range limits examined
```

```
        add     ax,8                ;make sure that ymax
                                    ;exceeds ymin by at least 8
        cmp     ax,ymax_s           ;
        jng     y_ok                ;if ymax_s <= ymin_s+8
y_bad:  mov     ax,199              ;then set ymax_s,ymin_s
                                    ;to default values
        mov     ymax_s,ax           ;ymax_s default=199
        xor     ax,ax               ;ymin_s default=0
        mov     ymin_s,ax           ;

;..........x coordinate ranges set up
y_ok:   mov     di,es:[bp].xmax ;
        mov     ax,es:[di]          ;
        cmp     ax,639              ;make sure xmax_s <=639
        jg      x_bad               ;use default value if
                                    ;value sent is bad
        mov     xmax_s,ax           ;

mov     di,es:[bp].xmin ;
        mov     ax,es:[di]          ;
        mov     xmin_s,ax           ;

;..........x range limits examined
        cmp     ax,xmax_s           ;make sure that xmax
                                    ;exceeds xmin
        jnge    x_ok                ;if xmax_s < xmin_s
x_bad:  mov     ax,639              ;then set xmax_s,xmin_s
                                    ;to default values
        mov     xmax_s,ax           ;xmax_s default=199
        xor     ax,ax               ;xmin_s default=0
        mov     xmin_s,ax           ;

;..........set up the pointers to the
        ;             four screen corners
```

```
        ; --ymin
x_ok:   xor     dx,dx           ;put lowest screen
                                ;memory location (=0) into dx
        mov     ax,ymin_s       ;first calculate y
                                ;contribution to offset of
        shr     ax,1            ;upper corners by
                                ;multiplying (ymin/2) by 80.
        jnc     y0_even         ;if ymin was not even
        mov     dx,2000H        ;then the upper corners
                                ;are odd pixels (2000H)
y0_even:mov     cl,80           ;[promised
                                ;multiplication by 80]
        mul     cl              ;
        add     dx,ax           ;y contribution to
                                ;offset is here
        mov     ulh_cor,dx      ;save partial result
        mov     urh_cor,dx      ;

; --ymax
        xor     dx,dx           ;put lowest screen
                                ;memory location (=0) into dx
        mov     ax,ymax_s       ;first calculate y
                                ;contribution to offset of
        shr     ax,1            ;lower corners by
                                ;multiplying (ymax/2) by 80.
        jnc     y1_even         ;if ymax was not even
        mov     dx,2000H        ;then the upper corners
                                ;are odd pixels (2000H)
y1_even:mov     cl,80           ;[promised
                                ;multiplication by 80]
        mul     cl              ;
        add     dx,ax           ;y contribution to
                                ;offset is here
        mov     llh_cor,dx      ;save partial result
        mov     lrh_cor,dx      ;

mov     ax,xmin_s       ;x contribution is
                                ;xmin/8
```

```
        mov     cl,3            ;calculated by shifting
                                ;right 3 bits
        shr     ax,cl           ;and
        add     ulh_cor,ax      ;adding the result to
                                ;the stored partial result
        add     llh_cor,ax      ;

mov     ax,xmax_s       ;x contribution is
                                ;   xmin/8
        mov     cl,3            ;calculated by shifting
                                ;right 3 bits
        shr     ax,cl           ;and
        add     urh_cor,ax      ;adding the result to
                                ;the stored partial result
        add     lrh_cor,ax      ;

;..........restore all registers which
        ;              were corrupted
        pop     ds              ;
        pop     di              ;
        pop     dx              ;
        pop     cx              ;
        pop     ax              ;

pop     bp              ;restore BASIC base
                                ;pointer before returning
        ret     8               ;delete 4 parameter
                                ;addresses (8 bytes) from
                                ;stack and return to
                                ;calling routine
swindow endp ;----------------------------------------;
        ; subroutine clrwindw                    ;
        ;----------------------------------------;
```

```
                                ;subroutine to clear
                                ;the screen window.

clrwindw        proc    far
                        public  clrwindw ;public symbols allow
                                         ;external references
                        assume  cs:cseg_gr,ss:dgroup
                        ;BASIC defines regs
                        assume  ds:dseg_wind,es:screen_memory push    bp      ;save base pointer for the
                                ;return to BASIC
                mov     bp,sp   ;point stack pointer at frame
                                ;structure ;.........save additional registers and
                                ;         set up data segments
                push   ax       ;
                push   bx       ;
                push   cx       ;
                push   dx       ;
                push   si       ;
                push   di       ;
                push   ds       ;
                push   es       ;

;.........set up data segments as
                                ;                 assumed
                mov    ax,dseg_wind     ;
                mov    ds,ax            ;
                mov    ax,screen_memory;
                mov    es,ax            ;

;.........clear screen by zeroing out
```

```
            ;           graphics memory
            ;              register usage:
            ;              ax - marker for
            ;                 rightmost column
            ;              bh - # x bytes
            ;              bl - pixel mask
            ;              cx - y
            ;                 coordinate counter
            ;              dx - # y lines
            ;              si - offset of
            ;                 top of column
            ;              di - offset of
            ;                 present byte
            ;....first clear leftmost part of window
    mov     dx,ymax_s       ;compute number of
                            ;vertical lines
    sub     dx,ymin_s       ;
    inc     dx              ;and save in dx mov     ax,urh_cor      ;compute number of
                            ;horizontal bytes
    sub     ax,ulh_cor      ;(a number 1-79)
    mov     bh,al           ;and save in bh
    xor     ax,ax           ;clear ax register to
                            ;indicate clearing of all
                            ;columns except the
                            ;rightmost one ;..........set up to blank leftmost
    ;               column
    mov     cx,xmin_s       ;compute mask for
                            ;blanking leftmost column
    call    mask0           ;

lea     di,even_pixels  ;get offset of
    add     di,ulh_cor      ;upper left hand corner
                            ; of window
```

| | | | |
|---|---|---|---|
| 35 | mov | si,di | ;save location in si |
| | | ;.........blank all columns except | |
| | | ; rightmost | |
| | nxt_col:call | clr_col | ; |
| 5 | xor | bl,bl | ;subsequent columns |
| | | ;blank all bits (bl mask=0) | |
| | inc | si | ;compute offset of |
| | | | ;present column |
| | mov | di,si | ;and load into di |
| 10 | dec | bh | ;see if there are any |
| | | | ;columns left |
| | jnz | nxt_col | ; |
| | | ;.........blank rightmost column | |
| 15 | mov | cx,xmax_s | ;compute mask for |
| | | | ;rightmost column |
| | inc | cx | ;include rightmost pixel |
| | and | cl,7 | ;using cx mod 8 |
| | mov | bl,0FFH | ;put mask in bl |
| 20 | jz | mask_r | ;if cx mod 8 <>0 then |
| | shr | bl,cl | ;shift mask |
| | | | ;appropriately |
| | jmp | 1st_clr | ; |
| | mask_r: xor | bl,bl | ;set bl mask to blank |
| 25 | | | ;all bits |
| | 1st_clr:call | clr_col | ;clear rightmost column |
| | | ;.........restore all registers which | |
| 30 | | ; were corrupted | |
| | pop | es | ; |
| | pop | ds | ; |
| | pop | di | ; |
| | pop | si | ; |
| 35 | pop | dx | ; |
| | pop | cx | ; |
| | pop | bx | ; |
| | pop | ax | ; |

```
        pop     bp              ;restore BASIC base
                                ;pointer before returning
        ret     0               ;delete 0 parameter
                                ;addresses (0 bytes) from
                                ;stack and return to
                                ;calling routine
clrwindw endp ;--------------------------------------;
        ; subroutine axes                      ;
        ;--------------------------------------;
                        ;subroutine to draw a box
                        ;enclosing the screen window.

axes            proc    far
                public  axes    ;public symbols allow
                                ;external references
                assume  cs:cseg_gr,ss:dgroup
                ;BASIC defines regs
                assume  ds:dseg_wind,es:screen_memory push    bp              ;save base pointer for the
                                ;return to BASIC
        mov     bp,sp           ;point stack pointer at frame
                                ;structure ;..........save additional registers and
                ;          set up data segments
        push    ax      ;
        push    bx      ;
        push    cx      ;
        push    dx      ;
        push    si      ;
        push    di      ;
```

```
                push    ds      ;
                push    es      ;

;..........set up data segments as
                ;           assumed
                mov     ax,dseg_wind    ;
                mov     ds,ax           ;
                mov     ax,screen_memory;
                mov     es,ax           ;

;..........draw box screen by setting
                ;               appropriate bits
                ;                   register usage:
                ;                       ax - marker for
                ;                           rightmost column
                ;                       bh - # x bytes
                ;                       bl - pixel mask
                ;                       cx - y
                ;                           coordinate counter
                ;                       dx - # y lines
                ;                       si - offset of
                ;                           top of column
                ;                       di - offset of
                ;                           present byte
                ;....first calculate number of
                ;       vertical,horizontal counts
                mov     dx,ymax_s       ;compute number of
                                        ;vertical lines
                sub     dx,ymin_s       ;
                inc     dx              ;and save in dx mov     ax,urh_cor      ;compute number of
                                        ;horizontal bytes
                sub     ax,ulh_cor      ;(a number 1-79)
                mov     bh,al           ;and save in bh
```

```
;..........left edge of box
        lea     di,even_pixels  ;get offset of
        add     di,ulh_cor      ;upper left hand corner
                                ;of window mov     cx,xmin_s       ;compute mask to draw
                                ;left end of top line
        call    mask0           ;[mask0 gives pixels to
                                ;left of x coordinate]
        xor     bl,0FFH         ;[requiring
                                ;complementation here]
        or      es:[di],bl      ;

mov     cx,xmin_s       ;compute mask for
                                ;setting leftmost box edge
        call    mask1           ;
        call    drw_ln          ;draw the left most
                                ;border of the box lea     di,even_pixels  ;get offset of
        add     di,llh_cor      ;lower left hand corner
                                ; of window
        mov     cx,xmin_s       ;compute mask to draw
                                ;left end of bottom line
        call    mask0           ;[mask0 gives pixels to
                                ;left of x coordinate]
        xor     bl,0FFH         ;[requiring
                                ;complementation here]
        or      es:[di],bl      ;

;..........bottom edge of box
        mov     bl,bh           ;save number of
                                ;horizontal bytes in bl
        call    hbar            ;draw horizontal bar ;..........top edge of box
```

```
        mov     bh,bl           ;get number of
                                ;horizontal bytes from bl
        lea     di,even_pixels  ;get offset of
        add     di,ulh_cor      ;upper left hand corner
                                ;of window
        call    hbar            ;draw horizontal bar ;..........right edge of box
        lea     di,even_pixels  ;get offset of
        add     di,urh_cor      ;upper left hand corner
                                ;of window mov     cx,xmax_s       ;compute mask to draw
                                ;right end of top line
        call    mask0           ;
        or      es:[di],bl      ;

mov     cx,xmax_s       ;compute mask for
                                ;setting rightmost box edge
        call    mask1           ;
        call    drw_ln          ;set rightmost box edge lea     di,even_pixels  ;get offset of
        add     di,lrh_cor      ;lower right hand corner
                                ;of window
        mov     cx,xmax_s       ;compute mask to draw
                                ;right end of bottom line
        call    mask0           ;
        or      es:[di],bl      ;

;..........restore all registers which
        ;              were corrupted
        pop     es              ;
        pop     ds              ;
        pop     di              ;
        pop     si              ;
        pop     dx              ;
```

```
                pop     cx      ;
        pop     bx      ;
                pop     ax      ;

pop     bp              ;restore BASIC base
                                        ;pointer before returning
                ret     0               ;delete 0 parameter
                                        ;addresses (0 bytes) from
                                        ;stack and return to
                                        ;calling routine
        axes endp ;-------------------------------------------------;
        ; subroutine scaler(indata_ptr,outdata_            ;
        ; ptr,numval)                                     ;
        ;-------------------------------------------------;
                        ;subroutine to scale data values within
                        ;limits
                        ;corresponding to data window. As a
                        ;convenience,
                        ;the data is inverted so ymax_d is at
                        ;top of
                        ;the window (screen values increase
                        ;towards
                        ;bottom of the screen)
                        ;
                        ;scaling occurs in two passes: first y
                        ;is scaled, then x
        scaler          proc    far
                        public  scaler  ;public symbols allow
                                                external references
                        assume  cs:cseg_gr,es:dgroup
                        ;BASIC defines regs
                        assume  ss:dgroup,ds:dseg_wind
```

```
        push    bp              ;save base pointer for the
                                ;return to BASIC
        mov     bp,sp           ;point stack pointer at frame
                                ;structure ;..........save additional registers and
                ;         set up extra data seg
        push    ax      ;
        push    bx      ;
        push    cx      ;
        push    dx      ;
        push    si      ;
        push    di      ;
        push    ds      ;

mov     ax,dseg_wind    ;set up extra data
                                ;segment as assumed
        mov     ds,ax           ;
                ;....get data from BASIC point by point
                ;              and scale according to
                ;         data window. (use di,bx as
                ;         holding registers)

mov     si,es:[bp].outdata_ptr
                ;get pointer for scaled data output
        mov     si,es:[si]      ;pointer is now in si
        mov     outptr,si       ;save output pointer mov     si,es:[bp].numval
                ;get number of points to scale into cx
        mov     cx,es:[si]      ;
        mov     numvalt,cx      ;save value for second
                                ;pass mov     si,es:[bp].indata_ptr
                ;get pointer to BASIC's array of data
        mov     si,es:[si]              ;pointer for
```

```
                mov     di,outptr       ;input is now in si
                                        ;pointer for
                                        ;output is now in di mov     bx,ymax_s       ;put screen scale into
                                        ;bx
                sub     bx,ymin_s       ;

mov     ax,bx           ;use half screen scale
                                        ;as a roundoff correction
                shr     ax,1            ;
                mov     rndoff,ax       ;

mov     bp,ymax_d       ;put data scale into bp
                sub     bp,ymin_d       ;
        getval: mov     ax,es:[si]      ;get data value from
                                        ;BASIC cmp     ax,ymin_d       ;if less than ymin_d
                jle     minval          ;then use minimum value
                sub     ax,ymax_d       ;if greater than ymax_d
                jge     maxval          ;then use maximum value
                neg     ax              ;ax now has distance
                                        ;from full scale mul     bx              ;multiply by screen
                                        ;scale (corrupts dx)
                add     ax,rndoff       ;add roundoff correction
                jnc     div_d           ;if no carry (ax,dx)
                                        ;pair is correct
                inc     dx              ;otherwise increment dx
                                        ;(carry from add)
        div_d:  div     bp              ;and divide by data
                                        ;scale
                add     ax,ymin_s       ;add screen offset value
                                        ;to get final scaled
                jmp     nextval         ;value
```

```
maxval: mov     ax,ymax_s           ;insert maximum value
        jmp     nextval             ;

minval: mov     ax,ymin_s           ;insert minimum value
        jmp     nextval             ;

nextval:mov     es:[di],ax          ;store y-scaled result
                                    ;in BASIC output array
        inc     si                  ;point to next data
                                    ;value (integer is 2 bytes)
        inc     si                  ;
        inc     di                  ;point to next output
                                    ;point for y-scaled data
        inc     di                  ;
        loop    getval              ;if cx shows points
                                    ;remain, scale them ;..........scale x-axis
        mov     di,outptr           ;point di to beginning
                                    ;of output array
        mov     cx,numvalt          ;restore counter for
                                    ;number of points mov     bp,xmax_s           ;put screen scale into
                                    ;bp
        sub     bp,xmin_s           ;

mov     bx,639              ;initialize bx_last to
                                    ;rightmost pixel
        mov     bx_last,bx          ;

xor     ax,ax               ;zero ax,bx to start
        xor     bx,bx               ;bx points to x-unscaled
                                    ;source get_ysc: mov    si,es:[di][bx]      ;get current value y
                                    ;scaled value into si
```

```
                mov     ax,bx           ;calculate twice x-
                                        ;coordinate plus 1
                inc     ax              ;(gives proper roundoff)

mul     bp              ;multiply by screen
                                        ;scale (corrupts dx)
        div_x:  div     numvalt         ;scale by number of
                                        ;input points
                and     ax,0FFFEH       ;trim off lsb for
                                        ;aligned access to words xchg    ax,bx           ;save source ptr in ax,
                                        ;using bx to point to
                                        ;offset of destination
                                        ;(which is a word)
                cmp     bx,bx_last      ;see if we are on the
                                        ;same x-coordinate
                jne     y_save          ;if not put a valid
                                        ;abcissa at this coordinate
                cmp     es:[di][bx],si  ;compare yscaled value
                                        ;to last yscaled value
                jle     y_more          ;stored. if y was
                                        ;greater or equal then keep it
        y_save: mov     es:[di][bx],si  ;else store yscaled
                                        ;value in output array
                mov     bx_last,bx      ;save current
                                        ;destination pointer y_more: xchg    bx,ax           ;restore bx register inc     bx              ;point to next input
                                        ;point
                inc     bx              ;
                loop    get_ysc         ;continue scaling x
                                        ;until counter cx is zero ;..........restore all registers which
```

```
                    ;           were corrupted
         pop    ds              ;
         pop    di              ;
         pop    si              ;
         pop    dx              ;
         pop    cx              ;
         pop    bx              ;
         pop    ax              ;

pop    bp              ;restore BASIC base
                                ;pointer before returning
         ret    6               ;delete 3 parameter
                                ;addresses (6 bytes) from
                                ;stack and return to
                                ;calling routine
   scaler  endp ;----------------------------------;
                      ; utility routines local to the window ;
                      ; module                               ;
                      ;----------------------------------;

;.........utility procedure for fast
                      ;         clearing of vertical cols
   clr_col proc   near mov    cx,dx            ;set up counter for
                                   ;clearing first column
   clr_lp: and    es:[di],bl       ;clear a graphics byte
                                   ;using mask
           xor    di,2000H         ;switch even/odd pixel
           test   di,2000H         ;if odd pixel go to
   loop                            ;        statement
           jnz    go_clr           ;
           add    di,80            ;go to next even/odd
                                   ;pair
```

```
go_clr: loop    clr_lp          ;continue clearing this
                                ;column
        ret                     ;

clr_col endp

;..........utility procedure for fast
                ;          drawing of vertical lines
drw_ln  proc    near mov     cx,dx           ;set up counter for
                                ;clearing first column
drw_lp: or      es:[di],bl      ;set a graphics bit
                                ;using mask
        xor     di,2000H        ;switch even/odd pixel
        test    di,2000H        ;if odd pixel go to loop
                                ;statement
        jnz     go_drw          ;
        add     di,80           ;go to next even/odd
                                ;pair
go_drw: loop    drw_lp          ;continue clearing this
                                ;column
        ret                     ;

drw_ln  endp

;..........utility for fast drawing of
                ;          horizontal lines
hbar    proc    near    ;requires di to have byte before
                        ;first byte of line
                        ;bh is used as a decrementing
                        ;byte counter for number
                        ;of bytes drawn dec     bh              ;check to make sure at
                                ;least one byte to plot
        jz      hbar_ok         ;if bh=0 then done
```

```
hbar_lp: inc    di                      ;go to next byte
         mov    byte ptr es:[di],0FFH   ;set byte
         dec    bh                      ;decrement number of
                                        ;bytes remaining
         jnz    hbar_lp                 ;continue if more bytes
                                        ;need to be drawn hbar_ok: ret                            ;

hbar     endp

;..........utility procedure for
         ;          computing bit mask for clears
mask0    proc   near    ;uses value in cx to compute bit
                        ;mask in bl and    cl,7                    ;using cx mod 8
         mov    bl,0FFH                 ;put mask in bl
         jz     mask0_ok                ;if cx mod 8 <>0 then
         shr    bl,cl                   ;shift mask
                                        ;appropriately
mask0_ok: xor   bl,0FFH                 ;complement mask to set
                                        ;bits to be retained
         ret mask0    endp ;..........utility procedure for
         ;          computing bit mask for drawing
mask1    proc   near    ;uses value in cx to compute bit
                        ;mask in bl
         and    cl,7                    ;using cx mod 8
         mov    bl,80H                  ;put mask in bl
         jz     mask1_ok                ;if cx mod 8 <>0 then
```

```
                shr     bl,cl           ;shift mask
                                        ;appropriately
        mask1_ok:ret mask1   endp cseg_gr ends
                end ; subroutine fgraph (data_ptr,numval,x_coord,line_type)
        ;       called from BASIC this routine graphs an array
        ;       on the screen
        ;       this routine is designed to allow rapid access
        ;       to the screen to allow
        ;       real time graph generation.
        ;

;-----------------------------------------------------------
        ;
        ;               arguments passed by BASIC
        ;
        ;
        ;       data_ptr        - offset of BASIC array
        ;                         containing y-coordinates of
        ;                         points to be plotted
        ;       numval          - number of values to plot
        ;       x_coord         - absolute (screen) x coordinate
        ;                         of first point
        ;                         succeeding values are plotted
        ;                         at succeeding pixels
        ;       line_type       - if 0 then just plot points
        ;                         if not zero this byte value
        ;                         gives the line mask for
        ;                         plotting various lines
        ;                         (eg. 55H interpolates a line
        ;                         between adjacent
```

```
;                           points with every other point
;                           on the interpolation
;                           line; in other words, a fine
                            dotted line)
;
;-----------------------------------------------------

;..........screen memory definition screen_memory   segment at 0B800H
even_pixels     db      8000 dup(?)     ;pixels with
                                        ;even y-coordinates
                org     2000H           ;beginning of
                                        ;high screen memory
odd_pixels      db      8000 dup(?)     ;pixels with odd
                                        ;y-coordinates
screen_memory   ends frame   struc                   ;define structure
savebp          dw      ?       ;caller's base pointer
save_es         dw      ?       ;save es on stack for
                                ;return to BASIC
saveret         dd      ?       ;return offset and
                                ;segment pushed by BASIC
line_type       dw      ?       ;mask for plotting
                                ;various line types
x_coord         dw      ?       ;x_coordinate of first
                                ;point to be plotted
numval          dw      ?       ;number of values in
                                ;graph_data(*) array
data_ptr        dw      ?       ;values to be graphed
                                ;are passed in an array
                                ;graph_data(*) pointed
                                ;to by this pointer.
frame   ends
```

```
cseg    segment 'code'
dgroup  group   data,stack,const,heap,memory
                ;defining link to BASIC
        assume  cs:cseg,ds:dgroup,ss:dgroup
                ;BASIC defines regs
        assume  es:screen_memory        ;use extra data
                                        ;segment to access the
                                        ;screen memory fgraph  proc    far
        public  fgraph                  ;public symbols allow
                                        ;external references push    es                      ;save BASIC's es
                                        ;register
        push    bp                      ;save base pointer for
                                        ;the return to BASIC
        mov     bp,sp                   ;point stack pointer at
                                        ;frame structure ;.........save additional registers
        push    ax                      ;
        push    bx                      ;
        push    cx                      ;
        push    dx                      ;
        push    si                      ;
        push    di                      ;

;this routine assumes that the proper
                ;graphics
                ;mode has been established (eg., <SCREEN
                ;2>)

mov     si,[bp].numval  ;get number of points
```

```
                                              ;remaining to be graphed.
               mov      ax,[si]              ;
               or       ax,ax                ;if number of
15                                           ;repetitions is zero we're done.
               jnz      setup                ;otherwise there is work
                                             ;remaining.
               jmp      finish               ;done 20
                        ;..........temporary storage area
                        ;          (aligned on word boundary)

even
25  numval_t   dw       ?                    ;number of points left
                                             ;to plot
    x_now      dw       ?                    ;byte offset in screen
                                             ;memory for x-coordinate
    last_x     dw       ?                    ;last x-coord (saved for
30                                           ;return to BASIC)
    last_y     dw       ?                    ;last y-coord (used only
                                             ;for line plots)
    last_di    dw       ?                    ;last screen offset
                                             ;(used only for line plots)
35  line_mask  db       ?                    ;line mask is the
                                             ;rotating buffer which is
                                             ;to generate various
                                             ;dotted/dashed lines pixel_mask db       ?                    ;pixel mask is used to
                                             ;set one pixel in the
5                                            ;screen memory (using an
                                             ;OR instruction)

setup: mov   last_di,0FFFFH    ;initialize last_di to
10                                 ;ffff
           mov   numval_t,ax       ;save number of points
                                   ;to plot
           mov   si,[bp].line_type ;get line type mask
```

|    |          |                  | ;from BASIC |
|----|----------|------------------|-------------|
| 15 | mov      | ax,[si]          | ;           |
|    | mov      | line_mask,al     | ;and store lower byte in ;local storage |
|    | mov      | si,[bp].x_coord  | ;get x coordinate of |
| 20 |          |                  | ;first point from BASIC |
|    | mov      | ax,[si]          | ; |
|    | mov      | bx,numval_t      | ;get number of points in ;order |
|    | dec      | bx               | ;to compute |
| 25 | add      | bx,ax            | ;the last x-coordinate |
|    | cmp      | bx,640           | ;x-coordinate is modulo ;640 |
|    | jle      | 1st_x            | ;if less than 640 store ;value |
| 30 | sub      | bx,640           | ;else make less than 640 |
|    | 1st_x: mov | last_x,bx      | ;store last_x value for ;return to BASIC |
|    | mov      | bx,seg even_pixels | ;set up screen |
| 35 |          |                  | ;memory as extra segment |
|    | mov      | es,bx            | ; (note: cannot move an ;immediate direct to es) |
|    | mov      | cl,al            | ;get low byte of x_ ;coordinate |
| 5  | and      | cl,7             | ;modulo 8 |
|    | mov      | pixel_mask,80H   | ;initialize pixel mask ;to first bit |
|    | jz       | mask_ok          | ;if x_coord mod 8 is ;zero, the mask is ok |
| 10 | shr      | pixel_mask,cl    | ;rotate mask bit to ;correct position |
|    | mask_ok:mov | cl,3          | ;x_coord/8 is byte ;offset for pixel |
| 15 | shr      | ax,cl            | ;this result is termed x_ |

```
                                            ;now
            mov     x_now,ax                ;

mov     di,[bp].data_ptr
20          ;use [si] with offset in bx to access y
            mov     si,[di]                 ;coordinates in BASIC
                                            ;data(*) array
            mov     bx,0                    ;initialize to first
                                            ;element of array
25          mov     dx,[si][bx]             ;get first y-coordinate
                                            ;from BASIC
            mov     last_y,dx               ;and initialize last_y get_y:  mov     dx,[si][bx]             ;get y-coordinate from
30                                          ;BASIC
            mov     ax,dx                   ;ax is used to calculate
                                            ;screen memory offset
            shr     ax,1                    ;divide by two to get
                                            ;rid of lsb
35          mov     cl,80                   ;80 bytes per line (lsb
                                            ;gives interlace)
            mul     cl                      ;ax is offset for y-
                                            ;coord in screen memory
            add     ax,x_now                ;add offset for x-
                                            ;coordinate to y offset in ax
5           mov     di,ax                   ;and put x,y offset into
                                            ;di
            test    dx,1                    ;if y_coordinate was
                                            ;even
            jz      ln_beg                  ;then we are ready to
10                                          ;plot a point or a line
            add     di,2000H                ;odd pixels require the
                                            ;interlace offset ln_beg: cmp     last_di,0FFFFH          ;if last_di is not ffff
15                                          ;(first point)
            jne     1st_di                  ;then go to set next
                                            ;pixel
```

```
              mov      last_di,di          ;else initialize di
                                           ;properly
    lst_di:   cmp      line_mask,0         ;if line mask is not 0
              jne      draw_line           ;then draw the
                                           ;approrpiate line
    set_px:   mov      al,pixel_mask       ;else set pixel using OR
                                           ;with mask
              or       even_pixels[di],al
              jmp      more                ;and go to next point ;..........drawing the required line draw_line:xchg     di,last_di          ;get old screen memory
                                           ;location to start
              mov      cx,last_y           ;cx will be the y
                                           ;distance to current pixel
              sub      cx,dx               ;dx still has current y-
                                           ;coord.
              jcxz     ln_done             ;if cx is zero then plot
                                           ;only one point
              jg       nxt_pxu             ;if last_y>y-coord then
                                           ;draw up on screen
                                           ;since lowest y is at
                                           ;top of screen ;..........draw a line down on screen
                       ;              (increasing y)

neg      cx                  ;cx was negative
              jmp      nxt_pix             ;only plot one point per
                                           ;y-coord if possible
    dn_lp:    shl      line_mask,1         ;set up line mask for
                                           ;next pixel
              jnc      nxt_pix             ;if no bits are shifted
                                           ;out then no pixel here
              or       line_mask,1         ;is msb was shifted out,
```

```
20                                          ;now set lsb
           mov      al,pixel_mask           ;load pixel mask and
           or       even_pixels[di],al      ;set pixel using
                                            ;OR with mask 25                  ;..........now find next pixel position
                    ;          for line
      nxt_pix:xor   di,2000H                ;change from high to low
                                            ;memory (or vice versa)
           test     di,2000H                ;if in high screen
30                                          ;memory
           jnz      dn_di                   ;then di points to next
                                            ;pixel
           add      di,80                   ;else go to next line in
                                            ;lower memory
35    dn_di: loop   dn_lp                   ;do another pixel in
                                            ;this line
           jmp      ln_done                 ;plot last pixel when
                                            ;done ;..........draw a line up on screen
 5                  ;          (decreasing y)

up_lp:  shl   line_mask,1             ;set up line mask for
                                            ;next pixel
           jnc      nxt_pxu                 ;if no bits are shifted
10                                          ;out then no pixel here
           or       line_mask,1             ;is msb was shifted out,
                                            ;now set lsb
           mov      al,pixel_mask           ;load pixel mask and
           or       even_pixels[di],al      ;set pixel using
15                                          ;OR with mask ;..........now find next pixel position
                    ;          for line
      nxt_pxu:xor   di,2000H                ;change from high to low
20                                          ;memory (or vice versa)
           test     di,2000H                ;if in low screen memory
```

```
            jz      up_di           ;then di points to next
                                    ;pixel
            sub     di,80           ;else go to next line in
                                    ;upper memory
    up_di:  loop    up_lp           ;do another pixel in
                                    ;this line
    ;       jmp     ln_done         ;plot last pixel when
                                    ;done(statement not needed
    ;                               here)

;..........finish up with line by
            ;          storing current data
    ln_done:shl     line_mask,1     ;set up line mask for
                                    ;next pixel
            jnc     end_pix         ;if no bits are shifted
                                    ;out then no pixel here
            or      line_mask,1     ;is msb was shifted out,
                                    ;now set lsb
            mov     al,pixel_mask   ;load pixel mask and
            or      even_pixels[di],al   ;set pixel using
                                         ;OR with mask
    end_pix:mov     last_y,dx       ;save present y-
                                    ;coordinate
            mov     last_di,di      ;save present
                                    ;pixel byte pointer ;..........prepare for next point if
            ;          there is one more:   dec     numval_t        ;one less point left now
            jz      finish          ;finished if none left
            inc     bx              ;if not done increment
                                    ;base index by 2 to point
            inc     bx              ;to next y-coord in
                                    ;BASIC array
```

```
        shr     pixel_mask,1        ;move pixel mask to next
                                    ;x-coord
        jnz     go_gety             ;if mask points to some
                                    ;pixel get the y-coord
        mov     pixel_mask,80H      ;otherwise set up mask
                                    ;for next 8 x-coordinates
        inc     x_now               ;x_now points to next
                                    ;byte (for next 8 pts)
        inc     last_di             ;fix last di to point to
                                    ;present column
        cmp     x_now,80            ;there are only 80 bytes
                                    ;per line, so
        jl      go_gety             ;if x_now<80 then x_now
                                    ;is ok to get next y
        mov     x_now,0             ;otherwise wrap around
                                    ;to x_now=0
        sub     last_di,80          ;also reset di to first
                                    ;column
go_gety:jmp     get_y               ;

;..........finish up and send present
        ;          pointers,mask to BASIC finish: mov     al,line_mask        ;get present line mask
        xor     ah,ah               ;zero upper byte
        mov     si,[bp].line_type   ;and
        mov     [si],ax             ;send to BASIC
        mov     ax,last_x           ;get last x-coordinate
        mov     si,[bp].x_coord     ;and send to BASIC
        mov     [si],ax             ;

;..........restore all registers which
        ;          were corrupted
        pop     di                  ;
        pop     si                  ;
        pop     dx                  ;
```

```
        pop     cx              ;
        pop     bx              ;
        pop     ax              ;
30 pop     es              ;restore the es register
                                ;and
        pop     bp              ;restore BASIC base
35                              ;pointer before returning
        ret     8               ;delete 4 parameter
                                ;addresses (8 bytes) from
                                ;stack and return to
                                ;calling routine
    fgraph  endp
5   cseg    ends
        end
```

APPENDIX C

```
5       ' CALIB - program to calibrate instruments using
        '   board#1
        ' last revision: 1985

10
        defint a-y
        ' only z denotes a real number
        dim buffer(12800)
        hrbpm=0
15      zfqlow=0.
        zfqres=0.
        zlfa=0.
        zrfa=0.
        cls
20

'define ports on 8253
```

```
            timer0=&h704
            timer1=&h705
25          timer2=&h706
            con8253=&h707

' set timer modes to 16 bit square wave rate
30          '    generators
            out con8253,&h36
            out con8253,&h76
            out con8253,&hB6

35      'for testing set timer 0 to 100Hz timebase
            out timer1,164
            out timer1,3 out timer2,0
            'set timer 0 to 1280Hz timebase
5           out timer2,5
            ' (2.38MHz/1864) (1864=2*256+104)
                                        'set timer 2 as a 1Hz
                                        '   clock at
                                        'startup
10          hrbpm=60                    '(gives a heart rate
                                        '   signal at
                                        '60bpm)
            out timer0,1                'set timer 0 as a flip
                                        '   flop
15          out timer0,0                '

' turn the gates on using the 8255 at bits 0,1,2
            '    on portc
20          porta=&H70C
            portb=&H70D
            portc=&H71E
            con8255=&H71F
            ' port A output port B input port C output
```

```
' first set all 8255 ports to output, then set
'   portc to
' 0FFH
out con8255,130
out portc,&H0FF ' first print out the present value of the
'   interrupt
' vectors
locate 4,1
gosub 10000

' install the interrupt with a dummy buffer and
'   print
' vectors
reseter=256
call wrbuffer(reseter)
reseter=128
call wrbuffer(reseter)
call instint
locate 5,1
gosub 10000

' now go through required startup subroutines
gosub 90
' set up breathing signal
gosub 70
' set up heart rate variations
gosub 50
' put some information on screen
gosub 80                    ' turn D/A on
locate 1,1
print "commands: h(rvar),i(nt
        on),q(uit),r(beats),b(reath),c(ounts)"
```

```
                    ' wait until user hits a key
30          savekey$=""
    40      while
len(savekey$)=0:savekey$=savekey$+inkey$:wend
            if savekey$="r" then gosub 50
            'print heart beats
35          if savekey$="q" then goto 9996   'quit
            if savekey$="c" then gosub 60    'print timers
            if savekey$="h" then gosub 70
            'set up heart rate variations unmask interrupts
            if savekey$="i" then gosub 80
            if savekey$="b" then gosub 90
5           'set up breathing signal
            savekey$=""
            goto 40

'print present value of heartbeats
10
    50      locate 7,1
            call rdbeat(n)
            print "present heart beats are: ";n;time$
            return
15

' print present value of counters
    60      out control,0              'latch timer0
            tlow0=inp(timer0)
20          thigh0=inp(timer0)
            out control,&h40           'latch timer1
            tlow1=inp(timer1)
            thigh1=inp(timer1)
            out control,&h80           'latch timer2
25          tlow2=inp(timer2)
            thigh2=inp(timer2)
            locate 8,1
            print "timer0:
";tlow0+thigh0*16;tab(20);"                   timer1:
30               ";tlow1+thigh1*16;
```

```
            print tab(40);"timer2: ";tlow2+thigh2*16
            return

' set up the heart rate variations
            '      respiratory frequency is given by
            '        1280Hz/buffer
            '         length
            '        low frequency is 1280Hz/low frequency
            '         divider
            '
70          if numval<=0 then beep:print "setup analog
               buffer first":return
71          locate 17,1
            print "present lfa,rfa(bpm)= ";zlfa,zrfa,"at
    freqs(Hz):";zfqlow,zfqres
            input "lfa,rfa,low freq: ",zlfan,zrfan,zfqlown
            if zlfan>30. then beep:goto 71 else zlfa=zlfan
            if zrfan>30. then beep:goto 71 else zrfa=zrfan
            if zfqlown<.02 or zfrlown>zfqres then beep:goto
    71 else
            zfqlow=zfqlown
            locate 21,1
            print "mean heart rate(bpm)= ";hrbpm
72          locate 22,1
            input "new mean heart rate(bpm): ",newhrbpm
            if newhrbpm>150 or newhrbpm<30 then beep:goto 72
    else
            hrbpm=newhrbpm
                'clear screen after input
            locate 17,1
            print space$(72)
            print space$(72)
            print space$(72)
            print space$(72)
            print space$(72)
```

```
                ' now compute values for hrsetup subroutine
35              meandiv=76800#/hrbpm    '1280*60 ticks/min gives
                                        '      ticks/beat
                rfascal=76800#/(hrbpm-zrfa)-76800#/(hrbpm+zrfa)
                                ' rfascal is the total excursion
                                '      of respiration
                lfascal=76800#/(hrbpm-zlfa)-76800#/(hrbpm+zlfa)
5                               ' lfascal is the total excursion
                                '      of low frequency
                lowdiv=meandiv-(rfascal+lfascal)/2# tbaserst=1280#/zfqlow
10              locate 17,1
                print "tbaserst,rfascal,lfascal,lowdiv:
                        ";tbaserst;rfascal;lfascal;
                print lowdiv
                call hrsetup(tbaserst,rfascal,lfascal,lowdiv)
15
                return 20              ' print out interrupt controller parameters
        80      locate 10,1
                mask=inp(&h21)
                mask=maskx or 24
                out &h21,mask
25              mask=inp(&h21)
                print "8259 IMR(interrupt mask regsiter)=
";mask;"
                        =";hex$(mask)
                return
30

' this subroutine will change the analog buffer
        90      locate 12,1
```

```
input "enter breathing rate (bpm): ",brate
if brate>75 or brate<7 then beep:goto 90
zfqres=brate/60#
numval=76800#/brate
ztincr=8*ATN(1#)/numval
locate 12,40
color 31:print "calculating respiratory
signal...":color
        7
call exstint              ' turn off interrupts
                          '    while
            resetting buffer
reseter=256
call wrbuffer(reseter)
for itime=0 to numval
    ztnow=ztnow+ztincr
    analogval=127*(1#+SIN(ztnow))
    call wrbuffer(analogval)
next itime
call instint
locate 12,40
print "respiratory signal active now    "
return ' exstall the interrupt and print vector
9996  cls
      locate 4,1
      gosub 10000
      call exstint
      locate 5,1
      gosub 10000
      locate 21,1
9999  stop ' subroutine to print out the interrupt vectors
```

```
                    page    66,80
; bdzint.asm - an assembler routine to handle interrupts
;              from IRQ3
; Last revision: 1 April 1985
;
;

;-------------------------------;
                        ;   8088 interrupt location     ;
                        ;-------------------------------;

abs0            segment at 0      ;absolute memory segment
                                          ;allows placement of
                                          ;interrupt address
                                          ;future timebase
                                          ;  interrupt handler
                                          ;  resides at int 0B
        IRQ3_int        dw       2 dup(?);offset value is a word org      0CH*4    ;heart beat interrupt
                                          ;handler resides at int
                                          ; 0C
        IRQ4_int        dw       2 dup(?);offset value is a word abs0            ends              ;

;-------------------------------;
                        ; int_buffer: area to save DOS  ;
                        ;         dummy interrupt ptr   ;
                        ;-------------------------------;

int_buffer      segment           ;data segment containing
                                          ;user interrupt buffer
        save_int        dw       4 dup(?);offset for two DOS
                                          ;interrupts saved
                                          ;to be restored using
```

```
                                        ;exstint int_buffer      ends            ;

;----------------------------;
                        ; working storage for        ;
                        ; time base interrupts       ;
                        ;----------------------------;

dseg_tbase      segment         ;data segment for timebase
                                  ; interrupt
  heartbeats      dw       ?      ;keep track of heart beats
                                  ; here (for debugging)
  base_rate       dw       ?      ;lowest divisor for heart
                                  ; rate
  lfa_scal        db       ?      ;low frequency modulation
  rfa_scal        db       ?      ;high frequency modulation
  tbase_ctr       dw       ?      ;counter for timebase
                                  ; interrupt
                                  ;(use for low frequency
                                  ;   generation)
  tbase_rst       dw       ?      ;reset value for tbase_ctr
                                  ; used to set low frequency
  tbase_ptr       dw       ?      ;pointer to present analog
                                  ; value
  tbase_len       dw       ?      ;length of analog data buffer
  tbase_buffer    db   2800dup(?) ;buffer for A/D values
  dseg_tbase      ends            ;

;------------------------------------;
                        ; setup structures to allow access to;
                        ; arguments pased by BASIC           ;
                        ;------------------------------------;
```

```
                    ; subroutine rdbeat(BASIC_beats)
     frame_rd       struc           ;define the stack
                                    ;structure for passing
                                    ;arguments to BASIC
     savebp1        dw      ?       ;caller's base pointer
     saveret1       dd      ?       ;return offset and
                                    ;segment pushed by BASIC
     BASIC_beats    dw      ?       ;place to return heart
                                    ;beats to BASIC
     frame_rd       ends ;subroutine wrbuffer (analog)
     frame_wr       struc   ;define the stack structure
                            ;   for passing
                            ;arguments from BASIC to
                            ;   analog buffer
     savebp2        dw      ?       ;caller's base pointer
     saveret2       dd      ?       ;return offset and segment
                                    ;   pushed by BASIC
     analog         dw      ?       ;place to receive analog value
                                    ;   from BASIC
     frame_wr       ends ;subroutine hrsetup(B_lreset,
                    ;   Brfa_scal,Blfa_scal,Bbase_
                    ;   rate)
     frame_hr       struc   ;define the stack structure for
                            ;   passing
                            ;arguments from BASIC to heart
                            ;   rate controls
     savebp3        dw      ?       ;caller's base pointer
     saveret3       dd      ?       ;return offset and segment pushed
                                    ;   by BASIC
     Bbase_rate     dw      ?       ;BASIC's lowest divider for heart
                                    ;   rate
     Blfa_scal      dw      ?       ;BASIC's low frequency scaler
                                    ;   (amplitude)
     Brfa_scal      dw      ?       ;BASIC's high frequency scaler
```

```
                            ; (amplitude)
       B_lreset   dw    ?   ;BASIC's low frequency timer
                            ;   reset value
       frame_hr   ends ;..........code segment begins here cseg_calibs       segment 'code'
       basic_dgroup      group    data,stack,const,heap,memory
                                  ;defining link to BASIC
       porta     equ     0700H    ;port definitions for
                                  ;8255 port expander
       portb     equ     0708H    ;these addresses are
                                  ;decoded on the homemade
       portc     equ     0710H    ;board
       control   equ     0718H    ;control word in the
                                  ;8255
       timer0    equ     0720H    ;8253 timer0 register
       timer1    equ     0721H    ;8253 timer1 register
       timer2    equ     0722H    ;8253 timer2 register
       con8253   equ     0723H    ;8253 control register ;-------------------------------------------------;
       ; timebase interrupt handler (not accessible to   ;
       ; BASIC)                                          ;
       ;-------------------------------------------------;
                   ;this routine reads the A/D every timer0
                   ;tick
                   ;with the next point in the analog
                   ;buffer tbase_int         proc    far     ;this procedure is not
                                         ;made public
                         assume  cs:cseg_sync,ds:dseg_
                            base,es:nothing,ss:nothing
                         push    ax      ;save registers used
```

```
                                            ;during interrupt
                    push    bx      ;
                    push    dx      ;
                    push    ds      ;

mov     ax,dseg_base    ;set up segment
                                            ;register for data area
                    mov     ds,ax           ;

;..........increment counter used for
                              ;low frequency generation
                    dec     tbase_ctr       ;decrement
                                            ; interrupt counter
                    jnz     ctr_ok          ;if not zero then
                                            ;   continue
                    mov     ax,tbase_rst    ;else reload reset
                                            ;value
                    mov     tbase_ctr,ax ;
                    ctr_ok:
                    ;..........get analog value from
                    ;buffer and send to DAC mov     bx,tbase_ptr    ;get pointer to
                                            ;analog data
                    dec     bx              ;
                    mov     al,tbase_buffer[bx]  ;get analog
                                            ;          value mov     dx,porta        ;send analog value
                                            ;to DAC
                    out     dx,al           ;

mov     dx,control      ;toggle the write
                                            ;latch for the DAC
                    mov     al,6            ;by using direct bit
```

```
                    out     dx,al           ;reset
                                            ;and
            inc     al              ;reset commands
            out     dx,al           ;

dec     tbase_ptr       ;point to next
                                    ;value
            jnz     tbase_eoi       ;if zero, reset
                                    ;pointer
            mov     ax,tbase_len    ;reset with buffer
                                    ;length
            mov     tbase_ptr,ax    ;

;.........acknowledge interrupt to
            ;           8259A
tbase_eoi:  mov     al,20H          ;send EOI to 8259A
            out     20H,al          ;

pop     ds              ;restore registers which
                                    ;were used
            pop     dx              ;
            pop     bx              ;
            pop     ax              ;
            iret                    ;return to place where
                                    ;interrupt occurred debugmsg1   db      'this is the end of the time
                     base interrupt' tbase_int   endp

;-------------------------------------------------;
; heart beat interrupt handler (not accessible    ;
; to BASIC)                                       ;
;-------------------------------------------------;
```

```
;this routine updates the timer1 rate generator
;every heart beat with the divider necessary to
;generate the next heart beat
;
;the respiratory modulation is given by a scaler
;    (0-255)
;times the present value of the respiratory
;    signal.
;the low frequency modulation is given by scaler
;    (0-255)
;times a value selected from the respiratory
;    buffer.
;the value selected is the
;    (tbase_ctr/tbase_rst)*buffer_length
;element hbeat_int       proc    far         ;this procedure is not
                                    ;made public
                assume  cs:cseg_calibs,ds:dseg_tbase
                assume  es:nothing,ss:nothing
                push    ax          ;save registers during
                                    ;interrupt
                push    bx          ;
                push    cx          ;
                push    dx          ;
                push    ds          ;

mov     ax,dseg_tbase    ;set up segment
                                         ;register for data area
                mov     ds,ax            ;

inc     heartbeats       ;increment heart
                                         ;  beat counter ;........calculate low frequency
                ;               modulation
                ; (the tbase buffer is used as a trig
```

; table here)

```
        mov     ax,tbase_ctr        ;get number of
                                    ;1280Hz pulses
        dec     ax                  ;
        mul     tbase_len           ;scale by length
                                    ;of respiratory
                                    ; buffer
        div     tbase_rst           ;divided by reset
                                    ;value to get
                                        pointer
        mov     bx,ax               ;to low frequency
                                    ; modulation
        mov     al,tbase_buffer[bx] ;get
                                    ; sinusoidal
                                    ; modulation
        mul     lfa_scal            ;and scale
                                    ; appropriately
        mov     cx,ax               ;cx accumulate
                                    ;divider for
                                    ; 1280Hz clock ;........calculate respiratory
;            modulation
        mov     bx,tbase_ptr        ;get present
                                    ;respiration
                                    ;signal
        mov     al,tbase_buffer[bx] ;from
                                    ;buffer
        mul     rfa_scal            ;scale with rfa
                                    ;scaler
        add     cx,ax               ;and add to cx add     cx,base_rate        ;finally add base
                                    ;rate to get
                                    ; value for
                                    ;timer1 (heart
                                    ;rate generator
                                    ; on
```

```
                ;............ send new divider to 8253
                ;    timer
        mov     al,76H          ;set timer 1 to
                                ;square wave
                                ; generator
        mov     dx,con8253      ;
        out     dx,al           ;

mov     dx,timer1       ;send divider to
                                ;time1
        mov     al,cl           ;low byte first
        out     dx,al           ;
        mov     al,ch           ;high byte next
        out     dx,al           ;
                ;..........acknowledge interrupt to
                ;          8259A
        mov     al,20H  ;send EOI to 8259A
        out     20H,al  ;

pop     ds      ;restore registers and
        pop     dx      ;
        pop     cx      ;
        pop     bx      ;
        pop     ax      ;
        iret            ;return to place where
                        ;interrupt occurred debugmsg2       db      'this is the end of the heart
                        beat interrupt' hbeat_int       endp

;--------------------------------------------------;
```

; subroutine instint (install_interrupts) ;
;------------------------------------------------;

```
instint         proc    far
                public  instint
                ;public symbol allows external references
                ;es,ds used to access interrupt and must
                ;  be restored movsw
                ;uses (ds:si)(es:di) addr
                assume  cs:cseg_calibs,ss:basic_
                    dgroup,ds:basic_dgroup
                assume  es:int_buffer ;..........save registers
                push    ds              ;save ds register on the
                                        ; stack
                push    es              ;save es register on the
                                        ; stack push    bp              ;save BASIC base pointer
                                        ;   for return to BASIC
                mov     bp,sp           ;point stack pointer at
                                        ;frame reference to
                                        ;address of BASIC analog
                                        ;data buffer push    ax              ;save additional
                                        ;registers
                push    si              ;
                push    di              ;

;set up the segment registers as assumed mov     ax,int_buffer   ;
                ;es points to buffer area to save
                ;DOS dummy interrupt vector
                mov     es,ax           ;
                mov     ax,0            ;ds points to
```

```
                                ;abs0 (interrupt table)
                mov     ds,ax           ;
                assume  ds:abs0         ;

;setup access to interrupt vectors
                lea     di,save_int     ;load offset of
                                        ;save_int in es,di
                lea     si,IRQ3_int     ;load offset of
                                        ;IRQ3_int in ds,si
                movsw                   ;save DOS dummy
                                        ;interrupt vectors to be
                movsw                   ;restored later
                movsw                   ;now saving IRQ4
                movsw                   ;

;install the DAC timebase (IRQ3)
                mov     IRQ3_int+2,cseg_calibs
                mov     IRQ3_int,offset tbase_int;
                                        ;interrupt handler now
;install the heart beat (IRQ4) interrupt handler now
                mov     IRQ4_int+2,cseg_calibs;
                mov     IRQ4_int,offset hbeat_int;

;..........return to BASIC pop     di      ;restore additional
                                    registers
                pop     si      ;
                pop     ax      ;

pop     bp      ;restore BASIC's base
                                ;pointer and
                pop     es      ;segment registers
                                    before returning
                pop     ds      ;
                ret     0       ;delete 0 parameters (0
```

```
                                      ;bytes) from the stack
                                      ;and return to the
                                      ;calling routine debugmsg3     db      'this is the end of the
                             interrupt installation' instint       endp
                     ;---------------------------------------;
                     ; subroutine exstint (exstall_          ;
                     ; interrupts)                           ;
                     ;---------------------------------------;

exstint       proc    far
                     public  exstint ;public symbol allows
                                     ;external references
                     assume  cs:cseg_calibs,ss:basic_dgroup
                     assume  ds:int_buffer,es:abs0
                             ;es,ds used to access interrupt
                             ;vectors and must be restored
                             ;movsw uses (ds:si)(es:di) addr ;..........save registers push    ds      ;save ds register on the
                                     ; stack
                     push    es      ;save es register on the
                                     ; stack
                     push    bp      ;save BASIC base pointer
                                     ;    for return to BASIC
                     mov     bp,sp   ;point stack pointer at
                                     ;    frame reference to
                                     ;access arguments passed
                                     ;    by BASIC (none here)

push    ax      ;save additional
```

```
                                    ;registers
                    push    si      ;
                    push    di      ;
                                    ;set up the segment
                                    ;  registers as assumed
                    mov     ax,0            ;es points to
                                    ;abs0 (interrupt table)
                    mov     es,ax           ;
                    mov     ax,int_buffer   ;ds points to
                                    ;buffer area to save
                    mov     ds,ax           ;DOS dummy
                                    ;interrupt vector ;setup access to interrupt vectors
                    lea     di,IRQ3_int     ;load offset of
                                    ;IRQ3_int in es,di
                    lea     si,save_int     ;load offset of
                                    ;save_int in ds,si
                    movsw                   ;restore DOS
                                    ;dummy interrupt vectors
                    movsw                   ;for IRQ3
                    movsw                   ;and IRQ4
                    movsw                   ;

;..........return to BASIC pop     di      ;restore additional
                                            registers
                    pop     si      ;
                    pop     ax      ;

pop     bp      ;restore BASIC's base
                    pop     es      ;pointer and segment
                    pop     ds      ;registers before
                                    ;returning
                    ret     0       ;delete 0 parameters (0
                                    ;bytes) from the stack
```

```
                                        ;and return to the
                                        ;calling routine
        debugmsg4       db      'this is the end of the
                                interrupt exstallation' exstint         endp

;-------------------------------------;
                        ; subroutine rdbeat (read_heart_beats ;
                        ;-------------------------------------;

rdbeat          proc    far
                        public  rdbeat    ;public symbol allows
                                          ;external references
                        assume  cs:cseg_calibs,es:dseg_tbase
                        assume  ds:basic_dgroup,ss:basic_dgroup ;..........save registers push    bp        ;save BASIC base pointer
                                          ;for return to BASIC
                        mov     bp,sp     ;point stack pointer at
                                          ;frame reference to
                                          ;access arguments passed
                                          ;by BASIC (one here)

push    ax        ;save additional
                                          ;registers
                        push    es        ;
                        push    di        ;

mov     ax,dseg_tbase    ;set up segment
```

```
                        mov     es,ax               ;register for data area
                                                    ;

mov     ax,heartbeats       ;get
                                                    ;beats from local memory
                        mov     di,[bp].BASIC_beats ;
                        mov     [di],ax             ;send
                                                    ;beats to BASIC ;..........return to BASIC pop     di                  ;restore additional
                                                     registers
                        pop     es                  ;
                        pop     ax                  ;

pop     bp                  ;restore BASIC's base
                                                    ;pointer,
                        ret     2                   ;delete 2 parameters (4
                                                    ;bytes) from the stack
                                                    ;and return to the
                                                    ;calling routine debugmsg5       db      'this is the end of the heart
                                 beat read routine' rdbeat  endp

;----------------------------------------;
                        ; subroutine wrbuffer(analog)            ;
                        ;----------------------------------------;

wrbuffer        proc    far
                        public wrbuffer    ;public symbol allows
                                           ;external references
```

```
        assume  cs:cseg_calibs,es:dseg_tbase
        assume  ds:basic_dgroup,ss:basic_dgroup ;..........save registers push    bp              ;save BASIC base pointer
                                ;for return to BASIC
        mov     bp,sp           ;point stack pointer at
                                ;frame reference to
                                ;access arguments passed
                                ;by BASIC (one here)

push    ax              ;save additional
                                ;registers
        push    bx              ;
        push    es              ;
        push    si              ;
        mov     ax,dseg_tbase   ;set up segment
                                ;register for data area
        mov     es,ax           ;

mov     si,[bp].analog  ;get analog value
                                ;from BASIC
        mov     ax,[si]         ;
        test    ah,0FFH         ;if upper byte is
                                ;zero
        jz      new_buff        ;then install a
                                ;new point in the
                                ;buffer
        mov     tbase_len,0     ;otherwise reset
                                ;the buffer
        mov     tbase_ptr,1     ;
        jmp     wr_ret          ;
        mov     bx,tbase_len    ;get present
                                ;pointer and use
                                ;it
        mov     tbase_buffer[bx],al     ;to store
```

```
                                                      ;buffer value
                        inc     tbase_len             ;point to next
                                                      ;buffer value ;..........return to BASIC pop     si              ;restore additional
                                                ;registers
    wr_ret:             pop     es              ;wr_ret:
                        pop     bx              ;
                        pop     ax              ;

pop     bp              ;restore BASIC's base
                                                ;pointer,
                        ret     2               ;delete 1 parameters (2
                                                ;bytes) from the stack
                                                ;and return to the
                                                ;calling routine debugmsg6           db      'this is the end of the buffer
                                 write routine' wrbuffer            endp

;-----------------------------------------------------------;
    ; subroutine hrsetup(B_lreset,Brfa_scal,Blfa_scal,          ;
    ; Bbase_rate)                                               ;
    ;-----------------------------------------------------------;
                        proc    far
                        public  hrsetup         ;public symbol allows
                                                    external references
                        assume  cs:cseg_calibs,es:dseg_tbase
                        assume  ds:basic_dgroup,ss:basic_dgroup ;...........save registers
```

```
        push    bp              ;save BASIC base
                                ;pointer for return
                                ;to BASIC
        mov     bp,sp           ;point stack pointer
                                ;at frame
                                ;reference to
                                ;access arguments
                                ;passed by BASIC
                                ;(one here)

push    ax              ;save additional
                                ;registers
        push    es              ;
        push    si              ;

mov     ax,dseg_tbase   ;set up segment
                                ;register for
                                ;data area
        mov     es,ax           ;

mov     si,[bp].Bbase_rate   ;get lowest
                                     ;divisor for heart
        mov     ax,[si]         ;rate from BASIC
        mov     base_rate,ax    ;and save in local
                                ;    data
                                ;    segment
        mov     si,[bp],Blfa_sacl   ;get low freq
                                    ;   modulation
                                    ;   scale
        mov     ax,[si]         ;       from BASIC
        mov     lfa_scal,al     ;and save LSbyte in
                                ;local data
                                ;   segment mov     si,[bp].Brfa_scal   ;get high freq
                                    ;   modulation scale
        mov     ax,[si]         ;from BASIC
        mov     rfa_scal,al             ;and save
```

```
                                       ;LSbyte in local data
                                       ;segment
        mov    si,[bp].B_lreset   ;get low freq
                                  ;   timer reset value
        mov    ax,[si]            ;from BASIC
        mov    tbase_rst,ax       ;and save in
                                  ;  local data segment ;..........return to BASIC pop    si                 ;restore additional
                                  ;registers
        pop    es                 ;
        pop    ax                 ;

pop    bp                 ;restore BASIC's base
                                  ;pointer,
        ret    8                  ;delete 4 parameters (8
                                  ;  bytes) from the stack
                                  ;and return to the
                                  ;  calling routine debugmsg 7     db     'this is the end of the heart rate
                       setup routine' hrsetup        endp cseg_calibs    ends end
```

What is claimed is:

1. A method for diagnosis of malfunctions of the cardiovascular control system in a patient comprising the steps of:
   monitoring a power spectrum of heart rate fluctuations in the patient; and
   identifying a level below 0.1 (beats/min)$^2$ in the power spectrum of heart rate fluctuations at a frequency between 0.04 and 0.10 Hz as indicative of cardiovascular instability.

2. A method for diagnosis of malfunctions of the cardiovascular control system in a patient comprising the steps of:
   monitoring a power spectrum of heart rate fluctuations in the patient; and
   identifying a marked increase above 10 (beats/min.)$^2$ in a peak in the heart rate fluctuation power spectrum at a frequency between 0.04 to 0.10 Hz as indicative of cardiovascular stress.

3. A method for diagnosis of malfunctions of the cardiovascular control system in a patient comprising the steps of:
   monitoring a power spectrum of heart rate fluctuations in the patient; and
   identifying a ratio of the area under a heart rate power spectrum peak at a frequency between 0.04 and 0.1 Hz to the area under a peak in the respiratory heart rate fluctuation power spectrum centered at the mean respiratory rate as having an absolute value less than 2.0 for longer than or equal to one hour as indicative of cardiac instability.

4. A method for diagnosis of malfunctions of the cardiovascular control system in a patient comprising the steps of:
   monitoring a power spectrum of heart rate fluctuations in the patient; and
   identifying a ratio of the area under a heart rate power spectrum peak at a frequency between 0.04 and 0.1 Hz to the area under a peak in the respiratory heart rate fluctuation power spectrum centered at the mean respiratory rate as having an absolute value greater than or 50 as indicative of cardiovascular stress.

* * * * *